US012157768B2

(12) United States Patent
Chen et al.

(10) Patent No.: US 12,157,768 B2
(45) Date of Patent: Dec. 3, 2024

(54) ANTI-LILRB2 ANTIBODIES AND METHODS OF USE THEREOF

(71) Applicants: ICAHN SHOOL OF MEDICINE AT MOUNT SINAI, New York, NY (US); THE METHODIST HOSPITAL, Houston, TX (US)

(72) Inventors: Shu-Hsia Chen, Houston, TX (US); Ping-Ying Pan, Houston, TX (US)

(73) Assignees: Icahn School of Medicine at Mount Sinai, New York, NY (US); The Methodist Hospital, Houston, TX (US)

( * ) Notice: Subject to any disclaimer, the term of this patent is extended or adjusted under 35 U.S.C. 154(b) by 841 days.

(21) Appl. No.: 17/276,324

(22) PCT Filed: Sep. 17, 2019

(86) PCT No.: PCT/US2019/051529
§ 371 (c)(1),
(2) Date: Mar. 15, 2021

(87) PCT Pub. No.: WO2020/061059
PCT Pub. Date: Mar. 26, 2020

(65) Prior Publication Data

US 2022/0056128 A1 Feb. 24, 2022

Related U.S. Application Data

(60) Provisional application No. 62/732,299, filed on Sep. 17, 2018, provisional application No. 62/732,334, filed on Sep. 17, 2018.

(51) Int. Cl.
*C07K 16/28* (2006.01)
*A61K 45/06* (2006.01)
(Continued)

(52) U.S. Cl.
CPC .......... *C07K 16/2803* (2013.01); *A61K 45/06* (2013.01); *A61P 35/00* (2018.01); *A61K 2039/505* (2013.01)

(58) Field of Classification Search
None
See application file for complete search history.

(56) References Cited

U.S. PATENT DOCUMENTS

2015/0284460 A1 10/2015 Nedospasov et al.
2016/0011217 A1 1/2016 Matsumura et al.
2018/0086829 A1 3/2018 Zhang et al.

FOREIGN PATENT DOCUMENTS

WO 2014/164519 A1 10/2014
WO 2015/179633 A1 11/2015
(Continued)

OTHER PUBLICATIONS

Deng Mi et al: "A motif in LILRB2 critical for Angpt12 binding and activation", Blood, American Society of Hematology, US, vol. 124, No. 6, Aug. 7, 2014 (Aug. 7, 2014), pp. 924-935.
(Continued)

*Primary Examiner* — Karl J Puttlitz
(74) *Attorney, Agent, or Firm* — Fox Rothschild LLP

(57) ABSTRACT

Antibodies and antibody fragments that specifically bind to LILRB2 are disclosed. Also provided herein are compositions comprising antibodies and antibody fragments that specifically bind to LILRB2 and methods of use thereof. Also provided are related chimeric antigen receptors (CARs) and cells comprising same (e.g., T cells, natural killer cells, or macrophages), and uses of the CARs and cells in targeting tumors and killing them, asthma treatment, or in targeting and removing infected cells (e.g., to treat infections or infectious diseases), or in suppressing immune system cells, as involved in autoimmune disease or transplant rejection.

19 Claims, 106 Drawing Sheets

Specification includes a Sequence Listing.

(51) Int. Cl.
*A61P 35/00* (2006.01)
*A61K 39/00* (2006.01)

(56) References Cited

FOREIGN PATENT DOCUMENTS

| | | | |
|---|---|---|---|
| WO | 2016/111947 | A2 | 7/2016 |
| WO | 2016/144728 | A2 | 9/2016 |
| WO | 2018091661 | A1 | 5/2018 |
| WO | 2018/187518 | A1 | 10/2018 |

OTHER PUBLICATIONS

Wu Ching-Lien et al: "Multiplex bead-based immunoassay for the free soluble forms of the HLA-G receptors, ILT2 and ILT4", Human Immunology, New York, NY, US, vol. 77, No. 9, Feb. 10, 2016 (Feb. 10, 2016), pp. 720-726.
Extended European Search Report mailed May 17, 2022 in European Patent Application No. 19863793.6, 14 pages.
Zhang, J. et al., "Leukocyte immunoglobulin-like receptors in human diseases: an overview of their distribution, function, and potential application for immunotherapies", Journal of Leukocyte Biology. Aug. 2017, Epub Mar. 28, 2017, vol. 102, No. 2; pp. 351-360.
An, H et al. "Soluble LILRA3 promotes neurite outgrowth and synapses formation through a high-affinity interaction with Nogo 66," Journal of Cell Science. Mar. 15, 2016, Epub Jan. 29, 2016, vol. 129, No. 6; pp. 1198-1209.
International Search Report and Written Opinion mailed Feb. 6, 2020, in International Application No. PCT/US2019/051529, 12 pages.

AntiLILRB2, TNFα raw

AntiLILRB2, IL-10 raw

5x10³/well for 3.5 days in 2% FBS RPMI, Ab 5ug/ml

IL-4 (min) | IgG 0 5 10 30 | αLILRB2 0 5 10 30
p-STAT6
actin

IL-4 (min) | IgG 0 5 10 30 | αLILRB2 0 5 10 30
SOCS1
SOCS3
Tubulin

— | IgG | αLILRB2
p-Akt
actin

IP:42D1 (IgG, αLILRB2) | Input (IgG, αLILRB2)
LILRB2
p-SHP1
SHP1
actin

CD16
PD-L1
CD163
CD14
HLA-DR
MFI
IgG
αLILRB2

Avg Radiance [p/s/cm²/sr]
(number x 104)
Ig
αLILRB2
αPD1
Combo

TNFα pg/ml

CD14+CD16-
*, p= 0.016
CD14-CD16-
ns
MFI of GFP E. Coli

TO FIG. 17A-2

FROM FIG. 17A-1

TO FIG. 17A-3

FROM FIG. 17A-2

FROM FIG. 18B-1

TO FIG. 18B-5

FROM FIG. 18B-2

FROM FIG. 18B-4

TO FIG. 18B-6

FROM FIG. 18B-3

FROM FIG. 18B-5

TO FIG. 18C-2

FROM FIG. 18C-1

TO FIG. 18C-3

FROM FIG. 18C-2

TO FIG. 18C-4

FROM FIG. 18C-3

TO FIG. 18C-5

FROM FIG. 18C-4

TO FIG. 18C-6

FROM FIG. 18C-5

TO FIG. 18C-7

FROM FIG. 18C-6

TO FIG. 18C-8

FROM FIG. 18C-7

TO FIG. 23B-2

AntiLILRB2, T cell proliferation raw

AntiLILRB2, T cell proliferation raw

FROM FIG. 23B-1

AntiLILRB2, T cell proliferation subtracted

AntiLILRB2, T cell proliferation subtracted

FROM FIG. 23C-1

AntiLILRB2, IFNg fold change

AntiLILRB2, IFNg fold change

FROM FIG. 23D-1

FROM FIG. 23E-1

AntiLILRB2, IFNg subtracted

FIG. 23G

| | Isotype | B1 | B2 | B3 | B4 | A1 | A2 | A4 | A5 | A6 |
|---|---|---|---|---|---|---|---|---|---|---|
| 4D3 | IgG2a | - | X | - | - | X | - | - | - | - |
| 12H6 | IgG2a | - | X | - | - | X | - | - | - | - |
| 8B5 | IgG2a | - | X | - | - | X | - | - | - | - |
| 15C6 | IgG2a | - | X | - | - | X | - | - | - | x |
| 4E7 | IgG2a | - | X | - | - | X | - | - | - | - |
| 4E2 | IgG2a | - | X | - | - | X | - | - | X | X |
| 8G10 | IgG2a | - | X | - | - | X | - | - | - | - |
| 50B9 | IgG2a | - | X | - | - | X | - | - | - | - |
| 33G2 | IgG2a | - | X | - | - | x | - | - | - | - |
| 51H9 | IgG2a | - | X | - | - | X | - | x | - | x |

```
                              SEQUENCE LISTING


<160> NUMBER OF SEQ ID NOS: 380

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Asp Ile Val Lys Asn
1               5


<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gln Ser Val Asp Asn Tyr Gly Tyr Ser Tyr
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Val Asp Tyr Asp Gly Asp Ser Tyr
1               5                   10


<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ile Gly Thr Ser
1               5


<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Asp Met Asn Thr Ala
1               5
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Gln Asn Ile Asn Val Trp
1 5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gln Asp Ile Ser Asn Tyr
1 5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Arg Thr Leu Val Arg Leu
1 5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Lys Ser Val Ser Ile Ser Gly Tyr Ser Tyr
1 5 10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Gln Ser Leu Val Asn Ser Tyr Gly Ile Thr Tyr
1 5 10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 11

Ser Ser Val Ser Ser Ser Cys
1               5


<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Asn Ile Tyr Ser Asn
1               5


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gln Asp Ile Val Asn Tyr
1               5


<210> SEQ ID NO 14

<400> SEQUENCE: 14

000


<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Asn Ile Tyr Cys Thr
1               5


<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gly Val Asp Thr Ala
1               5


<210> SEQ ID NO 17

<400> SEQUENCE: 17

000


<210> SEQ ID NO 18
<211> LENGTH: 6
<212> TYPE: PRT
```

-continued

<213> ORGANISM: Artificial Sequence
<220> FEATURE:
<223> OTHER INFORMATION: Description of Artificial Sequence: Synthetic
      peptide

<400> SEQUENCE: 18

Gln Asp Ile Arg Asn Tyr
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gly Ile Val Asn Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Asp Val Thr Asn Ala
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Asp Val Ser Thr Ala
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Val Ile Thr Asn Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ser Val Ser Tyr
1               5

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Lys Ser Val Ser Thr Ser Gly Tyr Ser Tyr
1 5 10

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Gln Gly Ile Ser Asn Tyr
1 5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gln Ser Leu Leu Asn Ser Ser Asn Gln Lys Asn Tyr
1 5 10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gln Asp Ile Asn Ser Tyr
1 5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gln Asp Val Gly Thr Ala
1 5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Lys Ser Val Ser Thr Ser Gly Phe Asn Tyr
1 5 10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Gln Asp Val Thr Thr Ala
1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Asp Val Ser Asn Ala
1 5

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Gln Ser Val Asp Tyr Tyr Gly Asp Ser Tyr
1 5 10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Ser Val Asp Tyr Gly Gly Asp Ser Tyr
1 5 10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Gln Asp Val Thr Lys Pro
1 5

<210> SEQ ID NO 35
<211> LENGTH: 3

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Tyr Ala Thr
1

<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Ala Ala Ser
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Ile Ala Ser
1

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Phe Ala Ser
1

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Ser Ala Ser
1

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Lys Ala Ser

1

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Tyr Thr Ser
1

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Leu Ala Ser
1

<210> SEQ ID NO 43
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gly Ile Ser
1

<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Ser Thr Ser
1

<210> SEQ ID NO 45
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Trp Ala Ser
1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Leu Thr Ser
1

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Val Thr Ser
1

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Arg Ala Asn
1

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Ala Ala Thr
1

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Cys Leu Gln Phe Tyr Glu Phe Pro Leu Thr Phe
1 5 10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Cys Gln His Ile Lys Glu Asp Thr Phe Ser Phe
1 5 10

<210> SEQ ID NO 52

<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Cys Gln Gln Ser Asn Glu Asp Pro Phe Thr Phe
1 5 10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Cys Gln Gln Ser Asn Gly Trp Pro Leu Thr Phe
1 5 10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Cys Gln Gln His Tyr Ser Thr Leu Pro Thr Phe
1 5 10

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Cys Gln Gln Gly Gln Ser Tyr Pro Leu Thr Phe
1 5 10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Cys Gln Gln Ser Asn Glu Asp Thr Phe Thr Phe
1 5 10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Cys Gln Gln Ser Asn Ser Trp Pro Leu Thr Phe
1 5 10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Cys Leu His Phe Tyr Glu Phe Pro Leu Glu Phe
1 5 10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Cys Gln His Ser Arg Glu Leu Pro Phe Thr Phe
1 5 10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Cys Leu Gln Gly Thr His Gln Pro Trp Thr Phe
1 5 10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Cys Gln Gln Tyr Lys Trp Leu Pro Ile Thr Phe
1 5 10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Cys Gln His Phe Trp Asp Ile Pro Tyr Thr Phe
1 5 10

<210> SEQ ID NO 63
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 63

Trp Thr Phe Ser Gly Cys Thr Gly Leu Glu Ile Gln
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Cys Gln His Ile Arg Glu Leu Thr Arg
1               5

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Cys Gln His Phe Trp Asp Ile Pro Tyr Glu Phe
1               5                   10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Cys Gln Gln Gly Asn Met Leu Pro Trp Thr Phe
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Gln Gln Tyr Ser Lys Leu Pro Trp Thr Phe
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Cys Gln Gln Tyr Ser Ser Tyr Pro Leu Thr Phe
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Cys Gln Gln Gly Asn Thr Leu Pro Trp Thr Phe
1 5 10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Cys Gln Gln Tyr Ser Glu Leu Pro Trp Thr Phe
1 5 10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Cys Gln Gln His Tyr Ser Phe Pro Tyr Thr Phe
1 5 10

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Cys Gln Gln His Tyr Ser Thr Pro Leu Thr Phe
1 5 10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Cys Gln Gln Tyr Gly Lys Phe Pro Cys Thr Phe
1 5 10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

-continued

Cys Gln Gln Trp Ser Ser Asn Pro Leu Thr Phe
1 5 10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Cys Gln His Ser Arg Glu Leu Pro Tyr Thr Phe
1 5 10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Cys Gln Gln Trp Ser Ser Asn Pro Pro Thr Phe
1 5 10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Ile Asn Pro Ser Asn Gly Gly Thr
1 5

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Cys Gln His Ile Arg Glu Leu Pro Trp Thr Phe
1 5 10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Cys Leu Gln Tyr Asp Glu Phe Pro Leu Thr Phe
1 5 10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Cys Gln His Phe Trp Gly Thr Pro Pro Thr Phe
1 5 10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Cys His Gln Tyr Ile Thr Tyr Pro Leu Thr Phe
1 5 10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Cys Gln His Phe Trp Gly Thr Pro Trp Thr Phe
1 5 10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Cys Gln Gln His Tyr Asn Thr Pro Leu Thr Phe
1 5 10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Cys Gln Gln Ile Asn Glu Asp Pro Phe Thr Phe
1 5 10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Cys Gln Gln Tyr Ser Glu Phe Pro Trp Thr Phe
1 5 10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Cys Gln Gln Tyr Ser Gly Tyr Pro Ser Thr Phe
1 5 10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

Ser Ser Val Ser Ser Ser Tyr
1 5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Cys Gln Gln Trp Asn Tyr Pro Leu Thr Phe
1 5 10

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gly Tyr Ala Phe Thr Asn Phe Phe
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Gly Tyr Ser Phe Thr Phe Phe Trp
1 5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Gly Tyr Ser Phe Thr Thr Tyr Trp
1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Gly Tyr Thr Phe Thr Asp Phe Glu
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Gly Tyr Thr Phe Thr Asn Tyr Trp
1 5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Tyr Thr Phe Thr Ser Tyr Trp
1 5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Tyr Ile Phe Thr Ser Asn Trp
1 5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Asp Tyr Thr Phe Thr Gly Tyr Trp
1 5

<210> SEQ ID NO 97
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 97

Gly Tyr Thr Phe Thr Asp Tyr Glu
1               5


<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Tyr Ser Phe Thr Asn Tyr Leu
1               5


<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Tyr Ala Phe Thr Asn Tyr Leu
1               5


<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Tyr Thr Phe Thr Asp Tyr Asn
1               5


<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Phe Ser Asn Tyr Gly
1               5


<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Tyr Ser Ile Thr Ser Gly Tyr Tyr
1               5
```

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Gly Tyr Thr Phe Thr Gly Tyr Gly
1 5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Gly Tyr Ser Phe Thr Asn Tyr Phe
1 5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Gly Phe Thr Phe Ser Asn Tyr Arg
1 5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Gly Phe Pro Phe Thr Asn Tyr Leu
1 5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Gly Tyr Thr Phe Thr Ser Tyr Gly
1 5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Gly Phe Thr Phe Ser Asp Tyr Tyr
1 5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Gly Tyr Ala Phe Ser Ser Ser Trp
1 5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Gly His Ser Ile Thr Ser Gly Tyr Tyr
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Gly Tyr Thr Phe Thr Thr Tyr Gly
1 5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gly Tyr Thr Phe Thr Asp Tyr Tyr
1 5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gly Tyr Thr Phe Thr Glu Tyr Pro
1 5

<210> SEQ ID NO 114
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

Gly Tyr Thr Phe Thr Gly Tyr Trp
1 5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 115

Gly Asn Thr Phe Thr Gly Tyr Trp
1 5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 116

Gly Tyr Ala Phe Thr Ser Tyr Trp
1 5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 117

Gly Tyr Ser Phe Thr Ser Tyr Trp
1 5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Trp Leu Pro His Ala Ser Gly Tyr Tyr
1 5

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Cys Gln Gln Ile Asn Thr Leu Pro Trp Thr Phe 1 5 10

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Ile Asn Pro Gly Ser Gly Gly Thr
1 5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Ile Asp Pro Ser Asp Asn Tyr Thr
1 5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Ile Asp Pro Ser Asp Ser Tyr Thr
1 5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Ile Asp Pro Glu Thr Gly Gly Ser
1 5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Ile Asp Pro Thr Gly Gly Ser
1 5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Ile Asp Pro Ser Asp Thr Tyr Thr
1 5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Ile His Pro Ser Asp Ser Asp Thr
1 5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Ile Tyr Pro Gly Ser Asp Thr Thr
1 5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Ile Leu Pro Glu Ser Gly Ser Thr
1 5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Ile Asn Pro Gly Ser Gly Gly Lys
1 5

<210> SEQ ID NO 130
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Cys Gln Gln His Tyr Ser Thr Pro Pro Thr Phe
1 5 10

<210> SEQ ID NO 131

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 131

Met Tyr Pro Gly Ser Gly Asn Thr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Thr Ser Ser Gly Gly Asn Ser Thr
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Ile Ser Tyr Glu Gly Ser Asn
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Ile Ser Tyr Lys Gly Ser Asn
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Ile Tyr Pro Arg Ser Ser Asn Thr
1               5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Ile Asn Pro Gly Ser Gly Gly Ile
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Ile Thr Val Lys Ser Asp Asn Tyr Gly Ala
1               5                   10

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Ile Tyr Pro Arg Ser Gly Asn Thr
1               5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Ile Tyr Pro Gly Ser Gly Asn Thr
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Ile Ser Asn Gly Gly Gly Asn Thr
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 141

Ile Ser Tyr Asp Gly Ser Thr
1               5

<210> SEQ ID NO 142
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 142

Ile His Pro Asn Ser Asp Thr Thr
1               5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Tyr Pro Gly Asp Gly Asp Thr
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ile Phe Tyr Asp Gly Ser Asn
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile His Pro Asn Ser Gly Asn Thr
1               5

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Ala Arg Gly Gly Ile Tyr Tyr Gly Pro Thr Gly Phe Ala Tyr Trp
1               5                   10                  15

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Met Asn Thr Tyr Ser Gly Val Pro
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

Ile Tyr Thr Asp Thr Gly Glu Pro
1 5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Ile Leu Ser Gly Ser Asp Ser Thr
1 5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Ile Leu Pro Gly Ser Asp Ser Thr
1 5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Ile Ser Tyr Gly Gly Gly Asn Thr
1 5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Ile Tyr Pro Gly Thr Asn Ser Thr
1 5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Ile Asp Pro Tyr Asp Thr Tyr Thr
1 5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Phe Asp Pro Glu Thr Gly Gly Ser
1 5

<210> SEQ ID NO 155
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Ile Ile Tyr Asp Gly Asn Asn
1 5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Ile Leu Pro His Ile Gly Tyr Pro
1 5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

Ile Asn Thr Tyr Ser Gly Val Pro
1 5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Cys Ala Arg Asn Asp Ala Met Asp Tyr Trp
1 5 10

<210> SEQ ID NO 159
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 159

Cys Ala Arg Arg Trp Leu Leu His Glu Met Ala Tyr Trp
1               5                   10


<210> SEQ ID NO 160
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Ala Arg Arg Trp Leu Leu His Glu Met Asp Tyr Trp
1               5                   10


<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Thr Ile Tyr Phe Trp Tyr Phe Asp Val Trp
1               5                   10


<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Gly Arg Arg Trp Leu Leu Leu Glu Met Asp Tyr Trp
1               5                   10


<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Ala Leu Gly Ser Thr Val Pro Ser Phe Val Tyr Trp
1               5                   10


<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Ala Arg Phe Phe Ser Ser Pro Trp Phe Ala Tyr Trp
1               5                   10
```

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Cys Ala Arg Arg Ser Leu Gly Leu Ser Phe Asn Tyr Trp
1 5 10

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Cys Ala Arg Arg Trp Leu Leu Arg Glu Met Asp Tyr Trp
1 5 10

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Cys Ala Arg Arg Trp Leu Leu His Lys Met Asp Tyr Trp
1 5 10

<210> SEQ ID NO 168
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Cys Ala Arg Arg Pro Thr Thr Val Leu Gly Gly Val Tyr Phe Asp Tyr
1 5 10 15

Trp

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Cys Ala Arg Gly Phe Leu Tyr Phe Asp Val Trp
1 5 10

<210> SEQ ID NO 170
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Cys Ala Lys Glu Pro Ile Tyr Tyr Asp Tyr Asp Glu Ala Gly Phe Asp
1 5 10 15

His Trp

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Cys Ala Arg His Pro Tyr Tyr Ser Tyr Tyr Val Glu Asp Trp Phe Ala
1 5 10 15

Tyr Trp

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Cys Val Arg Tyr Phe Asp Phe Trp
1 5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Cys Ala Arg Tyr Phe Asp Val Trp
1 5

<210> SEQ ID NO 174
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Cys Ala Arg Arg Glu Gly Ala Pro Tyr Ala Met Asp Tyr Trp
1 5 10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 175

Cys Val Arg Tyr Phe Asp Val Trp 1 5

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (1)..(1)
<223> OTHER INFORMATION: Any amino acid

<400> SEQUENCE: 176

Xaa Ser Leu Glu Asn Ser Asn Gly Asn Thr Tyr
1 5 10

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 177

Cys Ser Arg Ser Tyr Gly Ser Ser Tyr Gly Phe Ala Tyr Trp
1 5 10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

Cys Ala Arg Arg Glu Gly Ala Pro Tyr Thr Met Asp Tyr Trp
1 5 10

<210> SEQ ID NO 179
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

Cys Thr Arg Gly Phe Leu Tyr Phe Asp Val Trp
1 5 10

<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

Cys Ala Arg Gln Gly Glu Glu Trp Tyr Phe Asp Val Trp
1 5 10

<210> SEQ ID NO 181
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Cys Thr Arg Tyr Phe Asp Val Trp
1               5


<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Cys Ala Ile Arg Tyr His Tyr Tyr Phe Asp Tyr Trp
1               5                   10


<210> SEQ ID NO 183
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Cys Thr Pro Ala Tyr Tyr Ser Asn Tyr Gly Ala Trp Phe Ala Tyr Trp
1               5                   10                  15


<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Cys Ala Ile Arg Tyr Arg Tyr Tyr Phe Asp Tyr Trp
1               5                   10


<210> SEQ ID NO 185
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Cys Ala Arg Ile Thr Val Val Ala Ser Tyr Tyr Ala Met Asp Tyr Trp
1               5                   10                  15


<210> SEQ ID NO 186
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Thr Arg Met Gly Leu Arg Arg Ser Leu Tyr Ala Met Asp Tyr Trp
```

1 5 10 15

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 187

Cys Ala Arg Gly Gly Leu Thr Thr Val Val Val Asp Trp Tyr Phe Asp
1 5 10 15

Val Trp

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Cys Ala Arg Ser Tyr Arg Ser Ser Tyr Val Asp Tyr Ala Met Asp Tyr
1 5 10 15

Trp

<210> SEQ ID NO 189
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 189

Cys Val Arg Gly Val Leu Leu Ser Thr Val Phe Met Pro Glu Phe Ala
1 5 10 15

Tyr Trp

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 190

Cys Ala Arg Arg Gly Leu Gly Leu Ser Phe Asn Asn Trp
1 5 10

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 191

Cys Thr Gly Arg Asp Leu Gly Ile Ser Phe Asn Ser Trp
1 5 10

```
<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Ala Arg Gly Tyr Leu Tyr Phe Asp Val Trp
1               5                   10


<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Cys Gly Arg Tyr Phe Asn Gly Trp
1               5


<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Cys Ala Lys Glu Pro Ile Tyr Tyr Asp Tyr Asp Glu Ala Gly Phe Asp
1               5                   10                  15

Tyr Trp


<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Thr Gln Pro Phe Leu Tyr Phe His Val Trp
1               5                   10


<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Cys Ala Arg Arg Gly Ser Tyr Asp Gly Phe Arg Leu Asp Tyr Trp
1               5                   10                  15


<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 197

Gln Asn Val Gly Thr Asn
1               5

<210> SEQ ID NO 198

<400> SEQUENCE: 198

000

<210> SEQ ID NO 199
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Gly Ile Asn Asn Tyr
1               5

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gln Ile Val Asp Tyr Asp Gly Asp Ser Tyr
1               5                   10

<210> SEQ ID NO 201
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Ile Ser
1

<210> SEQ ID NO 202
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Leu Val Ser
1

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln His Ile Arg Glu Leu Pro Tyr Thr
1 5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 204

Leu Gln Phe Tyr Glu Phe Pro Leu Thr
1 5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 205

Gln Gln Gly Asn Thr Leu Pro Trp Thr
1 5

<210> SEQ ID NO 206
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 206

Gln Gln Tyr Ser Lys Leu Pro Trp Thr
1 5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 207

Gln Gln Ile Asn Glu Asp Pro Phe Thr
1 5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 208

Gln Gln Tyr Asn Arg Tyr Pro Leu Thr
1 5

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 209

Cys Gln Gln Trp Ser Ser Asn Pro Ile Leu Val
1 5 10

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 210

Gln Gln Gly Gln Ser Tyr Pro Leu Thr
1 5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 211

Gln Gln Tyr Ile Thr Tyr Pro Leu Thr
1 5

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 212

Gln Gln Tyr Ser Gly Tyr Pro Ser
1 5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 213

Gln Gln Tyr Asn Lys Leu Pro Trp Thr
1 5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 214

Gln Gln Gly Asn Met Leu Pro Trp Thr
1 5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Gln Gln Ser Asn Glu Asp Pro Phe Thr
1 5

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gln His Ile Arg Glu Leu Thr
1 5

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Gly Tyr Thr Phe Thr Ala Tyr Gly
1 5

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Glu Tyr Thr Phe Thr Asp Tyr Tyr
1 5

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Gly Tyr Thr Phe Thr Arg Tyr Trp
1 5

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Gly Tyr Ile Phe Thr Ser Tyr Trp
1               5

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Gly Tyr Thr Phe Thr Ser Asn Trp
1               5

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Gly Tyr Thr Phe Thr Asn Tyr Asp
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Gly Tyr Thr Phe Thr Glu Tyr Tyr
1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Gly Phe Ala Phe Thr Asn Tyr Leu
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Gly Tyr Thr Phe Thr Asn His Leu
1               5

<210> SEQ ID NO 226
<211> LENGTH: 8
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 226

Phe Asn Pro Asn Ile Gly Asn Ala
1               5

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ile Tyr Pro Gly Gly Asp Thr Thr
1               5

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ile Tyr Pro Arg Ser Gly Asn Ala
1               5

<210> SEQ ID NO 229
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ile Asn Pro Tyr Asn Gly Gly Thr
1               5

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ile His Pro Asn Thr Thr Asp Thr
1               5

<210> SEQ ID NO 231
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ile Asn Pro Tyr Asn Gly Gly Ile
1               5

<210> SEQ ID NO 232
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 232

Ile His Pro Asn Ser Gly Ser Thr
1 5

<210> SEQ ID NO 233
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 233

Ala Arg Gly Gly Leu Thr Thr Val Val Val Asp Trp Tyr Phe Asp Val
1 5 10 15

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 234

Ala Arg Gly Gly Arg Thr Leu Thr
1 5

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 235

Gly Gln Tyr Gly Tyr Asp Val Asp Tyr Phe Asp Tyr
1 5 10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 236

Ala Arg Arg Trp Leu Leu Arg Glu Met Asp Tyr
1 5 10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 237

Ala Arg Glu Gly Phe Ser Ala Gly Tyr
1 5

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Ala Arg Phe Phe Ser Ser Pro Trp Phe Ala Tyr
1 5 10

<210> SEQ ID NO 239
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Ala Lys Glu Pro Ile Tyr Tyr Asp Tyr Asp Glu Ala Gly Phe Asp His
1 5 10 15

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Ala Ser Arg Arg Arg Leu Cys Tyr Gly Leu
1 5 10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Ala Arg Arg Glu Gly Ala Pro Tyr Ala Met Asp Tyr
1 5 10

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Ala Arg His Pro Tyr Tyr Ser Tyr Tyr Val Glu Asp Trp Phe Ala Tyr
1 5 10 15

<210> SEQ ID NO 243
<211> LENGTH: 14

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid

<400> SEQUENCE: 243

Gln Gln Pro His Leu Ser Ile His Trp Val Ile Xaa Val Ser
1               5                   10


<210> SEQ ID NO 244
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ala Arg Glu Gly Arg Gly Trp Tyr Phe Asp Val
1               5                   10


<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Thr Pro Ala Tyr Tyr Ser Asn Tyr Gly Ala Trp Phe Ala Tyr
1               5                   10


<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ala Arg Asn Asp Ala Met Asp Tyr
1               5


<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Arg Gly Phe Leu Tyr Phe Asp Val
1               5


<210> SEQ ID NO 248
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 248

Gln Asp Val Ser Ile Ala
1               5

<210> SEQ ID NO 249
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Ala Thr
1

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Cys Leu Gln Tyr Asp Glu Leu Leu Thr Phe
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Cys Gln His Phe Trp Asp Thr Pro Leu Thr Phe
1               5                   10

<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Tyr Thr Phe Thr Thr Tyr Thr
1               5

<210> SEQ ID NO 253
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Arg Val Ser
1

<210> SEQ ID NO 254
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 254

Ile Asn Pro Asn Ser Asp Tyr Thr
1 5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 255

Ile Leu Pro Gly Ser Gly Ser Thr
1 5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 256

Ile Asn Pro Gly Ser Gly Ser Thr
1 5

<210> SEQ ID NO 257
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 257

Cys Ala Arg Gly Glu Ser Ile Thr Thr Val Val Ala Asp Trp Tyr Phe
1 5 10 15

Asp Val Trp

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 258

Ile Asn Pro Asn Asn Gly Gly Thr
1 5

<210> SEQ ID NO 259
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Cys Gln Gln Tyr Asn Thr Pro Pro Trp Thr Phe
1 5 10

<210> SEQ ID NO 260
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Glu Ile Ser
1

<210> SEQ ID NO 261
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Cys Ala Arg Met Gly Arg Gly Ser Leu Tyr Gly Met Asp Tyr Trp
1 5 10 15

<210> SEQ ID NO 262
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Cys Ala Arg Ser Gly His Ser Tyr Ser Leu Tyr Val Met Gly Tyr Trp
1 5 10 15

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Cys Ala Arg Ser Gly His Asn Tyr Ser Leu Tyr Val Met Gly Tyr Trp
1 5 10 15

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Cys Ala Arg Gly Ala Leu Tyr Tyr Phe Asp Asn Trp
1 5 10

<210> SEQ ID NO 265
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 265

Gly Tyr Met Phe Thr Thr Tyr Gly
1               5


<210> SEQ ID NO 266
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Cys Ala Arg Ile Gly Asn Thr Asn Ser Leu Tyr Thr Val His Tyr Trp
1               5                   10                  15


<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Tyr Thr Phe Thr Asn Tyr Gly
1               5


<210> SEQ ID NO 268
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Cys Thr Arg Ile Gly Asn Thr Asn Ser Leu Tyr Thr Val His Tyr Trp
1               5                   10                  15


<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Tyr Ser Ile Thr Ser Gly His Tyr
1               5


<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Ser Tyr Asp Gly Asn Asn
1               5
```

<210> SEQ ID NO 271
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Cys Val Arg Gly Tyr Tyr Tyr Tyr Gly Ser Arg Ala Met Asp Tyr Trp
1 5 10 15

<210> SEQ ID NO 272
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Ile Ser Tyr Asp Gly Asn Asp
1 5

<210> SEQ ID NO 273
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Cys Val Arg Gly Tyr Tyr Tyr Tyr Gly Ser Arg Ala Met Asp Cys Trp
1 5 10 15

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Gly Phe Ser Phe Ser Asp Tyr Gly
1 5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Ile Ser Ser Gly Ser Ser Thr Ile
1 5

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Cys Gly Pro Ser Asp Tyr Trp Tyr Phe Asp Val Trp
1 5 10

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Gly Phe Thr Phe Ser Asp Tyr Gly
1 5

<210> SEQ ID NO 278
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Cys Ala Arg Asp Tyr Phe Tyr Gly Asn Asn Tyr Gly Phe Pro Tyr Trp
1 5 10 15

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Gly Tyr Thr Phe Ile Asn Tyr Tyr
1 5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Ile Tyr Pro Gly Asn Ile Asn Ser
1 5

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 281

Cys Ala Met Thr Asn Ser Ser Ala Met Asp Tyr Trp
1 5 10

<210> SEQ ID NO 282
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 282

Gly Tyr Thr Phe Ile Ser Tyr Tyr
1 5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Ile Tyr Pro Gly Asn Val Asn Thr
1 5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Gly Tyr Thr Phe Thr Ser Tyr Tyr
1 5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 285

Gly Phe Ser Leu Thr Asn Tyr Asp
1 5

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 286

Ile Trp Thr Gly Gly Asn Thr
1 5

<210> SEQ ID NO 287
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 287

Cys Val Arg Glu Gly Phe Arg Gln Gly Tyr Tyr Ala Met Asp Tyr Trp
1 5 10 15

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Ile Asp Thr Lys Asn Gly Gly Thr
1 5

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 289

Cys Ala Ser Gly Gly Arg Gly Tyr Trp
1 5

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 290

Ile Asn Thr Tyr Thr Gly Glu Pro
1 5

<210> SEQ ID NO 291
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 291

Cys Thr Arg Asn Tyr Tyr Arg Pro Tyr Tyr Tyr Ala Met Asp Tyr Trp
1 5 10 15

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 292

Gly Tyr Ser Phe Thr Gly Tyr Thr
1 5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 293

Ile Asn Pro Tyr Asn Asp Asn Thr
1 5

<210> SEQ ID NO 294
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Cys Ala Arg Glu Gly Asn Tyr Tyr Gly Ala Ser Pro Trp Phe Ala Tyr
1 5 10 15

Trp

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Gly Tyr Thr Phe Thr His Tyr Gly
1 5

<210> SEQ ID NO 296
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Ile Asn Thr Ser Thr Gly Glu Thr
1 5

<210> SEQ ID NO 297
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Cys Ala Arg Tyr Tyr Tyr Gly Ser Ser Arg Trp Arg Asp Tyr Trp Phe
1 5 10 15

Ala Tyr Trp

<210> SEQ ID NO 298
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Gln Ser Leu Leu Ile Ser Thr Asn Gln Lys Asn Tyr
1 5 10

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Cys Gln Gln His Tyr Ser Ile Pro Pro Thr Phe
1 5 10

<210> SEQ ID NO 300
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

Gln Ser Leu Phe Ile Ser Thr Asn Gln Lys Asn Tyr
1 5 10

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Cys Gln Gln His Tyr Ser Ser Pro Pro Thr Phe
1 5 10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Gln Ser Leu Leu Ile Ser Thr Asn Gln Ile Asn Tyr
1 5 10

<210> SEQ ID NO 303
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 303

Cys Gln Gln His Tyr Asp Pro Pro Leu Thr Phe
1 5 10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 304

Cys Gln His His Tyr Asp Pro Pro Leu Thr Phe
1 5 10

<210> SEQ ID NO 305
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Gln Asn Leu Leu Asn Ser Ser Asn Gln Lys Asn Tyr
1 5 10

<210> SEQ ID NO 306
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Cys Gln Gln His Tyr Asn Thr Pro Pro Thr Phe
1 5 10

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Cys Gln Gln His Tyr Ser Pro Pro Pro Thr Phe
1 5 10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Gln Ser Leu Leu Ile Ser Ser Asn Gln Asn Asn Tyr
1 5 10

<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Cys Gln Gln Gly His Thr Leu Pro Tyr Thr Phe
1 5 10

<210> SEQ ID NO 310
<211> LENGTH: 11

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 310

Cys Gln Gln Gly Asn Thr Leu Pro Tyr Thr Phe
1 5 10

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 311

Cys Gln Gln Tyr Asn Ser Tyr Pro Phe Thr Phe
1 5 10

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Gln Thr Ile Gly Thr Trp
1 5

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Cys Gln Gln Leu Tyr Ser Thr Pro Leu Thr Phe
1 5 10

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Gln Asn Ile Arg Thr Ala
1 5

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 315

Cys Leu Gln His Trp Asn Tyr Pro Phe Thr Phe 1 5 10

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Gln Asn Val Arg Thr Ala
1 5

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Leu Asn Val Arg Thr Ala
1 5

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Ser Leu Leu Tyr Ser Ser Asn Gln Lys Asn Tyr
1 5 10

<210> SEQ ID NO 319
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

Cys Gln Gln Tyr Tyr Ser Tyr Arg Thr Phe
1 5 10

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Gln Asn Val Tyr Thr Thr
1 5

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Cys Gln Gln Tyr Asn Ser Tyr Pro Tyr Thr Phe
1 5 10

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Glu Asn Ile Tyr Ser Tyr
1 5

<210> SEQ ID NO 323
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Asp Ala Lys
1

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Cys Gln His His Tyr Gly Phe Pro Tyr Thr Phe
1 5 10

<210> SEQ ID NO 325
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Glu Thr Val Asp Thr Tyr Gly Asn Arg Phe
1 5 10

<210> SEQ ID NO 326
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Arg Ala Ser
1

<210> SEQ ID NO 327

<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Cys Pro Gln His Tyr Ser Thr Leu Cys Thr Phe
1 5 10

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Gly Phe Thr Phe Thr Gly Tyr Trp
1 5

<210> SEQ ID NO 329
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 329

Ile Leu Pro Val Ser Gly Ile Thr
1 5

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Cys Ala Arg Arg Gly Ser Pro Tyr Phe Asp Tyr Trp
1 5 10

<210> SEQ ID NO 331
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Gly Phe Ser Leu Asn Thr Phe Asp Met Gly
1 5 10

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Ile Trp Trp Asp Asp Asp Lys
1               5

<210> SEQ ID NO 333
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Cys Gly Arg Lys Pro Gly Gly Tyr Gly Asn Tyr Val Leu
1               5                   10

<210> SEQ ID NO 334
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gly Phe Ser Leu Thr Arg Tyr Gly
1               5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Ile Trp Ser Gly Gly Ser Thr
1               5

<210> SEQ ID NO 336
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Cys Ala Arg Asp Gly Arg Val Tyr Ala Met Asp Tyr Trp
1               5                   10

<210> SEQ ID NO 337
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Leu Asn Pro Tyr Asn Gly Gly Thr
1               5

<210> SEQ ID NO 338
<211> LENGTH: 15
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 338

Cys Ala Arg Gly Ser Gly Asn Ser Phe Tyr Ala Met Asp Tyr Trp
1 5 10 15

<210> SEQ ID NO 339
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Ile Tyr Pro Gly Asn Val Asn Ser
1 5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 340

Ile Ser Tyr Asp Gly Ser Asn
1 5

<210> SEQ ID NO 341
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 341

Cys Thr Ser Ile Tyr Gly Arg Phe Val Tyr Trp
1 5 10

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 342

Gly Tyr Thr Phe Thr Asn Phe Trp
1 5

<210> SEQ ID NO 343
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 343

Cys Ala Arg Asn Ser Gly Asp Tyr Leu Val Tyr Phe Asp Ser Trp
1 5 10 15

<210> SEQ ID NO 344
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Gly Tyr Ser Phe Thr Gly Tyr Phe
1 5

<210> SEQ ID NO 345
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Ile Asn Pro Ser Thr Gly Asp Thr
1 5

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Cys Ala Arg Gly Ala Thr Val Val Asp Tyr Pro Phe Asp Tyr Trp
1 5 10 15

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Ile His Pro Asn Gly Gly Ser Thr
1 5

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Cys Thr Arg Gly Leu Thr Gly Leu Phe Ala Tyr Trp
1 5 10

<210> SEQ ID NO 349
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 349

Gly Thr Ser
1

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 350

Cys His Gln Tyr His Arg Ser Pro Phe Thr Phe
1 5 10

<210> SEQ ID NO 351
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 351

Asp Thr Ser
1

<210> SEQ ID NO 352
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 352

Cys Phe Gln Gly Ser Gly Tyr Pro Phe Thr Phe
1 5 10

<210> SEQ ID NO 353
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 353

Gln Ser Val Leu Tyr Ser Ser Asp Gln Lys Asn Tyr
1 5 10

<210> SEQ ID NO 354
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 354

Cys His Gln Tyr Leu Ser His Thr Phe
1 5

<210> SEQ ID NO 355
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 355

Gln Asp Val Asn Thr Ala
1 5

<210> SEQ ID NO 356
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 356

Cys Gln Gln Leu Tyr Lys Leu Pro Arg Thr Phe
1 5 10

<210> SEQ ID NO 357
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 357

Ser Ser Val Asn Tyr
1 5

<210> SEQ ID NO 358
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 358

Cys Gln Gln Phe Ser Ser Ser Pro Tyr Thr Phe
1 5 10

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 359

Cys Gln Gln Trp Arg Ser Tyr Gln Leu Thr Phe
1 5 10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Cys Leu Gln Tyr Asp Glu Phe Leu Leu Thr Phe
1 5 10

<210> SEQ ID NO 361
<211> LENGTH: 482
<212> TYPE: PRT
<213> ORGANISM: Homo sapiens

<400> SEQUENCE: 361

Met Thr Gly Ala Tyr Pro Lys Pro Thr Leu Ser Ala Gln Pro Ser Pro
1 5 10 15

Val Val Thr Ser Gly Gly Arg Val Thr Leu Gln Cys Glu Ser Gln Val
20 25 30

Ala Phe Gly Gly Phe Ile Leu Cys Lys Glu Gly Glu Asp Glu His Pro
35 40 45

Gln Cys Leu Asn Ser Gln Pro His Ala Arg Gly Ser Ser Arg Ala Ile
50 55 60

Phe Ser Val Gly Pro Val Ser Pro Asn Arg Arg Trp Ser His Arg Cys
65 70 75 80

Tyr Gly Tyr Asp Leu Asn Ser Pro Tyr Val Trp Ser Ser Pro Ser Asp
85 90 95

Leu Leu Glu Leu Leu Val Pro Gly Val Ser Lys Lys Pro Ser Leu Ser
100 105 110

Val Gln Pro Gly Pro Val Met Ala Pro Gly Glu Ser Leu Thr Leu Gln
115 120 125

Cys Val Ser Asp Val Gly Tyr Asp Arg Phe Val Leu Tyr Lys Glu Gly
130 135 140

Glu Arg Asp Leu Arg Gln Leu Pro Gly Arg Gln Pro Gln Ala Gly Leu
145 150 155 160

Ser Gln Ala Asn Phe Thr Leu Gly Pro Val Ser Arg Ser Tyr Gly Gly
165 170 175

Gln Tyr Arg Cys Tyr Gly Ala His Asn Leu Ser Ser Glu Cys Ser Ala
180 185 190

Pro Ser Asp Pro Leu Asp Ile Leu Ile Thr Gly Gln Ile Arg Gly Thr
195 200 205

Pro Phe Ile Ser Val Gln Pro Gly Pro Thr Val Ala Ser Gly Glu Asn
210 215 220

Val Thr Leu Leu Cys Gln Ser Trp Arg Gln Phe His Thr Phe Leu Leu
225 230 235 240

Thr Lys Ala Gly Ala Ala Asp Ala Pro Leu Arg Leu Arg Ser Ile His
245 250 255

Glu Tyr Pro Lys Tyr Gln Ala Glu Phe Pro Met Ser Pro Val Thr Ser
260 265 270

Ala His Ala Gly Thr Tyr Arg Cys Tyr Gly Ser Leu Asn Ser Asp Pro
275 280 285

Tyr Leu Leu Ser His Pro Ser Glu Pro Leu Glu Leu Val Val Ser Gly
290 295 300

Pro Ser Met Gly Ser Ser Pro Pro Pro Thr Gly Pro Ile Ser Thr Pro
305 310 315 320

Ala Gly Pro Glu Asp Gln Pro Leu Thr Pro Thr Gly Ser Asp Pro Gln
325 330 335

Ser Gly Leu Gly Arg His Leu Gly Val Val Ile Gly Ile Leu Val Ala
340 345 350

Val Val Leu Leu Leu Leu Leu Leu Leu Leu Leu Phe Leu Ile Leu Arg
355 360 365

His Arg Arg Gln Gly Lys His Trp Thr Ser Thr Gln Arg Lys Ala Asp
370 375 380

Phe Gln His Pro Ala Gly Ala Val Gly Pro Glu Pro Thr Asp Arg Gly
385 390 395 400

Leu Gln Trp Arg Ser Ser Pro Ala Ala Asp Ala Gln Glu Glu Asn Leu
405 410 415

Tyr Ala Ala Val Lys Asp Thr Gln Pro Glu Asp Gly Val Glu Met Asp
420 425 430

Thr Arg Ala Ala Ala Ser Glu Ala Pro Gln Asp Val Thr Tyr Ala Gln
435 440 445

Leu His Ser Leu Thr Leu Arg Arg Lys Ala Thr Glu Pro Pro Pro Ser
450 455 460

Gln Glu Arg Glu Pro Pro Ala Glu Pro Ser Ile Tyr Ala Thr Leu Ala
465 470 475 480

Ile His

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Cys Leu Gln Val Thr His Val Pro Phe Thr Phe
1 5 10

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 363

Gly Phe Thr Phe Ser Asn Tyr Ala
1 5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Ile Thr Asp Gly Gly Thr Tyr Thr
1 5

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Cys Ala Arg Asp Asp Tyr Tyr Gly Ser Ser Tyr Leu Gly Phe Ala Tyr
1 5 10 15

Trp

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 366
aggtccacag tattctccag g 21

<210> SEQ ID NO 367
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 367
aggtccacag tattctccag g 21

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 368
gctgatcgac cagatcgaca g 21

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
cggttgtagt cctgcttgc 19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 370
gggcttcaat gggtcaacg 19

<210> SEQ ID NO 371
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 371
gccttcggtg tatttccctg 20

<210> SEQ ID NO 372
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 372
cccagcaggt agcattccc 19

<210> SEQ ID NO 373
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 373
gcagcagttc ctccgtgtag 20

<210> SEQ ID NO 374
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Cys Ser Gly Cys Thr Tyr Ala Trp Lys His Leu
1 5 10

<210> SEQ ID NO 375
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (2)..(2)
<223> OTHER INFORMATION: Any amino acid

<400> SEQUENCE: 375

Arg Xaa Ser
1

<210> SEQ ID NO 376
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Cys Phe Gln Gly Ser His Val Pro Trp Thr Phe
1 5 10

<210> SEQ ID NO 377
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

```
<400> SEQUENCE: 377

Gly Tyr Ser Phe Thr Asn Tyr Trp
1               5


<210> SEQ ID NO 378
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 378

Cys Ala Arg Arg Trp Leu Leu Xaa Lys Met Asp Tyr Trp
1               5                   10


<210> SEQ ID NO 379
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Cys His Gln His Tyr Ser Phe Pro Tyr Thr Phe
1               5                   10


<210> SEQ ID NO 380
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380

tttttttttt tttttttt                                                  18
```

ANTI-LILRB2 ANTIBODIES AND METHODS OF USE THEREOF

CROSS-REFERENCE TO RELATED APPLICATIONS

The present application is a National Stage Application under 35 U.S.C. § 371 of International Application No. PCT/US2019/051529 filed Sep. 17, 2029, which claims the priority benefit of U.S. Provisional Application No. 62/732,299, filed Sep. 17, 2018, and U.S. Provisional Application No. 62/732,334, filed Sep. 17, 2018, the contents of all are incorporated by reference in their entirety herein.

FEDERALLY SPONSORED RESEARCH OR DEVELOPMENT

This invention was made with Government support under Grant Nos. CA 109322 R01 CA 188610, R01 CA 204191 and CA 127483 awarded by the National Institutes of Health. The Government has certain rights in the invention.

TECHNICAL FIELD

This invention relates generally to antibodies or antigen-binding fragments thereof that bind to modulate leukocyte immunoglobulin (Ig)-like receptor (LILR) B2 (LILRB2) ("anti-LILRB2 antibodies") and modulate LILRB2 signaling to induce acquisition of either the M1 or the M2 functional phenotype in myeloid cells, compositions comprising anti-LILRB2 antibodies, and uses thereof. The invention also relates to related chimeric antigen receptors (CARs) and cells comprising same (e.g., T cells, natural killer cells, or macrophages), and uses of the CARs and cells in targeting tumors and killing them, asthma treatment, or in targeting and removing infected cells (e.g., to treat infections or infectious diseases), or in suppressing immune system cells, as involved in autoimmune disease or transplant rejection.

BACKGROUND

Leukocyte immunoglobulin (Ig)-like receptor (LILR), also known as immunoglobulin like transcripts (ILTs), are a family of inhibitory and stimulatory cell surface receptors encoded within the leukocyte receptor complex and are expressed by immune cell types of both myeloid and lymphoid lineage. ILTs influence both innate and acquired immune systems and demonstrate wide-ranging effects of LILR signaling on immune cell activity. The inhibitory activities of inhibitory receptors (LILRBs) occur upon co-crosslinking with activating receptors.

Myeloid-derived suppressor cells (MDSCs) are myeloid progenitors with immune suppressive functions that have included Gr1+CD11b+CD115+Ly6C+ monocytic (M)-cells and Gr1+CD11b+Ly6G+ granulocytic (G)-cells in mice (Gabrilovich et al., Cancer Res. 67:425, 2007; Huang et al., Cancer Res. 66:1123-1131, 2006). Human MDSCs are characterized as CD33+CD14+CD16+, CD11b+ CD14LowCD33+ or Lin-HLA-DRLow-CD33+ myeloid cells (Chen et. al., Clin. Cancer Res., 21(18):4073-2742, 2015; Ostrand-Rosenberg et al., J. Immunol. 182:4499-4506, 2009; Raychaudhuri et al., Neuro. Oncol. 13:591-599, 2011). In recent years, MDSCs have been found to play an important role in the regulation of the immune response in infection, malignancy, transplantation, and other immune disorders (e.g., Yin et al., J. Immunol. 185:5828-5834, 2010).

MDSCs can be differentiated and polarized into M1- and M2-linage cells (M1-cells expressing iNOS, TNF-α, IFN-gR, MHC class I, and CCR7, and M2-cells expressing arginase, IL-10, CD36, CD206, CD163, PD-L1, DC-SIGN and CCR2). M2-cells possess an enhanced ability to suppress Teff activation and proliferation compared to their M1-like counterparts in co-cultures of T-cells and in vivo (Ma et al., Immunity 34:385-395, 2011). M2-cells also possess higher potency in Treg expansion than those with an M1 phenotype, both in vitro and in vivo (Ma et al., Immunity 34:385-395, 2011). As M2-cells suppress Teff activation and proliferation, and promote Treg expansion, M2-cells can be used to treat autoimmune diseases, where a decrease in pro-inflammatory immune response is desired.

M1-cells have increased direct tumor killing and promote the development of anti-tumoral immunity through the augmentation of free radicals, death ligand, HLA-DR and immunostimulating cytokines-TNFa, (see, e.g., Ma et al., Immunity 34:385-395, 2011), and therefore, M1-cells can be used to treat cancer or other disorders where an increase in pro-inflammatory immune response is desired.

SUMMARY

The present disclosure features antibodies and antigen-binding fragments thereof that bind to leukocyte immunoglobulin (Ig)-like receptor B2 ("LILRB2"), e.g., an anti-LILRB2 antibody or antigen-binding fragments thereof. These antibodies can be grouped into three classes: one class (Class I) includes LILRB2 antagonist antibodies and antigen-binding fragments thereof for use in the treatment of cancer; and second class (Class II) including LILRB2 agonist antibodies cross-binding to LILRA1 and antigen-binding fragments thereof for use in the treatment in immune suppression.

In one aspect, provided herein is an antibody or antigen-binding fragment thereof that binds to LILRB2, comprising: (a) a heavy chain variable region (VH) comprising a heavy chain complementarity determining region 1 (HCDR1) comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and a light chain variable region (VL) comprising: a light chain CDR 1 (LCDR1) comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216; (b) a VH comprising a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising SEQ ID NO:50; (c) a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:159; and a VL comprising: a LCDR1 comprising the amino acid sequence set forth in SEQ ID NO:2, a LCDR2 comprising the amino acid sequence set forth in SEQ ID NO:36, and a LCDR3 comprising the amino acid sequence set forth in SEQ ID NO:51; (d) a VH comprising: a HCDR1 comprising the amino acid sequence set forth in SEQ ID NO:91, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (e) a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53; (f) a VH comprising: a HCDR1 comprising the amino acid sequence set forth in SEQ ID NO:92, a HCDR2 comprising the amino acid sequence set forth in SEQ ID NO:124, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:53; (g) a VH comprising: a HCDR1 comprising the amino acid sequence set forth in SEQ ID NO:93, a HCDR2 comprising the amino acid sequence set forth in SEQ ID NO:125, and a HCDR3 comprising the amino acid sequence set forth in SEQ ID NO:162; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (h) a VH comprising: a HCDR1 comprising the amino acid sequence set forth in SEQ ID NO:93, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (i) a VH comprising: a HCDR1 comprising the amino acid sequence set forth in SEQ ID NO:95, a HCDR2 comprising the amino acid sequence set forth in SEQ ID NO:127, and a HCDR3 comprising the amino acid sequence set forth in SEQ ID NO:164; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (j) a VH comprising: a HCDR1 comprising the amino acid sequence set forth in SEQ ID NO:96, a HCDR2 comprising the amino acid sequence set forth in SEQ ID NO:128, and a HCDR3 comprising the amino acid sequence set forth in SEQ ID NO:165; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55; (k) a VH comprising: a HCDR1 comprising the amino acid sequence set forth in SEQ ID NO:94, a HCDR2 comprising the amino acid sequence set forth in SEQ ID NO:122, and a HCDR3 comprising the amino acid sequence set forth in SEQ ID NO:166; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:56; (l) a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (m) a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:167; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (n) a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (o) a VH comprising: a HCDR1 comprising the amino acid sequence set forth in SEQ ID NO:98, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:8, a LCDR2 comprising the amino acid sequence set forth in SEQ ID NO:35, and a LCDR3 comprising the amino acid sequence set forth in SEQ ID NO:58; (p) a VH comprising: a HCDR1 comprising the amino acid sequence set forth in SEQ ID NO:99, a HCDR2 comprising the amino acid sequence set forth in SEQ ID NO:129, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (q) a VH comprising: a HCDR1 comprising the amino acid sequence set forth in SEQ ID NO:100, a HCDR2 comprising the amino acid sequence set forth in SEQ ID NO:258, and a HCDR3 comprising the amino acid sequence set forth in SEQ ID NO:168; and a VL comprising: a LCDR1 comprising the amino acid sequence set forth in SEQ ID NO:9, a LCDR2 comprising the amino acid sequence set forth in SEQ ID NO:42, and a LCDR3 comprising the amino acid sequence set forth in SEQ ID NO:59; (r) a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (s) a VH comprising: a HCDR1 comprising the amino acid sequence set forth in SEQ ID NO:94, a HCDR2 comprising the amino acid sequence set forth in SEQ ID NO:131, and a HCDR3 comprising the amino acid sequence set forth in SEQ ID NO:169; and a VL comprising: a LCDR1 comprising the amino acid sequence set forth in SEQ ID NO:10, a LCDR2 comprising the amino acid sequence set forth in SEQ ID NO:43, and a LCDR3 comprising the amino acid sequence set forth in SEQ ID NO:60; (t) a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (u) a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:170; and a VL comprising: a LCDR1 comprising the amino acid sequence set forth in SEQ ID NO:11, a LCDR2 comprising the amino acid sequence set forth in SEQ ID NO:4, and a LCDR3 comprising the amino acid sequence set forth in SEQ ID NO:61; (v) a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:62; (w) a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:15, a LCDR2 comprising the amino acid sequence set forth in SEQ ID NO:49, and a LCDR3 comprising the amino acid sequence set forth in SEQ ID NO:65; (x) a VH comprising: a HCDR1 comprising the amino acid sequence set forth in SEQ ID NO:104, a HCDR2 comprising the amino acid sequence set forth in SEQ ID NO:136, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (y) a VH comprising: a HCDR1 comprising the amino acid sequence set forth in SEQ ID NO:105, a HCDR2 comprising the amino acid sequence set forth in SEQ ID NO:137, and a HCDR3 comprising the amino acid sequence set forth in SEQ ID NO:177; and a VL comprising: a LCDR1 comprising the amino acid sequence set forth in SEQ ID NO:16, a LCDR2 comprising the amino acid sequence set forth in SEQ ID NO:45, and a LCDR3 comprising the amino acid sequence set forth in SEQ ID NO:68; (z) a VH comprising: a HCDR1 comprising the amino acid sequence set forth in SEQ ID NO:107, a HCDR2 comprising the amino acid sequence set forth in SEQ ID NO:138, and a HCDR3 comprising the amino acid sequence set forth in SEQ ID NO:178; and a VL comprising: a LCDR1 comprising the amino acid sequence set forth in SEQ ID NO:18, a LCDR2 comprising the amino acid sequence set forth in SEQ ID NO:41, and a LCDR3 comprising the amino acid sequence set forth in SEQ ID NO:69; (aa) a VH comprising: a HCDR1 comprising the amino acid sequence set forth in SEQ ID NO:94, a HCDR2 comprising the amino acid sequence set forth in SEQ ID NO:139, and a HCDR3 comprising the amino acid sequence set forth in SEQ ID NO:179; and a VL comprising: a LCDR1 comprising the amino acid sequence set forth in SEQ ID NO:20, a LCDR2 comprising the amino acid sequence set forth in SEQ ID NO:39, and a LCDR3 comprising the amino acid sequence set forth in SEQ ID NO:71; (bb) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67; (cc) a VH comprising: a HCDR1 comprising the amino acid sequence set forth in SEQ ID NO:108, a HCDR2 comprising the amino acid sequence set forth in SEQ ID NO:140, and a HCDR3 comprising the amino acid sequence set forth in SEQ ID NO:180; and a VL comprising: a LCDR1 comprising the amino acid sequence set forth in SEQ ID NO:21, a LCDR2 comprising the amino acid sequence set forth in SEQ ID NO:45, and a LCDR3 comprising the amino acid sequence set forth in SEQ ID NO:72; (dd) a VH comprising: a HCDR1 comprising the amino acid sequence set forth in SEQ ID NO:102, a HCDR2 comprising the amino acid sequence set forth in SEQ ID NO:141, and a HCDR3 comprising the amino acid sequence set forth in SEQ ID NO:181; and a VL comprising: a LCDR1 comprising the amino acid sequence set forth in SEQ ID NO:22, a LCDR2 comprising the amino acid sequence set forth in SEQ ID NO:41, and a LCDR3 comprising the amino acid sequence set forth in SEQ ID NO:73; (ee) a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:182; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74; (ff) a VH comprising: a HCDR1 comprising the amino acid sequence set forth in SEQ ID NO:109, a HCDR2 comprising the amino acid sequence set forth in SEQ ID NO:143, and a HCDR3 comprising the amino acid sequence set forth in SEQ ID NO:183; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:75; (gg) a VH comprising: a HCDR1 comprising the amino acid sequence set forth in SEQ ID NO:110, a HCDR2 comprising the amino acid sequence set forth in SEQ ID NO:144, and a HCDR3 comprising the amino acid sequence set forth in SEQ ID NO:173; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:259; (hh) a VH comprising: a HCDR1 comprising the amino acid sequence set forth in SEQ ID NO:94, a HCDR2 comprising the amino acid sequence set forth in SEQ ID NO:145, and a HCDR3 comprising the amino acid sequence set forth in SEQ ID NO:185; and a VL comprising: a LCDR1 comprising the amino acid sequence set forth in SEQ ID NO:23, a LCDR2 comprising the amino acid sequence set forth in SEQ ID NO:47, and a LCDR3 comprising the amino acid sequence set forth in SEQ ID NO:76; (ii) a VH comprising: a HCDR1 comprising the amino acid sequence set forth in SEQ ID NO:111, a HCDR2 comprising the amino acid sequence set forth in SEQ ID NO:111, and a HCDR3 comprising the amino acid sequence set forth in SEQ ID NO:186; and a VL comprising: a LCDR1 comprising the amino acid sequence set forth in SEQ ID NO:26, a LCDR2 comprising the amino acid sequence set forth in SEQ ID NO:38, and a LCDR3 comprising the amino acid sequence set forth in SEQ ID NO:130; (jj) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:78; (kk) a VH comprising: a HCDR1 comprising the amino acid sequence set forth in SEQ ID NO:111, a HCDR2 comprising the amino acid sequence set forth in SEQ ID NO:147, and a HCDR3 comprising the amino acid sequence set forth in SEQ ID NO:187; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:79; (ll) a VH comprising: a HCDR1 comprising the amino acid sequence set forth in SEQ ID NO:95, a HCDR2 comprising the amino acid sequence set forth in SEQ ID NO:127, and a HCDR3 comprising the amino acid sequence set forth in SEQ ID NO:164; and a VL comprising: a LCDR1 comprising the amino acid sequence set forth in SEQ ID NO:28, a LCDR2 comprising the amino acid sequence set forth in SEQ ID NO:45, and a LCDR3 comprising the amino acid sequence set forth in SEQ ID NO:81; (mm) a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (nn) a VH comprising: a HCDR1 comprising the amino acid sequence set forth in SEQ ID NO:106, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (oo) a VH comprising: a HCDR1 comprising the amino acid sequence set forth in SEQ ID NO:99, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (pp) a VH comprising: a HCDR1 comprising the amino acid sequence set forth in SEQ ID NO:99, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (qq) a VH comprising: a HCDR1 comprising the amino acid sequence set forth in SEQ ID NO:111, a HCDR2 comprising the amino acid sequence set forth in SEQ ID NO:147, and a HCDR3 comprising the amino acid sequence set forth in SEQ ID NO:187; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:82; (rr) a VH comprising: a HCDR1 comprising the amino acid sequence set forth in SEQ ID NO:113, a HCDR2 comprising the amino acid sequence set forth in SEQ ID NO:148, and a HCDR3 comprising the amino acid sequence set forth in SEQ ID NO:189; and a VL comprising: a LCDR1 comprising the amino acid sequence set forth in SEQ ID NO:29, a LCDR2 comprising the amino acid sequence set forth in SEQ ID NO:42, and a LCDR3 comprising the amino acid sequence set forth in SEQ ID NO:59; (ss) a VH comprising: a HCDR1 comprising the amino acid sequence set forth in SEQ ID NO:114, a HCDR2 comprising the amino acid sequence set forth in SEQ ID NO:149, and a HCDR3 comprising the amino acid sequence set forth in SEQ ID NO:190; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55; (tt) a VH comprising: a HCDR1 comprising the amino acid sequence set forth in SEQ ID NO:115, a HCDR2 comprising the amino acid sequence set forth in SEQ ID NO:150, and a HCDR3 comprising the amino acid sequence set forth in SEQ ID NO:191; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55; (uu) a VH comprising: a HCDR1 comprising the amino acid sequence set forth in SEQ ID NO:108, a HCDR2 comprising the amino acid sequence set forth in SEQ ID NO:151, and a HCDR3 comprising the amino acid sequence set forth in SEQ ID NO:180; and a VL comprising: a LCDR1 comprising the amino acid sequence set forth in SEQ ID NO:30, a LCDR2 comprising the amino acid sequence set forth in SEQ ID NO:45, and a LCDR3 comprising the amino acid sequence set forth in SEQ ID NO:83; (vv) a VH comprising: a HCDR1 comprising the amino acid sequence set forth in SEQ ID NO:116, a HCDR2 comprising the amino acid sequence set forth in SEQ ID NO:152, and a HCDR3 comprising the amino acid sequence set forth in SEQ ID NO:192; and a VL comprising: a LCDR1 comprising the amino acid sequence set forth in SEQ ID NO:31, a LCDR2 comprising the amino acid sequence set forth in SEQ ID NO:39, and a LCDR3 comprising the amino acid sequence set forth in SEQ ID NO:71; (ww) a VH comprising: a HCDR1 comprising the amino acid sequence set forth in SEQ ID NO:93, a HCDR2 comprising the amino acid sequence set forth in SEQ ID NO:125, and a HCDR3 comprising the amino acid sequence set forth in SEQ ID NO:160; and a VL comprising: a LCDR1 comprising the amino acid sequence set forth in SEQ ID NO:32, a LCDR2 comprising the amino acid sequence set forth in SEQ ID NO:36, and a LCDR3 comprising the amino acid sequence set forth in SEQ ID NO:84; (xx) a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:170; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (yy) a VH comprising: a HCDR1 comprising the amino acid sequence set forth in SEQ ID NO:117, a HCDR2 comprising the amino acid sequence set forth in SEQ ID NO:153, and a HCDR3 comprising the amino acid sequence set forth in SEQ ID NO:167; and a VL comprising: a LCDR1 comprising the amino acid sequence set forth in SEQ ID NO:33, a LCDR2 comprising the amino acid sequence set forth in SEQ ID NO:36, and a LCDR3 comprising the amino acid sequence set forth in SEQ ID NO:52; (zz) a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (aaa) a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (bbb) a VH comprising: a HCDR1 comprising the amino acid sequence set forth in SEQ ID NO:97, a HCDR2 comprising the amino acid sequence set forth in SEQ ID NO:154, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57; (ccc) a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:85; (ddd) a VH comprising: a HCDR1 comprising the amino acid sequence set forth in SEQ ID NO:118, a HCDR2 comprising the amino acid sequence set forth in SEQ ID NO:155, and a HCDR3 comprising the amino acid sequence set forth in SEQ ID NO:193; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:85; (eee) a VH comprising: a HCDR1 comprising the amino acid sequence set forth in SEQ ID NO:93, a HCDR2 comprising the amino acid sequence set forth in SEQ ID NO:77, and a HCDR3 comprising the amino acid sequence set forth in SEQ ID NO:194; and a VL comprising: a LCDR1 comprising the amino acid sequence set forth in SEQ ID NO:24, a LCDR2 comprising the amino acid sequence set forth in SEQ ID NO:4, and a LCDR3 comprising the amino acid sequence set forth in SEQ ID NO:86; (fff) a VH comprising: a HCDR1 comprising the amino acid sequence set forth in SEQ ID NO:94, a HCDR2 comprising the amino acid sequence set forth in SEQ ID NO:156, and a HCDR3 comprising the amino acid sequence set forth in SEQ ID NO:195; and a VL comprising: a LCDR1 comprising the amino acid sequence set forth in SEQ ID NO:34, a LCDR2 comprising the amino acid sequence set forth in SEQ ID NO:39, and a LCDR3 comprising the amino acid sequence set forth in SEQ ID NO:87; (ggg) a VH comprising: a HCDR1 comprising the amino acid sequence set forth in SEQ ID NO:111, a HCDR2 comprising the amino acid sequence set forth in SEQ ID NO:157, and a HCDR3 comprising the amino acid sequence set forth in SEQ ID NO:1%; and a VL comprising: a LCDR1 comprising the amino acid sequence set forth in SEQ ID NO:23, a LCDR2 comprising the amino acid sequence set forth in SEQ ID NO:260, and a LCDR3 comprising the amino acid sequence set forth in SEQ ID NO:88; (hhh) a VH comprising: a HCDR1 comprising the amino acid sequence set forth in SEQ ID NO:109, a HCDR2 comprising the amino acid sequence set forth in SEQ ID NO:143, and a HCDR3 comprising the amino acid sequence set forth in SEQ ID NO:245; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:203; (iii) a VH comprising: a HCDR1 comprising the amino acid sequence set forth in SEQ ID NO:224, a HCDR2 comprising the amino acid sequence set forth in SEQ ID NO:120, and a HCDR3 comprising the amino acid sequence set forth in SEQ ID NO:246; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:204; (jjj) a VH comprising: a HCDR1 comprising the amino acid sequence set forth in SEQ ID NO:94, a HCDR2 comprising the amino acid sequence set forth in SEQ ID NO:139, and a HCDR3 comprising the amino acid sequence set forth in SEQ ID NO:247; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:205; (kkk) a VH comprising: a HCDR1 comprising the amino acid sequence set forth in SEQ ID NO:217, a HCDR2 comprising the amino acid sequence set forth in SEQ ID NO:157, and a HCDR3 comprising the amino acid sequence set forth in SEQ ID NO:233; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:206; (lll) a VH comprising: a HCDR1 comprising the amino acid sequence set forth in SEQ ID NO:218, a HCDR2 comprising the amino acid sequence set forth in SEQ ID NO:231, and a HCDR3 comprising the amino acid sequence set forth in SEQ ID NO:234; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:207; (mmm) a VH comprising: a HCDR1 comprising the amino acid sequence set forth in SEQ ID NO:219, a HCDR2 comprising the amino acid sequence set forth in SEQ ID NO:232, and a HCDR3 comprising the amino acid sequence set forth in SEQ ID NO:235; and a VL comprising: a LCDR1 comprising the amino acid sequence set forth in SEQ ID NO:197, a LCDR2 comprising the amino acid sequence set forth in SEQ ID NO:39, and a LCDR3 comprising the amino acid sequence set forth in SEQ ID NO:208; (nnn) a VH comprising: a HCDR1 comprising the amino acid sequence set forth in SEQ ID NO:220, a HCDR2 comprising the amino acid sequence set forth in SEQ ID NO:122, and a HCDR3 comprising the amino acid sequence set forth in SEQ ID NO:236; and a VL comprising: a LCDR1 comprising the amino acid sequence set forth in SEQ ID NO:198, a LCDR2 comprising the amino acid sequence set forth in SEQ ID NO:201, and a LCDR3 comprising the amino acid sequence set forth in SEQ ID NO:209; (ooo) a VH comprising: a HCDR1 comprising the amino acid sequence set forth in SEQ ID NO:94, a HCDR2 comprising the amino acid sequence set forth in SEQ ID NO:226, and a HCDR3 comprising the amino acid sequence set forth in SEQ ID NO:237; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:210; (ppp) a VH comprising: a HCDR1 comprising the amino acid sequence set forth in SEQ ID NO:221, a HCDR2 comprising the amino acid sequence set forth in SEQ ID NO:227, and a HCDR3 comprising the amino acid sequence set forth in SEQ ID NO:238; and a VL comprising: a LCDR1 comprising the amino acid sequence set forth in SEQ ID NO:28, a LCDR2 comprising the amino acid sequence set forth in SEQ ID NO:45, and a LCDR3 comprising the amino acid sequence set forth in SEQ ID NO:211; (qqq) a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:239; and a VL comprising: a LCDR1 comprising the amino acid sequence set forth in SEQ ID NO:11, a LCDR2 comprising the amino acid sequence set forth in SEQ ID NO:44, and a LCDR3 comprising the amino acid sequence set forth in SEQ ID NO:212; (rrr) a VH comprising: a HCDR1 comprising the amino acid sequence set forth in SEQ ID NO:103, a HCDR2 comprising the amino acid sequence set forth in SEQ ID NO:135, and a HCDR3 comprising the amino acid sequence set forth in SEQ ID NO:241; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:214; (sss) a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:242; and a VL comprising: a LCDR1 comprising the amino acid sequence set forth in SEQ ID NO:199, a LCDR2 comprising the amino acid sequence set forth in SEQ ID NO:41, and a LCDR3 comprising the amino acid sequence set forth in SEQ ID NO:206; (ttt) a VH comprising: a HCDR1 comprising the amino acid sequence set forth in SEQ ID NO:223, a HCDR2 comprising the amino acid sequence set forth in SEQ ID NO:229, and a HCDR3 comprising the amino acid sequence set forth in SEQ ID NO:243; and a VL comprising: a LCDR1 comprising the amino acid sequence set forth in SEQ ID NO:200, a LCDR2 comprising the amino acid sequence set forth in SEQ ID NO:36, and a LCDR3 comprising the amino acid sequence set forth in SEQ ID NO:215; (uuu) a VH comprising: a HCDR1 comprising the amino acid sequence set forth in SEQ ID NO:252, a HCDR2 comprising the amino acid sequence set forth in SEQ ID NO:254, and a HCDR3 comprising the amino acid sequence set forth in SEQ ID NO:257; and a VL comprising: a LCDR1 comprising the amino acid sequence set forth in SEQ ID NO:12, a LCDR2 comprising the amino acid sequence set forth in SEQ ID NO:249, and a LCDR3 comprising the amino acid sequence set forth in SEQ ID NO:251; (vvv) a VH comprising: a HCDR1 comprising the amino acid sequence set forth in SEQ ID NO:94, a HCDR2 comprising the amino acid sequence set forth in SEQ ID NO:256, and a HCDR3 comprising the amino acid sequence set forth in SEQ ID NO:169; and a VL comprising: a LCDR1 comprising the amino acid sequence set forth in SEQ ID NO:248, a LCDR2 comprising the amino acid sequence set forth in SEQ ID NO:39, and a LCDR3 comprising the amino acid sequence set forth in SEQ ID NO:71; (www) a VH comprising: a HCDR1 comprising the amino acid sequence set forth in SEQ ID NO:111, a HCDR2 comprising the amino acid sequence set forth in SEQ ID NO:131, and a HCDR3 comprising the amino acid sequence set forth in SEQ ID NO:169; and a VL comprising: a LCDR1 comprising the amino acid sequence set forth in SEQ ID NO:31, a LCDR2 comprising the amino acid sequence set forth in SEQ ID NO:39, and a LCDR3 comprising the amino acid sequence set forth in SEQ ID NO:71; (xxx) a VH comprising: a HCDR1 comprising the amino acid sequence set forth in SEQ ID NO:377, a HCDR2 comprising the amino acid sequence set forth in SEQ ID NO:125, and a HCDR3 comprising the amino acid sequence set forth in SEQ ID NO:378; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (yyy) a VH comprising: a HCDR1 comprising the amino acid sequence set forth in SEQ ID NO:363, a HCDR2 comprising the amino acid sequence set forth in SEQ ID NO:364, and a HCDR3 comprising the amino acid sequence set forth in SEQ ID NO:365; and a VL comprising: a LCDR1 comprising the amino acid sequence set forth in SEQ ID NO:176, a LCDR2 comprising the amino acid sequence set forth in SEQ ID NO:253, and a LCDR3 comprising the amino acid sequence set forth in SEQ ID NO:362; (zzz) a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:374, a LCDR2 comprising the amino acid sequence set forth in SEQ ID NO:375, and a LCDR3 comprising the amino acid sequence set forth in SEQ ID NO:376; (aaaa) a VH comprising: a HCDR1 comprising the amino acid sequence set forth in SEQ ID NO:267, a HCDR2 comprising the amino acid sequence set forth in SEQ ID NO:138, and a HCDR3 comprising the amino acid sequence set forth in SEQ ID NO:174; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:119; or (bbbb) a VH comprising: a HCDR1 comprising the amino acid sequence set forth in SEQ ID NO:18, a HCDR2 comprising the amino acid sequence set forth in SEQ ID NO:41, and a HCDR3 comprising the amino acid sequence set forth in SEQ ID NO:69; and a VL comprising: a LCDR1 comprising the amino acid sequence set forth in SEQ ID NO:107, a LCDR2 comprising the amino acid sequence set forth in SEQ ID NO:138, and a LCDR3 comprising the amino acid sequence set forth in SEQ ID NO:178. In some embodiments, the antibody or antigen-binding fragment thereof comprises: (a) a VH comprising: a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and a VL comprising: a LCDR1 comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216; (b) a VH comprising a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising SEQ ID NO:50; (c) a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53; (d) a VH comprising: a HCDR1 comprising the amino acid sequence set forth in SEQ ID NO:93, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; (e) a VH comprising: a HCDR1 comprising the amino acid sequence set forth in SEQ ID NO:96, a HCDR2 comprising the amino acid sequence set forth in SEQ ID NO:128, and a HCDR3 comprising the amino acid sequence set forth in SEQ ID NO:165; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55; (f) a VH comprising: a HCDR1 comprising the amino acid sequence set forth in SEQ ID NO:99, a HCDR2 comprising the amino acid sequence set forth in SEQ ID NO:129, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (g) a VH comprising: a HCDR1 comprising the amino acid sequence set forth in SEQ ID NO:107, a HCDR2 comprising the amino acid sequence set forth in SEQ ID NO:138, and a HCDR3 comprising the amino acid sequence set forth in SEQ ID NO:178; and a VL comprising: a LCDR1 comprising the amino acid sequence set forth in SEQ ID NO:18, a LCDR2 comprising the amino acid sequence set forth in SEQ ID NO:41, and a LCDR3 comprising the amino acid sequence set forth in SEQ ID NO:69; (h) a VH comprising: a HCDR1 comprising the amino acid sequence set forth in SEQ ID NO:94, a HCDR2 comprising the amino acid sequence set forth in SEQ ID NO:139, and a HCDR3 comprising the amino acid sequence set forth in SEQ ID NO:179; and a VL comprising: a LCDR1 comprising the amino acid sequence set forth in SEQ ID NO:20, a LCDR2 comprising the amino acid sequence set forth in SEQ ID NO:39, and a LCDR3 comprising the amino acid sequence set forth in SEQ ID NO:71; (i) a VH comprising: a HCDR1 comprising the amino acid sequence set forth in SEQ ID NO:108, a HCDR2 comprising the amino acid sequence set forth in SEQ ID NO:140, and a HCDR3 comprising the amino acid sequence set forth in SEQ ID NO:180; and a VL comprising: a LCDR1 comprising the amino acid sequence set forth in SEQ ID NO:21, a LCDR2 comprising the amino acid sequence set forth in SEQ ID NO:45, and a LCDR3 comprising the amino acid sequence set forth in SEQ ID NO:72; (j) a VH comprising: a HCDR1 comprising the amino acid sequence set forth in SEQ ID NO:102, a HCDR2 comprising the amino acid sequence set forth in SEQ ID NO:141, and a HCDR3 comprising the amino acid sequence set forth in SEQ ID NO:181; and a VL comprising: a LCDR1 comprising the amino acid sequence set forth in SEQ ID NO:22, a LCDR2 comprising the amino acid sequence set forth in SEQ ID NO:41, and a LCDR3 comprising the amino acid sequence set forth in SEQ ID NO:73; (k) a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:182; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74; (l) a VH comprising: a HCDR1 comprising the amino acid sequence set forth in SEQ ID NO:109, a HCDR2 comprising the amino acid sequence set forth in SEQ ID NO:143, and a HCDR3 comprising the amino acid sequence set forth in SEQ ID NO:183; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:75; (m) a VH comprising: a HCDR1 comprising the amino acid sequence set forth in SEQ ID NO:110, a HCDR2 comprising the amino acid sequence set forth in SEQ ID NO:144, and a HCDR3 comprising the amino acid sequence set forth in SEQ ID NO:173; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:259; (n) a VH comprising: a HCDR1 comprising the amino acid sequence set forth in SEQ ID NO:111, a HCDR2 comprising the amino acid sequence set forth in SEQ ID NO:147, and a HCDR3 comprising the amino acid sequence set forth in SEQ ID NO:187; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:79; (o) a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50; (p) a VH comprising: a HCDR1 comprising the amino acid sequence set forth in SEQ ID NO:94, a HCDR2 comprising the amino acid sequence set forth in SEQ ID NO:156, and a HCDR3 comprising the amino acid sequence set forth in SEQ ID NO:195; and a VL comprising: a LCDR1 comprising the amino acid sequence set forth in SEQ ID NO:34, a LCDR2 comprising the amino acid sequence set forth in SEQ ID NO:39, and a LCDR3 comprising the amino acid sequence set forth in SEQ ID NO:87; (q) a VH comprising: a HCDR1 comprising the amino acid sequence set forth in SEQ ID NO:111, a HCDR2 comprising the amino acid sequence set forth in SEQ ID NO:157, and a HCDR3 comprising the amino acid sequence set forth in SEQ ID NO:196; and a VL comprising: a LCDR1 comprising the amino acid sequence set forth in SEQ ID NO:23, a LCDR2 comprising the amino acid sequence set forth in SEQ ID NO:260, and a LCDR3 comprising the amino acid sequence set forth in SEQ ID NO:88; (r) a VH comprising: a HCDR1 comprising the amino acid sequence set forth in SEQ ID NO:218, a HCDR2 comprising the amino acid sequence set forth in SEQ ID NO:231, and a HCDR3 comprising the amino acid sequence set forth in SEQ ID NO:234; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:207; or (s) a VH comprising: a HCDR1 comprising the amino acid sequence set forth in SEQ ID NO:252, a HCDR2 comprising the amino acid sequence set forth in SEQ ID NO:254, and a HCDR3 comprising the amino acid sequence set forth in SEQ ID NO:257; and a VL comprising: a LCDR1 comprising the amino acid sequence set forth in SEQ ID NO:12, a LCDR2 comprising the amino acid sequence set forth in SEQ ID NO:249, and a LCDR3 comprising the amino acid sequence set forth in SEQ ID NO:251. In some embodiments, the antibody or antigen-binding fragment thereof comprises: a VH comprising: a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and a VL comprising: a LCDR1 comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216. In some embodiments, the antibody or antigen-binding fragment thereof is an antagonist of LILRB2 activity.

In another aspect, provided herein is an antibody or antigen-binding fragment thereof that binds to LILRB2, comprising: (a) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:172; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:63; (b) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67; (c) a VH comprising a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:24, a LCDR2 comprising the amino acid sequence set forth in SEQ ID NO:202, and a LCDR3 comprising SEQ ID NO:64; (d) a VH comprising: a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:14, a LCDR2 comprising the amino acid sequence set forth in SEQ ID NO:41, and a LCDR3 comprising the amino acid sequence set forth in SEQ ID NO:64; (e) a VH comprising: a HCDR1 comprising the amino acid sequence set forth in SEQ ID NO:94, a HCDR2 comprising the amino acid sequence set forth in SEQ ID NO:126, and a HCDR3 comprising the amino acid sequence set forth in SEQ ID NO:163; and a VL comprising: a LCDR1 comprising the amino acid sequence set forth in SEQ ID NO:5, a LCDR2 comprising the amino acid sequence set forth in SEQ ID NO:39, and a LCDR3 comprising the amino acid sequence set forth in SEQ ID NO:54; (f) a VH comprising: a HCDR1 comprising the amino acid sequence set forth in SEQ ID NO:103, a HCDR2 comprising the amino acid sequence set forth in SEQ ID NO:135, and a HCDR3 comprising the amino acid sequence set forth in SEQ ID NO:174; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:66; (g) a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:184; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74; (h) a VH comprising: a HCDR1 comprising the amino acid sequence set forth in SEQ ID NO:222, a HCDR2 comprising the amino acid sequence set forth in SEQ ID NO:228, and a HCDR3 comprising the amino acid sequence set forth in SEQ ID NO:240; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:213; (i) a VH comprising: a HCDR1 comprising the amino acid sequence set forth in SEQ ID NO:114, a HCDR2 comprising the amino acid sequence set forth in SEQ ID NO:255, and a HCDR3 comprising the amino acid sequence set forth in SEQ ID NO:146; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:250; or (j) a VH comprising: a HCDR1 comprising the amino acid sequence set forth in SEQ ID NO:112, a HCDR2 comprising the amino acid sequence set forth in SEQ ID NO:258, and a HCDR3 comprising the amino acid sequence set forth in SEQ ID NO:188; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:80. In some embodiments, the antibody or antigen-binding fragment comprises: (a) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:172; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:63; (b) a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67; (c) a VH comprising a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:19, a LCDR2 comprising the amino acid sequence set forth in SEQ ID NO:41, and a LCDR3 comprising SEQ ID NO:70; (d) a VH comprising: a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:14, a LCDR2 comprising the amino acid sequence set forth in SEQ ID NO:41, and a LCDR3 comprising the amino acid sequence set forth in SEQ ID NO:64; (e) a VH comprising: a HCDR1 comprising the amino acid sequence set forth in SEQ ID NO:94, a HCDR2 comprising the amino acid sequence set forth in SEQ ID NO:126, and a HCDR3 comprising the amino acid sequence set forth in SEQ ID NO:163; and a VL comprising: a LCDR1 comprising the amino acid sequence set forth in SEQ ID NO:5, a LCDR2 comprising the amino acid sequence set forth in SEQ ID NO:39, and a LCDR3 comprising the amino acid sequence set forth in SEQ ID NO:54; (f) a VH comprising: a HCDR1 comprising the amino acid sequence set forth in SEQ ID NO:103, a HCDR2 comprising the amino acid sequence set forth in SEQ ID NO:135, and a HCDR3 comprising the amino acid sequence set forth in SEQ ID NO:174; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:66; (g) a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:184; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74; (h) a VH comprising: a HCDR1 comprising the amino acid sequence set forth in SEQ ID NO:222, a HCDR2 comprising the amino acid sequence set forth in SEQ ID NO:228, and a HCDR3 comprising the amino acid sequence set forth in SEQ ID NO:240; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:213; (i) a VH comprising: a HCDR1 comprising the amino acid sequence set forth in SEQ ID NO:114, a HCDR2 comprising the amino acid sequence set forth in SEQ ID NO:255, and a HCDR3 comprising the amino acid sequence set forth in SEQ ID NO:146; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:250; or (j) a VH comprising: a HCDR1 comprising the amino acid sequence set forth in SEQ ID NO:112, a HCDR2 comprising the amino acid sequence set forth in SEQ ID NO:258, and a HCDR3 comprising the amino acid sequence set forth in SEQ ID NO:188; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:80. In some embodiments, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:172; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:63. In some embodiments, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67. In some embodiments, the antibody or antigen-binding fragment thereof is an agonist of LILRB2 activity.

In one embodiment, the foregoing antibody or antigen-binding fragment thereof is an antigen-binding fragment of the antibody.

In one embodiment, the foregoing antibody or antigen-binding fragment thereof is an antibody. In one embodiment, the antibody comprises an IgG1 heavy chain constant region. In one embodiment, the antibody comprises an IgG2 heavy chain constant region. In one embodiment, the antibody comprises a kappa light chain constant region.

In another aspect, provided herein is an isolated nucleic acid molecule encoding any one of the foregoing antibodies or antigen-binding fragments thereof.

In another aspect, provided herein is a vector comprising a nucleic acid molecule encoding any one of the foregoing antibodies or antigen-binding fragments thereof.

In another aspect, provided herein is a vector comprising a first nucleic acid molecule and a second nucleic acid molecule, wherein the first nucleic acid molecule encodes the VH of any one of the foregoing antibodies or antigen-binding fragments thereof, and wherein the second nucleic acid molecule encodes the VL of the antibody or antigen-binding fragment thereof.

In another aspect, provided herein is a host cell comprising one or more nucleic acid molecules encoding any one of the foregoing antibodies or antigen-binding fragments thereof. In one embodiment, the host cell is a prokaryotic or eukaryotic cell.

In another aspect, provided herein is a host cell comprising any one of the foregoing vectors. In one embodiment, the host cell is a prokaryotic or eukaryotic cell.

In another aspect, provided herein is a method for producing any one of the foregoing antibodies or antigen-binding fragments thereof, comprising: (a) culturing any one of the foregoing host cells under conditions suitable for expression of the antibody or antigen-binding fragment thereof by the host cell; and (b) recovering the antibody or antigen-binding fragment thereof.

In another aspect, provided herein is a pharmaceutical composition comprising any one of the foregoing antibodies or antigen-binding fragments thereof and a suitable pharmaceutical carrier. In one embodiment, the pharmaceutical composition further comprises a chemotherapeutic agent or an analgesic. In one embodiment, the pharmaceutical composition further comprises one or more additional agents selected from the group consisting of: a myeloid-derived suppressor cell, a mobilizing agent, a c-jun N-terminal kinase inhibitor, an anti-inflammatory agent, and an immunosuppressive agent. In one embodiment, the pharmaceutical composition is formulated for intravenous, intramuscular, oral, subcutaneous, intraperitoneal, intrathecal, intratumoral or intramuscular administration to a subject.

In another aspect, provided herein is a method of treating cancer in a mammal in need thereof, the method comprising administering to the mammal a therapeutically effective amount of any one of the foregoing antibodies or antigen-binding fragments thereof or the foregoing pharmaceutical composition. In one embodiment, the method further comprises administering to the mammal a chemotherapeutic agent or an analgesic. In one embodiment, the method further comprises administering to the mammal an immune checkpoint inhibitor. In one embodiment, the cancer is a lymphoma, a leukemia, or a breast cancer. In one embodiment, the antibody is an antagonist of LILRB2.

In another aspect, provided herein is a method of treating cancer in a mammal in need thereof, comprising administering to the mammal any one of the foregoing antibodies or antigen-binding fragments thereof or the pharmaceutical composition and a PD-1 or PD-L1 inhibitor. In one embodiment, the cancer is a lymphoma, a leukemia, or a breast cancer. In one embodiment, the antibody is an antagonist of LILRB2.

In another aspect, provided herein is a method of treating an infection in a mammal in need thereof, comprising administering to the mammal any one of the foregoing antibodies or antigen-binding fragments thereof or the pharmaceutical composition. In one embodiment, the infection is a bacterial infection. In one embodiment, the antibody is an antagonist of LILRB2.

In another aspect, provided herein is a method of decreasing a pro-inflammatory immune response in a mammal in need thereof, the method comprising administering to the mammal a therapeutically effective amount of any one of the foregoing antibodies or antigen-binding fragments thereof or the pharmaceutical. In one embodiment, the mammal has been diagnosed as having inflammation, an autoimmune disease, or transplant rejection. In one embodiment, the mammal is selected for organ or tissue transplantation.

In another aspect, provided herein is a method of treating inflammation, an autoimmune disease, or transplant rejection in a mammal in need thereof, the method comprising administering to the mammal a therapeutically effective amount of any one of the foregoing antibodies or antigen-binding fragments thereof or the pharmaceutical composition. In one embodiment, the mammal has been diagnosed as having inflammation, an autoimmune disease, or transplant rejection. In one embodiment, the mammal is selected for organ or tissue transplantation.

In one embodiment of the foregoing methods, the method further comprises administering to the mammal one or more additional agents selected from the group consisting of: a myeloid-derived suppressor cell, a mobilizing agent, a c-jun N-terminal kinase inhibitor, an anti-inflammatory agent, and an immunosuppressive agent.

In one embodiment of the foregoing methods, the mammal is a human.

In another aspect, provided herein is a chimeric antigen receptor (CAR), comprising the VH and VL of an antibody described herein. In one embodiment, the VH comprises a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and the VL comprises a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53. In one embodiment, the VH comprises a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and the VL comprises a LCDR1 comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216.

In another aspect, provided herein is a polynucleotide encoding any one of the foregoing CARs.

In another aspect, provided herein is a vector comprising a polynucleotide encoding any one of the foregoing CARs.

In another aspect, provided herein is a cell comprising any one of the foregoing CARs. In another aspect, provided herein is a cell comprising a polynucleotide encoding any one of the foregoing CARs. In another aspect, provided herein is a cell comprising a vector comprising a polynucleotide encoding any one of the foregoing CARs. In one embodiment, the cell is a T cell. In one embodiment, the cell is a natural killer cell. In one embodiment, the cell is a macrophage.

In another aspect, provided herein is a pharmaceutical composition comprising any one of the foregoing CARs and a suitable pharmaceutical carrier. In another aspect, provided herein is a pharmaceutical composition comprising a cell comprising any one of the foregoing CARs and a suitable pharmaceutical carrier. In another aspect, provided herein is a pharmaceutical composition comprising a cell comprising a polynucleotide encoding any one of the foregoing CARs and a suitable pharmaceutical carrier. In another aspect, provided herein is a pharmaceutical composition comprising a cell comprising a vector comprising a polynucleotide encoding any one of the foregoing CARs and a suitable pharmaceutical carrier.

In another aspect, provided herein is a method of producing a CAR, comprising (a) culturing one of the foregoing cells (e.g., a cell comprising a polynucleotide encoding any one of the foregoing CARs or a cell comprising a vector comprising a polynucleotide encoding any one of the foregoing CARs) and (b) isolating the CAR.

In another aspect, provided herein is a method of treating cancer in a mammal in need thereof, the method comprising administering to the mammal a therapeutically effective amount of any one of the foregoing CARs, any one of the foregoing cells, or any one of the foregoing pharmaceutical compositions. In one embodiment, the cancer is a lymphoma, a leukemia, a colon cancer, or a breast cancer. In one embodiment, the mammal is a human.

In another aspect, provided herein is a method of treating asthma in a mammal in need thereof, the method comprising administering to the mammal a therapeutically effective amount of any one of the foregoing CARs, any one of the foregoing cells, or any one of the foregoing pharmaceutical compositions. In one embodiment, the mammal is a human.

In another aspect, provided herein is a method of treating an infection in a mammal in need thereof, the method comprising administering to the mammal a therapeutically effective amount of any one of the foregoing CARs, any one of the foregoing cells, or any one of the foregoing pharmaceutical compositions. In one embodiment, the mammal is a human.

In another aspect, provided herein is a method of treating inflammation, an autoimmune disease, or transplant rejection in a mammal in need thereof, the method comprising administering to the mammal a therapeutically effective amount of any one of the foregoing CARs, any one of the foregoing cells, or any one of the foregoing pharmaceutical compositions. In one embodiment, the mammal is a human.

In one aspect, the disclosure provides an antibody or antigen-binding fragment thereof that specifically binds to LILRB2, wherein the antibody or antigen-binding fragment comprises a heavy chain complementarity determining region (CDR) 1 comprising an amino acid sequence as set forth in one of SEQ ID NOs: 111, 265, 267, 269, 274, 277, 279, 282, 284, 285, 112, 267, 292, and 295, or the amino acid sequence as set forth in one of SEQ ID NOs: 111, 265, 267, 269, 274, 277, 279, 282, 284, 285, 112, 267, 292, and 295 with a substitution at two or fewer amino acid positions, a heavy chain CDR 2 comprising an amino acid sequence as set forth in one of SEQ ID NOs: 147, 157, 270, 272, 275, 280, 283, 286, 288, 290, 293, and 296, or the amino acid sequence as set forth in one of SEQ ID NOs: 147, 157, 270, 272, 275, 280, 283, 286, 288, 290, 293, and 296 with a substitution at two or fewer amino acid positions, and a heavy chain CDR 3 comprising an amino acid sequence as set forth in one of SEQ ID NOs: 261-264, 266, 268, 271, 273, 276, 278, 281, 287, 289, 291, 294, and 297, or the amino acid sequence as set forth in one of SEQ ID NOs:

261-264, 266, 268, 271, 273, 276, 278, 281, 287, 289, 291, 294, and 297 with a substitution at two or fewer amino acid positions.

In one aspect, the disclosure provides an antibody or antigen-binding fragment thereof that specifically binds to LILRB2, wherein the antibody or antigen-binding fragment comprises a light chain CDR 1 comprising an amino acid sequence as set forth in one of SEQ ID NOs: 298, 300, 302, 305, 26, 308, 7, 197, 312, 314, 316, 317, 318, 320, 322, 325, and 31, or the amino acid sequence as set forth in one of SEQ ID NOs: 298, 300, 302, 305, 26, 308, 7, 197, 312, 314, 316, 317, 318, 320, 322, 325, and 31 with a substitution at two or fewer amino acid positions, a light chain CDR 2 comprising an amino acid sequence as set forth in one of SEQ ID NOs: 38, 41, 44, 49, 42, 45, 39, 323, and 326, or the amino acid sequence as set forth in one of SEQ ID NOs: 38, 41, 44, 49, 42, 45, 39, 323, and 326 with a substitution at two or fewer amino acid positions, and a light chain CDR 3 comprising an amino acid sequence as set forth in one of SEQ ID NOs: 299, 301, 303, 304, 306, 307, 130, 309, 310, 311, 313, 315, 319, 321, 324, 52, and 327, or the amino acid sequence as set forth in one of SEQ ID NOs: 299, 301, 303, 304, 306, 307, 130, 309, 310, 311, 313, 315, 319, 321, 324, 52, and 327 with a substitution at two or fewer amino acid positions.

In one aspect, the disclosure provides an antibody or antigen-binding fragment thereof specifically binds to LILRB2, wherein the antibody or antigen-binding fragment thereof comprises a heavy chain variable region comprising complementarity determining region (CDR)1, CDR2, and CDR3, consisting of the amino acid sequences: (i) GYTFTTYG (SEQ ID NO: 111), MNTYSGVP (SEQ ID NO: 147), and CARMGRGSLYGMDYW (SEQ ID NO: 261, respectively; (ii) GYTFTTYG (SEQ ID NO: 111), INTYSGVP (SEQ ID NO: 157) and CARSGHSYSLYVMGYW (SEQ ID NO: 262), respectively; (iii) GYTFTTYG (SEQ ID NO: 111), INTYSGVP (SEQ ID NO: 157) and CARSGHNYSLYVMGYW (SEQ ID NO: 263), respectively; (iv) GYTFTTYG (SEQ ID NO: 111), INTYSGVP (SEQ ID NO: 157) and CARGALYYFDNW (SEQ ID NO: 264), respectively; (v) GYMFTTYG (SEQ ID NO: 265), INTYSGVP (SEQ ID NO: 157) and CARIGNTNSLYTVHYW (SEQ ID NO: 266), respectively; (vi) GYTFTTYG (SEQ ID NO: 111), INTYSGVP (SEQ ID NO: 157) and CARIGNTNSLYTVHYW (SEQ ID NO: 266), respectively; (vii) GYTFTNYG (SEQ ID NO: 267), INTYSGVP (SEQ ID NO: 157) and CARIGNTNSLYTVHYW (SEQ ID NO: 266), respectively; (viii) GYTFTTYG (SEQ ID NO: 111), INTYSGVP (SEQ ID NO: 157) and CTRIGNTNSLYTVHYW (SEQ ID NO: 268), respectively; (ix) GYSITSGHY (SEQ ID NO: 269), ISYDGNN (SEQ ID NO: 270) and CVRGYYYYGSRAMDYW (SEQ ID NO: 271), respectively; (x) GYSITSGHY (SEQ ID NO: 269), ISYDGND (SEQ ID NO: 272) and CVRGYYYYGSRAMDCW (SEQ ID NO: 273), respectively; (xi) GFSFSDYG (SEQ ID NO: 274), ISSGSSTI (SEQ ID NO: 275) and CGPSDYWYFDVW (SEQ ID NO: 276), respectively; (xii) GFTFSDYG (SEQ ID NO: 277), ISSGSSTI (SEQ ID NO: 275) and CARDYFYGNNYGFPYW (SEQ ID NO: 278), respectively; (xiii) GYTFINYY (SEQ ID NO: 279), IYPGNINS (SEQ ID NO: 280) and CAMTNSSAMDYW (SEQ ID NO: 281), respectively; (xiv) GYTFISYY (SEQ ID NO: 282), IYPGNVNT (SEQ ID NO: 283) and CAMTNSSAMDYW (SEQ ID NO: 281), respectively; (xv) GYTFTSYY (SEQ ID NO: 284), IYPGNVNT (SEQ ID NO: 283) and CAMTNSSAMDYW (SEQ ID NO: 281), respectively; (xvi) GFSLTNYD (SEQ ID NO: 285), IWTGGNT (SEQ ID NO: 286) and CVREG- FRQGYYAMDYW (SEQ ID NO: 287), respectively; (xvii) GYTFTDYY (SEQ ID NO: 112), IDTKNGGT (SEQ ID NO: 288) and CASGGRGYW (SEQ ID NO: 289), respectively; (xviii) GYTFTNYG (SEQ ID NO: 267), INTYTGEP (SEQ ID NO: 290) and CTRNYYRPYYYAMDYW (SEQ ID NO: 291), respectively; (xix) GYSFTGYT (SEQ ID NO: 292), INPYNDNT (SEQ ID NO: 293) and CAREGNYYGASPWFAYW (SEQ ID NO: 294), respectively; and (xx) GYTFTHYG (SEQ ID NO: 295), INTSTGET (SEQ ID NO: 2%) and CARYYYGSSRWRDYWFAYW (SEQ ID NO: 297), respectively.

In one aspect, the disclosure provides an antibody or antigen-binding fragment thereof specifically binds to LILRB2, wherein the antibody or antigen-binding fragment thereof comprises a heavy chain variable region comprising complementarity determining region (CDR)1, CDR2, and CDR3, consisting of the amino acid sequences: consisting of the amino acid sequences: (i) GYTFTTYG (SEQ ID NO: 111), MNTYSGVP (SEQ ID NO: 147), and CARMGRGSLYGMDYW (SEQ ID NO: 261, respectively; (ii) GYTFTTYG (SEQ ID NO: 111), INTYSGVP (SEQ ID NO: 157) and CARSGHSYSLYVMGYW (SEQ ID NO: 262), respectively; (iii) GYTFTTYG (SEQ ID NO: 111), INTYSGVP (SEQ ID NO: 157) and CARSGHNYSLYVMGYW (SEQ ID NO: 263), respectively; (iv) GYTFTTYG (SEQ ID NO: 111), INTYSGVP (SEQ ID NO: 157) and CARGALYYFDNW (SEQ ID NO: 264), respectively; (v) GYMFTTYG (SEQ ID NO: 265), INTYSGVP (SEQ ID NO: 157) and CARIGNTNSLYTVHYW (SEQ ID NO: 266), respectively; (vi) GYTFTTYG (SEQ ID NO: 111), INTYSGVP (SEQ ID NO: 157) and CARIGNTNSLYTVHYW (SEQ ID NO: 266), respectively; (vii) GYTFTNYG (SEQ ID NO: 267), INTYSGVP (SEQ ID NO: 157) and CARIGNTNSLYTVHYW (SEQ ID NO: 266), respectively; (viii) GYTFTTYG (SEQ ID NO: 111), INTYSGVP (SEQ ID NO: 157) and CTRIGNTNSLYTVHYW (SEQ ID NO: 268), respectively; (ix) GYSITSGHY (SEQ ID NO: 269), ISYDGNN (SEQ ID NO: 270) and CVRGYYYYGSRAMDYW (SEQ ID NO: 271), respectively; (x) GYSITSGHY (SEQ ID NO: 269), ISYDGND (SEQ ID NO: 272) and CVRGYYYYGSRAMDCW (SEQ ID NO: 273), respectively; (xi) GFSFSDYG (SEQ ID NO: 274), ISSGSSTI (SEQ ID NO: 275) and CGPSDYWYFDVW (SEQ ID NO: 276), respectively; (xii) GFTFSDYG (SEQ ID NO: 277), ISSGSSTI (SEQ ID NO: 275) and CARDYFYGNNYGFPYW (SEQ ID NO: 278), respectively; (xiii) GYTFINYY (SEQ ID NO: 279), IYPGNINS (SEQ ID NO: 280) and CAMTNSSAMDYW (SEQ ID NO: 281), respectively; (xiv) GYTFISYY (SEQ ID NO: 282), IYPGNVNT (SEQ ID NO: 283) and CAMTNSSAMDYW (SEQ ID NO: 281), respectively; (xv) GYTFTSYY (SEQ ID NO: 284), IYPGNVNT (SEQ ID NO: 283) and CAMTNSSAMDYW (SEQ ID NO: 281), respectively; (xvi) GFSLTNYD (SEQ ID NO: 285), IWTGGNT (SEQ ID NO: 286) and CVREGFRQGYYAMDYW (SEQ ID NO: 287), respectively; (xvii) GYTFTDYY (SEQ ID NO: 112), IDTKNGGT (SEQ ID NO: 288) and CASGGRGYW (SEQ ID NO: 289), respectively; (xviii) GYTFTNYG (SEQ ID NO: 267), INTYTGEP (SEQ ID NO: 290) and CTRNYYRPYYYAMDYW (SEQ ID NO: 291), respectively; (xix) GYSFTGYT (SEQ ID NO: 292), INPYNDNT (SEQ ID NO: 293) and CAREGNYYGASPWFAYW (SEQ ID NO: 294), respectively; and (xx) GYTFTHYG (SEQ ID NO: 295), INTSTGET (SEQ ID NO: 2%) and CARYYYGSSRWRDYWFAYW (SEQ ID NO: 297), respectively; and a light chain variable region comprising CDR1, CDR2, and CDR3, consisting of the amino acid sequences: (xxi) QSLLISTNQKNY (SEQ ID NO: 298), FAS (SEQ ID NO: 38) and CQQHYSIPPTF (SEQ ID NO: 299), respectively; (xxii) QSLFISTNQKNY (SEQ ID NO: 300), FAS (SEQ ID NO: 38) and CQQHYSSPPTF (SEQ ID NO: 301), respectively; (xxiii) QSLLISTNQINY (SEQ ID NO: 302), FAS (SEQ ID NO: 38) and CQQHYDPPLTF (SEQ ID NO: 303), respectively; (xxiv) QSLLISTNQKNY (SEQ ID NO: 298), FAS (SEQ ID NO: 38) and CQHHYDPPLTF (SEQ ID NO: 304), respectively; (xxv) QNLLNSSNQKNY (SEQ ID NO: 305), FAS (SEQ ID NO: 38) and CQQHYNTPPTF (SEQ ID NO: 306), respectively; (xxvi) QSLLNSSNQKNY (SEQ ID NO: 26), FAS (SEQ ID NO: 38) and CQQHYSPPPTF (SEQ ID NO: 307), respectively; (xxvii) QSLLISSNQNNY (SEQ ID NO: 308), FAS (SEQ ID NO: 38) and CQQHYSTPPTF (SEQ ID NO: 130), respectively; (xxviii) QDISNY (SEQ ID NO: 7), YTS (SEQ ID NO: 41) and CQQGHTLPYTF (SEQ ID NO: 309), respectively; (xxix) QDISNY (SEQ ID NO: 7), YTS (SEQ ID NO: 41) and CQQGNTLPYTF (SEQ ID NO: 310), respectively; (xxx) QNVGTN (SEQ ID NO: 197), STS (SEQ ID NO: 44) and CQQYNSYPFTF (SEQ ID NO: 311), respectively; (xxxi) QTIGTW (SEQ ID NO: 312), AAT (SEQ ID NO: 49) and CQQLYSTPLTF (SEQ ID NO: 313), respectively; (xxxii) QNIRTA (SEQ ID NO: 314), LAS (SEQ ID NO: 42) and CLQHWNYPFTF (SEQ ID NO: 315), respectively; (xxxiii) QNVRTA (SEQ ID NO: 316), LAS (SEQ ID NO: 42) and CLQHWNYPFTF (SEQ ID NO: 315), respectively; (xxxiv) LNVRTA (SEQ ID NO: 317), LAS (SEQ ID NO: 42) and CLQHWNYPFTF (SEQ ID NO: 315), respectively; (xxxv) QSLLYSSNQKNY (SEQ ID NO: 318), WAS (SEQ ID NO: 45) and CQQYYSYRTF (SEQ ID NO: 319), respectively; (xxxvi) QNVYTT (SEQ ID NO: 320), SAS (SEQ ID NO: 39) and CQQYNSYPYTF (SEQ ID NO: 321), respectively; (xxxvii) ENIYSY (SEQ ID NO: 322), DAK (SEQ ID NO: 323) and CQHHYGFPYTF (SEQ ID NO: 324), respectively; and (xxxviii) QDVSNA (SEQ ID NO: 31), SAS (SEQ ID NO: 39) and CPQHYSTLCTF (SEQ ID NO: 327), respectively.

In some aspects, the isolated antibody or antigen-binding fragment is an antagonist of LILRB2 activity.

In one aspect, the disclosure provides an antibody or antigen-binding fragment thereof that specifically binds to LILRB2, wherein the antibody or antigen-binding fragment comprises a heavy chain complementarity determining region (CDR) 1 comprising an amino acid sequence as set forth in one of SEQ ID NOs: 279, 284, 94, 112, 328, 331, 334, 102, 342, and 344, or the amino acid sequence as set forth in one of SEQ ID NOs: 279, 284, 94, 112, 328, 331, 334, 102, 342, and 344 with a substitution at two or fewer amino acid positions, a heavy chain CDR 2 comprising an amino acid sequence as set forth in one of SEQ ID NOs: 283, 329, 332, 335, 337, 339, 340, 232, 345, and 347, or the amino acid sequence as set forth in one of SEQ ID NOs: 283, 329, 332, 335, 337, 339, 340, 232, 345, and 347 with a substitution at two or fewer amino acid positions, and a heavy chain CDR 3 comprising an amino acid sequence as set forth in one of SEQ ID NOs: 330, 333, 336, 338, 341, 343, 346, and 348, or the amino acid sequence as set forth in one of SEQ ID NOs: 330, 333, 336, 338, 341, 343, 346, and 348 with a substitution at two or fewer amino acid positions.

In one aspect, the disclosure provides an antibody or antigen-binding fragment thereof that specifically binds to LILRB2, wherein the antibody or antigen-binding fragment comprises light chain CDR 1 comprising an amino acid sequence as set forth in one of SEQ ID NOs: 298, 300, 302, 305, 26, 308, 7, 197, 312, 314, 316, 317, 318, 320, 322, 325, and 31, or the amino acid sequence as set forth in one of SEQ ID NOs: 314, 316, 87, 23, 353, 355, 91, 357, 12, and 27, or the amino acid sequence as set forth in one of SEQ ID NOs: 314, 316, 87, 23, 353, 355, 91, 357, 12, and 27 with a substitution at two or fewer amino acid positions, a light chain CDR 2 comprises an amino acid sequence as set forth in one of SEQ ID NOs: 41, 42, 45, 349, 351, 97, 40, and 48, or the amino acid sequence as set forth in one of SEQ ID NOs: 41, 42, 45, 349, 351, 97, 40, and 48 with a substitution at two or fewer amino acid positions, and a light chain CDR 3 comprises an amino acid sequence as set forth in one of SEQ ID NOs: 315, 350, 352, 354, 356, 104, 358, 359, 55, and 360, or the amino acid sequence as set forth in one of SEQ ID NOs: 315, 350, 352, 354, 356, 104, 358, 359, 55, and 360 with a substitution at two or fewer amino acid positions.

In one aspect, the disclosure provides an antibody or antigen-binding fragment thereof specifically binds to LILRB2, wherein the antibody or antigen-binding fragment thereof comprises a heavy chain variable region comprising complementarity determining region (CDR)1, CDR2, and CDR3, consisting of the amino acid sequences: (xl) GFTFTGYW (SEQ ID NO: 328), ILPVSGIT (SEQ ID NO: 329) and CARRGSPYFDYW (SEQ ID NO: 330), respectively; (xli) GFSLNTFDMG (SEQ ID NO: 331), IWWDDDK (SEQ ID NO: 332) and CGRKPGGYGNYVL (SEQ ID NO: 333), respectively; (xlii) GFSLTRYG (SEQ ID NO: 334), IWSGGST (SEQ ID NO: 335) and CARDGRVYAMDYW (SEQ ID NO: 336), respectively; (xliii) GYTFTDYY (SEQ ID NO: 112), LNPYNGGT (SEQ ID NO: 337) and CARGSGNSFYAMDYW (SEQ ID NO: 338), respectively; (xliv) GYTFINYY (SEQ ID NO: 279), IYPGNVNS (SEQ ID NO: 339) and CAMTNSSAMDYW (SEQ ID NO: 281), respectively; (xlv) GYSITSGYY (SEQ ID NO: 102), ISYDGSN (SEQ ID NO: 340) and CTSIYGRFVYW (SEQ ID NO: 341), respectively; (xlvi) GFSLTRYG (SEQ ID NO: 334), IWSGGST (SEQ ID NO: 335) and CARDGRVYAMDYW (SEQ ID NO: 336), respectively; (xlvii) GYTFTNFW (SEQ ID NO: 342), IHPNSGST (SEQ ID NO: 232) and CARNSGDYLVYFDSW (SEQ ID NO: 343), respectively, (xlviii) GYSFTGYF (SEQ ID NO: 344), INPSTGDT (SEQ ID NO: 345) and CARGATVVDYPFDYW (SEQ ID NO: 346), respectively, or (xlix) GYTFTSYW (SEQ ID NO: 94), IHPNGGST (SEQ ID NO: 347) and CTRGLTGLFAYW SEQ ID NO: 348), respectively.

In one aspect, the disclosure provides an antibody or antigen-binding fragment thereof specifically binds to LILRB2, wherein the antibody or antigen-binding fragment thereof comprises a heavy chain variable region comprising complementarity determining region (CDR)1, CDR2, and CDR3, consisting of the amino acid sequences: consisting of the amino acid sequences: (xl) GFTFTGYW (SEQ ID NO: 328), ILPVSGIT (SEQ ID NO: 329) and CARRGSPYFDYW (SEQ ID NO: 330), respectively; (xli) GFSLNTFDMG (SEQ ID NO: 331), IWWDDDK (SEQ ID NO: 332) and CGRKPGGYGNYVL (SEQ ID NO: 333), respectively; (xlii) GFSLTRYG (SEQ ID NO: 334), IWSGGST (SEQ ID NO: 335) and CARDGRVYAMDYW (SEQ ID NO: 336), respectively; (xliii) GYTFTDYY (SEQ ID NO: 112), LNPYNGGT (SEQ ID NO: 337) and CARGSGNSFYAMDYW (SEQ ID NO: 338), respectively; (xliv) GYTFINYY (SEQ ID NO: 279), IYPGNVNS (SEQ ID NO: 339) and CAMTNSSAMDYW (SEQ ID NO: 281), respectively; (xlv) GYSITSGYY (SEQ ID NO: 102), ISYDGSN (SEQ ID NO: 340) and CTSIYGRFVYW (SEQ ID NO: 341), respectively; (xlvi) GFSLTRYG (SEQ ID NO: 334), IWSGGST (SEQ ID NO: 335) and CARDGRVYAMDYW (SEQ ID NO: 336), respectively; (xlvii) GYTFTNFW (SEQ ID NO: 342), IHPNSGST (SEQ ID NO: 232) and CARNSGDYLVYFDSW (SEQ ID NO: 343), respectively, (xlviii) GYSFTGYF (SEQ ID NO: 344), INPSTGDT (SEQ ID NO: 345) and CARGATVVDYPFDYW (SEQ ID NO: 346), respectively, or (xlix) GYTFTSYW (SEQ ID NO: 94), IHPNGGST (SEQ ID NO: 347) and CTRGLTGLFAYW (SEQ ID NO: 348), respectively; and a light chain variable region comprising CDR1, CDR2, and CDR3, consisting of the amino acid sequences: (l) SSVSSSY (SEQ ID NO: 87), GTS (SEQ ID NO: 349) and CHQYHRSPFTF (SEQ ID NO: 350), respectively; (li) SSVSY (SEQ ID NO: 23), DTS (SEQ ID NO: 351) and CFQGSGYPFTF (SEQ ID NO: 352), respectively; (lii) QSVLYSSDQKNY (SEQ ID NO: 353), WAS (SEQ ID NO: 45) and CHQYLSHTF (SEQ ID NO: 354), respectively; (liii) QDVNTA (SEQ ID NO: 355), WAS (SEQ ID NO: 45) and CQQLYKLPRTF (SEQ ID NO: 356), respectively; (lv) QNIRTA (SEQ ID NO: 314), LAS (SEQ ID NO: 42) and CLQHWNYPFTF (SEQ ID NO: 315), respectively; (lvi) SSVNY (SEQ ID NO: 357), YTS (SEQ ID NO:41) and CQQFSSSPYTF (SEQ ID NO: 358), respectively; (lvii) QNVRTA (SEQ ID NO: 316), LAS (SEQ ID NO: 42) and CLQHWNYPFTF (SEQ ID NO: 315), respectively; (lviii) SSVSY (SEQ ID NO: 23), DTS (SEQ ID NO: 351) and CQQWRSYQLTF (SEQ ID NO: 359), respectively; (lvix), QNINVW (SEQ ID NO: 6), KAS (SEQ ID NO: 40) and CQQGQSYPLTF (SEQ ID NO: 55)), respectively; and (lvx), QDINSY (SEQ ID NO: 27), RAN (SEQ ID NO: 48) and CLQYDEFLLTF (SEQ ID NO: 360), respectively.

In some aspects, the isolated antibody or antigen-binding fragment is an agonist of LILRB2 activity.

In some aspects, the disclosure provides an isolated nucleic acid molecule encoding the anti-LILRB2 antibody or antigen-binding fragment thereof as disclosed herein. The disclosure also provides a vector comprising a nucleic acid molecule encoding the anti-LILRB2 antibody or antigen-binding fragment thereof as disclosed herein. Host cells, including prokaryotic or eukaryotic cells, comprising a vector comprising a nucleic acid molecule encoding the anti-LILRB2 antibody or antigen-binding fragment thereof as disclosed herein are also provided herein.

In some aspects, the disclosure provides methods for producing an anti-LILRB2 antibody or antigen-binding fragment thereof comprising the steps of (a) culturing a host cell comprising a vector comprising a nucleic acid molecule encoding the anti-LILRB2 antibody or antigen-binding fragment thereof under conditions suitable for expression of the LILRB2 antibody or antigen-binding fragment thereof by the host cell; and (b) recovering the LILRB2 antibody or antigen-binding fragment thereof.

Compositions comprising the anti-LILRB2 antibody or antigen-binding fragment thereof and a suitable pharmaceutical carrier are disclosed herein. In some aspects, the compositions further comprise a chemotherapeutic agent or an analgesic.

In some aspects, the compositions further comprise a one or more additional agents selected from the group consisting of: a myeloid-derived suppressor cell, a mobilizing agent, a c-jun N-terminal kinase inhibitor, an anti-inflammatory agent, and an immunosuppressive agent.

The compositions of the present disclosure can be formulated, for example, for intravenous, intramuscular, oral, subcutaneous, intraperitoneal, intrathecal, intratumoral or intramuscular administration.

In some aspects, the disclosure provides methods for treating cancer in a subject, the method comprising administering to the subject a therapeutically effective amount of the antibody or antigen-binding fragment thereof that specifically binds to LILRB2 as described herein. In some aspects, the methods further comprise administering to the mammal a chemotherapeutic agent or an analgesic.

In one aspect, this disclosure provides a pharmaceutical composition comprising the anti-LILRB2 antibody or antigen-binding fragment thereof (e.g., Fab or scFv) described herein and a pharmaceutically acceptable carrier.

In certain embodiments of the above aspects, the antibody or antigen-binding fragment thereof has an apparent monovalent affinity of about 150 pM to about 100 nM.

In certain embodiments of all of the above aspects, the antibody or the antigen-binding fragment thereof is an Fab, an Fab', an F(ab')2, an Facb, an Fv, an Fd, a diabody, an scFv, or an sc(Fv)2. In a specific embodiment, the antibody or the antigen-binding fragment thereof is an Fab.

As used herein, the term "one or more" includes at least one, more suitably, one, two, three, four, five, ten, twenty, fifty, one-hundred, five-hundred, etc., of the item to which "one or more" refers.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1C are graphs showing the production of TNF-α from human peripheral blood mononuclear cells (PBMC) obtained from healthy donors after incubation with anti-LILRB2 purified antibodies (5 μg/ml), or isotype control overnight for 16 hours following stimulation with LPS (50 ng/ml) for 24 hours. Anti-LILRB2 monoclonal antibodies (mAbs) were ranked in order of clones that suppress TNF alpha release to those that enhance TNF alpha secretion. The levels of TNF-α were determined by ELISA. Clone ranking based on the relative fold change in TNF alpha release from FIG. 1A is presented. The secretion of TNF alpha is shown in FIG. 1A (fold change with Ig control). The overall difference in TNF alpha levels from FIG. 1B is presented in FIG. 1C (by subtraction of Ig control).

FIGS. 2A-2C are graphs showing the production of IL-10 from PBMCs obtained from healthy donors after treatment with purified LILRB2 antibodies (5 μg/ml), or isotype control overnight for 16 hours following stimulation with LPS (50 ng/ml) for 24 hours. Supernatants were collected and IL-10 concentrations were measured by ELISA. Clone ranking based on TNF alpha from FIG. 1A is presented. The relative fold change in IL-10 release is presented in FIG. 2A (by fold change with Ig control). The secretion of IL-10 is shown in FIG. 2B. The overall difference in IL-10 concentrations from FIG. 2B is presented in FIG. 2C (by subtraction of Ig control).

FIG. 2D is the flow cytometric analysis on the effect of LILRB2 antibodies on the M1/M2 markers of tumor-associated macrophages from multiple lung cancer patients. Tumor infiltrated lymphocytes were isolated and treated with LILRB2 antagonistic antibody (P_5G5) for 2 days in the presence of IFNgamma. The test cells were harvested for cytometric analysis in upper panel and the statistic analysis on multiple patients is shown in lower panel.

FIG. 2E is the flow cytometric analysis on the effect of LILRB2 antibodies on the M1/M2 markers in multiple healthy donors. M1-type macrophages were differentiated from CD33+ myeloid cells sorted from healthy donor in the presence of GM-CSF 100 ng/ml and agonistic anti-LILRB2 Ab (12H6, 5 μg/ml) for 6 days and IFNgamma (25 ng/ml) and LPS (25 ng/ml) for the last 24 hours. The test cells were harvested for cytometric analysis in upper panel and the statistic analysis on multiple healthy donors is shown in lower panel.

FIG. 2F is mass cytometry analysis of antagonistic and agonistic LILRB2 antibodies on OKT3-stimulated PBMCs from multiple healthy donors. PBMCs were obtained from healthy donors and treated with purified LILRB2 antagonistic (C_1H3) and agonistic (C_8B5) antibodies (5 μg/ml), or isotype control overnight for 16 hours following stimulation with OKT3 (0.01 μg/ml) for 3 days. The test cells were harvested for cytometric analysis (heat map, Left panel and Disney figure, Right panel). Left panel represents the heatmaps showing the expression of the indicated markers in the immune cells subsets (PBMC, CD4 and CD8 T cells). Right panel represents t-SNE map displaying data on subsets of $1\times10^6$ PBMCs, CD4 and CD8 T cells analyzed with our 38-antibody panel and colored by marker expression normalized based on IgG control.

FIG. 3A is a graph showing OKT3-mediated T cell proliferation (CPM) following stimulation of PBMC from healthy donors. PBMC were cultured with LILRB2 antagonistic antibodies overnight (16 hours) and stimulated with a low dose (0.01 μg/ml) of anti-CD3 (OKT3) for 3 days. After 3 days of treatment, [$^3$H]-thymidine was added for the last 8 hours of culture followed by measurement on a scintillation counter. Clone ranking based on TNF alpha from FIG. 1A is presented. The relative fold change in T-cell proliferation (CPM) is shown in FIG. 3A (based on fold change with Ig control).

FIG. 3B is a graph showing IFN-γ production from OKT3-mediated T cell proliferation of PBMC from healthy donors. PBMC were cultured with LILRB2 antagonistic antibodies overnight (16 hours) and stimulated with a low dose (0.01 μg/ml) of anti-CD3 (OKT3) for 3 days. Supernatants were collected from FIG. 3A and IFN-γ concentrations were measured by ELISA (based on fold change with Ig control).

(agonist). FIG. 3C is a set of flow cytometric data from OKT3-stimulated human PBMC labeled with CFSE. CFSE-labeled PBMCs were cultured with LILRB2 agonistic antibodies overnight (16 hours) and stimulated with a low dose (0.01 μg/ml) of anti-CD3 (OKT3) for 3 days. After 3 days of culture, viable CD4 T cells (left panel) and CD8 T cells (middle panel) were analyzed by flow cytometry. The representative flow plots were showed as CFSE dilution of CD4 and CD8 T cells (left and middle panels) and proliferation index (right middle for CD4 cells and right lower panel for CD8 cells). Supernatants were harvested for IFNgamma detection shown in right upper panel.

FIG. 3D is a set of flow cytometric data from cultured human PBMC (responders) labeled with CFSE, and stimulated with irradiated (30 Gy) unrelated donor PBMCs (stimulators) in presence of IgG isotype control or the indicated LILRB2 antibodies (5 μg/ml). The ratio of responder/stimulator was 1/2. After 5 days of co-culture, viable CD4 T cells (left panel) and CD8 T cells (right panel) were analyzed by flow cytometry. The representative flow plots are shown as CFSE dilution.

FIG. 4A is a graph showing the proliferation of LILRB2-transduced human myeloid leukemia cells (THP1) following treatment with anti-LILRB2 antibody (5 μg/ml), or isotype control for 42 hours. LILRB2+ THP-1 cell proliferation was assessed by [$^3$H]-thymidine incorporation. Cells were pulsed with [$^3$H]-thymidine for the last 8 hours of culture.

FIG. 4B is a graph showing the proliferation of LILRB2-transduced human breast cancer cells (MCF7) following treatment with anti-LILRB2 antibody (5 μg/ml), or isotype control for 4 days. LILRB2+ MCF7 cell proliferation was assessed by [$^3$H]-thymidine incorporation. Cells were pulsed with [$^3$H]-thymidine for the last 8 hours of culture.

FIGS. 5A-5B are graphs showing migration/invasive activity of LILRB2$^+$ MDAMB231 breast cancer cells. FIG. 5A shows the scratch assay performing to evaluate the migration activity of LILRB2$^+$ MDAMB231. Scratched the cell monolayer in a straight line and treated with anti-LILRB2 mAbs or control Ig (5 μg/ml) in serum-free medium. After 24 hours, the migratory ability of LILRB2$^+$ MDAMB231 cells was determined by scratch closure on the basis of the area that are measured by Image J. FIG. 5B shows the transwell assay performed to evaluate the invasive activity of LILRB2$^+$ MDAMB231. $1\times10^5$ cells were seeded in the upper chamber in the presence of LILRB2 antagonistic antibody (C_5C12) or control Ig (5 μg/ml). After 24 hours, the transwell membrane was stained with Crystal Violet and cells per field were counted. Photos are shown to indicate the migrated cells at the upper panel. Statistical analysis of upper panels in FIGS. 5A-5B are shown in lower panels.

FIG. 6A are graphs showing the effect of LILRB2 antagonistic antibody (P_5G5) on enhancement of adjuvant effect (left panel) and phagocytic activities of human monocytes on GFP-expressing *Escherichia coli* (middle and right panels). Left Panel, MISTRG mice were intravenously injected with IgG control or LILRB2 antagonistic antibody (P_5G5) (150 μg/mouse) for two days, and then intraperitoneally challenged with 5 nmol. After 2 hours, the serums were collected from test mice and subjected to ELISA analysis for TNFα levels. Middle and Right Panels, humanized MISTRG mice were intraperitoneally injected with LILRB2 antagonistic antibody (P_5G5) or control Ig (150 μg/mouse) for 48 hours. Peripheral blood cells were isolated and incubated with *E. coli* expressing GFP at the ratio of $2\times10^8$ *E. Coli* per $1\times10^7$ peripheral blood cells for 4h at 37° C. The cells were harvested and washed with PBS and analyzed by gating on viable CD45$^+$CD33$^+$ population.

FIG. 6B is a graph showing tumor growth of LLC cells were suppressed by LILRB2 antagonistic clone (P_5G5) in BAC LILRB2/3 transgenic mice in conjunction with anti-PDL1. Test mice were subcutaneously (sc) implanted with $4\times10^5$ LLC cells. When the tumor size reached 2-3 mm diameter, LILRB2 antagonistic clone, clone P_5G5 (open circle) or control IgG (open diamond) (150 μg/mouse, every three days) were infused through I.V. injection. Anti-PDL-1 (150 μg/mouse, every three days) was started from second time injection of LILRB2 antibody, clone P_5G5 (open square) or control IgG (open triangle). The tumor volume was determined every 2-3 days; shown in FIG. 6B.

FIG. 6C is a graph showing the anti-tumor effect of LILRB2 antagonistic antibodies (P_5G5) on tumor growth of Luciferase-expressed-A549 in HLA-A2 matching humanized NCG mice model. Test mice were intravenously (iv) injected with $2\times10^6$ A549 cells. LILRB2 antagonistic clone, clone P_5G5 or control IgG were infused through I.V. injection on day 3 (200 μg/mouse, every three days). HLA-A2 matched PBMC from same donors were infused on day 3 and day 13. Anti-PD-1 (200 μg/mouse) was started on day 4 and given every week for three weeks. The statistical analysis on luciferase activity in lungs after 25 days of luciferase-expressed A549 tumor inoculation in HLA-A2$^+$ PBMC humanized NCG mice was quantified by bioluminescence signals (Avg Radiance [p/s/cm$^2$/sr]) and is shown in FIG. 6C.

FIG. 7A is a schematic of the experiment. FIGS. 7B-C depicts graphs showing the co-stimulatory effect of anti-LILRB2 on human PBMC proliferation and interferon gamma secretion. $1\times10^1$ total PBMC from healthy donors were cultured with stimulated with anti-LILRB2 Abs (5 μg/ml) in the presence of 1 μg/ml of a-PD-1, 1 μg/ml of 4-1BBL, 100 ng/ml of OX40L or 1 μg/ml of GITRL overnight (16 hours) a low dose of anti-CD3 (OKT3, 0.01 μg/ml) plus for 3 days. After 3 days of treatment, T cells proliferation was assessed by [$^3$H]-thymidine incorporation. Thymidine was added for the last 8 hours of culture followed by measurement on a scintillation counter. The effect of on T cell proliferation (CPM) is shown in FIG. 7B. Supernatants were harvested for detection of interferon gamma production shown in FIG. 7C.

FIG. 8A: Fold change of TNFα and CD86 MFI levels relative to IgG-treated samples. PBMC were cultured for 48 hours with LILRB2 reactive hybridoma supernatant followed by 6 hours of LPS stimulation (50 ng/ml) in the presence of brefeldin A. MFI values represent cells gated on CD33$^+$ monocytes. FIG. 8B: Raw CD86 and TNFα data of highlighted clones (red line) from FIG. 8A. Data are overlaid Ig control-treated PBMC (black line). FIG. 8C: LILRB and LILRA1 receptor recognition of highlighted clones in FIG. 8A. Antibody binding was detected using goat polyclonal anti-mouse IgG secondary antibody. FIG. 8D: Expression of LILRB2 on THP1 parental cells and LILRB2 retroviral transduced cells. FIG. 8E: Bio-layer interferometry data testing LILRB2-His association to (t=1-600s) and dissociation from (t=600-1450s) immobilized anti-LILRB2 (10 μg/ml). Concentrations of LILRB2-His and calculated anti-LILRB2 affinity (Clone A) are shown.

FIG. 9A: Representative brightfield microscopy images of MCSF M(−) macrophages matured in the presence of mIgG2a or anti-LILRB2 (αLILRB2, 1 μg/ml). FIG. 9B: Representative levels of CD14 and CD163 expression by M(−) in the presence of mIgG2a (blue line) or anti-LILRB2 (red line). FIG. 9C: Pooled paired MFI data from FIG. 9B collected from healthy donors (n=10) over multiple experiments. FIG. 9D: Secreted TNFα and IL10 from macrophages in FIG. 9C following 16 hour LPS (50 ng/mL) stimulation and detection by ELISA. FIG. 9E: Fold changes in IRF3, 4, 5 and 7 mRNA expression relative to mean value in IgG-treated immature macrophages cultured in the presence of MCSF (50 ng/ml) for 2 days. p-value was calculated by using 2-tailed, Student t-test. FIG. 9F: Representative PD-L1 expression in M(LPS) and M(IL4) matured in the presence of mIgG2a (black) and anti-LILRB2 (red). FIG. 9G: Pooled paired MFI data from FIG. 9F collected from healthy donors (n=11) over multiple experiments. FIG. 9H: Representative DC-SIGN expression of M(LPS) and M(IL4) matured in the context of mIgG2a (black) and anti-LILRB2 (red). FIG. 9I: Pooled paired MFI data from FIG. 9H collected from healthy donors (n=11) over multiple experiments. p-value was calculated by using 2-tailed, paired t-test.

FIG. 10A-FIG. 10C: THP1 LILRB2$^+$ cells were cultured with IgG or anti-LILRB2 (αLILRB2, 1 μg/ml) for 24 hours followed by acute stimulation with LPS (FIG. 10A), IFNγ (FIG. 10B), or IL4 (FIG. 10C) for 5, 10, and 30 min. FIG. 10A: Immunoblot of phosphorylated NFκB, ERK1/2 and p38 in response to LPS (50 ng/mL) stimulation. FIG. 10B: Immunoblot of phosphorylated NFκB, ERK1/2, p38, and STAT1 in response to IFNγ (20 ng/mL) stimulation. FIG. 10C: Immunoblot of phosphorylated STAT6 in response to IL4 (20 ng/mL) stimulation. FIG. 10D: Immunoblot of SOCS1 and SOCS3 in response to IL4 (20 ng/mL) stimulation. FIG. 10E: Immunoblot of phosphorylated AKT from primary MCSF macrophages matured in the presence of IgG or anti-LILRB2. Representative data from 3 independent PBMC donors. FIG. 10F: LILRB2, pSHP1, and total SHP1 immunoblotting from IgG and anti-LILRB2 treated macrophages. Results from anti-LILRB2 (42D1) immunoprecipitate (top) and total input lysate (bottom).

FIG. 10G: LILRB2 antagonism inhibits monocyte/macrophage-mediated suppression of Teff responses. Total CD4 and CD8 T cell counts determined by flow cytometry of 72 hour MLRs containing mature DCs, sorted allogeneic T cells, and titrated ratios of MCSF macrophages matured in the presence of IgG (black line) or anti-LILRB2 (red line). FIG. 10H: Supernatants from MLRs in FIG. 10G were analyzed for secreted IFNγ by ELISA. FIG. 10I: Total PBMC were incubated with anti-LILRB2 (5 μg/ml) or IgG overnight followed by anti-PD-1 treatment (1 μg/ml) in the presence of OKT3 stimulation (0.01 μg/ml) for three days. Supernatants were harvested for IFNγ detection by ELISA. Data are from a representative experiment of three independent experiments and presented as mean f SEM, and p values were calculated by one way ANOVA, Tukey's multiple comparison test.

FIG. 11A: Volcano plots of normalized gene enrichment scores and enrichment p-values of anti-LILRB2 (αLILRB2) treatment versus IgG treatment in monocyte-derived macrophage conditions M(LPS) (left) and M(IL4) (right). Statistically significant DEGs above the enrichment cutoff (DEGs with FC≥1.5 and p-value<0.01 with FDR) are shown in red. FIG. 11B: Overlapping and unique DEGs from M(LPS) and M(IL4) conditions in response to anti-LILRB2 treatment. Venn-diagram (top) depicting overlap of DEGs between M(LPS)+anti-LILRB2 vs. M(LPS)+IgG and M(IL4)+anti-LILRB2 vs. M(IL4)+IgG (FC≥1.5 and p-value<0.01 with FDR). Summarized gene ontology of overlapping DEGs are shown. Functional terms associated with the 66 shared LILRB2-regulated genes between M(LPS) and M(IL4) are listed below. FIG. 11C: 2D principal component analysis of Illumina BeadArray datasets. M(LPS)+IgG (blue), M(LPS)+anti-LILRB2 (red), M(IL4)+IgG (black) and M(IL4)+anti-LILRB2 (green); n=3 per group are shown. FIG. 11D: Heatmap visualization of normalized DEGs associated with immune function changes as a result of LILRB2 antagonism in M(IL4) by comparing M(IL4)+anti-LILRB2 versus M(IL4)+IgG conditions. DEGs are ranked top to bottom by fold change: red (increased), green (decreased), black (unchanged). Data is normalized by row z-score.

FIG. 12A: FACS gating analysis of primary human CD33+monocytes (1×10$^5$ cells/well) with 5 days co-culture of A549 cells (1×10$^3$ cells/well). FIG. 12B: CD14, CD16, CD163, and DC-SIGN expression among live CD33$^+$CD14$^+$ myeloid cells from FIG. 12A. IgG treated cells (black line) are overlaid by anti-LILRB2 treated cells (αLILRB2, red line). FIG. 12C: FACS gating strategy for identifying human CD45$^+$CD33$^+$ macrophages from NSG-SGM3 immuno-deficient mice subcutaneously inoculated with A549 tumor and CD33+monocytes 12 days earlier. FIG. 12D: One representative data from one donor was shown. Data were averaged from 4 tumor samples/group, 2 mice/group. Data were compared using two-tailed Student's t-test. Individual data from five donors were presented in FIG. 20B. Combined data from all five donors for CD14, HLADR and CD16 is presented in FIG. 20D. Data were averaged from 4-8 tumor samples/group/donor, 2-4 mice/group/donor, three independent experiments, paired t-test. FIG. 12E: HLA-A2 matched humanized NCG mice were used to assess in vivo anti-tumor responses by LILRB2 blockade (αLILRB2) together with anti-PD-1 (αPD1) treatment in a LUC-A549 (HLA-A2$^+$) xenograft mouse model. The statistical analysis on luciferase activity in lungs after 19 days of luciferase-expressed A549 tumor inoculation in HLA-A2+PBMC humanized NCG mice were quantified by bioluminescence signals (Avg Radiance [p/s/cm$^2$/sr]) and shown in bar graph. (n=3-6 mice per group), one way ANOVA, Tukey's multiple comparison test. FIG. 12F: ELISA analysis on serum TNFα levels from CpG challenged mice are shown, n=5 (two-tailed Student's t-test). FIG. 12G: The mean fluorescence intensity of GFP-expressing *E. Coli* in viable CD14$^+$CD16$^-$ and CD14$^+$CD16$^-$ cells in CD45$^+$CD33$^+$ population from IgG or anti-LILRB2-treated humanized MISTRG mice were analyzed (N=3, duplicates per mouse). *, $p<0.05$, ns.=no significance. Data were compared using two-tailed Student's t-test.

FIG. 13A: LILRB2 and LILRB3 expression in CD11b-gated viable peripheral blood cells. FIG. 13B: Total peripheral blood cells were harvested for flow cytometric analysis after LPS stimulation in the presence of IgG or anti-LILRB2 (αLILRB2) and supernatants were collected for ELISA assay. Representative dot plots of the $CD86^+MHCII^+$ population in CD11b-gated cells. FIG. 13C: Statistical analysis on percentage of $CD86^+MHCII^+$ cells in CD11b-gated cells from FIG. 13B (n=3). FIG. 13D: Statistical analysis on TNFα secretion from total peripheral blood cells (n=3). FIG. 13E: Lewis Lung carcinoma (LLC)-tumor model in LILRB2 transgenic mice. Experimental mice treated with Ig control or anti-LILRB2 (αLILRB2) or/and anti-PD-L1 (αPDL1). Left, LLC tumor growth was measured every two or three days and the average tumor volume per group+/−SEM (Standard Error of the Mean) reported, N=5-6. Right, Tumor weight. Statistical significance was determined using two way ANOVA comparison of groups on day 23, p-value: *, $p<0.05$, **, $p<0.01$. FIG. 13F: Tumor infiltrating lymphocytes were purified for flow cytometric analysis of $Ly6G^+$ $Ly6C^{int}$ granulocytic MDSC and $Ly6G^-Ly6C^{hi}$ monocytic MDSC in the $CD11b^+$ cell population. Upper panels, representative flow cytometric analysis on MDSC from tumor of test mice treated with Ig control or anti-LILRB2+ anti-PDL1. Bottom panels, pooled MFI data from Left figure collected from tumor-bearing mice (n=3-5 mice/group, one way ANOVA, Tukey's multiple comparison test). FIG. 13G: Splenocytes and tumor infiltrating lymphocytes were isolated for flow cytometric analysis of $CD25^+FoxP3^+$ Treg in $CD4^+$ cell population. Left, representative flow cytometric analysis on Treg from spleen and tumor of test mice treated with Ig control or anti-LILRB2+anti-PDL1. Right, pooled MFI data collected from same tumor-bearing mice (n=4-6 mice per group, one way ANOVA, Tukey's multiple comparison test).

FIG. 14A: Characterization of myeloid cell populations isolated from NSCLC excised tumor. Cells were gated on DAPI-$CD45^+$ live leukocyte cells. PMN-MDSC, M-MDSC, DC, and TAM populations were identified. FIG. 14B: Representative LILRB1-4 staining among $CD33^+$ gate from FIG. 14A. FIG. 14C: LILRB MFI of multiple patient biopsies (N=5-6) shown gated on the MDSC (left) and TAM (right) gate. FIG. 14D: Lung cancer-derived TIL were cultured with M-CSF plus IFNγ with Ig controls or anti-LILRB2 (αLILRB2) for 48 hours. The supernatants were evaluated for TNFα and IL10 secretion. (*, $p<0.05$, n=15, paired t-test). FIG. 14E: Lung cancer-derived TILs from FIG. 14D were collected from multiple patients for flow cytometric analysis for expression of CD163, CD14, and PD-L1 (n=11) as well as DC-SIGN and CD16 (n=7) (paired t-test). FIG. 14F: Proposed mechanisms for LILRB2 antagonism on the M1/M2 polarization.

FIG. 23G shows the cross-reactivity of the anti-LILRB2 agonist antibodies to the LILRA family.

FIG. 30: Weekly BLI of mice treated with untransduced T cells (left) or anti-LILRB2-CAR-T cells (right) were taken from the back of mice.

FIG. 31: Weekly BLI of mice treated with untransduced T cells (left) or anti-LILRB2-CAR-T cells (right) were taken from the abdomen were showed.

FIG. 32: Each shape represents an individual mouse in the treatment group. Plot of total flux (p/s) as a function of time demonstrated that anti-LILRB2 CAR-T cells (right) decrease leukemia burden as compared to the control T cell-treated (left) mice.

FIG. 33: The quantification results of leukemia burden were showed in total flux (left panel) and average radiance (right panel). Mice treated with anti-LILRB2 CAR-T cells showed decrease of the tumor burden compared to the untransduced T cell-treated mice.

FIG. 35A: Anti-LILRB2 overcame MDSC-mediated inhibition of AML killing by LILRB4 CAR-T. LILRB4 CAR-T cells were co-cultured with MDSC and AML cells, THP-1, which express LILRB4, in the presence of an anti-LILRB2 antibody or control immunoglobulin for three days. The residual THP-1 and MDSC cells were identified by staining of CD33 and CD14 markers. Anti-LILRB2 enhanced the LILRB4 CAR-T mediated THP-1 killing as compared with control immunoglobulin. FIG. 35B: Anti-LILRB2 overcame MDSC-mediated suppression of CAR-T proliferation. CFSE-labeled Her2 CAR-T cells were stimulated with Her2+SCC-47 tumor cells for 3 days in the presence of MDSCs and anti-LILRB2. The proliferation of CD4 and CD8 T cells were assessed using CFSE dilution by flow cytometry. The ratio of CAR-T cells, tumor cells, and MDSCs was 10:1:5.

DETAILED DESCRIPTION

Figure 1A:
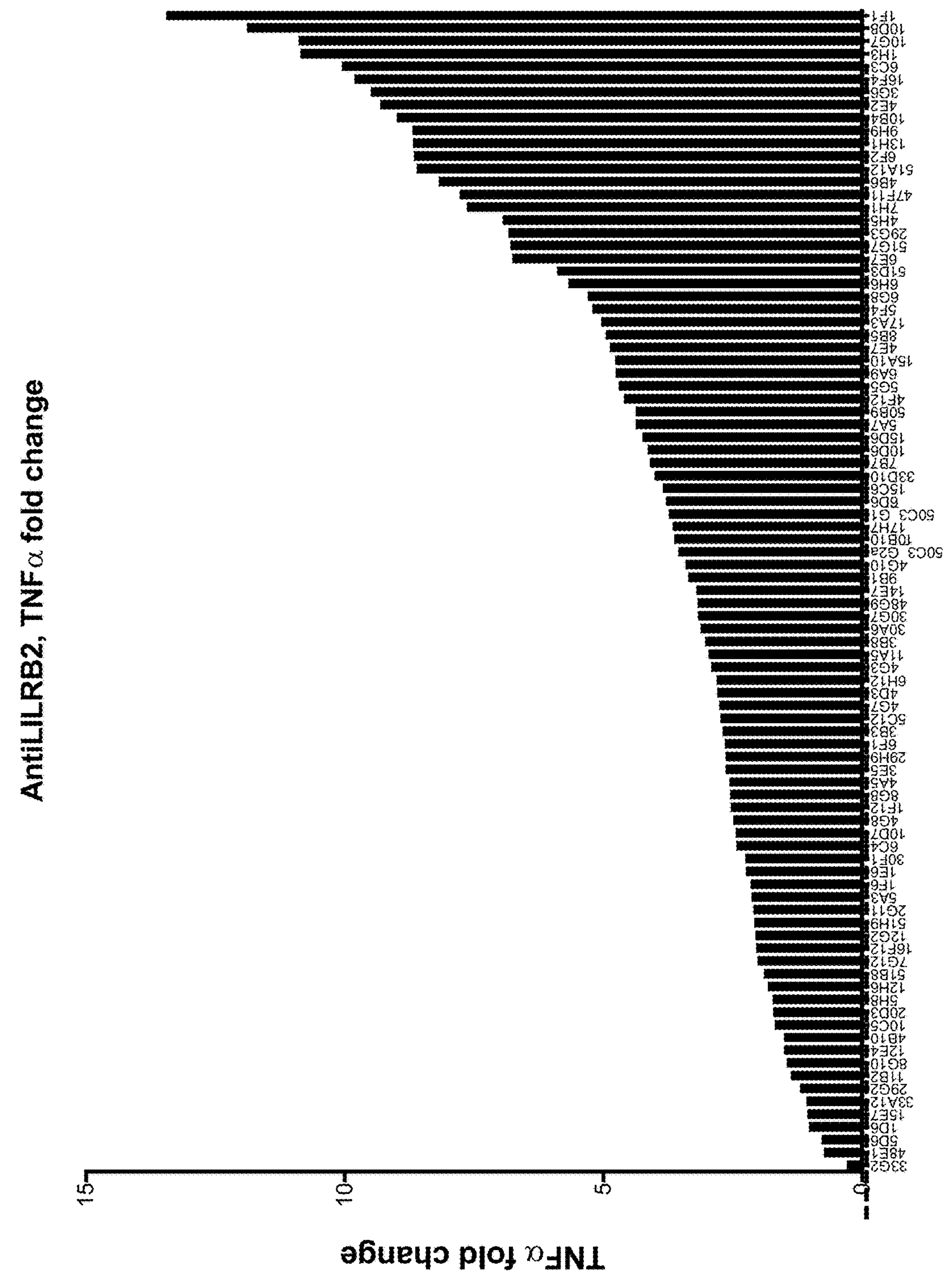
FIGS. 1A-1C: The effect of anti LILRB2 on TNFalpha production from human PBMC.

This disclosure features antibodies and antigen-binding fragments that specifically bind LILRB2.

The disclosure also provides polynucleotides encoding the antibodies and antigen-binding fragments thereof described herein. In addition, this disclosure relates to methods of using the anti-LILRB2 antibodies and antigen-binding fragments thereof in the treatment of cancer or stimulating a pro-inflammatory immune response.

The disclosure also relates to related chimeric antigen receptors (CARs) and cells comprising same (e.g., T cells, natural killer cells, or macrophages), and uses of the CARs and cells in targeting tumors and killing them, asthma treatment, or in targeting and removing infected cells (e.g., to treat infections or infectious diseases), or in suppressing immune system cells, as involved in autoimmune disease or transplant rejection.

In order to provide a clear understanding of the specification and claims, the following definitions are provided below.

Definitions

It is understood that wherever embodiments are described herein with the language "comprising," otherwise analogous embodiments described in terms of "consisting of" and/or "consisting essentially of" are also provided.

The term "antibody" means an immunoglobulin molecule that recognizes and specifically binds to a target, such as a protein (e.g., the LILRB2, a subunit thereof, or the receptor complex), polypeptide, peptide, carbohydrate, polynucleotide, lipid, or combinations of the foregoing through at least one antigen recognition site within the variable region of the immunoglobulin molecule. A typical antibody comprises at least two heavy (HC) chains and two light (LC) chains interconnected by disulfide bonds. Each heavy chain is comprised of a "heavy chain variable region" or "heavy chain variable domain" (abbreviated herein as VH) and a heavy chain constant region. The heavy chain constant region is comprised of three domains, CH1, CH2, and CH3. Each light chain is comprised of a "light chain variable region" or "light chain variable domain" (abbreviated herein as $V_L$) and a light chain constant region. The light chain constant region is comprised of one domain, C1. The $V_H$ and $V_L$ regions can be further subdivided into regions of hypervariablity, termed Complementarity Determining Regions (CDR), interspersed with regions that are more conserved, termed framework regions (FRs). Each $V_H$ and $V_L$ region is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. As used herein, the term "antibody" encompasses intact polyclonal antibodies, intact monoclonal antibodies, antibody fragments (such as Fab, Fab', F(ab')2, Fd, Facb, and Fv fragments), single chain Fv (scFv), minibodies (e.g., sc(Fv)2, diabody), multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, radioisotopes, small molecule drugs, polypeptides, etc.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and including more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

Bispecific antibodies are described, e.g., in U.S. Pat. No. 5,932,448, incorporated by reference, disclosing making of bispecific antibodies with Fab' portions joined by a leucine zipper; U.S. Pat. No. 7,538,196, incorporated by reference, disclosing making of bispecific antibodies where portions are joined with a linker; and U.S. Pat. No. 8,148,496, incorporated by reference, disclosing a multivalent a multivalent Fv antibody construct having at least four variable domains which are linked with each other via peptide linkers.

The term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human. See, e.g., U.S. Pat. Nos. 5,585,089; 5,225,539 (incorporated by reference).

The term "antigen binding fragment" refers to a portion of an intact antibody and refers to the antigenic determining variable regions of an intact antibody. It is known in the art that the antigen binding function of an antibody can be performed by fragments of a full-length antibody. Examples of antigen-binding antibody fragments include, but are not limited to Fab, Fab', F(ab')2, Facb, Fd, and Fv fragments, linear antibodies, single chain antibodies, and multispecific antibodies formed from antibody fragments. In some instances, antibody fragments may be prepared by proteolytic digestion of intact or whole antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab; and plasmin digestion of whole antibodies yields Facb fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced. The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced. The term "Fv" refers to an antibody fragment that consists of one NH and one N domain held together by noncovalent interactions.

As used herein the term "scFv" or "scFv molecule" includes binding molecules which consist of one light chain variable domain ($V_L$) or a portion thereof, and one heavy chain variable domain ($V_H$) or a portion thereof, wherein each variable domain (or a portion thereof) is derived from the same or different antibodies. Single chain Fv molecules preferably comprise an scFv linker interposed between the $V_H$ domain and the $V_L$ domain. Exemplary scFv molecules are known in the art and are described, for example, in U.S. Pat. No. 5,892,019; Ho et al, *Gene,* 77:51 (1989); Bird et al., *Science,* 242:423 (1988); Pantoliano et al, *Biochemistry,* 30: 101 17 (1991); Milenic et al, *Cancer Research,* 51:6363 (1991); Takkinen et al, *Protein Engineering,* 4:837 (1991). The term "scFv linker" as used herein refers to a moiety interposed between the $V_L$ and $V_H$ domains of the scFv. The scFv linkers preferably maintain the scFv molecule in an antigen-binding conformation. In one embodiment, a scFv linker comprises or consists of an scFv linker peptide. In certain embodiments, an scFv linker peptide comprises or consists of a Gly-Ser peptide linker. In other embodiments, an scFv linker comprises a disulfide bond.

The terms "LILRB2 antibody," "anti-LILRB2 antibody," "anti-LILRB2," "antibody that binds to LILRB2" and any grammatical variations thereof refer to an antibody that is capable of specifically binding to the LILRB2 with sufficient affinity such that the antibody is useful as a therapeutic agent or diagnostic reagent in targeting LILRB2. The extent of binding of an anti-LILRB2 antibody disclosed herein to an unrelated, non-LILRB2 protein is less than about 10% of the binding of the antibody to LILRB2 as measured, e.g., by a radioimmunoassay (RIA), BIACORE™ (using recombinant LILRB2 as the analyte and antibody as the ligand, or vice versa), or other binding assays known in the art. In certain embodiments, an antibody that binds to LILRB2 has a dissociation constant (KD) of <1 μM, <100 nM, <50 nM, <10 nM, or <1 nM.

The term "% identical" between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is b12seq, part of the BLAST suite of program available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org (ClustalX is a version of the ClustalW2 program ported to the Windows environment). Another suitable program is MUSCLE, available from www.drive5.com/muscle. ClustalW2 and MUSCLE are alternatively available, e.g., from the EBI.

The term "therapeutic agent" refers to any biological or chemical agent used in the treatment of a disease or disorder. Therapeutic agents include any suitable biologically active chemical compounds, biologically derived components such as cells, peptides, antibodies, CARs (and cells comprising CARs), and polynucleotides, and radiochemical therapeutic agents such as radioisotopes. In some embodiments, the therapeutic agent comprises a chemotherapeutic agent or an analgesic.

The terms "treat," and "treating," as used herein with reference to a disorder associated with increased cellular death, e.g., ischemia, refer to a decrease in the occurrence of tissue and/or cellular damage in an animal or human. The prevention may be complete, e.g., the total absence of tissue damage in a subject. The prevention may also be partial, such that the occurrence of tissue damage in a subject is less than that which would have occurred without the therapeutic agent.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than that which would have occurred without the present invention.

LILRB2

By the term "leukocyte immunoglobulin (Ig)-like receptor B2" or "LILRB2" is meant a mammalian (e.g., human) LILRB2 protein or mRNA, or a LILRB2 protein or mRNA derived from a mammalian (e.g., human) LILRB2 protein or mRNA. Non-limiting examples of LILRB2 proteins and mRNA are described herein. Additional examples of LILRB2 proteins and mRNA are known in the art.

The amino acid sequence of a human LILRB2 are provided below: (NP_001265333.2)

```
                                          (SEQ ID NO: 361)
MTGAYPKPTLSAQPSPVVTSGGRVTLQCESQVAFGGFILCKEGEDEHPQ

CLNSQPHARGSSRAIFSVGPVSPNRRWSHRCYGYDLNSPYVWSSPSDLL

ELLVPGVSKKPSLSVQPGPVMAPGESLTLQCVSDVGYDRFVLYKEGERD

LRQLPGRQPQAGLSQANFTLGPVSRSYGGQYRCYGAHNLSSECSAPSDP

LDILITGQIRGTPFISVQPGPTVASGENVTLLCQSWRQFHTFLLTKAGA

ADAPLRLRSIHEYPKYQAEFPMSPVTSAHAGTYRCYGSLNSDPYLLSHP

SEPLELVVSGPSMGSSPPPTGPISTPAGPEDQPLTPTGSDPQSGLGRHL

GVVIGILVAVVLLLLLLLLLFLILRHRRQGKHWTSTQRKADFQHPAGAV

GPEPTDRGLQWRSSPAADAQEENLYAAVKDTQPEDGVEMDTRAAASEAP

QDVTYAQLHSLTLRRKATEPPPSQEREPPAEPSIYATLAIH
```

and its variants.

By the term "LILRB2 agonist" is meant an agent that specifically binds to LILRB2 protein and activates LILRB2 signaling pathways in a mammalian cell. Non-limiting examples of LILRB2 agonists are described herein. Examples of LILRB2 signaling pathways are described in the WO2013/181438 and US. Publication No. US 2050174203, each of which is incorporated herein in its entirety.

By the term "LILRB2 antagonist" is meant an agent that specifically binds to LILRB2 protein and decreases the activity, activation or function of the LILRB2 signaling pathways in a mammalian cell. Non-limiting examples of LILRB2 antagonist are described herein.

Anti-LILRB2 Antibodies

This disclosure provides antibodies and antigen-binding fragments thereof that specifically bind to LILRB2. Examples of anti-LILRB2 antagonist antibodies (murine) are provided in Table 1.

TABLE 1

Murine Anti-LILRB2 CDR* Amino Acid Sequences

| | variable Light (VL) chain CDR sequences | | | Variable Heavy (VH) chain CDR sequences | | |
|---|---|---|---|---|---|---|
| ID | LC CDR1 | LC CDR2 | LC CDR3 JUNCTION | HC CDR1 | HC CDR2 | HC CDR3 JUNCTION |
| 1F1 | QDIVKN (SEQ ID NO: 1) | YAT (SEQ ID NO: 35) | CLQFYEFP LTF (SEQ ID NO: 50) | GYAFTNFF (SEQ ID NO: 89) | INPGSGGT (SEQ ID NO: 120) | CARNDAM DYW (SEQ ID NO: 158) |
| 10D8 | QSVDNYG YSY (SEQ ID NO: 2) | AAS (SEQ ID NO: 36) | CQHIKEDT FSF (SEQ ID NO: 51) | GYSFTFFW (SEQ ID NO: 90) | IDPSDNYT (SEQ ID NO: 121) | CARRWLLH EMAYW (SEQ ID NO: 159) |
| 10G7 | QSVDYDG DSY (SEQ ID NO: 3) | AAS (SEQ ID NO: 36) | CQQSNEDP FTF (SEQ ID NO: 52) | GYSFTTYW (SEQ ID NO: 91) | IDPSDSYT (SEQ ID NO: 122) | CARRWLLH EMDYW (SEQ ID NO: 160) |
| 1H3 | QSIGTS (SEQ ID NO: 4) | IAS (SEQ ID NO: 37) | CQQSNGW PLTF (SEQ ID NO: 53) | GYTFTDFE (SEQ ID NO: 92) | IDPETGGS (SEQ ID NO: 123) | CTIYFWYF DVW (SEQ ID NO: 161) |
| 6C3 | QSIGTS (SEQ ID NO: 4) | FAS (SEQ ID NO: 38) | CQQSNGW PLTF (SEQ ID NO: 53) | GYTFTDFE (SEQ ID NO: 92) | IDPTGGS (SEQ ID NO: 124) | CTIYFWYF DVW (SEQ ID NO: 161) |
| 16F4 | QSVDYDG DSY (SEQ ID NO: 3) | AAS (SEQ ID NO: 36) | CQQSNEDP FTF (SEQ ID NO: 52) | GYTFTNYW (SEQ ID NO: 93) | IDPSDTYT (SEQ ID NO: 125) | CGRRWLLL EMDYW (SEQ ID NO: 162) |
| 3G6 | QSVDYDG DSY (SEQ ID NO: 3) | AAS (SEQ ID NO: 36) | CQQSNEDP FTF (SEQ ID NO: 52) | GYTFTNYW (SEQ ID NO: 93) | IDPSDSYT (SEQ ID NO: 122) | CARRWLLH EMDYW (SEQ ID NO: 160) |
| 9H9 | QSVDYDG DSY (SEQ ID NO: 3) | AAS (SEQ ID NO: 36) | CQQSNEDP FTF (SEQ ID NO: 52) | GYIFTSNW (SEQ ID NO: 95) | IYPGSDTT (SEQ ID NO: 127) | CARFFSSP WFAYW (SEQ ID NO: 164) |
| 13H1 | QNINVW (SEQ ID NO: 6) | KAS (SEQ ID NO: 40) | CQQGQSYP LTF (SEQ ID NO: 55) | DYTFTGYW (SEQ ID NO: 96) | ILPESGST (SEQ ID NO: 128) | CARRSLGL SFNYW (SEQ ID NO: 165) |
| 6F2 | QSVDYDG DSY (SEQ ID NO: 3) | AAS (SEQ ID NO: 36) | CQQSNEDT FTF (SEQ ID NO: 56) | GYTFTSYW (SEQ ID NO: 94) | IDPSDSYT (SEQ ID NO: 122) | CARRWLLR EMDYW (SEQ ID NO: 166) |
| 51A12 | QSIGTS (SEQ ID NO: 4) | FAS (SEQ ID NO: 38) | CQQSNSWP LTF (SEQ ID NO: 57) | GYTFTDYE (SEQ ID NO: 97) | IDPETGGS (SEQ ID NO: 123) | CTIYFWYF DVW (SEQ ID NO: 161) |
| 4B6 | QSVDYDG DSY (SEQ ID NO: 3) | AAS (SEQ ID NO: 36) | CQQSNEDP FTF (SEQ ID NO: 52) | GYSFTFFW (SEQ ID NO: 90) | IDPSDNYT (SEQ ID NO: 121) | CARRWLLH KMDYW (SEQ ID NO: 167) |
| 47F11 | QSIGTS (SEQ ID NO: 4) | FAS (SEQ ID NO: 38) | CQQSNSWP LTF (SEQ ID NO: 57) | GYTFTDYE (SEQ ID NO: 97) | IDPETGGS (SEQ ID NO: 123) | CTIYFWYF DVW (SEQ ID NO: 161) |
| 7H1 | RTL VRL (SEQ ID NO: 8) | YAT (SEQ ID NO: 35) | CLHFYEFP LEF (SEQ ID NO: 58) | GYSFTNYL (SEQ ID NO: 98) | INPGSGGT (SEQ ID NO: 120) | CARNDAM DYW (SEQ ID NO: 158) |

TABLE 1-continued

Murine Anti-LILRB2 CDR* Amino Acid Sequences

| ID | variable Light (VL) chain CDR sequences | | | Variable Heavy (VH) chain CDR sequences | | |
|---|---|---|---|---|---|---|
| | LC CDR1 | LC CDR2 | LC CDR3 JUNCTION | HC CDR1 | HC CDR2 | HC CDR3 JUNCTION |
| 4H5 | QDIVKN (SEQ ID NO: 1) | YAT (SEQ ID NO: 35) | CLQFYEFP LTF (SEQ ID NO: 50) | GYAFTNYL (SEQ ID NO: 99) | INPGSGGK (SEQ ID NO: 129) | CARNDAM DYW (SEQ ID NO: 158) |
| 29G3 | KSVSISGY SY (SEQ ID NO: 9) | LAS (SEQ ID NO: 42) | CQHSRELP FTF (SEQ ID NO: 59) | GYTFTDYN (SEQ ID NO: 100) | INPNNGGT (SEQ ID NO: 258) | CARRPTTV LGGVYFDY W (SEQ ID NO: 168) |
| 51G7 | QSIGTS (SEQ ID NO: 4) | FAS (SEQ ID NO: 38) | CQQSNSWP LTF (SEQ ID NO: 57) | GYTFTDYE (SEQ ID NO: 97) | IDPETGGS (SEQ ID NO: 123) | CTIYFWYF DVW (SEQ ID NO: 161) |
| 6E7 | QSL VNSY GITY (SEQ ID NO: 10) | GIS (SEQ ID NO: 43) | CLQGTHQP WTF (SEQ ID NO: 60) | GYTFTSYW (SEQ ID NO: 94) | MYPGSGNT (SEQ ID NO: 131) | CARGFLYF DVW (SEQ ID NO: 169) |
| 51D3 | QSIGTS (SEQ ID NO: 4) | FAS (SEQ ID NO: 38) | CQQSNSWP LTF (SEQ ID NO: 57) | GYTFTDYE (SEQ ID NO: 97) | IDPETGGS (SEQ ID NO: 123) | CTIYFWYF DVW (SEQ ID NO: 161) |
| 6H6 | SSVSSSC (SEQ ID NO: 11) | STS (SEQ ID NO: 44) | CQQYKWL PITF (SEQ ID NO: 61) | GYTFTSYW (SEQ ID NO: 94) | INPSNGGT (SEQ ID NO: 77) | CAKEPIYY DYDEAGFD HW (SEQ ID NO: 170) |
| 17A3 | ENIYSN (SEQ ID NO: 12) | AAT (SEQ ID NO: 49) | CQHFWDIP YTF (SEQ ID NO: 62) | GFTFSNYG (SEQ ID NO: 101) | TSSGGNST (SEQ ID NO: 132) | CARHPYYS YYVEDWF AYW (SEQ ID NO: 171) |
| 6A9 | ENIYCT (SEQ ID NO: 15) | AAT (SEQ ID NO: 49) | CQHFWDIP YEF (SEQ ID NO: 65) | GFTFSNYG (SEQ ID NO: 101) | TSSGGNST (SEQ ID NO: 132) | CARHPYYS YYVEDWF AYW (SEQ ID NO: 171) |
| 17H7 | QDIVKN (SEQ ID NO: 1) | YAT (SEQ ID NO: 35) | CLQFYEFP LTF (SEQ ID NO: 50) | GYSFTNYF (SEQ ID NO: 104) | INPGSGGI (SEQ ID NO: 136) | CARNDAM DYW (SEQ ID NO: 158) |
| 10B10 | QGVDTA (SEQ ID NO: 16) | WAS (SEQ ID NO: 45) | CQQYSSYP LTF (SEQ ID NO: 68) | GFTFSNYR (SEQ ID NO: 105) | ITVKSDNYGA (SEQ ID NO: 137) | CSRSYGSS YGFAYW (SEQ ID NO: 177) |
| 11A5 | QDIRNY (SEQ ID NO: 18) | YTS (SEQ ID NO: 41) | CQQGNTLP WTF (SEQ ID NO: 69) | GYTFTSYG (SEQ ID NO: 107) | IYPRSGNT (SEQ ID NO: 138) | CARREGAP YTMDYW (SEQ ID NO: 178) |
| 5C12 | QDVTNA (SEQ ID NO: 20) | SAS (SEQ ID NO: 39) | CQQHYSFP YTF (SEQ ID NO: 71) | GYTFTSYW (SEQ ID NO: 94) | IYPGSGNT (SEQ ID NO: 139) | CTRGFLYF DVW (SEQ ID NO: 179) |
| 6F1 | QDIVNY (SEQ ID NO: 13) | YTS (SEQ ID NO: 41) | CQQYSKLP WTF (SEQ ID NO: 67) | GYSITSGYY (SEQ ID NO: 102) | ISYEGSN (SEQ ID NO: 133) | CVRYFDV W (SEQ ID NO: 175) |
| 4A5 | QDVSTA (SEQ ID NO: 21) | WAS (SEQ ID NO: 45) | CQQHYSTP LTF (SEQ ID NO: 72) | GFTFSDYY (SEQ ID NO: 108) | ISNGGGNT (SEQ ID NO: 140) | CARQGEEW YFDVW (SEQ ID NO: 180) |
| 5A3 | QVITNY (SEQ ID NO: 22) | YTS (SEQ ID NO: 41) | CQQYGKFP CTF (SEQ ID NO: 73) | GYSITSGYY (SEQ ID NO: 102) | ISYDGST (SEQ ID NO: 141) | CTRYFDVW (SEQ ID NO: 181) |
| 51H9 | SSVSY (SEQ ID NO: 23) | LTS (SEQ ID NO: 46) | CQQWSSNP LTF (SEQ ID NO: 74) | GYTFTSYW (SEQ ID NO: 94) | IHPNSDTT (SEQ ID NO: 142) | CAIRYHYY FDYW (SEQ ID NO: 182) |

TABLE 1-continued

Murine Anti-LILRB2 CDR* Amino Acid Sequences

| ID | variable Light (VL) chain CDR sequences: LC CDR1 | LC CDR2 | LC CDR3 JUNCTION | Variable Heavy (VH) chain CDR sequences: HC CDR1 | HC CDR2 | HC CDR3 JUNCTION |
|---|---|---|---|---|---|---|
| 10C5 | KSVSTSGYSY (SEQ ID NO: 24) | LAS (SEQ ID NO: 42) | CQHSRELPYTF (SEQ ID NO: 75) | GYAFSSSW (SEQ ID NO: 109) | IYPGDGDT (SEQ ID NO: 143) | CTPAYYSNYGAWFAYW (SEQ ID NO: 183) |
| 11B2 | QGISNY (SEQ ID NO: 25) | YTS (SEQ ID NO: 41) | CQQYNTPPWTF (SEQ ID NO: 259) | GHSITSGYY (SEQ ID NO: 110) | IFYDGSN (SEQ ID NO: 144) | CARYFDVW (SEQ ID NO: 173) |
| 29G2 | SSVSY (SEQ ID NO: 23) | VTS (SEQ ID NO: 47) | CQQWSSNPPTF (SEQ ID NO: 76) | GYTFTSYW (SEQ ID NO: 94) | IHPNSGNT (SEQ ID NO: 145) | CARITVVASYYAMDYW (SEQ ID NO: 185) |
| 33A12 | QSLLNSSNQKNY (SEQ ID NO: 26) | FAS (SEQ ID NO: 38) | CQQHYSTPPTF (SEQ ID NO: 130) | GYTFTTYG (SEQ ID NO: 111) | GYTFTTYG (SEQ ID NO: 111) | CTRMGLRRSLYAMDYW (SEQ ID NO: 186) |
| 15E7 | KSVSTSGYSY (SEQ ID NO: 24) | LAS (SEQ ID NO: 42) | CQHIRELPWTF (SEQ ID NO: 78) | GYSITSGYY (SEQ ID NO: 102) | ISYEGSN (SEQ ID NO: 133) | CVRYFDVW (SEQ ID NO: 175) |
| 5D6 | QDINSY (SEQ ID NO: 27) | RAN (SEQ ID NO: 48) | CLQYDEFPLTF (SEQ ID NO: 79) | GYTFTTYG (SEQ ID NO: 111) | MNTYSGVP (SEQ ID NO: 147) | CARGGLTTVVVDWYFDVW (SEQ ID NO: 187) |
| 8G8 | QDVGTA (SEQ ID NO: 28) | WAS (SEQ ID NO: 45) | CHQYITYPLTF (SEQ ID NO: 81) | GYIFTSNW (SEQ ID NO: 95) | IYPGSDTT (SEQ ID NO: 127) | CARFFSSPWFAYW (SEQ ID NO: 164) |
| 1F6 | QDIVKN (SEQ ID NO: 1) | YAT (SEQ ID NO: 35) | CLQFYEFPLTF (SEQ ID NO: 50) | GYAFTNFF (SEQ ID NO: 89) | INPGSGGT (SEQ ID NO: 120) | CARNDAMDYW (SEQ ID NO: 158) |
| 29H9 | QDIVKN (SEQ ID NO: 1) | YAT (SEQ ID NO: 35) | CLQFYEFPLTF (SEQ ID NO: 50) | GFPFTNYL (SEQ ID NO: 106) | INPGSGGT (SEQ ID NO: 120) | CARNDAMDYW (SEQ ID NO: 158) |
| 5F4 | QDIVKN (SEQ ID NO: 1) | YAT (SEQ ID NO: 35) | CLQFYEFPLTF (SEQ ID NO: 50) | GYAFTNYL (SEQ ID NO: 99) | INPGSGGT (SEQ ID NO: 120) | CARNDAMDYW (SEQ ID NO: 158) |
| 6H12 | QDIVKN (SEQ ID NO: 1) | YAT (SEQ ID NO: 35) | CLQFYEFPLTF (SEQ ID NO: 50) | GYAFTNYL (SEQ ID NO: 99) | INPGSGGT (SEQ ID NO: 120) | CARNDAMDYW (SEQ ID NO: 158) |
| 5H8 | ENIYSN (SEQ ID NO: 12) | AAT (SEQ ID NO: 49) | CQHFWGTPWTF (SEQ ID NO: 82) | GYTFTTYG (SEQ ID NO: 111) | MNTYSGVP (SEQ ID NO: 147) | CARGGLTTVVVDWYFDVW (SEQ ID NO: 187) |
| 6C4 | KSVSTSGFNY (SEQ ID NO: 29) | LAS (SEQ ID NO: 42) | CQHSRELPFTF (SEQ ID NO: 59) | GYTFTEYP (SEQ ID NO: 113) | IYTDTGEP (SEQ ID NO: 148) | CVRGVLLSTVFMPEFAYW (SEQ ID NO: 189) |
| 16F12 | QNINVW (SEQ ID NO: 6) | KAS (SEQ ID NO: 40) | CQQGQSYPLTF (SEQ ID NO: 55) | GYTFTGYW (SEQ ID NO: 114) | ILSGSDST (SEQ ID NO: 149) | CARRGLGLSFNNW (SEQ ID NO: 190) |
| 1E6 | QNINVW (SEQ ID NO: 6) | KAS (SEQ ID NO: 40) | CQQGQSYPLTF (SEQ ID NO: 55) | GNTFTGYW (SEQ ID NO: 115) | ILPGSDST (SEQ ID NO: 150) | CTGRDLGISFNSW (SEQ ID NO: 191) |
| 30G7 | QDVTTA (SEQ ID NO: 30) | WAS (SEQ ID NO: 45) | CQQHYNTPLTF (SEQ ID NO: 83) | GFTFSDYY (SEQ ID NO: 108) | ISYGGGNT (SEQ ID NO: 151) | CARQGEEWYFDVW (SEQ ID NO: 180) |

TABLE 1-continued

Murine Anti-LILRB2 CDR* Amino Acid Sequences

| ID | variable Light (VL) chain CDR sequences | | | Variable Heavy (VH) chain CDR sequences | | |
|---|---|---|---|---|---|---|
| | LC CDR1 | LC CDR2 | LC CDR3 JUNCTION | HC CDR1 | HC CDR2 | HC CDR3 JUNCTION |
| 10D7 | QDVSNA (SEQ ID NO: 31) | SAS (SEQ ID NO: 39) | CQQHYSFP YTF (SEQ ID NO: 71) | GYAFTSYW (SEQ ID NO: 116) | IYPGTNST (SEQ ID NO: 152) | CARGYLYF DVW (SEQ ID NO: 192) |
| 12G2 | QSVDYYG DSY (SEQ ID NO: 32) | AAS (SEQ ID NO: 36) | CQQINEDP FTF (SEQ ID NO: 84) | GYTFTNYW (SEQ ID NO: 93) | IDPSDTYT (SEQ ID NO: 125) | CARRWLLH EMDYW (SEQ ID NO: 160) |
| 33D10 | QSVDYDG DSY (SEQ ID NO: 3) | AAS (SEQ ID NO: 36) | CQQSNEDP FTF (SEQ ID NO: 52) | GYTFTSYW (SEQ ID NO: 94) | INPSNGGT (SEQ ID NO: 77) | CAKEPIYY DYDEAGFD HW (SEQ ID NO: 170) |
| 3B8 | QSVDYGG DSY (SEQ ID NO: 33) | AAS (SEQ ID NO: 36) | CQQSNEDP FTF (SEQ ID NO: 52) | GYSFTSYW (SEQ ID NO: 117) | IDPYDTYT (SEQ ID NO: 153) | CARRWLLH KMDYW (SEQ ID NO: 167) |
| 48G9 | QSIGTS (SEQ ID NO: 4) | FAS (SEQ ID NO: 38) | CQQSNSWP LTF (SEQ ID NO: 57) | GYTFTDYE (SEQ ID NO: 97) | IDPETGGS (SEQ ID NO: 123) | CTIYFWYF DVW (SEQ ID NO: 161) |
| 7G12 | QSIGTS (SEQ ID NO: 4) | FAS (SEQ ID NO: 38) | CQQSNSWP LTF (SEQ ID NO: 57) | GYTFTDFE (SEQ ID NO: 92) | IDPETGGS (SEQ ID NO: 123) | CTIYFWYF DVW (SEQ ID NO: 161) |
| 4G3 | QSIGTS (SEQ ID NO: 4) | FAS (SEQ ID NO: 38) | CQQSNSWP LTF (SEQ ID NO: 57) | GYTFTDYE (SEQ ID NO: 97) | FDPETGGS (SEQ ID NO: 154) | CTIYFWYF DVW (SEQ ID NO: 161) |
| 4B10 | QGISNY (SEQ ID NO: 25) | YTS (SEQ ID NO: 41) | CQQYSEFP WTF (SEQ ID NO: 85) | GYAFTNFF (SEQ ID NO: 89) | INPGSGGT (SEQ ID NO: 120) | CARNDAM DYW (SEQ ID NO: 158) |
| 12E4 | QGISNY (SEQ ID NO: 25) | YTS (SEQ ID NO: 41) | CQQYSEFP WTF (SEQ ID NO: 85) | WLPHASGY Y (SEQ ID NO: 118) | IIYDGNN (SEQ ID NO: 155) | CGRYFNG W (SEQ ID NO: 193) |
| 1F12 | KSVSTSG YSY (SEQ ID NO: 24) | STS (SEQ ID NO: 44) | CQQYSGYP STF (SEQ ID NO: 86) | GYTFTNYW (SEQ ID NO: 93) | INPSNGGT (SEQ ID NO: 77) | CAKEPIYY DYDEAGFD YW (SEQ ID NO: 194) |
| 3B3 | QDVTKP (SEQ ID NO: 34) | SAS (SEQ ID NO: 39) | CHQHYSFP YTF (SEQ ID NO: 87) | GYTFTSYW (SEQ ID NO: 94) | ILPHIGYP (SEQ ID NO: 156) | CTQPFLYF HVW (SEQ ID NO: 195) |
| 33G2 | SSVSY (SEQ ID NO: 23) | EIS (SEQ ID NO: 260) | CQQWNYP LTF (SEQ ID NO: 88) | GYTFTTYG (SEQ ID NO: 111) | INTYSGVP (SEQ ID NO: 157) | CARRGSYD GFRLDYW (SEQ ID NO: 196) |
| 15A10 | KSVSTSG YSY (SEQ ID NO: 24) | LAS (SEQ ID NO: 42) | QHIRELPY T (SEQ ID NO: 203) | GYAFSSSW (SEQ ID NO: 109) | IYPGDGDT (SEQ ID NO: 143) | TPAYYSNY GAWFAY (SEQ ID NO: 245) |
| 14E7 | QDIVKN (SEQ ID NO: 1) | YAT (SEQ ID NO: 35) | LQFYEFPL T (SEQ ID NO: 204) | GFAFTNYL (SEQ ID NO: 224) | INPGSGGT (SEQ ID NO: 120) | ARNDAMD Y (SEQ ID NO: 246) |
| 3E5 | QDISNY (SEQ ID NO: 7) | YTS (SEQ ID NO: 41) | QQGNTLP WT (SEQ ID NO: 205) | GYTFTSYW (SEQ ID NO: 94) | IYPGSGNT (SEQ ID NO: 139) | TRGFLYFD V (SEQ ID NO: 247) |
| 5A7 | QGISNY (SEQ ID NO: 25) | YTS (SEQ ID NO: 41) | QQYSKLP WT (SEQ ID NO: 206) | GYTFTAYG (SEQ ID NO: 217) | INTYSGVP (SEQ ID NO: 157) | ARGGLTTV VVDWYFD V (SEQ ID NO: 233) |

TABLE 1-continued

Murine Anti-LILRB2 CDR* Amino Acid Sequences

| | variable Light (VL) chain CDR sequences | | | Variable Heavy (VH) chain CDR sequences | | |
|---|---|---|---|---|---|---|
| ID | LC CDR1 | LC CDR2 | LC CDR3 JUNCTION | HC CDR1 | HC CDR2 | HC CDR3 JUNCTION |
| 30A6 | QSVDYDG DSY (SEQ ID NO: 3) | AAS (SEQ ID NO: 36) | QQINEDPF T (SEQ ID NO: 207) | EYTFTDYY (SEQ ID NO: 218) | INPYNGGI (SEQ ID NO: 231) | ARGGRTLT (SEQ ID NO: 234) |
| 51B8 | QNVGTN (SEQ ID NO: 197) | SAS (SEQ ID NO: 39) | QQYNRYPL T (SEQ ID NO: 208) | GYTFTRYW (SEQ ID NO: 219) | IHPNSGST (SEQ ID NO: 232) | GQYGYDV DYFDY (SEQ ID NO: 235) |
| 15D6 | SSVSSSY (SEQ ID NO: 87) | SIS (SEQ ID NO: 201) | CQQWSSNP ILV (SEQ ID NO: 209) | GYIFTSYW (SEQ ID NO: 220) | IDPSDSYT (SEQ ID NO: 122) | ARRWLLRE MDY (SEQ ID NO: 236) |
| 4G8 | QNINVW (SEQ ID NO: 6) | KAS (SEQ ID NO: 40) | QQGQSYPL T (SEQ ID NO: 210) | GYTFTSYW (SEQ ID NO: 94) | FNPNIGNA (SEQ ID NO: 226) | AREGFSAG Y (SEQ ID NO: 237) |
| 10D6 | QDVGTA (SEQ ID NO: 28) | WAS (SEQ ID NO: 45) | QQYITYPL T (SEQ ID NO: 211) | GYTFTSNW (SEQ ID NO: 221) | IYPGGDTT (SEQ ID NO: 227) | ARFFSSPWF AY (SEQ ID NO: 238) |
| 6D6 | SSVSSSC (SEQ ID NO: 11) | STS (SEQ ID NO: 44) | QQYSGYPS (SEQ ID NO: 212) | GYTFTSYW (SEQ ID NO: 94) | INPSNGGT (SEQ ID NO: 77) | AKEPIYYD YDEAGFDH (SEQ ID NO: 239) |
| 50C3_G2A | QDISNY (SEQ ID NO: 7) | YTS (SEQ ID NO: 41) | QQGNMLP WT (SEQ ID NO: 214) | GYTFTGYG (SEQ ID NO: 103) | IYPRSSNT (SEQ ID NO: 135) | ARREGAPY AMDY (SEQ ID NO: 241) |
| 6G8 | QGINNY (SEQ ID NO: 199) | YTS (SEQ ID NO: 41) | QQYSKLP WT (SEQ ID NO: 206) | GFTFSNYG (SEQ ID NO: 101) | TSSGGNST (SEQ ID NO: 132) | ARHPYYSY YVEDWFA Y (SEQ ID NO: 242) |
| 50C3_G1 | QIVDYDG DSY (SEQ ID NO: 200) | AAS (SEQ ID NO: 36) | QQSNEDPF T (SEQ ID NO: 215) | GYTFTEYY (SEQ ID NO: 223) | INPYNGGT (SEQ ID NO: 229) | QQPHLSIH WVIXVS (SEQ ID NO: 243) |
| 5G5 | KSVSTSG YSY (SEQ ID NO: 24) | LVS (SEQ ID NO: 202) | QHIRELT (SEQ ID NO: 216) | GYTFTNHL (SEQ ID NO: 225) | IHPNTTDT (SEQ ID NO: 230) | AREGRGW YFDV (SEQ ID NO: 244) |
| 20D3 | ENIYSN (SEQ ID NO: 12) | GAT (SEQ ID NO: 249) | CQHFWDT PLTF (SEQ ID NO: 251) | GYTFTTYT (SEQ ID NO: 252) | INPNSDYT (SEQ ID NO: 254) | CARGESITT VVADWYF DVW (SEQ ID NO: 257) |
| 4G10 | QDVSIA (SEQ ID NO: 248) | SAS (SEQ ID NO: 39) | CQQHYSFP YTF (SEQ ID NO: 71) | GYTFTSYW (SEQ ID NO: 94) | INPGSGST (SEQ ID NO: 256) | CARGFLYF DVW (SEQ ID NO: 169) |
| 6H2 | QDVSNA (SEQ ID NO: 31) | SAS (SEQ ID NO: 39) | CQQHYSFP YTF (SEQ ID NO: 71) | GYTFTTYG (SEQ ID NO: 111) | MYPGSGNT (SEQ ID NO: 131) | CARGFLYF DVW (SEQ ID NO: 169) |
| 30F1 | | | | | | |
| 10B4 | QSVDYDG DSY (SEQ ID NO: 3) | AAS (SEQ ID NO: 36) | CQQSNEDP FTF (SEQ ID NO: 52) | GYSFTNYW (SEQ ID NO: 377) | IDPSDTYT (SEQ ID NO: 125) | CARRWLLX KMDYW, wherein X is any amino acid (SEQ ID NO: 378) |

TABLE 1-continued

Murine Anti-LILRB2 CDR* Amino Acid Sequences

| ID | LC CDR1 (variable Light (VL) chain CDR sequences) | LC CDR2 | LC CDR3 JUNCTION | HC CDR1 (Variable Heavy (VH) chain CDR sequences) | HC CDR2 | HC CDR3 JUNCTION |
|---|---|---|---|---|---|---|
| 4F12 | XSLENSN GNTY, wherein X is any amino acid (SEQ ID NO: 176) | RVS (SEQ ID NO: 253) | CLQVTHVP FTF (SEQ ID NO: 362) | GFTFSNYA (SEQ ID NO: 363) | ITDGGTYT (SEQ ID NO: 364) | CARDDYYG SSYLGFAY W (SEQ ID NO: 365) |
| 4G7 | | | | | | |
| 7B7 | CSGCTYA WKHL (SEQ ID NO: 374) | RXS, wherein X is any amino acid (SEQ ID NO: 375) | CFQGSHVP WTF (SEQ ID NO: 376) | GFTFSNYG (SEQ ID NO: 101) | TSSGGNST (SEQ ID NO: 132) | CARHPYYS YYVEDWF AYW (SEQ ID NO: 171) |
| 9B1 | QDISNY (SEQ ID NO: 7) | YTS (SEQ ID NO: 41) | CQQINTLP WTF (SEQ ID NO: 119) | GYTFTNYG (SEQ ID NO: 267) | IYPRSGNT (SEQ ID NO: 138) | CARREGAP YAMDYW (SEQ ID NO: 174) |
| 11E5 | QDIRNY (SEQ ID NO: 18) | YTS (SEQ ID NO: 41) | CQQGNTLP WTF (SEQ ID NO: 69) | GYTFTSYG (SEQ ID NO: 107) | IYPRSGNT (SEQ ID NO: 138) | CARREGAP YTMDYW (SEQ ID NO: 178) |

*The CDRs are based on Kabat Numbering System

Examples of anti-LILRB2 agonist antibodies (murine) are provided in Table 2.

TABLE 2

Murine Anti-LILRB2 CDR Amino Acid Sequences

| ID | LC CDR1 (variable Light (VL) chain CDR sequences) | LC CDR2 | LC CDR3 JUNCTION | HC CDR1 (Variable Heavy (VH) chain CDR sequences) | HC CDR2 | HC CDR3 JUNCTION |
|---|---|---|---|---|---|---|
| 4D3 | QGIVNY (SEQ ID NO: 19) | YTS (SEQ ID NO: 41) | CQQYSELP WTF (SEQ ID NO: 70) | GYSITSGYY (SEQ ID NO: 102) | ISYKGSN (SEQ ID NO: 134) | CARYFDVW (SEQ ID NO: 173) |
| 8B5 | QDIVNY (SEQ ID NO: 13) | YTS (SEQ ID NO: 41) | WTFSGCTG LEIQ (SEQ ID NO: 63) | GYSITSGYY (SEQ ID NO: 102) | ISYEGSN (SEQ ID NO: 133) | CVRYFDFW (SEQ ID NO: 172) |
| 4E7 | KSVSTSGY SY (SEQ ID NO: 24) | LVS (SEQ ID NO: 202) | CQHIRELTR (SEQ ID NO: 64) | GYSITSGYY (SEQ ID NO: 102) | ISYKGSN (SEQ ID NO: 134) | CARYFDVW (SEQ ID NO: 173) |
| 12H6 | QDIVNY (SEQ ID NO: 13) | YTS (SEQ ID NO: 41) | CQQYSKLP WTF (SEQ ID NO: 67) | GYSITSGYY (SEQ ID NO: 102) | ISYEGSN (SEQ ID NO: 133) | CVRYFDVW (SEQ ID NO: 175) |
| 15C6 | QDIVNY (SEQ ID NO: 13) | YTS (SEQ ID NO: 41) | CQQYSKLP WTF (SEQ ID NO: 67) | GYSITSGYY (SEQ ID NO: 102) | ISYEGSN (SEQ ID NO: 133) | CVRYFDVW (SEQ ID NO: 175) |
| 4E2 | QDMNTA (SEQ ID NO: 5) | SAS (SEQ ID NO: 39) | CQQHYSTL PTF (SEQ ID NO: 54) | GYTFTSYW (SEQ ID NO: 94) | IHPSDSDT (SEQ ID NO: 126) | CALGSTVPS FVYW (SEQ ID NO: 163) |

TABLE 2-continued

Murine Anti-LILRB2 CDR Amino Acid Sequences

| ID | variable Light (VL) chain CDR sequences: LC CDR1 | LC CDR2 | LC CDR3 JUNCTION | Variable Heavy (VH) chain CDR sequences: HC CDR1 | HC CDR2 | HC CDR3 JUNCTION |
|---|---|---|---|---|---|---|
| 50B9 | QDISNY (SEQ ID NO: 7) | YTS (SEQ ID NO: 41) | CQQGNMLP WTF (SEQ ID NO: 66) | GYTFTGYG (SEQ ID NO: 103) | IYPRSSNT (SEQ ID NO: 135) | CARREGAP YAMDYW (SEQ ID NO: 174) |
| 8G10 | SSVSY (SEQ ID NO: 23) | LTS (SEQ ID NO: 46) | CQQWSSNP LTF (SEQ ID NO: 74) | GYTFTSYW (SEQ ID NO: 94) | IHPNSDTT (SEQ ID NO: 142) | CAIRYRYY FDYW (SEQ ID NO: 184) |
| 2G11 | QDIVNY (SEQ ID NO: 13) | YTS (SEQ ID NO: 41) | QQYNKLP WT (SEQ ID NO: 213) | GYTFTNYD (SEQ ID NO: 222) | IYPRSGNA (SEQ ID NO: 228) | ASRRRLCY GL (SEQ ID NO: 240) |
| 1D6 | QDINSY (SEQ ID NO: 27) | RAN (SEQ ID NO: 48) | CLQYDELL TF (SEQ ID NO: 250) | GYTFTGYW (SEQ ID NO: 114) | ILPGSGST (SEQ ID NO: 255) | CARGGIYY GPTGFAYW (SEQ ID NO: 146) |
| 48E1 | ENIYSN (SEQ ID NO: 12) | AAT (SEQ ID NO: 49) | CQHFWGTP PTF (SEQ ID NO: 80) | GYTFTDYY (SEQ ID NO: 112) | INPNNGGT (SEQ ID NO: 258) | CARSYRSS YVDYAMD YW (SEQ ID NO: 188) |

*The CDRs are based on Kabat Numbering System

Although the above Tables discloses the CDRs according to Kabat (Kabat et al., Sequences of Proteins of Immunological Interest, 5th Ed. Public Health Service, National Institutes of Health, Bethesda, Md. (1991)), the antibodies of this disclosure can comprise CDRs according to any CDR definition (e.g., Kabat, Chothia, enhanced Chothia, contact, IMGT, AbM). The CDRs of an antibody according to the different CDR definitions can be determined, e.g., by using the AbYsis database (ABySS: a parallel assembler for short read sequence data. Simpson J T et al. Genome Res. (2009)).

In certain embodiments, these antibodies or antigen-binding fragments thereof have at least one, at least two, at least three, at least four, at least five, or all six of the CDRs of as disclosed in Tables 1 and 2 (wherein the CDRs can be according to any CDR definition).

In one embodiment, the antibody or antigen-binding fragment thereof comprises a VH comprising a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and a VL comprising: a LCDR1 comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216.

In one embodiment, the antibody or antigen-binding fragment thereof comprises a VH comprising a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising SEQ ID NO:50.

In one embodiment, the antibody or antigen-binding fragment thereof comprises a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:159; and a VL comprising: a LCDR1 comprising the amino acid sequence set forth in SEQ ID NO:2, a LCDR2 comprising the amino acid sequence set forth in SEQ ID NO:36, and a LCDR3 comprising the amino acid sequence set forth in SEQ ID NO:51.

In one embodiment, the antibody or antigen-binding fragment thereof comprises a VH comprising: a HCDR1 comprising the amino acid sequence set forth in SEQ ID NO:91, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53.

In one embodiment, the antibody or antigen-binding fragment thereof comprises a VH comprising: a HCDR1 comprising the amino acid sequence set forth in SEQ ID NO:92, a HCDR2 comprising the amino acid sequence set forth in SEQ ID NO:124, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:53.

In one embodiment, the antibody or antigen-binding fragment thereof comprises a VH comprising: a HCDR1 comprising the amino acid sequence set forth in SEQ ID NO:93, a HCDR2 comprising the amino acid sequence set forth in SEQ ID NO:125, and a HCDR3 comprising the amino acid sequence set forth in SEQ ID NO:162; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:93, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:95, a HCDR2 comprising the amino acid sequence set forth in SEQ ID NO:127, and a HCDR3 comprising the amino acid sequence set forth in SEQ ID NO:164; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:96, a HCDR2 comprising the amino acid sequence set forth in SEQ ID NO:128, and a HCDR3 comprising the amino acid sequence set forth in SEQ ID NO:165; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:122, and a HCDR3 comprising the amino acid sequence set forth in SEQ ID NO:166; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:56.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:167; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:98, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:8, a LCDR2 comprising the amino acid sequence set forth in SEQ ID NO:35, and a LCDR3 comprising the amino acid sequence set forth in SEQ ID NO:58.

In one embodiment, the antibody or antigen-binding fragment thereof comprises a VH comprising: a HCDR1 comprising the amino acid sequence set forth in SEQ ID NO:99, a HCDR2 comprising the amino acid sequence set forth in SEQ ID NO:129, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:100, a HCDR2 comprising the amino acid sequence set forth in SEQ ID NO:258, and a HCDR3 comprising the amino acid sequence set forth in SEQ ID NO:168; and a VL comprising: a LCDR1 comprising the amino acid sequence set forth in SEQ ID NO:9, a LCDR2 comprising the amino acid sequence set forth in SEQ ID NO:42, and a LCDR3 comprising the amino acid sequence set forth in SEQ ID NO:59.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:131, and a HCDR3 comprising the amino acid sequence set forth in SEQ ID NO:169; and a VL comprising: a LCDR1 comprising the amino acid sequence set forth in SEQ ID NO:10, a LCDR2 comprising the amino acid sequence set forth in SEQ ID NO:43, and a LCDR3 comprising the amino acid sequence set forth in SEQ ID NO:60.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:170; and a VL comprising: a LCDR1 comprising the amino acid sequence set forth in SEQ ID NO:11, a LCDR2 comprising the amino acid sequence set forth in SEQ ID NO:4, and a LCDR3 comprising the amino acid sequence set forth in SEQ ID NO:61.

In one embodiment, the antibody or antigen-binding fragment thereof comprises a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:62.

In one embodiment, the antibody or antigen-binding fragment thereof comprises a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:15, a LCDR2 comprising the amino acid sequence set forth in SEQ ID NO:49, and a LCDR3 comprising the amino acid sequence set forth in SEQ ID NO:65.

In one embodiment, the antibody or antigen-binding fragment thereof comprises a VH comprising: a HCDR1 comprising the amino acid sequence set forth in SEQ ID NO:104, a HCDR2 comprising the amino acid sequence set forth in SEQ ID NO:136, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:105, a HCDR2 comprising the amino acid sequence set forth in SEQ ID NO:137, and a HCDR3 comprising the amino acid sequence set forth in SEQ ID NO:177; and a VL comprising: a LCDR1 comprising the amino acid sequence set forth in SEQ ID NO:16, a LCDR2 comprising the amino acid sequence set forth in SEQ ID NO:45, and a LCDR3 comprising the amino acid sequence set forth in SEQ ID NO:68.

In one embodiment, the antibody or antigen-binding fragment thereof comprises a VH comprising: a HCDR1 comprising the amino acid sequence set forth in SEQ ID NO:107, a HCDR2 comprising the amino acid sequence set forth in SEQ ID NO:138, and a HCDR3 comprising the amino acid sequence set forth in SEQ ID NO:178; and a VL comprising: a LCDR1 comprising the amino acid sequence set forth in SEQ ID NO:18, a LCDR2 comprising the amino acid sequence set forth in SEQ ID NO:41, and a LCDR3 comprising the amino acid sequence set forth in SEQ ID NO:69.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:139, and a HCDR3 comprising the amino acid sequence set forth in SEQ ID NO:179; and a VL comprising: a LCDR1 comprising the amino acid sequence set forth in SEQ ID NO:20, a LCDR2 comprising the amino acid sequence set forth in SEQ ID NO:39, and a LCDR3 comprising the amino acid sequence set forth in SEQ ID NO:71.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67.

In one embodiment, the antibody or antigen-binding fragment thereof comprises a VH comprising: a HCDR1 comprising the amino acid sequence set forth in SEQ ID NO:108, a HCDR2 comprising the amino acid sequence set forth in SEQ ID NO:140, and a HCDR3 comprising the amino acid sequence set forth in SEQ ID NO:180; and a VL comprising: a LCDR1 comprising the amino acid sequence set forth in SEQ ID NO:21, a LCDR2 comprising the amino acid sequence set forth in SEQ ID NO:45, and a LCDR3 comprising the amino acid sequence set forth in SEQ ID NO:72.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:141, and a HCDR3 comprising the amino acid sequence set forth in SEQ ID NO:181; and a VL comprising: a LCDR1 comprising the amino acid sequence set forth in SEQ ID NO:22, a LCDR2 comprising the amino acid sequence set forth in SEQ ID NO:41, and a LCDR3 comprising the amino acid sequence set forth in SEQ ID NO:73.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:182; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74.

In one embodiment, the antibody or antigen-binding fragment thereof comprises a VH comprising: a HCDR1 comprising the amino acid sequence set forth in SEQ ID NO:109, a HCDR2 comprising the amino acid sequence set forth in SEQ ID NO:143, and a HCDR3 comprising the amino acid sequence set forth in SEQ ID NO:183; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:75.

In one embodiment, the antibody or antigen-binding fragment thereof comprises a VH comprising: a HCDR1 comprising the amino acid sequence set forth in SEQ ID NO:110, a HCDR2 comprising the amino acid sequence set forth in SEQ ID NO:144, and a HCDR3 comprising the amino acid sequence set forth in SEQ ID NO:173; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:259.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:145, and a HCDR3 comprising the amino acid sequence set forth in SEQ ID NO:185; and a VL comprising: a LCDR1 comprising the amino acid sequence set forth in SEQ ID NO:23, a LCDR2 comprising the amino acid sequence set forth in SEQ ID NO:47, and a LCDR3 comprising the amino acid sequence set forth in SEQ ID NO:76.

In one embodiment, the antibody or antigen-binding fragment thereof comprises a VH comprising: a HCDR1 comprising the amino acid sequence set forth in SEQ ID NO:111, a HCDR2 comprising the amino acid sequence set forth in SEQ ID NO:111, and a HCDR3 comprising the amino acid sequence set forth in SEQ ID NO:186; and a VL comprising: a LCDR1 comprising the amino acid sequence set forth in SEQ ID NO:26, a LCDR2 comprising the amino acid sequence set forth in SEQ ID NO:38, and a LCDR3 comprising the amino acid sequence set forth in SEQ ID NO:130.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:78.

In one embodiment, the antibody or antigen-binding fragment thereof comprises a VH comprising: a HCDR1 comprising the amino acid sequence set forth in SEQ ID NO:111, a HCDR2 comprising the amino acid sequence set forth in SEQ ID NO:147, and a HCDR3 comprising the amino acid sequence set forth in SEQ ID NO:187; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:79.

In one embodiment, the antibody or antigen-binding fragment thereof comprises a VH comprising: a HCDR1 comprising the amino acid sequence set forth in SEQ ID NO:95, a HCDR2 comprising the amino acid sequence set forth in SEQ ID NO:127, and a HCDR3 comprising the amino acid sequence set forth in SEQ ID NO:164; and a VL comprising: a LCDR1 comprising the amino acid sequence set forth in SEQ ID NO:28, a LCDR2 comprising the amino acid sequence set forth in SEQ ID NO:45, and a LCDR3 comprising the amino acid sequence set forth in SEQ ID NO:81.

In one embodiment, the antibody or antigen-binding fragment thereof comprises a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:106, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:99, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:99, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:50.

In one embodiment, the antibody or antigen-binding fragment thereof comprises a VH comprising: a HCDR1 comprising the amino acid sequence set forth in SEQ ID NO:111, a HCDR2 comprising the amino acid sequence set forth in SEQ ID NO:147, and a HCDR3 comprising the amino acid sequence set forth in SEQ ID NO:187; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:82.

In one embodiment, the antibody or antigen-binding fragment thereof comprises a VH comprising: a HCDR1 comprising the amino acid sequence set forth in SEQ ID NO:113, a HCDR2 comprising the amino acid sequence set forth in SEQ ID NO:148, and a HCDR3 comprising the amino acid sequence set forth in SEQ ID NO:189; and a VL comprising: a LCDR1 comprising the amino acid sequence set forth in SEQ ID NO:29, a LCDR2 comprising the amino acid sequence set forth in SEQ ID NO:42, and a LCDR3 comprising the amino acid sequence set forth in SEQ ID NO:59.

In one embodiment, the antibody or antigen-binding fragment thereof comprises a VH comprising: a HCDR1 comprising the amino acid sequence set forth in SEQ ID NO:114, a HCDR2 comprising the amino acid sequence set forth in SEQ ID NO:149, and a HCDR3 comprising the amino acid sequence set forth in SEQ ID NO:190; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55.

In one embodiment, the antibody or antigen-binding fragment thereof comprises a VH comprising: a HCDR1 comprising the amino acid sequence set forth in SEQ ID NO:115, a HCDR2 comprising the amino acid sequence set forth in SEQ ID NO:150, and a HCDR3 comprising the amino acid sequence set forth in SEQ ID NO:191; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55.

In one embodiment, the antibody or antigen-binding fragment thereof comprises a VH comprising: a HCDR1 comprising the amino acid sequence set forth in SEQ ID NO:108, a HCDR2 comprising the amino acid sequence set forth in SEQ ID NO:151, and a HCDR3 comprising the amino acid sequence set forth in SEQ ID NO:180; and a VL comprising: a LCDR1 comprising the amino acid sequence set forth in SEQ ID NO:30, a LCDR2 comprising the amino acid sequence set forth in SEQ ID NO:45, and a LCDR3 comprising the amino acid sequence set forth in SEQ ID NO:83.

In one embodiment, the antibody or antigen-binding fragment thereof comprises a VH comprising: a HCDR1 comprising the amino acid sequence set forth in SEQ ID NO:116, a HCDR2 comprising the amino acid sequence set forth in SEQ ID NO:152, and a HCDR3 comprising the amino acid sequence set forth in SEQ ID NO:192; and a VL comprising: a LCDR1 comprising the amino acid sequence set forth in SEQ ID NO:31, a LCDR2 comprising the amino acid sequence set forth in SEQ ID NO:39, and a LCDR3 comprising the amino acid sequence set forth in SEQ ID NO:71.

In one embodiment, the antibody or antigen-binding fragment thereof comprises a VH comprising: a HCDR1 comprising the amino acid sequence set forth in SEQ ID NO:93, a HCDR2 comprising the amino acid sequence set forth in SEQ ID NO:125, and a HCDR3 comprising the amino acid sequence set forth in SEQ ID NO:160; and a VL comprising: a LCDR1 comprising the amino acid sequence set forth in SEQ ID NO:32, a LCDR2 comprising the amino acid sequence set forth in SEQ ID NO:36, and a LCDR3 comprising the amino acid sequence set forth in SEQ ID NO:84.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:170; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:117, a HCDR2 comprising the amino acid sequence set forth in SEQ ID NO:153, and a HCDR3 comprising the amino acid sequence set forth in SEQ ID NO:167; and a VL comprising: a LCDR1 comprising the amino acid sequence set forth in SEQ ID NO:33, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:97, a HCDR2 comprising the amino acid sequence set forth in SEQ ID NO:154, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:57.

In one embodiment, the antibody or antigen-binding fragment thereof comprises a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:85.

In one embodiment, the antibody or antigen-binding fragment thereof comprises a VH comprising: a HCDR1 comprising the amino acid sequence set forth in SEQ ID NO:118, a HCDR2 comprising the amino acid sequence set forth in SEQ ID NO:155, and a HCDR3 comprising the amino acid sequence set forth in SEQ ID NO:193; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:85.

In one embodiment, the antibody or antigen-binding fragment thereof comprises a VH comprising: a HCDR1 comprising the amino acid sequence set forth in SEQ ID NO:93, a HCDR2 comprising the amino acid sequence set forth in SEQ ID NO:77, and a HCDR3 comprising the amino acid sequence set forth in SEQ ID NO:194; and a VL comprising: a LCDR1 comprising the amino acid sequence set forth in SEQ ID NO:24, a LCDR2 comprising the amino acid sequence set forth in SEQ ID NO:44, and a LCDR3 comprising the amino acid sequence set forth in SEQ ID NO:86.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:156, and a HCDR3 comprising the amino acid sequence set forth in SEQ ID NO:195; and a VL comprising: a LCDR1 comprising the amino acid sequence set forth in SEQ ID NO:34, a LCDR2 comprising the amino acid sequence set forth in SEQ ID NO:39, and a LCDR3 comprising the amino acid sequence set forth in SEQ ID NO:87.

In one embodiment, the antibody or antigen-binding fragment thereof comprises a VH comprising: a HCDR1 comprising the amino acid sequence set forth in SEQ ID NO:111, a HCDR2 comprising the amino acid sequence set forth in SEQ ID NO:157, and a HCDR3 comprising the amino acid sequence set forth in SEQ ID NO:1%; and a VL comprising: a LCDR1 comprising the amino acid sequence set forth in SEQ ID NO:23, a LCDR2 comprising the amino acid sequence set forth in SEQ ID NO:260, and a LCDR3 comprising the amino acid sequence set forth in SEQ ID NO:88.

In one embodiment, the antibody or antigen-binding fragment thereof comprises a VH comprising: a HCDR1 comprising the amino acid sequence set forth in SEQ ID NO:109, a HCDR2 comprising the amino acid sequence set forth in SEQ ID NO:143, and a HCDR3 comprising the amino acid sequence set forth in SEQ ID NO:245; and a VL comprising: a LCDR1 comprising the amino acid sequence set forth in SEQ ID NO:24, a LCDR2 comprising the amino acid sequence set forth in SEQ ID NO:42, and a LCDR3 comprising the amino acid sequence set forth in SEQ ID NO:203.

In one embodiment, the antibody or antigen-binding fragment thereof comprises a VH comprising: a HCDR1 comprising the amino acid sequence set forth in SEQ ID NO:224, a HCDR2 comprising the amino acid sequence set forth in SEQ ID NO:120, and a HCDR3 comprising the amino acid sequence set forth in SEQ ID NO:246; and a VL comprising: a LCDR1 comprising the amino acid sequence set forth in SEQ ID NO:1, a LCDR2 comprising the amino acid sequence set forth in SEQ ID NO:35, and a LCDR3 comprising the amino acid sequence set forth in SEQ ID NO:204.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:139, and a HCDR3 comprising the amino acid sequence set forth in SEQ ID NO:247; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:205.

In one embodiment, the antibody or antigen-binding fragment thereof comprises a VH comprising: a HCDR1 comprising the amino acid sequence set forth in SEQ ID NO:217, a HCDR2 comprising the amino acid sequence set forth in SEQ ID NO:157, and a HCDR3 comprising the amino acid sequence set forth in SEQ ID NO:233; and a VL comprising: a LCDR1 comprising the amino acid sequence set forth in SEQ ID NO:25, a LCDR2 comprising the amino acid sequence set forth in SEQ ID NO:41, and a LCDR3 comprising the amino acid sequence set forth in SEQ ID NO:206.

In one embodiment, the antibody or antigen-binding fragment thereof comprises a VH comprising: a HCDR1 comprising the amino acid sequence set forth in SEQ ID NO:218, a HCDR2 comprising the amino acid sequence set forth in SEQ ID NO:231, and a HCDR3 comprising the amino acid sequence set forth in SEQ ID NO:234; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:207.

In one embodiment, the antibody or antigen-binding fragment thereof comprises a VH comprising: a HCDR1 comprising the amino acid sequence set forth in SEQ ID NO:219, a HCDR2 comprising the amino acid sequence set forth in SEQ ID NO:232, and a HCDR3 comprising the amino acid sequence set forth in SEQ ID NO:235; and a VL comprising: a LCDR1 comprising the amino acid sequence set forth in SEQ ID NO:197, a LCDR2 comprising the amino acid sequence set forth in SEQ ID NO:39, and a LCDR3 comprising the amino acid sequence set forth in SEQ ID NO:208.

In one embodiment, the antibody or antigen-binding fragment thereof comprises a VH comprising: a HCDR1 comprising the amino acid sequence set forth in SEQ ID NO:220, a HCDR2 comprising the amino acid sequence set forth in SEQ ID NO:122, and a HCDR3 comprising the amino acid sequence set forth in SEQ ID NO:236; and a VL comprising: a LCDR1 comprising the amino acid sequence set forth in SEQ ID NO:87, a LCDR2 comprising the amino acid sequence set forth in SEQ ID NO:201, and a LCDR3 comprising the amino acid sequence set forth in SEQ ID NO:209.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:226, and a HCDR3 comprising the amino acid sequence set forth in SEQ ID NO:237; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:210.

In one embodiment, the antibody or antigen-binding fragment thereof comprises a VH comprising: a HCDR1 comprising the amino acid sequence set forth in SEQ ID NO:221, a HCDR2 comprising the amino acid sequence set forth in SEQ ID NO:227, and a HCDR3 comprising the amino acid sequence set forth in SEQ ID NO:238; and a VL comprising: a LCDR1 comprising the amino acid sequence set forth in SEQ ID NO:28, a LCDR2 comprising the amino acid sequence set forth in SEQ ID NO:45, and a LCDR3 comprising the amino acid sequence set forth in SEQ ID NO:211.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:77, and a HCDR3 comprising the amino acid sequence set forth in SEQ ID NO:239; and a VL comprising: a LCDR1 comprising the amino acid sequence set forth in SEQ ID NO:11, a LCDR2 comprising the amino acid sequence set forth in SEQ ID NO:4, and a LCDR3 comprising the amino acid sequence set forth in SEQ ID NO:212.

In one embodiment, the antibody or antigen-binding fragment thereof comprises a VH comprising: a HCDR1 comprising the amino acid sequence set forth in SEQ ID NO:103, a HCDR2 comprising the amino acid sequence set forth in SEQ ID NO:135, and a HCDR3 comprising the amino acid sequence set forth in SEQ ID NO:241; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:214.

In one embodiment, the antibody or antigen-binding fragment thereof comprises a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:242; and a VL comprising: a LCDR1 comprising the amino acid sequence set forth in SEQ ID NO:199, a LCDR2 comprising the amino acid sequence set forth in SEQ ID NO:41, and a LCDR3 comprising the amino acid sequence set forth in SEQ ID NO:206.

In one embodiment, the antibody or antigen-binding fragment thereof comprises a VH comprising: a HCDR1 comprising the amino acid sequence set forth in SEQ ID NO:223, a HCDR2 comprising the amino acid sequence set forth in SEQ ID NO:229, and a HCDR3 comprising the amino acid sequence set forth in SEQ ID NO:243; and a VL comprising: a LCDR1 comprising the amino acid sequence set forth in SEQ ID NO:200, a LCDR2 comprising the amino acid sequence set forth in SEQ ID NO:36, and a LCDR3 comprising the amino acid sequence set forth in SEQ ID NO:215.

In one embodiment, the antibody or antigen-binding fragment thereof comprises a VH comprising: a HCDR1 comprising the amino acid sequence set forth in SEQ ID NO:252, a HCDR2 comprising the amino acid sequence set forth in SEQ ID NO:254, and a HCDR3 comprising the amino acid sequence set forth in SEQ ID NO:257; and a VL comprising: a LCDR1 comprising the amino acid sequence set forth in SEQ ID NO:12, a LCDR2 comprising the amino acid sequence set forth in SEQ ID NO:249, and a LCDR3 comprising the amino acid sequence set forth in SEQ ID NO:251.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:256, and a HCDR3 comprising the amino acid sequence set forth in SEQ ID NO:169; and a VL comprising: a LCDR1 comprising the amino acid sequence set forth in SEQ ID NO:248, a LCDR2 comprising the amino acid sequence set forth in SEQ ID NO:39, and a LCDR3 comprising the amino acid sequence set forth in SEQ ID NO:71.

In one embodiment, the antibody or antigen-binding fragment thereof comprises a VH comprising: a HCDR1 comprising the amino acid sequence set forth in SEQ ID NO:111, a HCDR2 comprising the amino acid sequence set forth in SEQ ID NO:131, and a HCDR3 comprising the amino acid sequence set forth in SEQ ID NO:169; and a VL comprising: a LCDR1 comprising the amino acid sequence set forth in SEQ ID NO:31, a LCDR2 comprising the amino acid sequence set forth in SEQ ID NO:39, and a LCDR3 comprising the amino acid sequence set forth in SEQ ID NO:71.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:172; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:63.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:133, and a HCDR3 comprising the amino acid sequence set forth in SEQ ID NO:175; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:67.

In one embodiment, the antibody or antigen-binding fragment thereof comprises a VH comprising a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:24, a LCDR2 comprising the amino acid sequence set forth in SEQ ID NO:202, and a LCDR3 comprising SEQ ID NO:64.

In one embodiment, the antibody or antigen-binding fragment thereof comprises a VH comprising: a HCDR1 comprising the amino acid sequence set forth in SEQ ID NO:102, a HCDR2 comprising the amino acid sequence set forth in SEQ ID NO:134, and a HCDR3 comprising the amino acid sequence set forth in SEQ ID NO:173; and a VL comprising: a LCDR1 comprising the amino acid sequence set forth in SEQ ID NO:14, a LCDR2 comprising the amino acid sequence set forth in SEQ ID NO:41, and a LCDR3 comprising the amino acid sequence set forth in SEQ ID NO:64.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:126, and a HCDR3 comprising the amino acid sequence set forth in SEQ ID NO:163; and a VL comprising: a LCDR1 comprising the amino acid sequence set forth in SEQ ID NO:5, a LCDR2 comprising the amino acid sequence set forth in SEQ ID NO:39, and a LCDR3 comprising the amino acid sequence set forth in SEQ ID NO:54.

In one embodiment, the antibody or antigen-binding fragment thereof comprises a VH comprising: a HCDR1 comprising the amino acid sequence set forth in SEQ ID NO:103, a HCDR2 comprising the amino acid sequence set forth in SEQ ID NO:135, and a HCDR3 comprising the amino acid sequence set forth in SEQ ID NO:174; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO:66.

In one embodiment, the antibody or antigen-binding fragment thereof comprises a VH comprising: a HCDR1 comprising the amino acid sequence set forth in SEQ ID NO:94, a HCDR2 comprising the amino acid sequence set forth in SEQ ID NO:142, and a HCDR3 comprising the amino acid sequence set forth in SEQ ID NO:184; and a VL comprising: a LCDR1 comprising the amino acid sequence set forth in SEQ ID NO:23, a LCDR2 comprising the amino acid sequence set forth in SEQ ID NO:46, and a LCDR3 comprising the amino acid sequence set forth in SEQ ID NO:74.

In one embodiment, the antibody or antigen-binding fragment thereof comprises a VH comprising: a HCDR1 comprising the amino acid sequence set forth in SEQ ID NO:222, a HCDR2 comprising the amino acid sequence set forth in SEQ ID NO:228, and a HCDR3 comprising the amino acid sequence set forth in SEQ ID NO:240; and a VL comprising: a LCDR1 comprising the amino acid sequence set forth in SEQ ID NO:13, a LCDR2 comprising the amino acid sequence set forth in SEQ ID NO:41, and a LCDR3 comprising the amino acid sequence set forth in SEQ ID NO:213.

In one embodiment, the antibody or antigen-binding fragment thereof comprises a VH comprising: a HCDR1 comprising the amino acid sequence set forth in SEQ ID NO:114, a HCDR2 comprising the amino acid sequence set forth in SEQ ID NO:255, and a HCDR3 comprising the amino acid sequence set forth in SEQ ID NO:146; and a VL comprising: a LCDR1 comprising the amino acid sequence set forth in SEQ ID NO:27, a LCDR2 comprising the amino acid sequence set forth in SEQ ID NO:48, and a LCDR3 comprising the amino acid sequence set forth in SEQ ID NO:250.

In one embodiment, the antibody or antigen-binding fragment thereof comprises a VH comprising: a HCDR1 comprising the amino acid sequence set forth in SEQ ID NO:112, a HCDR2 comprising the amino acid sequence set forth in SEQ ID NO:258, and a HCDR3 comprising the amino acid sequence set forth in SEQ ID NO:188; and a VL comprising: a LCDR1 comprising the amino acid sequence set forth in SEQ ID NO:12, a LCDR2 comprising the amino acid sequence set forth in SEQ ID NO:49, and a LCDR3 comprising the amino acid sequence set forth in SEQ ID NO:80.

In one embodiment, the antibody or antigen-binding fragment thereof comprises a VH comprising: a HCDR1 comprising the amino acid sequence set forth in SEQ ID NO:377, a HCDR2 comprising the amino acid sequence set forth in SEQ ID NO:125, and a HCDR3 comprising the amino acid sequence set forth in SEQ ID NO:378; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52.

In one embodiment, the antibody or antigen-binding fragment thereof comprises a VH comprising: a HCDR1 comprising the amino acid sequence set forth in SEQ ID NO:363, a HCDR2 comprising the amino acid sequence set forth in SEQ ID NO:364, and a HCDR3 comprising the amino acid sequence set forth in SEQ ID NO:365; and a VL comprising: a LCDR1 comprising the amino acid sequence set forth in SEQ ID NO:176, a LCDR2 comprising the amino acid sequence set forth in SEQ ID NO:253, and a LCDR3 comprising the amino acid sequence set forth in SEQ ID NO:362.

In one embodiment, the antibody or antigen-binding fragment thereof comprises a VH comprising: a HCDR1 comprising the amino acid sequence set forth in SEQ ID NO:101, a HCDR2 comprising the amino acid sequence set forth in SEQ ID NO:132, and a HCDR3 comprising the amino acid sequence set forth in SEQ ID NO:171; and a VL comprising: a LCDR1 comprising the amino acid sequence set forth in SEQ ID NO:374, a LCDR2 comprising the amino acid sequence set forth in SEQ ID NO:375, and a LCDR3 comprising the amino acid sequence set forth in SEQ ID NO:376.

In one embodiment, the antibody or antigen-binding fragment thereof comprises a VH comprising: a HCDR1 comprising the amino acid sequence set forth in SEQ ID NO:267, a HCDR2 comprising the amino acid sequence set forth in SEQ ID NO:138, and a HCDR3 comprising the amino acid sequence set forth in SEQ ID NO:174; and a VL comprising: a LCDR1 comprising the amino acid sequence set forth in SEQ ID NO:7, a LCDR2 comprising the amino acid sequence set forth in SEQ ID NO:41, and a LCDR3 comprising the amino acid sequence set forth in SEQ ID NO: 119.

In one embodiment, the antibody or antigen-binding fragment thereof comprises a VH comprising: a HCDR1 comprising the amino acid sequence set forth in SEQ ID NO:18, a HCDR2 comprising the amino acid sequence set forth in SEQ ID NO:41, and a HCDR3 comprising the amino acid sequence set forth in SEQ ID NO:69; and a VL comprising: a LCDR1 comprising the amino acid sequence set forth in SEQ ID NO:107, a LCDR2 comprising the amino acid sequence set forth in SEQ ID NO:138, and a LCDR3 comprising the amino acid sequence set forth in SEQ ID NO:178.

The $V_H$ and or $V_L$ region of the anti-LILRB2 antibodies or antigen-binding fragments thereof described herein can be linked to a constant region (e.g., a wild-type human Fc region or an Fc region that includes one or more alterations). In some embodiments, the antibody has a light chain constant region derived from a human kappa sequence. In some embodiments, the antibody has a light chain constant region derived from a human lambda sequence. In a specific embodiment, the light chain constant region comprises a human subgroup kappa 1 sequence. In certain embodiments, the antibody has an isotype selected from the group consisting of IgG1, IgG2, IgG3, and IgG4 (e.g., a human IgG1, human IgG2, human IgG3, or human IgG4 isotype). In certain embodiments, the antibody has a human IgG1 isotype. In certain embodiments, the antibody has a human IgG1 isotype and a human kappa light chain constant region. In certain embodiments, the antibody has a human IgG2 isotype. In certain embodiments, the antibody has a human IgG2 isotype and a human kappa light chain constant region. The heavy chain constant region can be a wild-type human Fc region, or a human Fc region that includes one or more amino acid substitutions. The antibodies can have mutations that stabilize the disulfide bond between the two heavy chains of an immunoglobulin, such as mutations in the hinge region of IgG4, as disclosed in the art (e.g., Angal et al, Mol. Immunol, 30: 105-08 (1993)). See also, e.g., U.S. 2005/0037000. The heavy chain constant region can also have substitutions that modify the properties of the antibody (e.g., decrease one or more of: Fc receptor binding, antibody glycosylation, deamidation, binding to complement, or methionine oxidation). In some instances, the antibodies may have mutations such as those described in U.S. Pat. Nos. 5,624,821 and 5,648,260. In some embodiments, the antibody is modified to reduce or eliminate effector function. In some embodiments, the heavy chain constant region has one or more of the following mutations: S228P; N297Q; and T299A (numbering according to Kabat). The heavy chain constant region can be chimeric, e.g., the Fc region can comprise the CHI and CH2 domains of an IgG antibody of the IgG4 isotype, and the CH3 domain from an IgG antibody of the IgG1 isotype (see, e.g., U.S. Patent Appl. No. 2012/0100140A1 which is incorporated by reference in its entirety herein). In a specific embodiment, the humanized anti-LILRB2 antibodies described herein have a chimeric constant region comprising the CHI and CH2 domains of an IgG antibody of the IgG4 isotype, and the CH3 domain from an IgG antibody of the IgG1 isotype and further contain the S228P and N297Q mutations (numbering according to Kabat).

Antigen-binding fragments of the anti-LILRB2 antibodies are also encompassed by this disclosure. In some embodiments, the anti-LILRB2 antibody or antigen-binding molecule thereof comprises or consists of (i) a single chain Fv ("scFv"); (ii) a diabody; (iii) an sc(Fv)2; (iv) a polypeptide chain of an antibody; (v) F(ab')2; or (vi) F(ab). In one embodiment, the antigen-binding fragment is an Fab molecule. The fragment antigen-binding (Fab fragment) is a region on an antibody that binds to antigens. It is composed of one constant and one variable domain of each of the heavy and the light chain. These domains shape the paratope, i.e., the antigen-binding site. The enzyme papain can be used to cleave an immunoglobulin monomer into two Fab fragments and an Fc fragment. Recombinant methods can also be used to make an Fab molecule. In another embodiment, the antigen-binding fragment is a single-chain fragment variable (scFv). An scFv is comprised of the variable regions of the heavy and light chains of an antibody. It is only half the size of the Fab fragment and yet retains the original specificity of the parent immunoglobulin. Methods of making an ScFv are well known in the art (see, e.g., Ahmad et al, Clinical and Developmental Immunology, vol. 2012, Article ID 980250, 15 pages, 2012. doi: 10.1 155/2012/980250).

In certain embodiments, the anti-LILRB2antibody or antigen-binding molecule thereof can be a targeting moiety. These targeting moieties are useful in ferrying an agent of interest (e.g., a therapeutic agent, a small molecule drug) to a cell.

The present disclosure also provides "chimeric molecules" comprising, for example, at least one of the LILRB2 antibodies or antigen-binding fragments thereof disclosed herein that is linked and/or conjugated and/or otherwise associated with at least one heterologous moiety. In certain embodiments, the heterologous moiety is an agent that to be ferried or delivered to a cell or its local environment. Such an agent can be e.g., a therapeutic agent such as a chemotherapeutic agent. A chimeric molecule disclosed herein encompasses any molecule comprising (i) a LILRB2 antibody or antigen-binding molecule thereof disclosed herein (e.g., an Fab or scFv), and (ii) at least one (e.g., one two, three, four) heterologous moiety (e.g., a therapeutic moiety, a chemotherapeutic agent, a half-life extending moiety) and optionally including one or more linkers. In some embodiments, a chimeric molecule is a chimeric protein, i.e., a chimeric molecule in which all its components (heterologous moieties and/or linkers) are polypeptides. Other chimeric molecules can comprise non-polypeptide heterologous moieties (e.g., PEG, lipids, carbohydrates, nucleic acids, small molecule therapeutic agents, radionuclides, fluorescent probes, etc.) and/or non-polypeptide linkers.

In some embodiments, a chimeric molecule comprises a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric molecule can include for example, a protein derived from at least two different biological sources. A biological source can include any non-synthetically produced nucleic acid or amino acid sequence (e.g., a genomic or cDNA sequence, a plasmid or viral vector, a native virion or a mutant or analog, as further described herein, of any of the above). A synthetic source can include a protein or nucleic acid sequence produced chemically and not by a biological system (e.g., solid phase synthesis of amino acid sequences). A chimeric molecule can also include a protein derived from at least 2 different synthetic sources or a protein derived from at least one biological source and at least one synthetic source. A chimeric molecule can also comprise a first amino acid sequence derived from a first source, covalently or non-covalently linked to a nucleic acid, derived from any source or a small organic or inorganic molecule derived from any source. The chimeric molecule can also comprise a linker molecule between the first and second amino acid sequence or between the first amino acid sequence and the nucleic acid, or between the first amino acid sequence and the small organic or inorganic molecule.

The heterologous moiety or moieties of the chimeric molecules disclosed herein can comprise, consist of, or consist essentially of, for example, prophylactic and/or therapeutic agents (e.g., chemotherapeutic agent or analgesic), molecules capable of improving a pharmacokinetic (PK) property (e.g., plasma half-life extending moieties), and detectable moieties (e.g., fluorescent molecules or radionuclides). In some embodiments, the heterologous moiety comprises a clotting factor (e.g., a Factor VII). In some embodiments, a heterologous moiety comprises a molecule that can modify a physicochemical property of a chimeric molecule lacking such heterologous moiety. In other embodiments, the incorporation of a heterologous moiety into a chimeric molecule can improve one or more pharmacokinetic properties without significantly affecting its biological activity or function. In other embodiments, a heterologous moiety increases stability of the chimeric molecule of the invention or a fragment thereof.

In some embodiments, the heterologous moiety is a polypeptide comprising, consisting essentially of, or consisting of at least about 10, 100, 200, 300, 400, 500, 600, 700, 800, 900, 1000, 1 100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In some embodiments, the chimeric molecule comprises at least one heterologous moiety that is a "half-life extending moiety." Half-life extending moieties can comprise, for example, (i) XTEN polypeptides; (ii) Fc; (iii) albumin, (iv) albumin binding polypeptide or fatty acid, (v) the C-terminal peptide (CTP) of the 0 subunit of human chorionic gonadotropin, (vi) PAS; (vii) HAP; (viii) transferrin; (ix) polyethylene glycol (PEG); (x) hydroxyethyl starch (HES), (xi) polysialic acids (PSAs); (xii) a clearance receptor or fragment thereof which blocks binding of the chimeric molecule to a clearance receptor; (xiii) low complexity peptides; (xiv) vWF; or (xv) any combinations thereof. In some embodiments, the half-life extending moiety comprises an Fc region. In other embodiments, the half-life extending moiety comprises two Fc regions fused by a linker. Exemplary heterologous moieties also include, e.g., FcRn binding moieties (e.g., complete Fc regions or portions thereof which bind to FcRn), single chain Fc regions (scFc regions, e.g., as described in U.S. Publ. No. 2008-0260738, and Intl. Publ. Nos. WO 2008-012543 and WO 2008-1439545), or processable scFc regions. In some embodiments, a heterologous moiety can include an attachment site for a non-polypeptide moiety such as polyethylene glycol (PEG), hydroxyethyl starch (HES), polysialic acid, or any derivatives, variants, or combinations of these moieties.

In certain embodiments, a chimeric molecule of the disclosure comprises at least one (e.g., one, two, three, or four) half-like extending moiety which increases the in vivo half-life of the chimeric molecule compared with the in vivo half-life of the corresponding chimeric molecule lacking such heterologous moiety. In vivo half-life of a chimeric molecule can be determined by any method known to those of skill in the art, e.g., activity assays (chromogenic assay or one stage clotting aPTT assay), ELISA, etc. In some embodiments, the presence of one or more half-life extending moiety results in the half-life of the chimeric molecule to be increased compared to the half-life of the corresponding chimeric molecule lacking such one or more half-life extending moieties. The half-life of the chimeric molecule comprising a half-life extending moiety is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding chimeric molecule lacking such half-life extending moiety.

In one embodiment, the half-life of the chimeric molecule comprising a half-life extending moiety is about 1.5-fold to about 20-fold, about 1.5 fold to about 15 fold, or about 1.5 fold to about 10 fold longer than the in vivo half-life of the corresponding chimeric molecule lacking such half-life extending moiety. In another embodiment, the half-life of chimeric molecule comprising a half-life extending moiety is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding chimeric molecule lacking such half-life extending moiety.

Characterization of Antibodies

The LILRB2 binding properties of the antibodies described herein may be measured by any standard method, e.g., one or more of the following methods: OCTET®, Surface Plasmon Resonance (SPR), BIACORET™ analysis, Enzyme Linked Immunosorbent Assay (ELISA), EIA (enzyme immunoassay), RIA (radioimmunoassay), and Fluorescence Resonance Energy Transfer (FRET).

The binding interaction of a protein of interest (an anti-LILRB2 antibody or functional fragment thereof) and a target (e.g., LILRB2) can be analyzed using the OCTET® systems. In this method, one of several variations of instruments (e.g., OCTET® QKe and QK), made by the FortéBio company are used to determine protein interactions, binding specificity, and epitope mapping. The OCTET® systems provide an easy way to monitor real-time binding by measuring the changes in polarized light that travels down a custom tip and then back to a sensor.

The binding interaction of a protein of interest (an anti-LILRB2 antibody or functional fragment thereof) and a target (e.g., LILRB2) can be analyzed using Surface Plasmon Resonance (SPR). SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which is measured as an indication of real-time reactions between biological molecules. Methods for using SPR are described, for example, in U.S. Pat. No. 5,641,640; Raether (1988) Surface Plasmons Springer Verlag; Sjolander and Urbaniczky (1991) Anal. Chem. 63:2338-

2345; Szabo et al. (1995) Curr. Opin. Struct. Biol. 5:699-705 and on-line resources provide by BIAcore International AB (Uppsala, Sweden). Information from SPR can be used to provide an accurate and quantitative measure of the equilibrium dissociation constant (Kd), and kinetic parameters, including Kon and Koff, for the binding of a biomolecule to a target.

Epitopes can also be directly mapped by assessing the ability of different anti-LILRB2 antibody or functional fragment thereof to compete with each other for binding to human LILRB2 using BIACORE chromatographic techniques (Pharmacia BIAtechnology Handbook, "Epitope Mapping", Section 6.3.2, (May 1994); see also Johne et al. (1993) J. Immunol. Methods, 160:191-198).

When employing an enzyme immunoassay, a sample containing an antibody, for example, a culture supernatant of antibody-producing cells or a purified antibody is added to an antigen-coated plate. A secondary antibody labeled with an enzyme such as alkaline phosphatase is added, the plate is incubated, and after washing, an enzyme substrate such as p-nitrophenylphosphate is added, and the absorbance is measured to evaluate the antigen binding activity.

Additional general guidance for evaluating antibodies, e.g., Western blots and immunoprecipitation assays, can be found in Antibodies: A Laboratory Manual, ed. by Harlow and Lane, Cold Spring Harbor press (1988)).

Figure 2C:
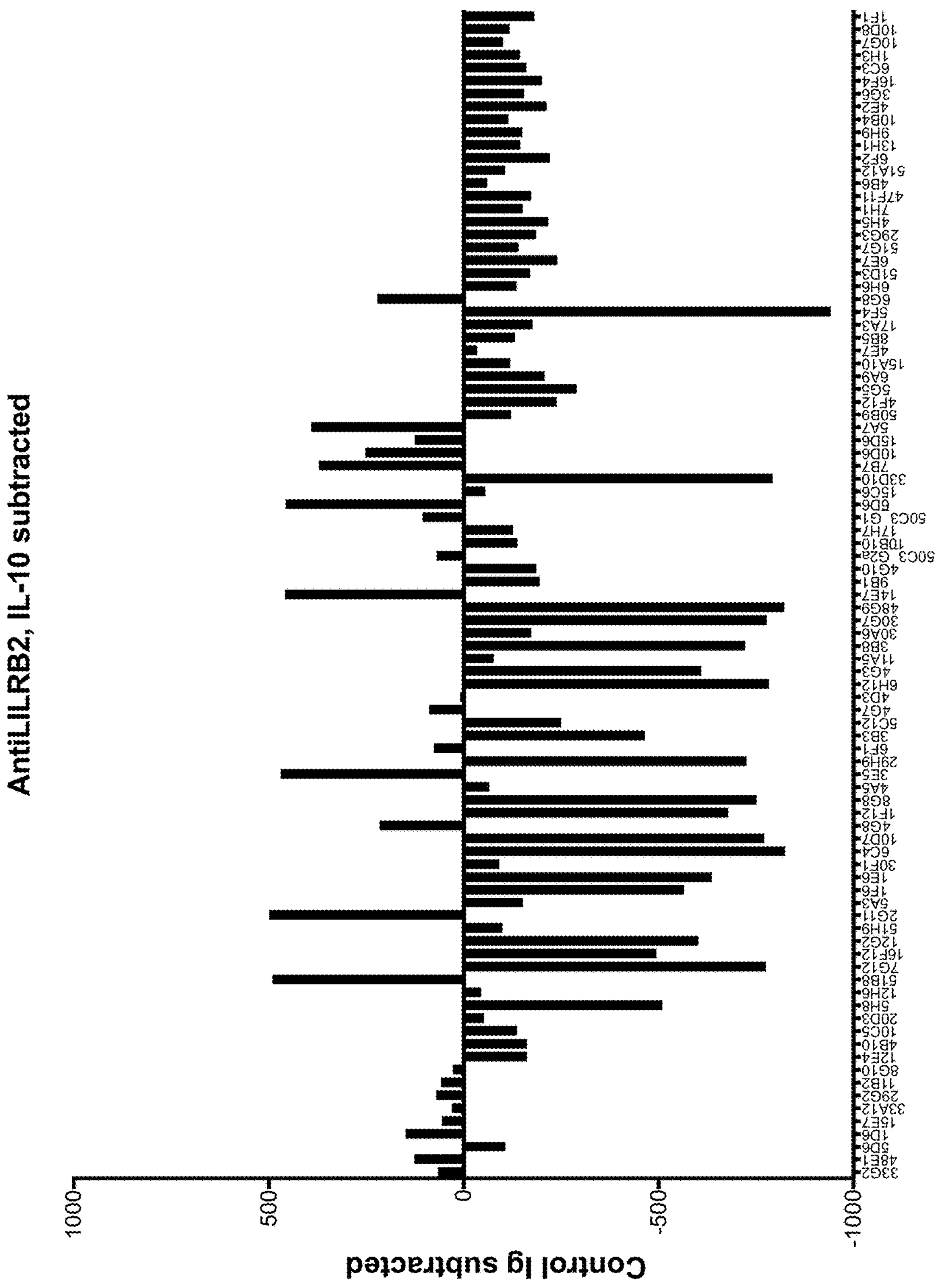
Figure 3A:
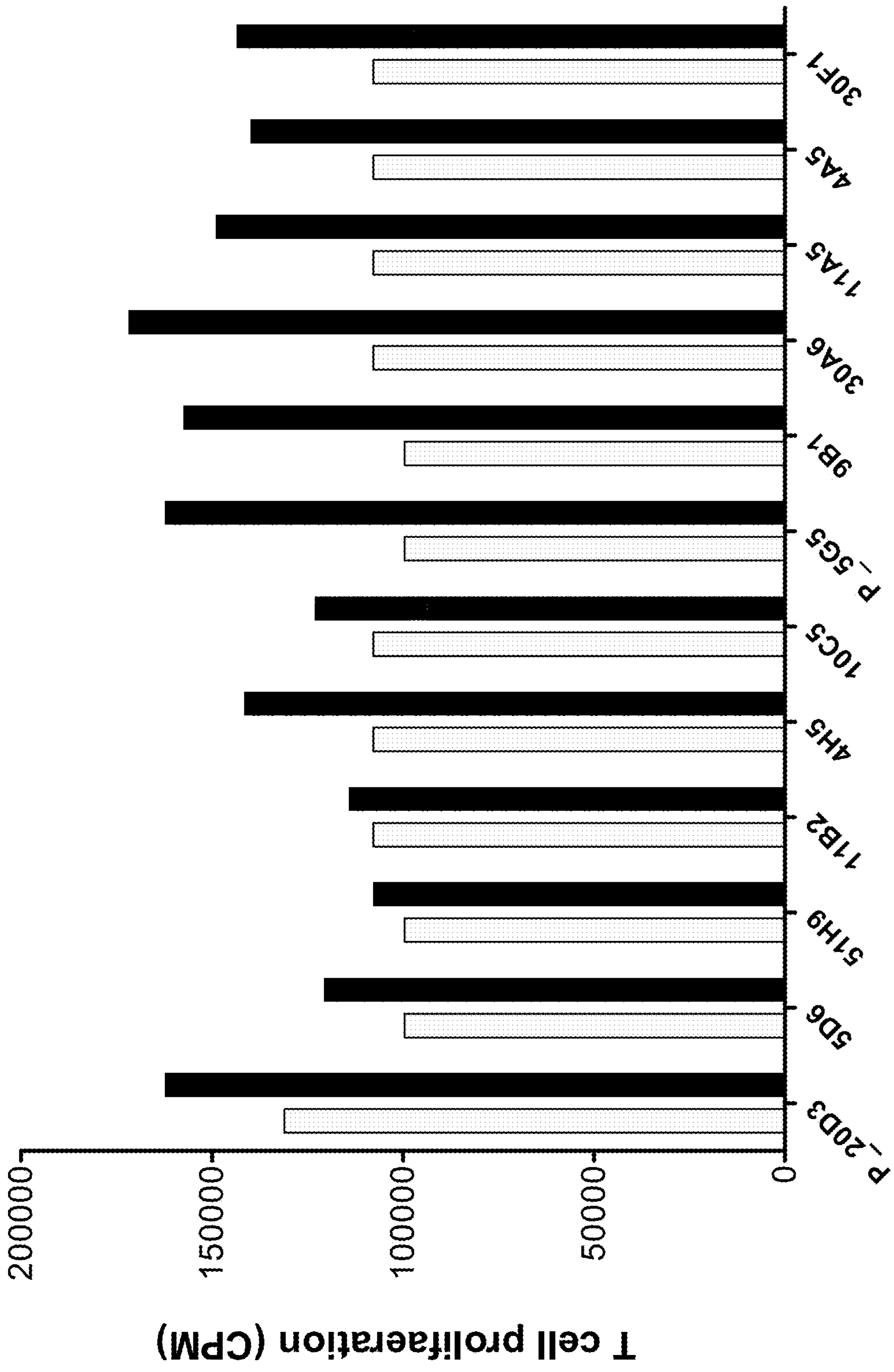
FIG. 3A: The effect of anti LILRB2 on the T proliferation of human PBMC stimulated with low dose of antiOKT3 (Antagonist).
Figure 3B:
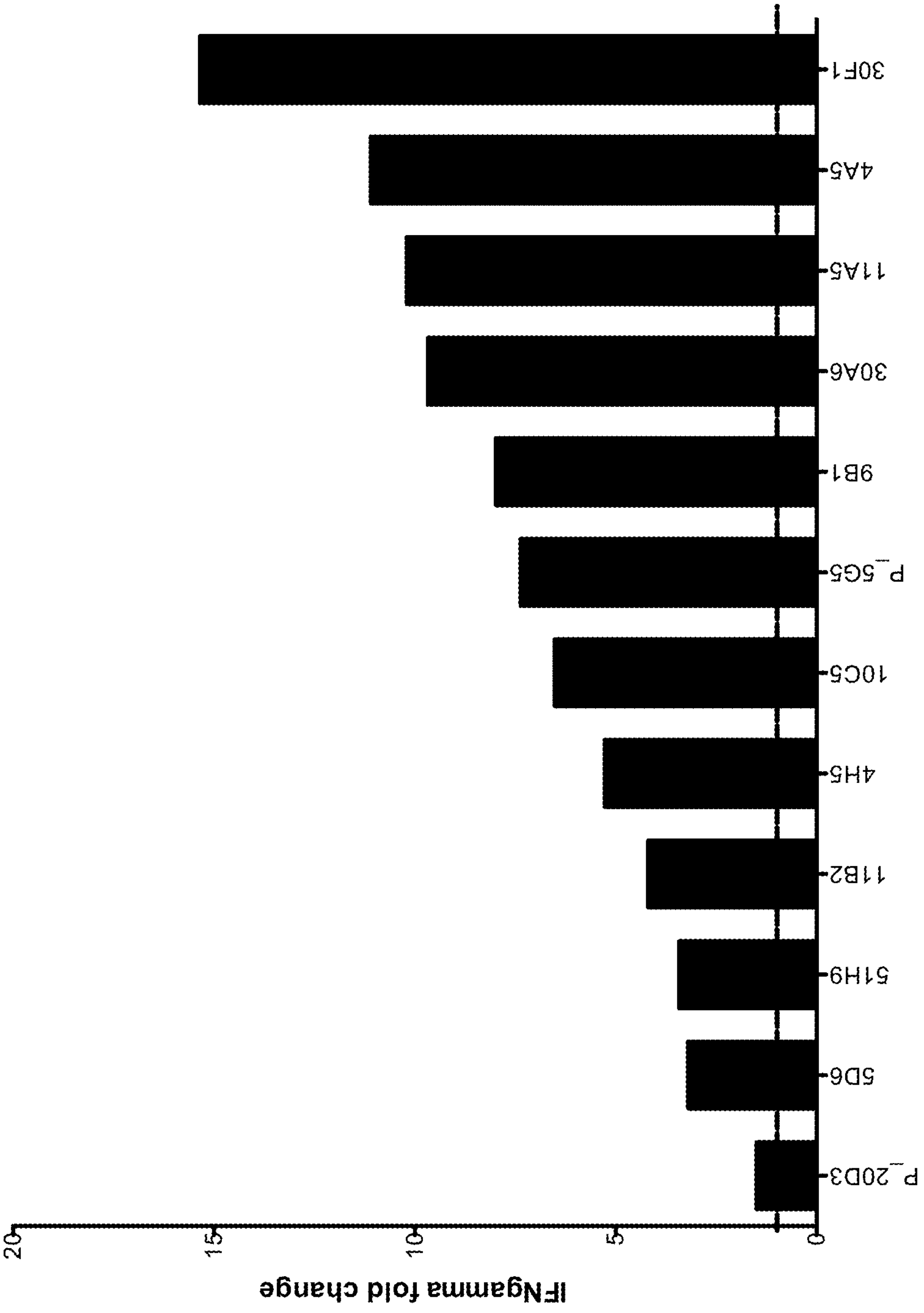
FIG. 3B: The effect of anti LILRB2 on interferon gamma production of human PBMC stimulated with low dose of antiOKT3 (Antagonist).
Figures 1, 3C:
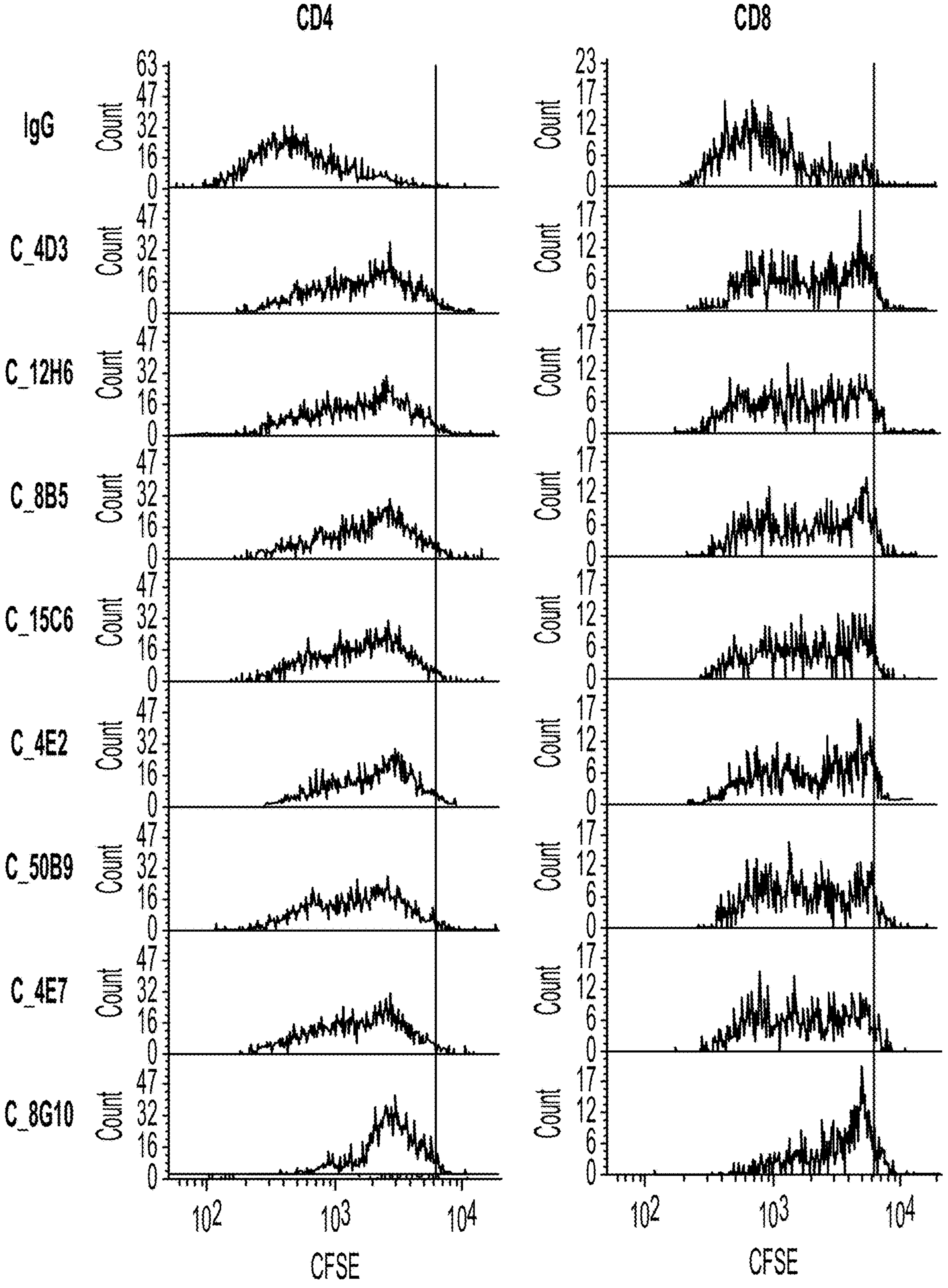
FIG. 3C: The effect of anti LILRB2 on T cells proliferation from human PBMC stimulated with low dose of OKT3

For characterization of antagonistic and agonistic bioactivity of antibodies, the inventors performed the LPS-stimulated PBMC (top priority, majorly targeting to myeloid cells) and OKT3-stimulated PBMC (majorly targeting to T cells) as pilot screening strategies. The antagonistic Abs can increase TNFa along with decreased/unchanged IL-10 secretion, meanwhile, increased/unchanged T cell proliferation (TNFa>1.5 fold, IL-10<1.1 fold). On the other hand, agonistic Abs can increase IL-10 secretion together with decreased/unchanged TNFα secretion, meanwhile, decreased T cell proliferation (IL-10>1.2 fold, TNFα<1.1 fold and T cell proliferation<0.8 fold). The effects of Ab candidates on LPS- and OKT3-stimulated PBMC were shown in Table 3-6. Noteworthy that antagonistic and agonistic bioactivity of Ab candidates screened from T cell-based assays majority are consistent, but few may not consistent with that from myeloid cell-based assays. Besides, the Ab candidates were subjected to test LILRB2 reporter assay, M1/M2 differentiation/human MDSC markers by CD163, CD206, HLA-DR, PD-L1 and CD14, CD16 (FIG. 2C) as well as mix lymphocytes reaction (FIG. 3C). The antagonists can decrease the M2 differentiation (down-regulated CD163, CD206, PD-L1), increase HLA-DR and decrease human MDSC CD33+CD14+CD16+, in contrast, the agonists can counter-regulate or maintain above parameters. These assay provided very important parameters to decide the activity or compare the efficiency/potency of Ab candidates.

Anti-LILRB2 Chimeric Antigen Receptors (CARs)

Also provided herein are chimeric antigen receptor (CAR), comprising the VH and VL of an antibody described herein. In one embodiment, the VH comprises a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and the VL comprises a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53. In one embodiment, the VH comprises a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and the VL comprises a LCDR1 comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216.

Methods of making CARs are known in the art.

Also provided herein are polynucleotide(s) encoding a CAR described herein.

Also provided herein is a vector comprising a polynucleotide encoding a CAR described herein.

Also provided herein is a cell comprising a CAR described herein. Also provided herein is a cell comprising a polynucleotide encoding a CAR described herein. Also provided herein is a cell comprising a vector comprising a polynucleotide encoding a CAR described herein. In one embodiment, the cell is a T cell. In one embodiment, the cell is a natural killer cell. In one embodiment, the cell is a macrophage.

Also provided herein is a pharmaceutical composition comprising a CAR described herein and a suitable pharmaceutical carrier. Also provided herein is a pharmaceutical composition comprising a cell comprising a CAR described herein and a suitable pharmaceutical carrier. Also provided herein is a pharmaceutical composition comprising a cell comprising a polynucleotide encoding CAR described herein and a suitable pharmaceutical carrier. In another aspect, provided herein is a pharmaceutical composition comprising a cell comprising a vector comprising a polynucleotide encoding a CAR described herein and a suitable pharmaceutical carrier.

Also provided herein is a method of producing a CAR described herein, comprising (a) culturing a cell described hereis (e.g., a cell comprising a polynucleotide encoding a CAR described herein or a cell comprising a vector comprising a polynucleotide encoding a CAR) and (b) isolating the CAR.

Additional Agents

MDSCs

MDSCs have recently been recognized as one of the central regulators of the immune system. MDSCs represent a heterogeneous population of cells of myeloid origin that include myeloid progenitors, immature macrophages, immature granulocytes, and immature dendritic cells. MDSCs differentiate and polarize into $Gr1^+CD11b^+CD115^+Ly6C^+$ monocytic (M)-cells and $Gr1^+CD11b^+Ly6G^+$ granulocytic (G)-cells in mice (Gabrilovich et al., *Cancer Res.* 67:425, 2007; Huang et al., *Cancer Res.* 66:1123-1131, 2006; Movahedi et al., *Blood* 111:4233-4244, 2008). Human MDSCs are characterized as $CD11b^+CD14^{Low}CD33^+$ or Lin-HLA-DR-$^{Low-}CD33^+$ myeloid cells (Ostrand-Rosenberg et al., *J. Immunol.* 182:4499-4506, 2009; Raychaudhuri et al., *Neurol. Oncol.* 13:591-599, 2011). Mirroring the nomenclature of type 1 classical activation-like (M1) and type 2 alternative activation-like (M2) macrophages, MDSCs can be differentiated and polarized into M1- and M2-cells (M1-cells expressing iNOS, TNF-α, IFN-gR, MHC class I, and CCR7, and M2-cells expressing arginase, IL-10, CD36, CD206, and CCR2). Tumor-associated MDSCs exhibit predominantly M2-like phenotypes with pro-tumoral and immunosuppressive activities. M2-cells are phenotypically characterized by a number of enhanced signature markers such as IL-10, arginase, IL-10, Tie-2, CD36, CD206, IL-4R and CCR2 (Ma et al., *Immunity* 34:385-395, 2011). M1-cells have an elevation in the expression of iNOS, NO, TNF-α, IFN-γR, MHC I, and CCR7 (Ma et al., *Immunity* 34:385-395, 2011). M2-cells up-regulate the expression of arginase, CCL2, CCL5 and MMP-9. In contrast, M1-cells show elevated expression levels of TNF-α, Fas, and ICAM-1.

MDSCs exert immune suppression through cross-communication with T-cells, NK cells, dendritic cells, macrophages, and other immune cells via multiple mechanisms. The details of how MDSC cross-talk with other immune cells are described in Bunt et al. (*J. Leukoc. Biol.* 85:996-1004, 2009), Ostrand-Rosenberg et al. (*Nat. Rev. Immunol.* 12:253-268, 2012), and Sinha et al. (*J. Immunol.* 179:977-983, 2007). As far as T-cells are concerned, MDSCs can induce effector T-cell (Teff) inactivation and apoptosis (see, e.g., Apolloni et al., *J. Immunol.* 165:6723-6730, 2000) and expand regulatory T cells (Treg) (see, e.g., Adeegbe et al., *Cell Transplant.* 20:941-954, 2011). The regulation of T-cell suppression and Treg expansion by MDSC is cell contact-, MHC class II-, NO- and/or arginase-dependent. M2-cells possess an enhanced ability to suppress Teff activation and proliferation compared to their M1-like counterparts in co-cultures of T-cells (Ma et al., *Immunity* 34:385-395, 2011). M2-cells possess higher potency in Treg expansion than M1-cells, both in vitro and in vivo (Ma et al., *Immunity* 34:385-395, 2011). M2-cell-induced increase in Treg cells appears to be IL-10-, IL-4-, and IL-13-mediated and arginase-dependent (Ma et al., *Immunity* 34:385-395, 2011). Akin to the functionalities of M1/M2 cells, G1- and G2-cells possess anti-tumoral and pro-tumoral activities, respectively (Fridlender et al., *Cancer Cell* 16:183-194, 2009).

Polarization of MDSC subsets from one phenotype to the other is accompanied by functional changes. M2-cells accelerate tumor growth mainly by enhanced immune suppression involving an increase in arginase and immunosuppressive cytokines (see, e.g., Ma et al., Immunity 34:385-395, 2011). M1-cells have increased direct tumor killing and promote the development of anti-tumoral immunity through the augmentation of free radicals, death ligand, and immunostimulating cytokines (see, e.g., Ma et al., Immunity 34:385-395, 2011). The balance of M1/M2 polarization may have a significant influence on disease and health.

Methods of preparing and isolating MDSCs are known in the art. For example, MDSCs can be isolated using fluorescence-assisted cell sorting using antibodies that recognize any of the specific protein markers of the different MDSC subsets described herein. Exemplary methods for preparing and isolating MDSCs are described in U.S. Patent Application Publication No. 2008/0305079 and WO 11/087795 (each of which is herein incorporated by reference).

Mobilizing Agents

In some embodiments, the compositions further contain one or more mobilizing agents or are used in combination with one or more mobilizing agents. Mobilizing agents stimulate the release of MDSCs from the bone marrow of a mammal. Non-limiting examples of mobilizing agents include, for example, granulocyte colony stimulating factor (G-CSF), cyclophosphamide, AMD3100, Fms-like tyrosine kinase 3 ligand (Flt3-L), GM-CSF, M-CSF, IL-34, TSLP-1, SCF, FK560, S100 A8, and S100 A9.

In some embodiments, the disclosure provides a composition containing a mobilizing agent and at least one LILRB1, LILRB2, LILRB2, LILRB4, and/or LILRB5 agonist. In some embodiments, a composition contains a mobilizing agent, at least one LILRB1, LILRB2, LILRB2, LILRB4, and/or LILRB5 agonist, and at least one JNK inhibitor. In some embodiments, the disclosure provides a composition further containing a mobilizing agent and does not include MDSCs.

JNK Inhibitors

In some embodiments, the compositions further contain at least one JNK inhibitor or are used in combination with at least one JNK inhibitor. Non-limiting examples of JNK inhibitors include, for example, BI-78D3, SP600125, AEG 3482, JIP-1, SU 3327, TCS JNK 5a, and TCS JNK 6o. Additional examples of JNK inhibitors are described in WO 00/35906, WO 00/35909, WO 00/35921, WO 00/64872, WO 01/12609, WO 01/12621, WO 01/23378, WO 01/23379, WO 01/23382, WO 01/47920, WO 01/91749, WO 02/046170, WO 02/062792, WO 02/081475, WO 02/083648, and WO 03/024967, each of which are herein incorporated by reference.

Anti-Inflammatory Agents

In some instances, the composition can also contain one or more anti-inflammatory agents or are used in combination with one or more anti-inflammatory agents. Anti-inflammatory agents include, for example, corticosteroids, non-steroidal anti-inflammatory drugs (NSAIDs, e.g., cyclooxygenase I (COX I) inhibitors and cyclooxygenase II (COX-II) inhibitors), immune selective anti-inflammatory derivatives (ImSAIDs), and biologics. Any of the exemplary anti-inflammatory agents described herein or known in the art can be included in the compositions described herein.

Non-limiting examples of NSAIDs are salicylates (e.g., aspirin, diflusinal, and salsalate), propionic acid derivatives (e.g., ibuprofen, dexiboprofen, naproxen, fenoprofen, ketoprofen, dexketoprofen, flurbiprofen, oxaprozin, and loxoprofen), acetic acid derivatives (e.g., indomethacin, sulindac, etodolac, ketorolac, diclofenac, and nabunetone), enolic acid derivatives (e.g., piroxicam, meloxicam, tanoxicam, droxicam, lomoxicam, and isoxicam), fenamic acid derivatives (e.g., mefamic acid, meclofenamic acid, flufenamic acid, and tolfenamic acid), sulphonanilides (e.g., nimesulide), licofelone, and lysine clonixinate. In some embodiments, an NSAID is a COX-I inhibitor or a COX-II inhibitor. Non-limiting examples of COX-I inhibitors include aspirin, ibuprofen, and naproxen. Non-limiting examples of COX-II inhibitors include celecoxib, valdecoxib, and rofecoxib.

Non-limiting examples of ImSAIDs include FEG (Phe-Glu-Gly), its D-isomer feG, and SGP-T peptide. Non-limiting examples of corticosteroids include hydrocortisone, cortisone acetate, tixocortol pivalate, prednisolone, methylprednisolone, prednisone, triamcinolone acetonide, triamcinolone alcohol, mometasone, amcinonide, budesonide, desonide, fluocinolone, halcinonide, betamethasone, dexamethasone, and fluocortolone. Non-limiting examples of biologics include tocilizumab, certolizumab, etanercept, adalimumab, anakinra, abatacept, efalizumab, infliximab, rituximab, and golimumab.

Immunosuppressive Agents

The compositions described herein can also contain one or more immunosuppressive agents or can be used in combination with one or more immunosuppressive agents. Non-limiting examples of immunosuppressive agents include mycophenolate, ciclosporin, cyclosporine, tacrolimus, sirolimus, and pimecrolimus. Additional immunosuppressive agents are known in the art.

Chemotherapeutic Agents

In some embodiments, the compositions further contain one or more chemotherapeutic agents or are used in combination with one or more chemotherapeutic agents. Non-limiting examples of chemotherapeutic agents include alkylating agents (e.g., cyclophosphamide, mechlorethamine, chlorambucil, and melphalan), anthracyclines (e.g., daunorubicin, doxorubicin, epirubicin, idarubicin, mitoxantrone, and valrubicin), taxanes (e.g., paxlitaxel and docetaxel), epothilones, histone deacetylase inhibitors (e.g., vorinostat and romidepsin), topoisomerase II inhibitors (e.g., etoposide, teniposide, and tafluposide), kinase inhibitors (e.g., bortezomib, erlotinib, gefitinib, imatinib, and vismodegib), bevacizumab, cetuximab, ipilimumab, ipilimumab, ofatumumab, ocrelizumab, panitumab, rituximab, vemurafenib, herceptin, nucleotide analogs (e.g., azacitidine, azathioprine, capecitabine, cytarabine, doxifluridine, fluorouracil, gemcitabine, hydroxyurea, mercaptopurine, methotrexate, and thioguanine), peptide antibiotics (e.g., bleomycin and actinomycin), platinum-based agents (e.g., carboplatin, cisplatin, and oxaliplatin), retinoids (e.g., tretinoin, alitretinoin, and bexarotene), and vinca alkaloids (e.g., vinblastine, vincristine, vindesine, and vinorelbine).

Analgesics

In some embodiments, the composition can further contain one or more analgesics or are used in combination with one or more analgesics. Any of the exemplary analgesics described herein or known in the art can be included in the compositions described herein. Non-limiting examples of analgesics include opioid drugs (e.g., morphine, opium, codeine, oxycodone, hydrocodone, diamorphine, dihydromorphine, pethidine, buprenorphine, fentanyl, methadone, meperidine, pentazocine, dipipanone, and tramadol), acetaminophen, venlafaxine, flupirtine, nefopam, gabapentin, pregabalin, orphenadrine, cyclobenzaprine, trazodone, clonidine, duloxetine and amitriptyline.

Immune Checkpoint Inhibitors

In some embodiments, the composition can further contain one or more immune checkpoint inhibitor or are used in combination with one or more immune checkpoint inhibitor. Any of the exemplary analgesics described herein or known in the art can be included in the compositions described herein. Non-limiting examples of immune checkpoint inhibitors include antagonists (e.g., antagonistic antibodies antibodies) of programmed cell death protein 1 (PD1), cytotoxic T-lymphocyte-associated antigen 4 (CTLA-4), B and T-lymphocyte attenuator (BTLA), killer cell immunoglobulin-like receptor (KIR), lymphocyte activation gene 3 (LAG3), T-cell membrane protein 3 (TIM3), CD160, or adenosine A2a receptor (A2aR) and agonists (e.g., agonistic antibodies) of glucocorticoid-induced tumor necrosis factor receptor (GITR), Inducible T-cell costimulator (ICOS or CD278), OX40 (CD134), CD27, CD28, 4-1BB (CD137), CD40, lymphotoxin alpha (LT alpha), or LIGHT (lymphotoxin-like, exhibits inducible expression, and competes with herpes simplex virus glycoprotein D for HVEM, a receptor expressed by T lymphocytes). In specific embodiments, the immune-checkpoint inhibitor is an antagonist of PD-1 (e.g., an antagonistic antibody of PD-1). In specific embodiments, the immune-checkpoint inhibitor is an antagonist of PD-L 1 (e.g., an antagonistic antibody of PD-L1).

Methods of Producing Anti-LILRB2 Antibodies

The anti-LILRB2 antibodies (or antigen binding domain of an antibody or functional fragment thereof) of this disclosure may be produced in bacterial or eukaryotic cells. To produce the polypeptide of interest, a polynucleotide encoding the polypeptide is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., *E. coli*), the expression vector should have characteristics that permit amplification of the vector in the bacterial cells. Additionally, when *E. coli* such as JM109, DH5a, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for antibody secretion. For production into the periplasm of *E. coli*, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, 293, 293T, and NIH3T3 cells, the expression vector includes a promoter necessary for expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, the antibodies are produced in mammalian cells. Exemplary mammalian host cells for expressing a polypeptide include Chinese Hamster Ovary (CHO cells) (including dhfr− CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g., 293, 293E, 293T), COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

The antibodies of the present disclosure can be isolated from inside or outside (such as medium) of the host cell and purified as substantially pure and homogenous antibodies. Methods for isolation and purification commonly used for polypeptides may be used for the isolation and purification of antibodies described herein, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). The present disclosure also includes antibodies that are highly purified using these purification methods.

The present disclosure also provides a nucleic acid molecule or a set of nucleic acid molecules encoding an anti-LILRB2 antibody or antigen binding molecule thereof disclosed herein. In one embodiment, the invention includes a nucleic acid molecule encoding a polypeptide chain, which comprises a light chain of an anti-LILR3 antibody or antigen-binding molecule thereof as described herein. In one embodiment, the invention includes a nucleic acid molecule encoding a polypeptide chain, which comprises a heavy chain of an anti-LILR3 antibody or antigen-binding molecule thereof as described herein.

Also provided are a vector or a set of vectors comprising such nucleic acid molecule or the set of the nucleic acid molecules or a complement thereof, as well as a host cell comprising the vector.

The instant disclosure also provides a method for producing a LILRB2 or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a LILRB2 antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

For recombinant production, a polynucleotide sequence encoding a polypeptide (e.g., a LILRB2 antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a LILRB2 antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO J. 1:841). A variety of host-expression vector systems can be utilized to express the polypeptides described herein (e.g., a LILRB2 antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a LILRB2 antibody or antigen-binding molecule thereof disclosed herein, or any of the chimeric molecules disclosed herein) can also code for a signal sequence that will permit the polypeptide to be secreted. One skilled in the art will understand that while the polypeptide is translated, the signal sequence is cleaved by the cell to form the mature chimeric molecule. Various signal sequences are known in the art and familiar to the skilled practitioner. Alternatively, where a signal sequence is not included, the polypeptide (e.g., a LILRB2 antibody or antigen-binding molecule thereof disclosed herein, or any of the chimeric molecules disclosed herein) can be recovered by lysing the cells.

Pharmaceutical Compositions

The present disclosure also provides pharmaceutical compositions comprising one or more of: (i) a LILRB2 antibody or antigen-binding molecule thereof disclosed herein;

(ii) a nucleic acid molecule or the set of nucleic acid molecules encoding a LILRB2 antibody or antigen-binding molecule as disclosed herein; or (iii) a vector or set of vectors disclosed herein, and a pharmaceutically acceptable carrier.

An anti-LILRB2 antibodies or fragments thereof described herein can be formulated as a pharmaceutical composition for administration to a subject, e.g., to treat a disorder described herein. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

Pharmaceutical formulation is a well-established art, and is further described, e.g., in Gennaro (ed.), Remington: The Science and Practice of Pharmacy, 20th ed., Lippincott, Williams & Wilkins (2000) (ISBN: 0683306472); Ansel et al., Pharmaceutical Dosage Forms and Drug Delivery Systems, 7th Ed., Lippincott Williams & Wilkins Publishers (1999) (ISBN: 0683305727); and Kibbe (ed.), Handbook of Pharmaceutical Excipients American Pharmaceutical Association, 3rd ed. (2000) (ISBN: 091733096X).

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

In one embodiment, an antibody described herein is formulated with excipient materials, such as sodium citrate, sodium dibasic phosphate heptahydrate, sodium monobasic phosphate, Tween®-80, and a stabilizer. It can be provided, for example, in a buffered solution at a suitable concentration and can be stored at 2-8° C. In some other embodiments, the pH of the composition is between about 5.5 and 7.5 (e.g., 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5).

The pharmaceutical compositions can also include agents that reduce aggregation of the antibody when formulated. Examples of aggregation reducing agents include one or more amino acids selected from the group consisting of methionine, arginine, lysine, aspartic acid, glycine, and glutamic acid. These amino acids may be added to the formulation to a concentration of about 0.5 mM to about 145 mM (e.g., 0.5 mM, 1 mM, 2 mM, 5 mM, 10 mM, 25 mM, 50 mM, 100 mM). The pharmaceutical compositions can also include a sugar (e.g., sucrose, trehalose, mannitol, sorbitol, or xylitol) and/or a tonicity modifier (e.g., sodium chloride, mannitol, or sorbitol) and/or a surfactant (e.g., polysorbate-20 or polysorbate-80).

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the antibodies may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

In one embodiment, the pharmaceutical formulation comprises an antibody at a concentration of about 0.005 mg/mL to 500 mg/mL (e.g., 0.005 mg/ml, 0.01 mg/ml, 0.05 mg/ml, 0.1 mg/ml, 0.5 mg/mL, 1 mg/mL, 5 mg/mL, 10 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 250 mg/mL, 300 mg/mL, 350 mg/mL, 400 mg/mL, 450 mg/mL, 500 mg/mL), formulated with a pharmaceutically acceptable carrier. In some embodiments, the antibody is formulated in sterile distilled water or phosphate buffered saline. The pH of the pharmaceutical formulation may be between 5.5 and 7.5 (e.g., 5.5, 5.6, 5.7, 5.8, 5.9, 6.0, 6.1, 6.2 6.3, 6.4 6.5, 6.6 6.7, 6.8, 6.9 7.0, 7.1, 7.3, 7.4, 7.5).

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Administration

The antibodies or antigen-binding fragment thereof, or nucleic acids encoding same can be administered to a subject, e.g., a subject in need thereof, for example, a human or animal subject, by a variety of methods. For many applications, the route of administration is one of: intravenous injection or parenteral, infusion (IV), subcutaneous injection (SC), intraperitoneally (IP), or intramuscular injection, intratumor (IT). Other modes of parenteral administration can also be used. Examples of such modes include: intraarterial, intrathecal, intracapsular, intraorbital, intracardiac, intradermal, transtracheal, subcuticular, intraarticular, subcapsular, subarachnoid, intraspinal, and epidural and intrasternal injection.

In one embodiment, the route of administration of the antibodies of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection can comprise a buffer (e.g., acetate, phosphate or citrate buffer), a surfactant (e.g. polysorbate), optionally a stabilizer agent (e.g., human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

The route and/or mode of administration of the anti-LILRB2 antibody or fragment thereof can also be tailored for the individual case, e.g., by monitoring the subject.

The antibody or fragment thereof can be administered as a fixed dose, or in a mg/kg dose. The dose can also be chosen to reduce or avoid production of antibodies against the anti-LILRB2 antibody or fragment thereof. Dosage regimens are adjusted to provide the desired response, e.g., a therapeutic response or a combinatorial therapeutic effect. Generally, doses of the antibody or fragment thereof (and optionally a second agent) can be used in order to provide a subject with the agent in bioavailable quantities. For example, doses in the range of 0.1-100 mg/kg, 0.5-100 mg/kg, 1 mg/kg-100 mg/kg, 0.5-20 mg/kg, 0.1-10 mg/kg, or 1-10 mg/kg can be administered. Other doses can also be used. In certain embodiments, a subject in need of treatment with an antibody or fragment thereof is administered the antibody or fragment thereof at a dose of between about 1 mg/kg to about 30 mg/kg. In some embodiments, a subject in need of treatment with anti-LILRB2 antibody or fragment thereof is administered the antibody or fragment thereof at a dose of 1 mg/kg, 2 mg/kg, 4 mg/kg, 5 mg/kg, 7 mg/kg 10 mg/kg, 12 mg/kg, 15 mg/kg, 20 mg/kg, 25 mg/kg, 28 mg/kg, 30 mg/kg, 35 mg/kg, 40 mg/kg, or 50 mg/kg. In a specific embodiment, the antibody or fragment thereof is administered subcutaneously at a dose of 1 mg/kg to 3 mg/kg. In another embodiment, the antibody or fragment thereof is administered intravenously at a dose of between 4 mg/kg and 30 mg/kg.

A composition may comprise about 1 mg/mL to 100 mg/ml or about 10 mg/mL to 100 mg/ml or about 50 to 250 mg/mL or about 100 to 150 mg/ml or about 100 to 250 mg/ml of the antibody or fragment thereof.

Dosage unit form or "fixed dose" as used herein refers to physically discrete units suited as unitary dosages for the subjects to be treated; each unit contains a predetermined quantity of antibody or fragment thereof calculated to produce the desired therapeutic effect in association with the required pharmaceutical carrier and optionally in association with the other agent. Single or multiple dosages may be given. Alternatively, or in addition, the antibody or fragment thereof may be administered via continuous infusion.

An antibody or fragment thereof dose can be administered, e.g., at a periodic interval over a period of time (a course of treatment) sufficient to encompass at least 2 doses, 3 doses, 5 doses, 10 doses, or more, e.g., once or twice daily, or about one to four times per week, or preferably weekly, biweekly (every two weeks), every three weeks, monthly, e.g., for between about 1 to 12 weeks, preferably between 2 to 8 weeks, more preferably between about 3 to 7 weeks, and even more preferably for about 4, 5, or 6 weeks. Factors that may influence the dosage and timing required to effectively treat a subject, include, e.g., the stage or severity of the disease or disorder, formulation, route of delivery, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein, the antibody or fragment thereof can be administered before the full onset of the disorder, e.g., as a preventative measure. The duration of such preventative treatment can be a single dosage of the antibody or fragment thereof or the treatment may continue (e.g., multiple dosages). For example, a subject at risk for the disorder or who has a predisposition for the disorder may be treated with the antibody or fragment thereof for days, weeks, months, or even years so as to prevent the disorder from occurring or fulminating.

In certain embodiments, the antibody or fragment thereof is administered subcutaneously at a concentration of about 1 mg/mL to about 500 mg/mL (e.g., 1 mg/mL, 2 mg/mL, 3 mg/mL, 4 mg/mL, 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, 75 mg/mL, 80 mg/mL, 85 mg/mL, 90 mg/mL, 95 mg/mL, 100 mg/mL, 125 mg/mL, 150 mg/mL, 175 mg/mL, 200 mg/mL, 225 mg/mL, 250 mg/mL, 275 mg/mL, 300 mg/mL, 325 mg/mL, 350 mg/mL, 400 mg/mL, 450 mg/mL). In one embodiment, the anti-LILRB2 antibody or fragment thereof is administered subcutaneously at a concentration of 50 mg/mL. In another embodiment, the antibody or fragment thereof is administered intravenously at a concentration of about 1 mg/mL to about 500 mg/mL. In one embodiment, the antibody or fragment thereof is administered intravenously at a concentration of 50 mg/mL.

The anti-LILRB2 antibody or fragment thereof can be administered to a patient in need thereof alone or in combination with (i.e., by co-administration or sequential administration) other therapeutic agents useful for treating a cancer or immunological disorder as described herein may be desirable. Such therapeutic agents can be chemical or biologic in nature. The term "biologic" or "biologic agent" refers to any pharmaceutically active agent made from living organisms and/or their products which is intended for use as a therapeutic. In one embodiment, the additional therapeutic proteins are included in the pharmaceutical composition of the present invention.

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides can be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Methods of Use

The antibodies, or antigen-binding fragments thereof of the disclosure can be useful in methods of treating a subject (e.g., a human) with a disease or condition. The disease or condition can include, but is not limited to, cancer or stimulating a pro-inflammatory immune response for anti-viral immune response or inhibition of chronic infections.

For example, the present invention includes the use of anti-LILRB2, including antagonists or agonists having anti-LILRB2 activity. The invention includes administering to a subject (e.g., a mammal, e.g., a human) the anti-LILRB2 antibodies or a fragment thereof and contemplates both human and veterinary therapeutic uses. Illustrative veterinary subjects include mammalian subjects, such as farm animals and domestic animals.

Provided herein are methods of stimulating a pro-inflammatory immune response in a mammal (e.g., human) that include administering to a mammal a therapeutically effective amount of an anti-LILRB2 antibody or fragment thereof as described herein.

In some embodiments, an increase in pro-inflammatory immune response in a mammal can be detected as an increase in the levels of one or more pro-inflammatory proteins in the mammal (e.g., an increase in one or more of C-reactive protein, IL-1α, IL-1β, TNF-α, IL-6, IL-8, IL-23, IL-17, and matrix metalloproteases) or an increase in the number of effector T-cells (Teff) in the mammal (e.g., as compared to the levels of the one or more pro-inflammatory proteins in the mammal and/or the levels of effector T-cells in the mammal prior to treatment or compared to the levels of the one or more pro-inflammatory proteins and/or the levels of effector T-cells present in a control, healthy mammal).

Provided herein are methods of treating in a mammal (e.g., human) that include administering to a mammal a therapeutically effective amount of an anti-LILRB2 antibody or antigen-binding fragment thereof as described herein (or a pharmaceutical composition comprising the antibody or antigen-binding fragment thereof).

In some embodiments, the mammal (e.g., human) has been previously diagnosed as having a cancer (e.g., any of the different types of cancer described herein). Non-limiting examples of cancer include: bladder cancer, breast cancer, colon cancer, colorectal cancer, endometrial cancer, kidney cancer, lung cancer, melanoma, pancreatic cancer, prostate cancer, thyroid cancer, bile duct cancer, bone cancer, brain cancer, cervical cancer, cardiac tumors, esophageal cancer, eye cancer, gallbladder cancer, gastric cancer, head and neck cancer, heart cancer, liver cancer, laryngeal cancer, leukemia, lip and oral cavity cancer, lymphoma, melanoma, mesothelioma, mouth cancer, nasal cavity and paranasal sinus cancer, nasopharyngeal cancer, non-Hodgkin lymphoma, ovarian cancer, penile cancer, pituitary tumor, retinoblastoma, sarcoma, skin cancer, testicular cancer, throat cancer, thyroid cancer, urethral cancer, uterine cancer, vaginal cancer, and vulvar cancer. In some embodiments, the cancer is a lymphoma, a leukemia, or a breast cancer. A mammal having cancer can present with one or more of the following symptoms: fatigue, lump or thickening that can be felt under the skin, weight changes, skin changes (e.g., yellowing, darkening or redness of the skin, sores that won't heal, or changes in existing moles), changes in bowel or bladder habits, persistent cough, difficulty swallowing, hoarseness, persistent indigestion or discomfort after eating, persistent, unexplained muscle or joint pain, and unexplained and persistent fevers or night sweats. The particular symptoms experienced by a mammal will depend on the particular type of cancer. A mammal can be diagnosed as having a cancer based on the observation of one or more symptoms of cancer in the mammal (e.g., any of the symptoms of cancer described herein or known in the art). A mammal can also be diagnosed as having a cancer based on imaging (e.g., magnetic resonance imaging, computed tomography, and/or X-ray) and/or tissue biopsy results. A mammal can also be diagnosed as having a cancer based using molecular diagnostic tests (e.g., based on the detection of prostate specific antigen, or mutations in breast cancer susceptibility 2 protein, breast cancer susceptibility 1 protein, or a tumor suppressor protein (e.g., p53)). Additional methods for diagnosing a mammal as having cancer are known in the art. Efficacy of treatment of a cancer can be detected by a decrease the number of symptoms of a cancer in a mammal (e.g., any of the symptoms of cancer described herein or known in the art) and/or a decrease in the frequency and/or severity of one or more symptoms of cancer in a mammal (e.g., any of the symptoms described herein or known in the art). An effective treatment of cancer in a mammal can also be assessed by a decrease in the rate of growth of a tumor in a mammal (e.g., compared to the rate of tumor growth in the mammal prior to administration of treatment or compared to a control mammal having the same type of cancer not administered a treatment or administered a different treatment). An effective treatment of cancer in a mammal can also be observed by an increase in the length of remission of cancer in the mammal (e.g., compared to a control mammal having the same type of cancer not administered a treatment or administered a different treatment).

The mammal may be female or male, and may be an adult or juvenile (e.g., an infant). The mammal may have been previously treated with a chemotherapeutic agent and/or analgesic and/or responded poorly to the chemotherapeutic agent and/or analgesic. The mammal may have non-metastatic cancer. In some embodiments, the mammal can have metastatic cancer. Where the mammal is an adult, the mammal may be, e.g., between 18 to 20 years old or at least or about 20, 25, 30, 35, 40, 45, 50, 55, 60, 65, 70, 75, 80, 85, 90, 95, or at least or about 100 years old.

Also provided are methods of treating cancer in a mammal (e.g., human) that include administering to the mammal a therapeutically effective amount of an anti-LILRB2 antibody or antigen-binding fragment thereof as described herein (or a pharmaceutical composition comprising the antibody or fragment thereof).

Also provided herein are methods of treating cancer in a mammal (e.g., human) in need thereof, comprising administering to the mammal an antibody or antigen-binding fragment thereof described herein (or a pharmaceutical composition comprising the antibody or antigen-binding fragment thereof) and a PD-1 or PD-L1 inhibitor.

In some embodiments, the methods of treating cancer described herein further comprise administering to the mammal a chemotherapeutic agent or an analgesic. In some embodiments, the methods of treating cancer described herein further comprise administering to the mammal an immune checkpoint inhibitor. In some embodiments, the methods of treating cancer described herein further comprise administering to the mammal one or more additional agents selected from the group consisting of: a myeloid-derived suppressor cell, a mobilizing agent, a c-jun N-terminal kinase inhibitor, an anti-inflammatory agent, and an immunosuppressive agent.

Also provided herein are methods of treating an infection in a mammal (e.g., human) in need thereof, comprising administering to the mammal an antibody or antigen-binding fragment thereof as described herein (or a pharmaceutical composition comprising the antibody or fragment thereof). In some embodiments, the infection is a bacterial infection.

Also provided herein are methods of decreasing a pro-inflammatory immune response in a mammal (e.g., human) in need thereof, the method comprising administering to the mammal a therapeutically effective amount of an antibody or antigen-binding fragment thereof as described herein (or a pharmaceutical composition comprising the antibody or fragment thereof). In some embodiments, the mammal has been diagnosed as having inflammation, an autoimmune disease, or transplant rejection. In some embodiments, the mammal is selected for organ or tissue transplantation.

Also provided herein are methods of treating inflammation, an autoimmune disease, or transplant rejection in a mammal (e.g., human) in need thereof, the method comprising administering to the mammal a therapeutically effective amount of an antibody or antigen-binding fragment thereof as described herein (or a pharmaceutical composition comprising the antibody or fragment thereof). In some embodiments, the mammal has been diagnosed as having inflammation, an autoimmune disease, or transplant rejection. In some embodiments, the mammal is selected for organ or tissue transplantation.

Also provided herein is a method of treating cancer in a mammal in need thereof, the method comprising administering to the mammal a therapeutically effective amount of a CAR described herein (or cells comprising or encoding a CAR described herein or a pharmaceutical composition comprising same) or a pharmaceutical composition comprising same. In one embodiment, the cancer is a lymphoma, a leukemia, a colon cancer, or a breast cancer. In one embodiment, the mammal is a human.

In another aspect, provided herein is a method of treating asthma in a mammal in need thereof, the method comprising administering to the mammal a therapeutically effective amount of a CAR described herein (or cells comprising or encoding a CAR described herein or a pharmaceutical composition comprising same) or a pharmaceutical composition comprising same. In one embodiment, the mammal is a human.

In another aspect, provided herein is a method of treating an infection in a mammal in need thereof, the method comprising administering to the mammal a therapeutically effective amount of a CAR described herein (or cells comprising or encoding a CAR described herein or a pharmaceutical composition comprising same) or a pharmaceutical composition comprising same. In one embodiment, the mammal is a human.

In another aspect, provided herein is a method of treating inflammation, an autoimmune disease, or transplant rejection in a mammal in need thereof, the method comprising administering to the mammal a therapeutically effective amount of a CAR described herein (or cells comprising or encoding a CAR described herein or a pharmaceutical composition comprising same) or a pharmaceutical composition comprising same. In one embodiment, the mammal is a human.

Devices and Kits for Therapy

Pharmaceutical compositions that include the anti-LILRB2 antibody or fragment thereof described herein can be administered with a medical device. The device can be designed with features such as portability, room temperature storage, and ease of use so that it can be used in emergency situations, e.g., by an untrained subject or by emergency personnel in the field, removed from medical facilities and other medical equipment. The device can include, e.g., one or more housings for storing pharmaceutical preparations that include an anti-LILRB2 antibody or fragment thereof, and can be configured to deliver one or more unit doses of the antibody or fragment thereof. The device can be further configured to administer a second agent, e.g., a chemotherapeutic agent, either as a single pharmaceutical composition that also includes the anti-LILRB2 antibody or fragment thereof or as two separate pharmaceutical compositions.

An anti-LILRB2 antibody or fragment thereof can be provided in a kit. In one embodiment, the kit includes (a) a container that contains a composition that includes an anti-LILRB2 antibody or fragment thereof as described herein, and optionally (b) informational material. The informational material can be descriptive, instructional, marketing or other material that relates to the methods described herein and/or the use of the agents for therapeutic benefit.

In an embodiment, the kit also includes a second agent for treating a disorder described herein. For example, the kit includes a first container that contains a composition that includes the anti-LILRB2 antibody or fragment thereof, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the anti-LILRB2 antibody or fragment thereof, e.g., in a suitable dose, dosage form, or mode of administration (e.g., a dose, dosage form, or mode of administration described herein), to treat a subject who has had or who is at risk for a disease as described herein. The information can be provided in a variety of formats, include printed text, computer readable material, video recording, or audio recording, or information that provides a link or address to substantive material, e.g., on the internet.

In addition to the anti-LILRB2 antibody or fragment thereof, the composition in the kit can include other ingredients, such as a solvent or buffer, a stabilizer, or a preservative. The anti-LILRB2 antibody or fragment thereof can be provided in any form, e.g., liquid, dried or lyophilized form, preferably substantially pure and/or sterile. When the agents are provided in a liquid solution, the liquid solution preferably is an aqueous solution. In certain embodiments, the anti-LILRB2 antibody or fragment thereof in the liquid solution is at a concentration of about 25 mg/mL to about 250 mg/mL (e.g., 40 mg/mL, 50 mg/mL, 60 mg/mL, 75 mg/mL, 85 mg/mL, 100 mg/mL, 125 mg/mL, 150 mg/mL, and 200 mg/mL). When the anti-LILRB2 antibody or fragment thereof is provided as a lyophilized product, the anti-LILRB2 antibody or fragment thereof is at about 75 mg/vial to about 200 mg/vial (e.g., 100 mg/vial, 108.5 mg/vial, 125 mg/vial, 150 mg/vial). The lyophilized powder is generally reconstituted by the addition of a suitable solvent. The solvent, e.g., sterile water or buffer (e.g., PBS), can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the anti-LILRB2 antibody or fragment thereof and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

The invention is further described in the following examples, which do not limit the scope of the invention described in the claims.

Monoclonal antibodies that specifically bind LILRB2 were generated (Examples 1 and 9) and characterized (Examples 2-9) as described below. The anti-LILRB2 antibodies exhibited pro- or anti-inflammatory responses as well as regulated T cell-mediated immunities through modulation of LILRB2 signaling. Additionally, anti-LILRB2 antibodies described below mediated anti-tumor responses on LILRB2-expressed tumor cells.

Example 1

Monoclonal antibodies that specifically bind LILRB2 were generated as described below. The anti-LILRB2 antibodies can exhibit pro- or anti-inflammatory responses as well as regulate T cell-mediated immunities through modulation of LILRB2 signaling. Additionally, LILRB2 antibodies can mediate anti-tumor responses on the LILRB2-expressed tumor cells.

Generation and Purification of Anti-LILRB2 Antibodies

Monoclonal antibodies generated from clonal hybridoma cells were cultured in ClonaCell-HY Medium A (StemCell Technologies) followed by adaptation to serum-free conditions using Hybridoma-SFM (ThermoFisher Scientific). Hybridoma cells were expanded in 50 mL of Hybridoma SFM for 2 weeks or until medium was exhausted. Antibody-containing supernatant was harvested by centrifugation followed by sterile 0.22 micron filtration. Antibodies were concentrated using Amicon Ultra-15 centrifugal filter concentrator with nominal molecular weight limit of 100 kDa (Millipore). Concentrated antibodies were then purified using Nab Protein A/G Spin Kit (Thermo Fisher Scientific) according to manufacturer's instructions. Purified antibodies were desalted using Zeba Spin Columns (Thermo Fisher Scientific).

Hybridoma IgL and IgH Chain Sequencing

RNA from hybridoma clones was extracted using Trizol extraction. cDNA was synthesized from purified RNA using OneStep RT-PCR Kit (Qiagen) according to manufacturer's instructions. PCR of Ig heavy and light chains was performed using degenerate primers. Amplified PCR products were subsequently sequenced (GeneWiz) and validated using IMGT/V-QUEST from The International Immunogenetics Information System.

Sequence of Hybridoma

Using degenerate primers flanking the mouse kappa and heavy chain Ig genes, the heavy and light chain genes and complementarity determining regions (CDRs) sequences were determined for the indicated clones. Total RNA isolated from early passage hybridomas was converted to cDNA using RT-PCR followed by PCR amplification of the heavy and light chain genes. PCR products were sequenced by Sanger sequencing followed by Ig-BLAST comparison to known allele framework from databases. Productive antibody sequences are listed in Tables 1, 2, 5 and 6, showing the closest aligning mouse alleles and CDRs1-3. The CDR amino acid sequences of selected anti-LILRB2 antibodies (murine) are provided in Tables 1, 2, and 5. The CDRs are based on Kabat Numbering System. Table 6 shows the closest aligning mouse alleles and CDRs1-3 for the selected anti-LILRB2 antibodies (murine).

Anti-LILRB2 antagonists promote TNF alpha secretion whereas Anti-LILRB2 agonist promotes IL-10 secretion from total peripheral blood mononuclear cells (PBMC) in the presence of low-dose LPS stimulation. The inventors screened several monoclonal antibodies (mAbs) for biological function with total PBMC under the inflammatory condition. The mAbs with antagonistic functional characteristics can further promote the TNF alpha production from total PBMC under the low dose of LPS stimulation, but do not affect the IL-10 secretion, meaning they are effective in treating cancer or infectious diseases. On the other hand, the agonistic clones can increase the IL-10 production (FIG. 1), for treating autoimmune diseases, inflammation or transplant rejection. Those clones that can induce TNF alpha secretion were considered as antagonists whereas those induce IL-10 are considered as agonists. Antagonistic anti-LILRB-1 antibodies are described in Table 1. Agonistic anti-LILRB-1 antibodies are described in Table 2.

The skilled artisan will understand that the name of the antibody (e.g., 5G5) and its hybridoma clonal name (e.g., P_5G5) are used interchangeably and refer to antibodies having the same sequences as each other. For example, 5G5 and P_5G5 may be used interchangeably to refer to an antibody having HCDR1-3 of SEQ ID NOs: 225, 230, and 244, respectively, and LCDR1-3 of SEQ ID NOs: 24, 202, and 216, respectively.

Example 2

Anti-LILRB2 Antibodies Modulate TNF Alpha Secretion In Vitro.

Figure 1B:
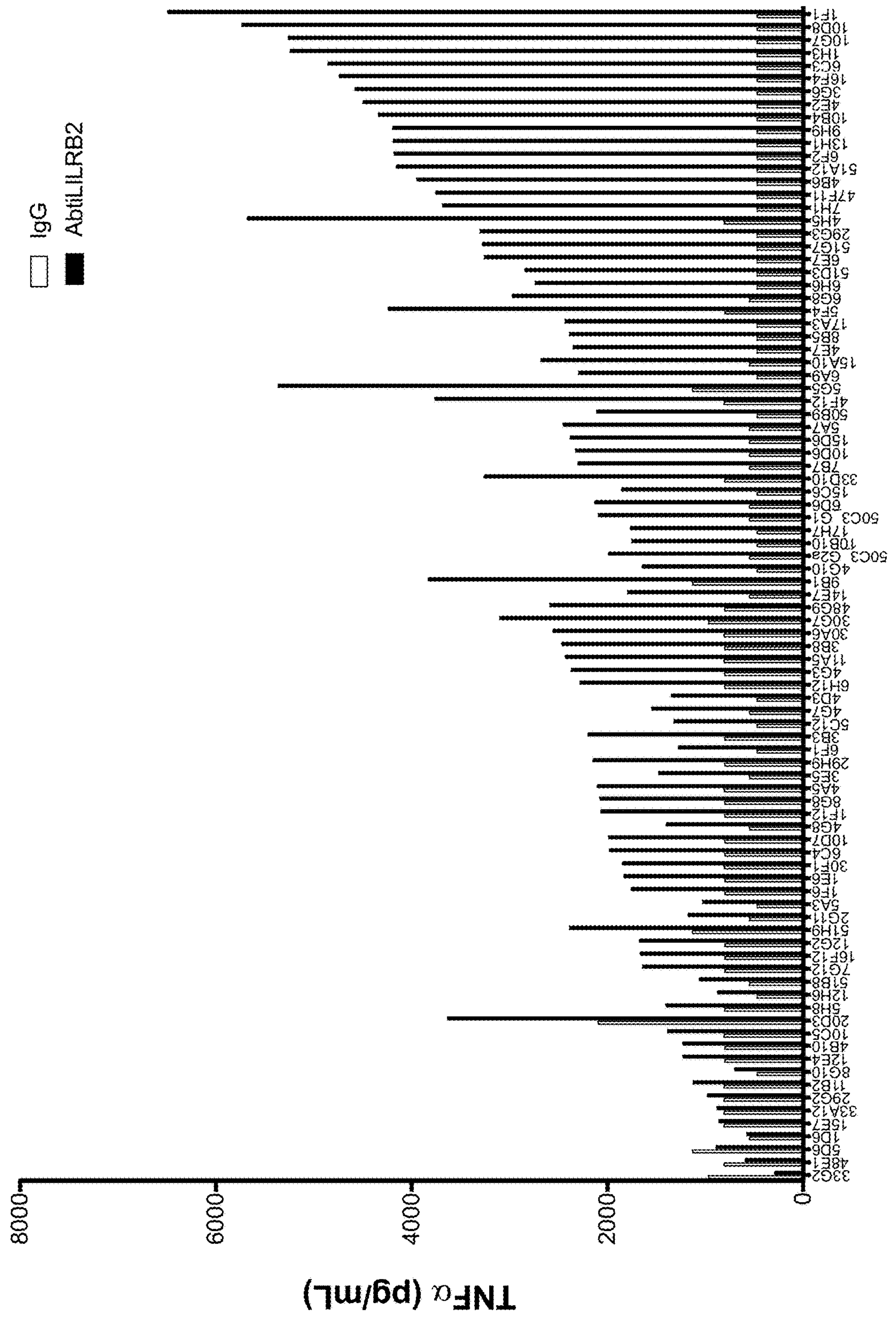
Figure 1C:
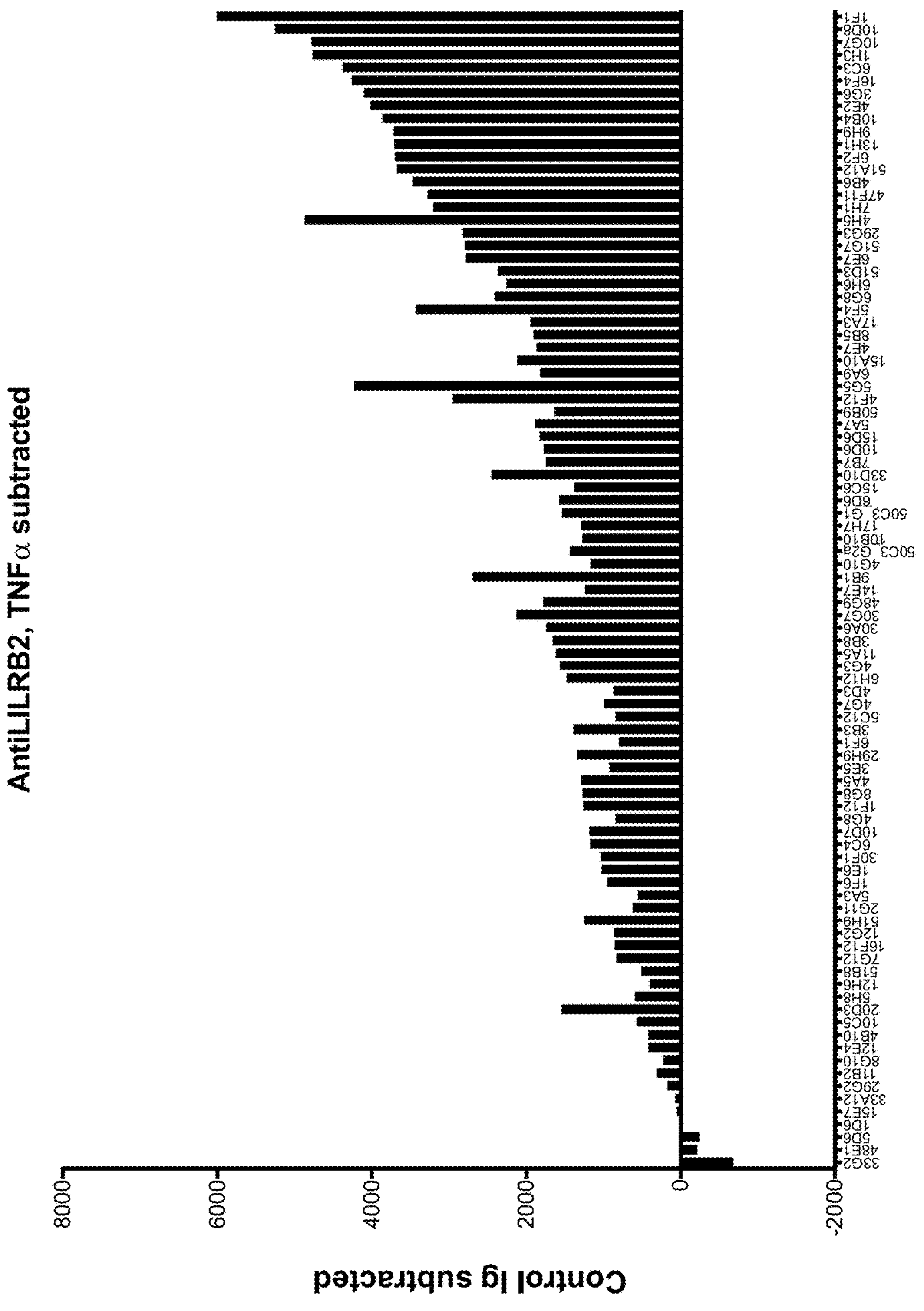

Total peripheral blood mononuclear cells (PBMC) obtained from healthy donors were incubated with anti-LILRB2 purified antibodies (5 μg/ml), or isotype control overnight for 16 hours following stimulation with LPS (50 ng/ml) for 24 hours. Supernatants were collected and TNF alpha concentrations were measured by ELISA (FIG. 1). Isotype treatment was used as a control. Anti-LILRB mAbs were ranked in order of clones that suppress TNF alpha release to those that enhance TNF alpha secretion by the relative fold change in TNF alpha release (FIG. 1A). The raw data of TNF alpha release is presented in FIG. 1B. The overall difference in TNF alpha levels from FIG. 1B is presented in FIG. 1C.

Raw data for Example 2 are provided in Table 3 and Table 4.

Example 3

Anti-LILRB2 Antibodies Modulate IL-10 Production In Vitro.

Figure 2A:
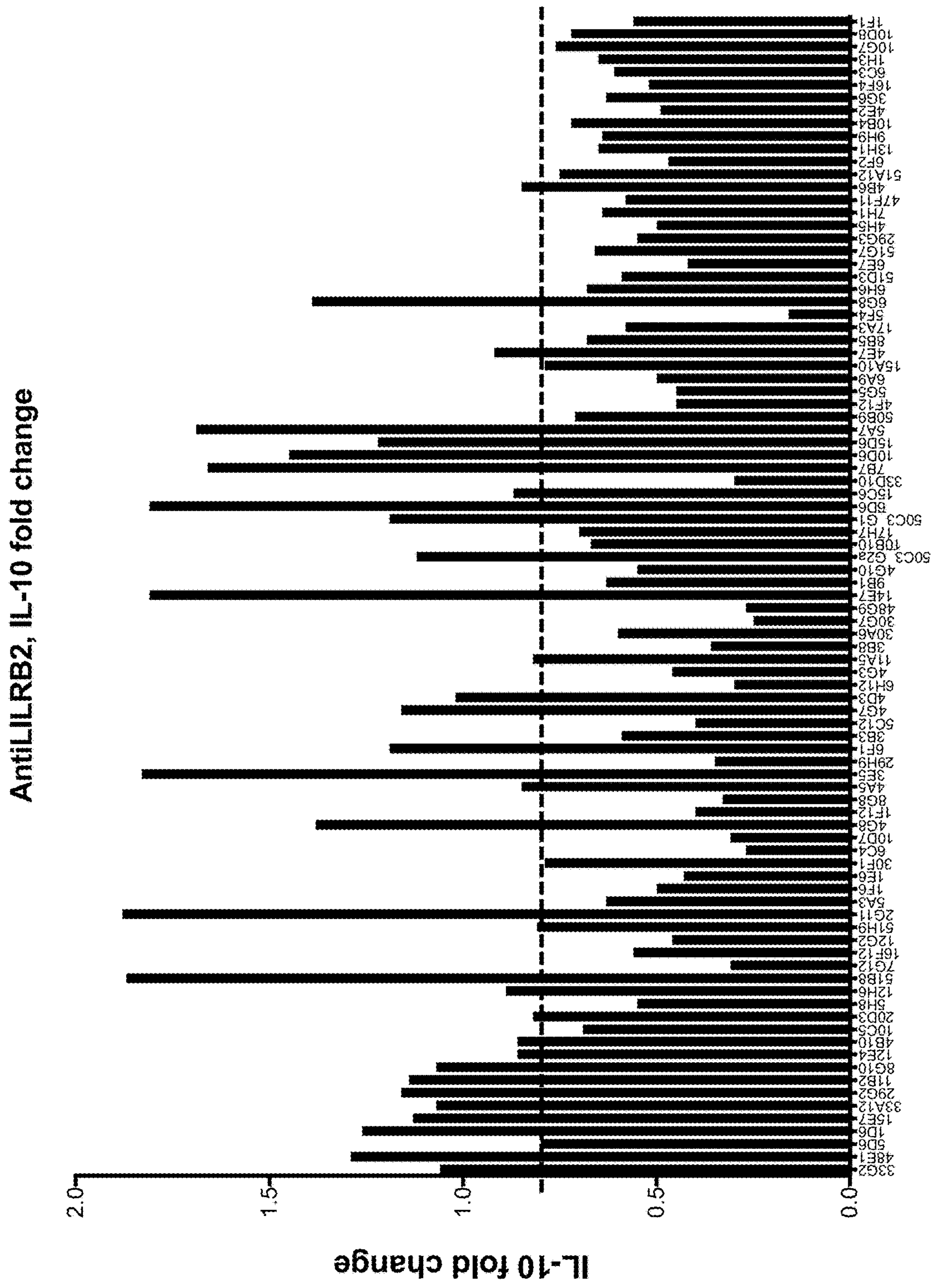
FIGS. 2A-2C: The effect of anti LILRB2 on IL-10 production from human PBMC.
Figure 2B:
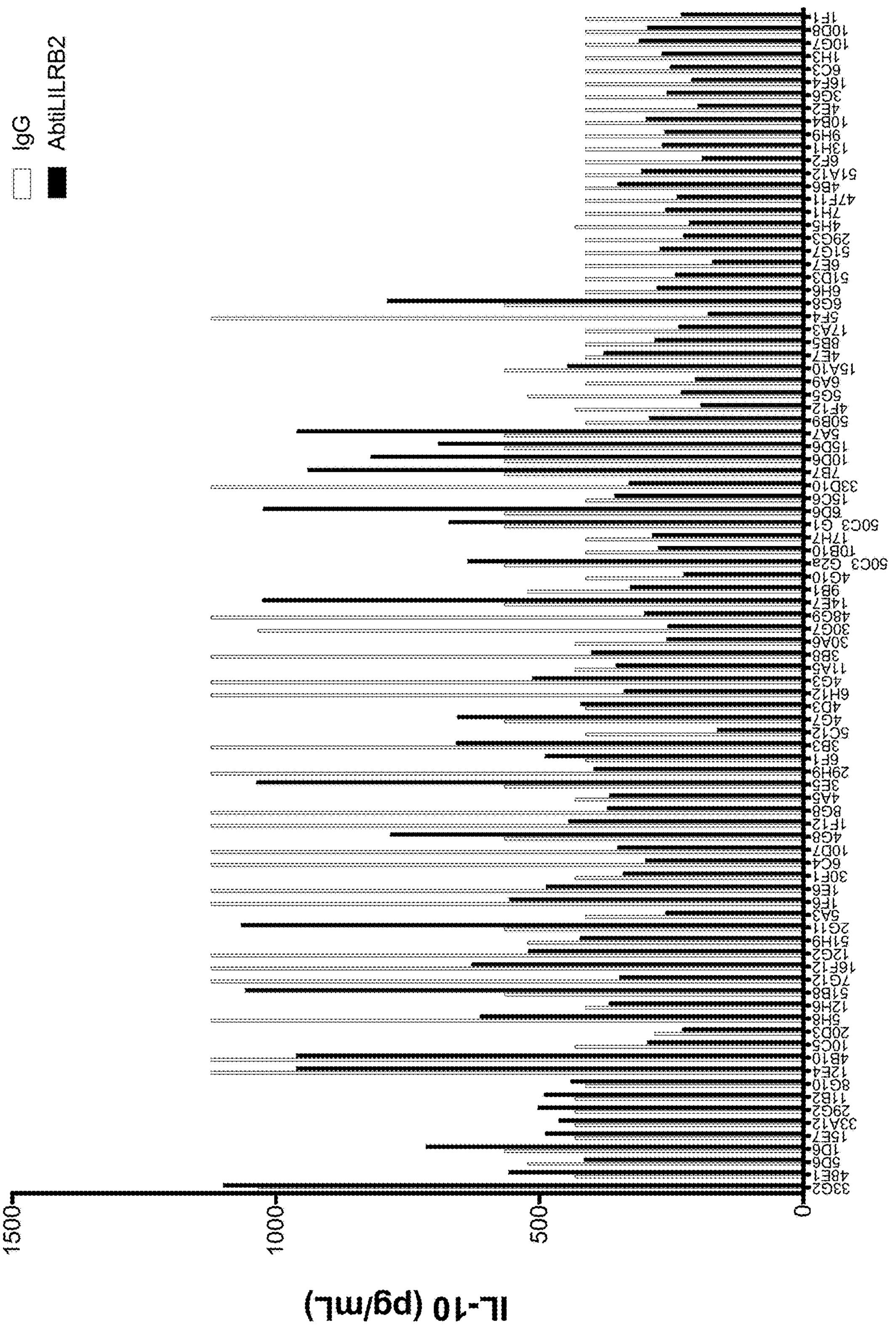
Figures 2, 3C:
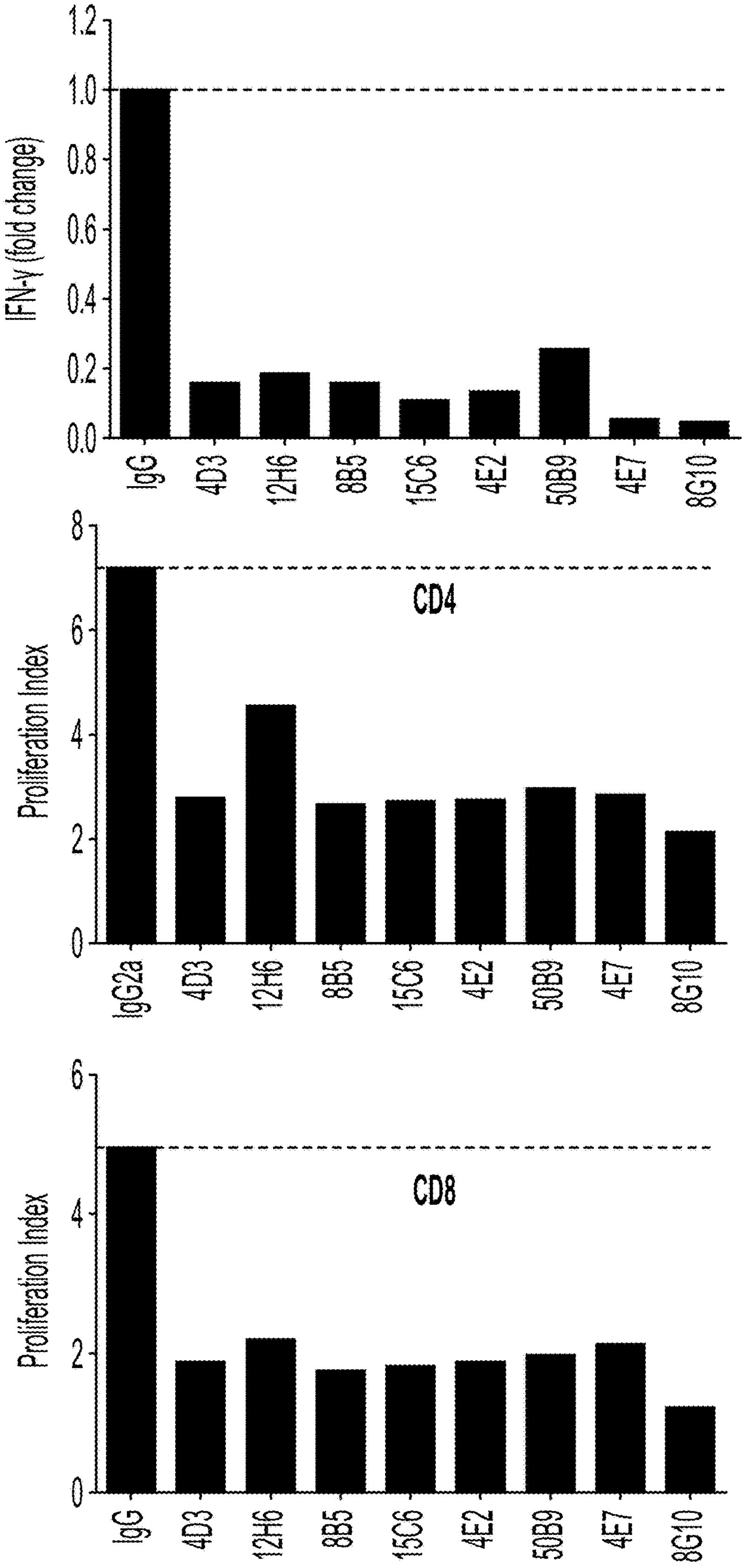

Total peripheral blood mononuclear cells (PBMC) obtained from healthy donors were incubated with anti-LILRB2 purified antibodies (5 μg/ml), or isotype control overnight for 16 hours following stimulation with lipopolysaccharide (LPS) (50 ng/ml) for 24 hours. Supernatants were collected and IL-10 concentrations were measured by ELISA (FIG. 2). Isotype treatment was used as a control. Anti-LILRB mAbs were ranked in order of clones that suppress IL-10 release to those that enhance IL-10 secretion by the relative fold change in IL-10 release (FIG. 2A). The raw data of IL-10 release is presented in FIG. 2B. The overall difference in IL-10 levels from FIG. 1B is presented in FIG. 2C.

Raw data for Example 3 is provided in Table 3 and Table 4.

The Effect on the Anti-LILRB2 on M1/M2 Differentiation

Figure 2D:
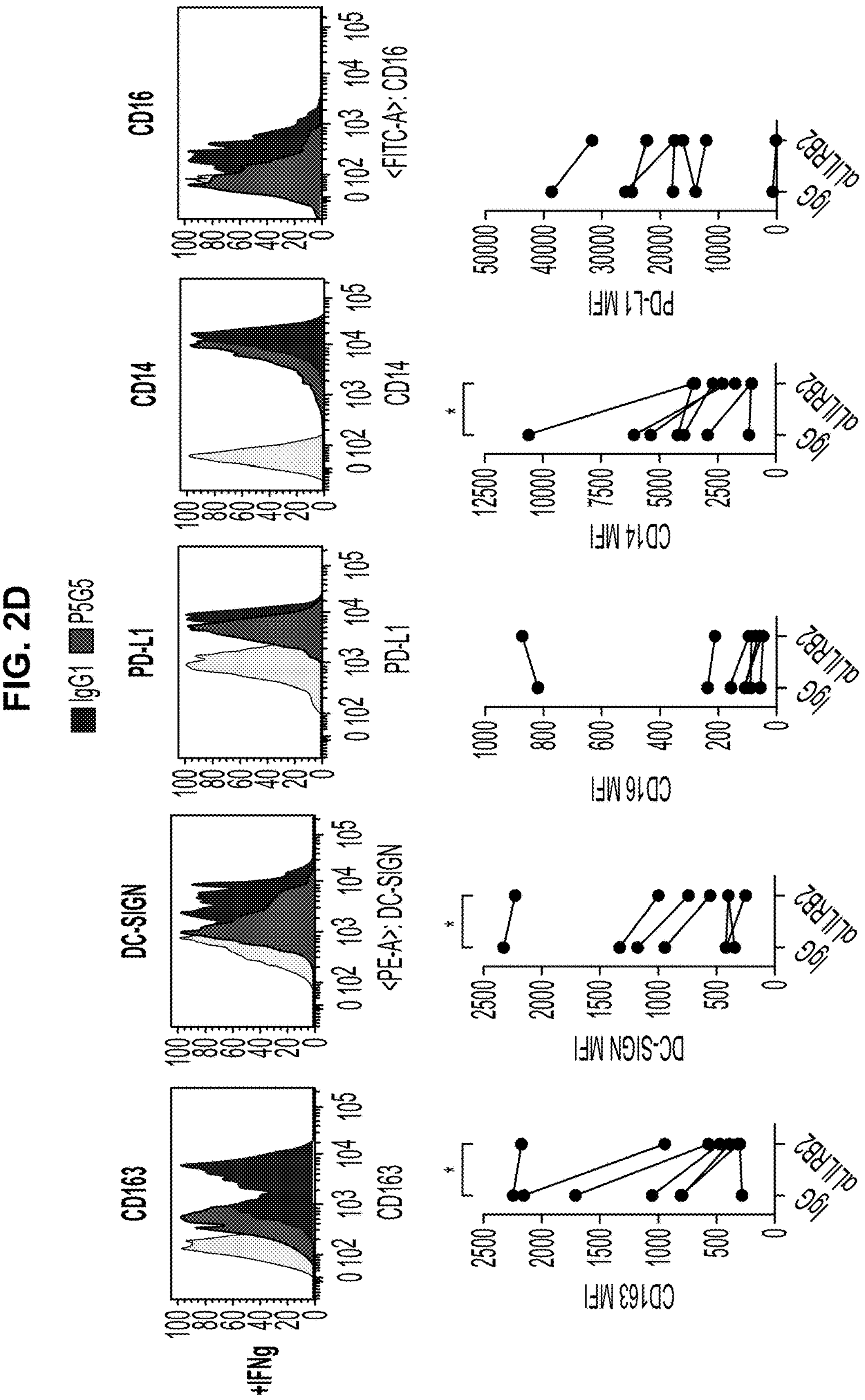
FIG. 2D: The effect of anti LILRB2 on M1/M2 differentiation/TAM markers from monocyte-derived macrophages (Antagonist).

FIG. 2D presents the flow cytometric analysis on the effect of LILRB2 antibodies on the M1/M2 markers of tumor-associated macrophages from multiple lung cancer patients. Tumor infiltrated lymphocytes were isolated and treated with LILRB2 antagonistic antibody (P_5G5) for 2 days in the presence of IFNgamma. The test cells were harvested for cytometric analysis (FIG. 2D, upper panel); the statistical analysis on multiple patients is shown in FIG. 2D, lower panel.

Figure 2E:
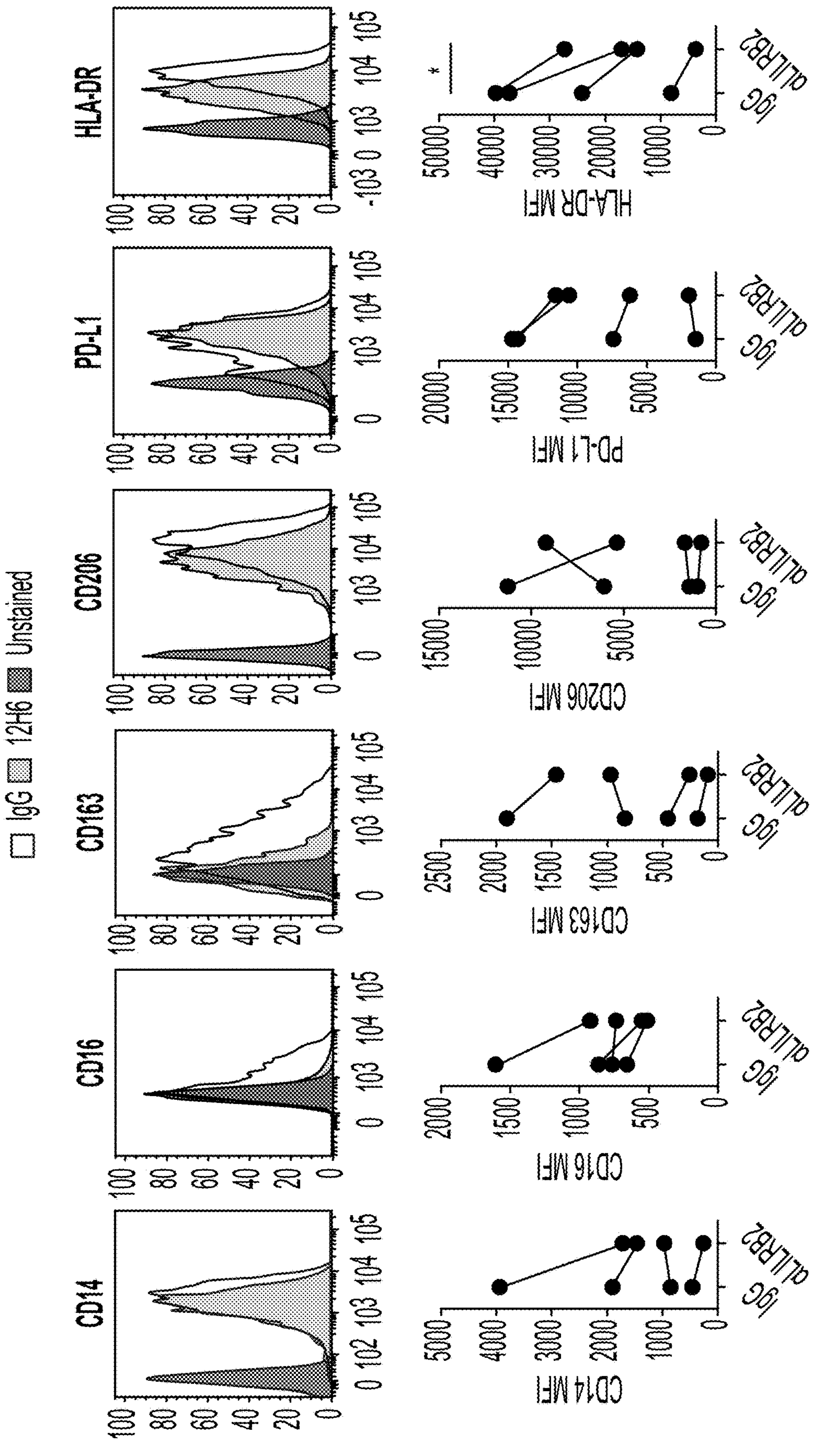
FIG. 2E: The effect of anti LILRB2 on M1/M2 differentiation/TAM markers from monocyte-derived macrophages (Agonist).

FIG. 2E shows the flow cytometric analysis on the effect of LILRB2 antibodies on the M1/M2 markers in multiple healthy donors. M1-type macrophages were differentiated from $CD33^+$ myeloid cells sorted from healthy donor in the presence of GM-CSF 100 ng/ml and agonistic anti-LILRB2 Ab (12H6, 5 μg/ml) for 6 days and IFNgamma (25 ng/ml) and LPS (25 ng/ml) for the last 24 hours. The test cells were harvested for cytometric analysis (FIG. 2E, upper panel); the statistical analysis on multiple healthy donors is shown in FIG. 2E, lower panel.

Figure 2F:
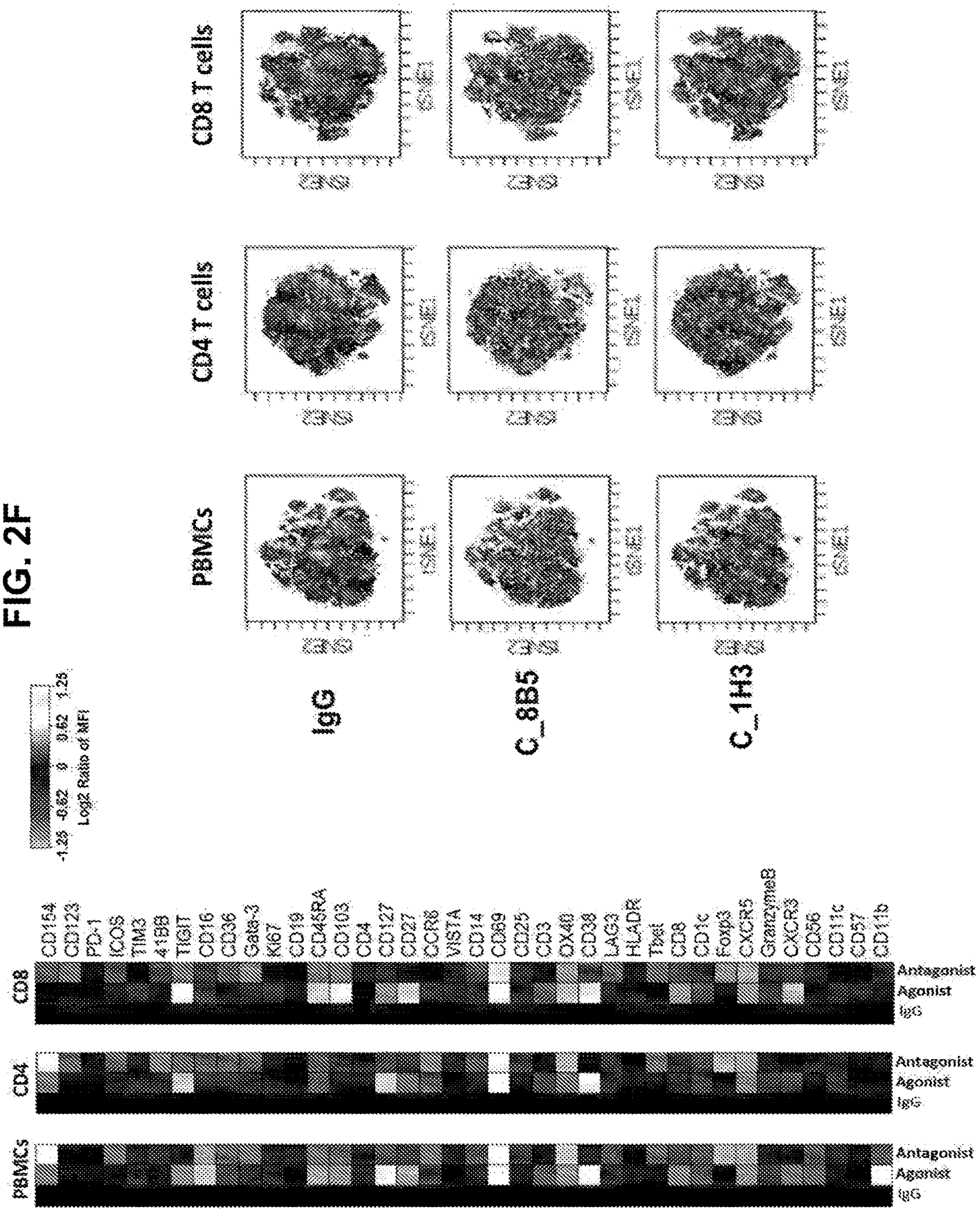
FIG. 2F: Mass cytometry analysis of anti-LILRB2 treated PBMCs stimulated with anti-CD3.

FIG. 2F shows the mass cytometry analysis of antagonistic and agonistic LILRB2 antibodies on OKT3-stimulated PBMCs from multiple healthy donors. PBMCs were obtained from healthy donors and treated with purified LILRB2 antagonistic (C_1H3) and agonistic (C_8B5) antibodies (5 μg/ml) or isotype control overnight for 16 hours following stimulation with OKT3 (0.01 μg/ml) for 3 days. The test cells were harvested for cytometric analysis (see heat map in FIG. 2F, left panel and Disney figure, Right panel). FIG. 2F, left panel represents the heatmaps showing the expression of the indicated markers in the immune cells subsets (PBMC, CD4 and CD8 T cells). FIG. 2F, right panel represents t-SNE map displaying data on subsets of $1\times10^6$ PBMCs, CD4 and CD8 T cells analyzed with our 38-antibody panel and colored by marker expression normalized based on IgG control.

Example 4

Anti-LILRB2 Antibodies Modulate T Cell Proliferation and IFN Gamma Secretion In Vitro.

Figure 3D:
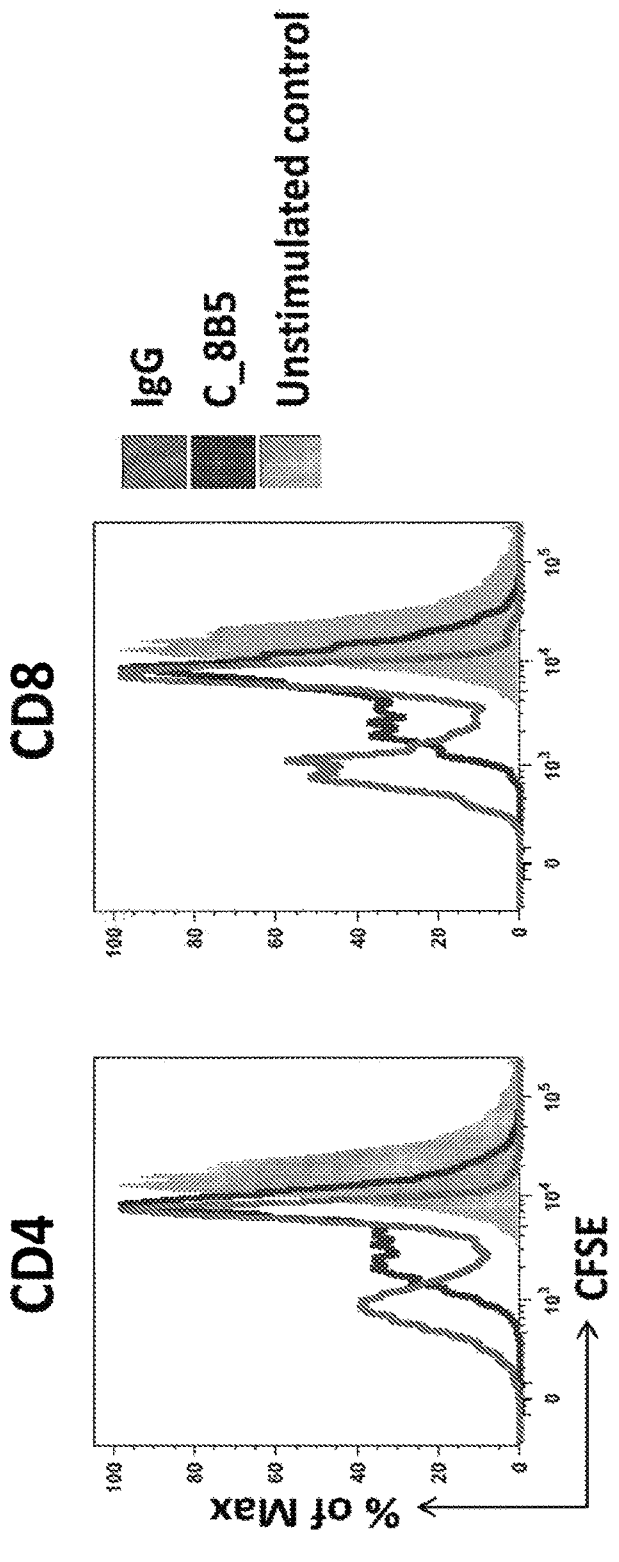
FIG. 3D: The effect of anti LILRB2 on T cell proliferation in MLR.

PBMCs were cultured with LILRB2 antagonistic antibodies overnight (16 hours) and stimulated with a low dose (0.01 μg/ml) of anti-CD3 (OKT3) for 3 days. After 3 days of treatment, [$^3$H]-thymidine was added for the last 8 hours of culture followed by measurement on a scintillation counter. T-cell proliferation (CPM) is shown in FIG. 3A. Supernatants were collected from the samples of FIG. 3A and IFN-γ concentrations were measured by ELISA (FIG. 3B). Isotype treatment was used as a control. FIGS. 3C-3D present the flow cytometric data from cultured human PBMCs (responders) labeled with CFSE, and stimulated with irradiated (30 Gy) unrelated donor PBMCs (stimulators) in the presence of IgG isotype control or the indicated LILRB2 antibodies (5 μg/ml). The ratio of responder/stimulator was 1/2. After 5 days of co-culture, viable CD4 T cells (left panel) and CD8 T cells (right panel) were analyzed by flow cytometry. The representative flow plots were shown as CFSE dilution and percent divided cells.

Anti-LILRB2 Antibodies Modulate IFN Gamma Release In Vitro.

PBMC were cultured with LILRB2 antagonistic antibodies overnight (16 hours) and stimulated with a low dose (0.01 μg/ml) anti-CD3 (OKT3) for 3 days. Supernatants were collected from the samples of FIG. 3A and IFN-γ concentrations were measured by ELISA (FIG. 3B). Isotype treatment was used as a control.

Anti-LILRB2 Antibodies Inhibited Allogeneic T Cell Proliferation In Vitro.

CFSE-labeled PBMCs were cultured with LILRB2 agonistic antibodies overnight (16 hours) and stimulated with a low dose (0.01 μg/ml) anti-CD3 (OKT3) for 3 days (FIG. 3C). After 3 days of culture, viable CD4 T cells (FIG. 3C, left panel) and CD8 T cells (FIG. 3C, middle panel) were analyzed by flow cytometry. The representative flow plots are shown as CFSE dilution of CD4 and CD8 T cells (FIG. 3C, left and middle panels) and proliferation index (FIG. 3C, right middle for CD4 cells and right lower panel for CD8 cells). Supernatants were harvested for IFNgamma detection shown in FIG. 3C, right upper panel.

OKT3-mediated T cell proliferation and IFN gamma secretion was strongly suppressed by agonistic clones, whereas antagonistic clones enhanced IFNgamma production and proliferation or exerted no effect on different healthy donors (FIGS. 3A-3B). Furthermore, the LILRB2 agonistic antibodies mediated suppression of mixed lymphocyte reactions (MLR) (FIG. 3D).

AntiLILRB2 can Inhibit the Proliferation of Cancer Cells of Multiple Cancer Types.

The inventors further tested the effect of LILRB2 mAbs on myeloid leukemia cell proliferation. The proliferative activity of U937 and HL60 cells was inhibited by antagonist clones.

Example 5

Proliferation of Leukemia Cells was Suppressed by Anti-LILRB2 Antibodies.

Figure 4A:
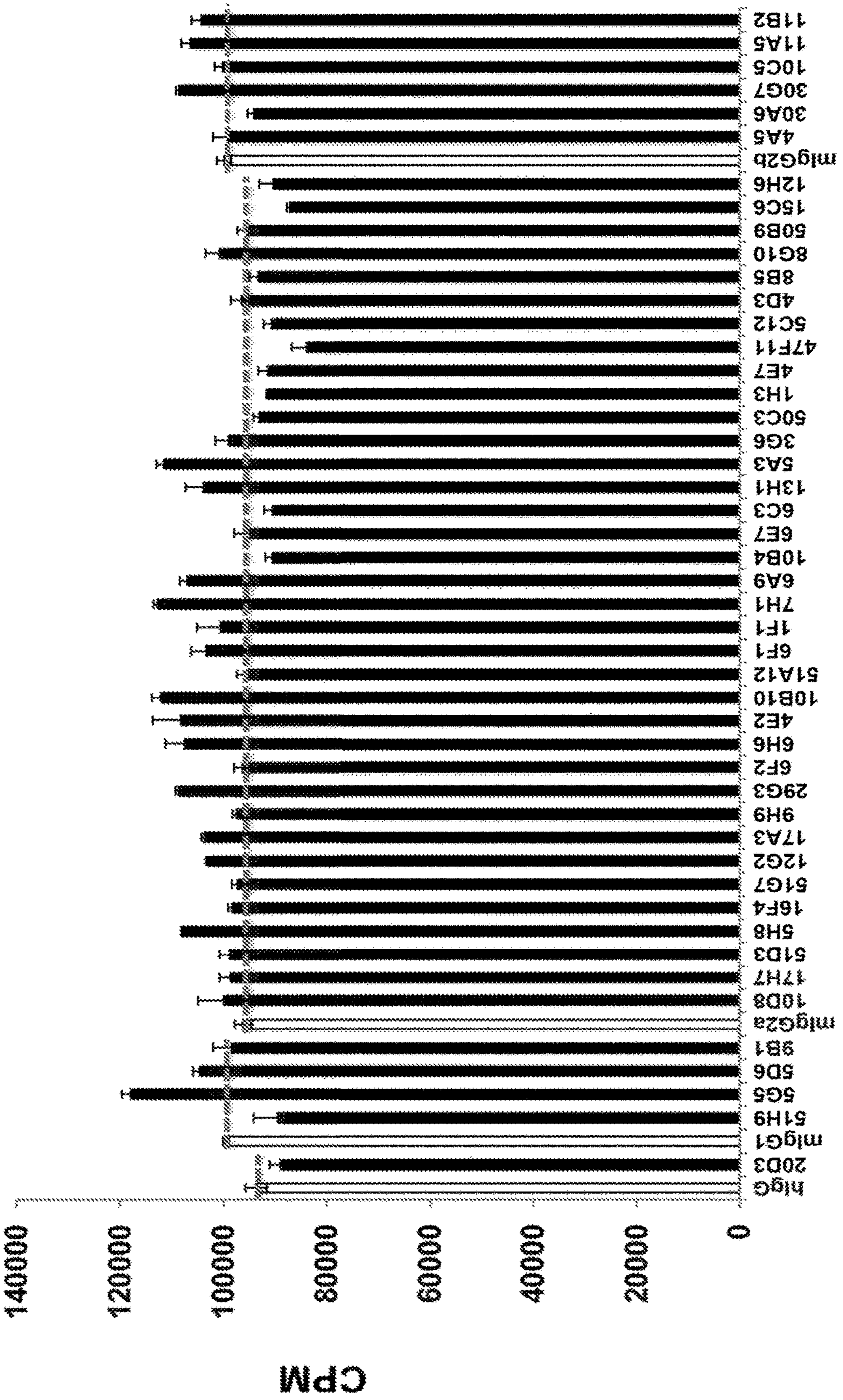
FIG. 4A: The effect of anti LILRB2 on human myeloid leukemia cell, THP-RB2, proliferation.

LILRB2-transduced U937 leukemia cells were treated with control Ig or anti-LILRB2 mAbs (5 microgram) for 42 days. U937 cell proliferation was assessed by [$^3$H]-thymidine incorporation. Cells were pulsed with [$^3$H]-thymidine for the last 8 hours of culture. The proliferation of LILRB2+ THP-1 cells (CPM) is shown in FIG. 4A.

Proliferation of LILRB2 Antagonistic Clones on Breast Cancer Cells

Figure 4B:
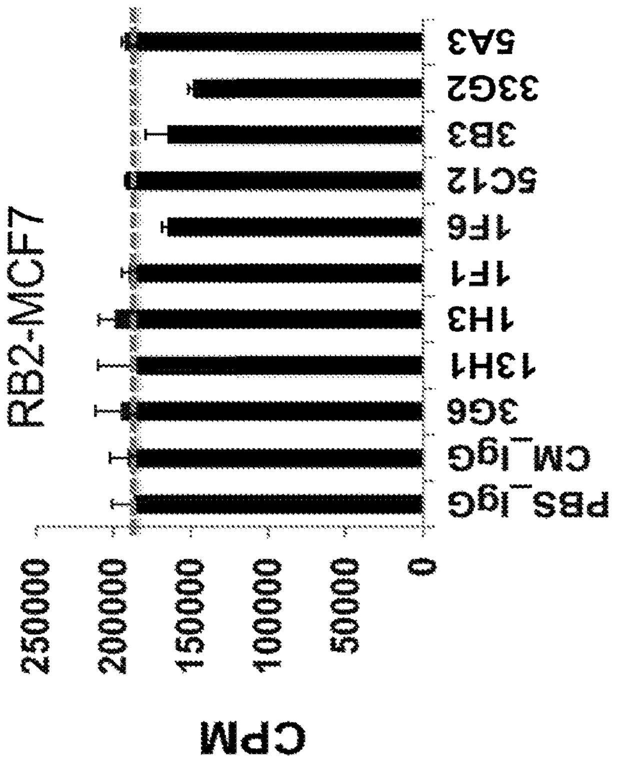
FIG. 4B: The effect of anti LILRB2 on human solid cancer, MCF7 proliferation.

LILRB2-transduced human breast cancer cells (MCF7) were treated with anti-LILRB2 antibody (5 μg/ml), or isotype control for 4 days. LILRB2+MCF7 cell proliferation was assessed by [$^3$H]-thymidine incorporation. Cells were pulsed with [$^3$H]-thymidine for the last 8 hours of culture. The proliferation of LILRB2+MCF7 cells (CPM) is shown in FIG. 4B.

Example 6

LILRB2 Antagonists Inhibit the Migratory Ability of LILRB2+MDAMB231 Breast Cancer Cells.

Figure 5B:
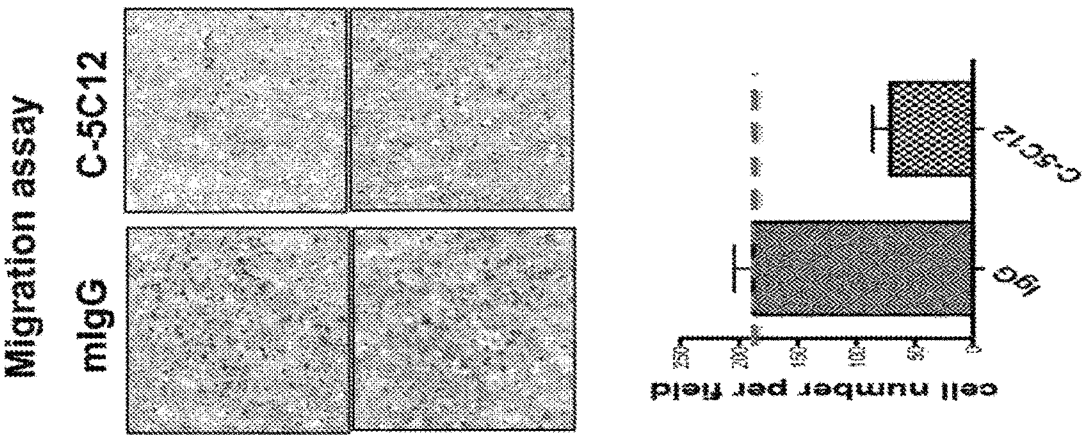
FIGS. 5A-5B: AntiLILRB3 decreases the migration of RB3+ breast cancer cells.
Figure 5A:
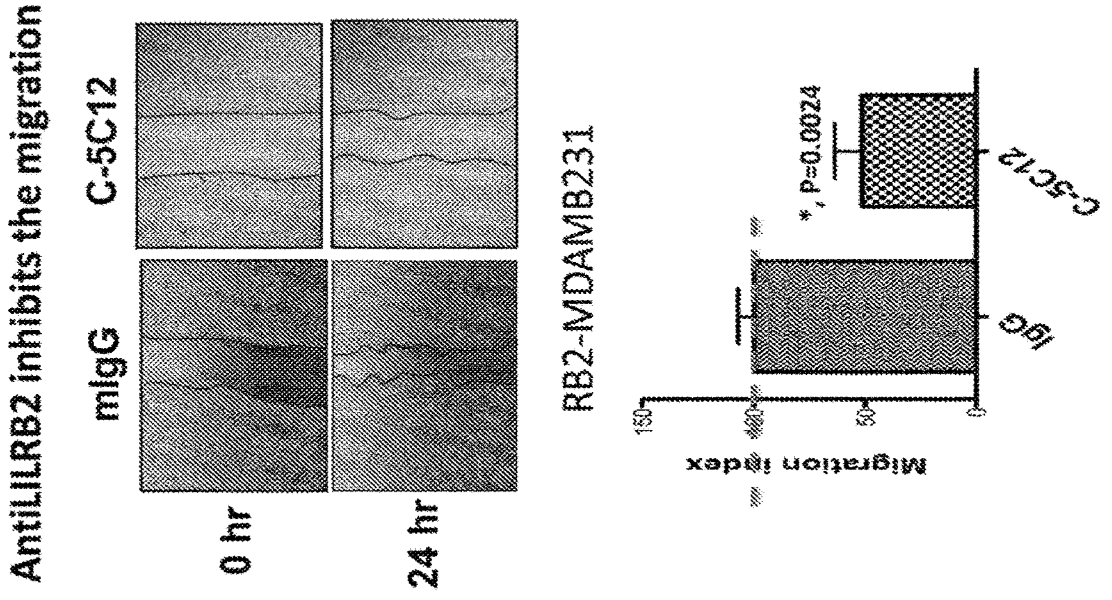

The migratory ability of LILRB2+MDAMB231 breast cancer cells was substantially inhibited by antagonistic clone C_5C12 at 5 microgram/ml concentrations by scratch assay (FIG. 5A) and transwell assay (FIG. 53).

Example 7

Figure 6A:
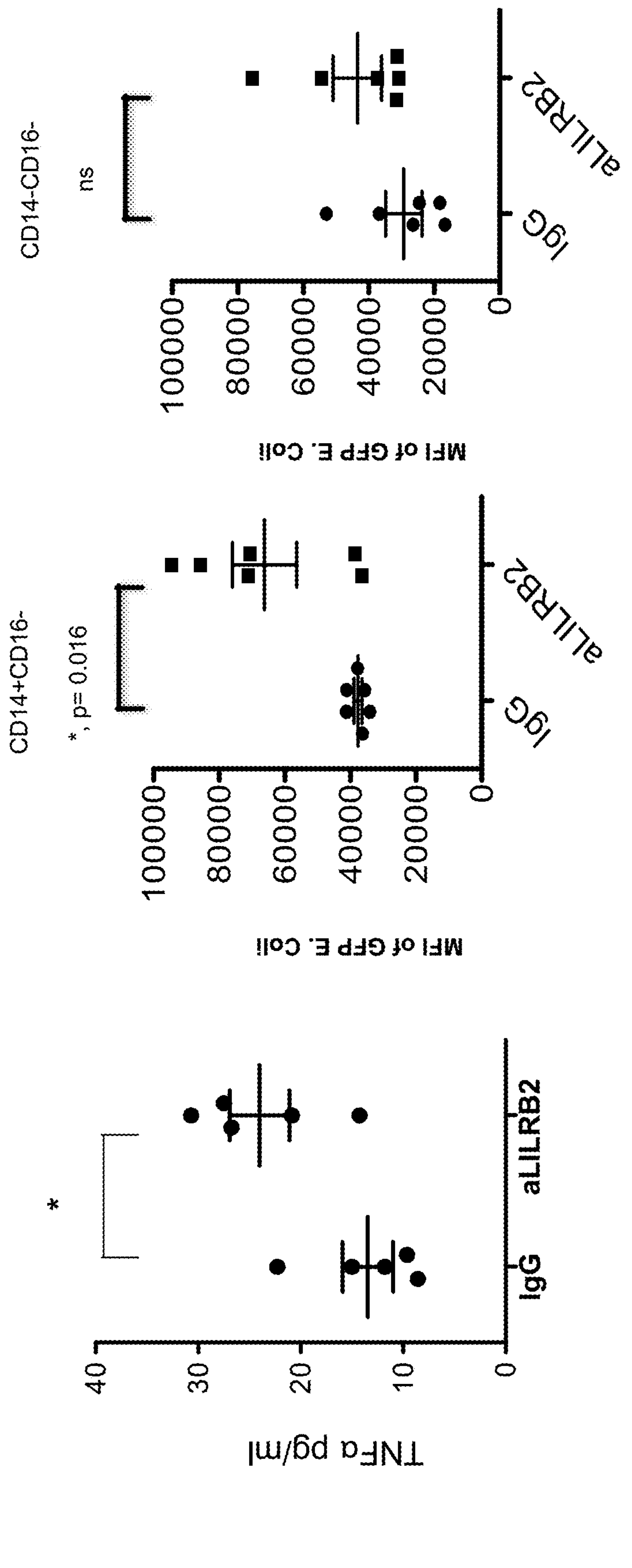
FIG. 6A: Antagonistic anti-LILRB2 enhance Vaccine adjuvant effect (CpG) and bacterial opsonization/phagocytosis.

Antagonistic Anti-LILRB2 Antibody Enhances Vaccine Adjuvant Effect (CpG) and Bacterial Opsonization/Phagocytosis MISTRG mice were intravenously injected with IgG control or LILRB2 antagonistic antibody (P_5G5) (150 μg/mouse) for two days, and then intraperitoneally challenged with 5 nmol. After 2 hours, the sera were collected from test mice and subjected to ELISA analysis for TNFα levels (FIG. 6A, left panel).

Humanized MISTRG mice were intraperitoneally injected with LILRB2 antagonistic antibody (P_5G5) or control Ig (150 μg/mouse) for 48 hours. Peripheral blood cells were isolated and incubated with *E. coli* expressing GFP at the ratio of $2\times10^8$ *E. Coli* per $1\times10^7$ peripheral blood cells for 4 hours at 37° C. The cells were harvested and washed with PBS and analyzed by gating on viable CD45$^+$ CD33$^+$ population. The result showed that antagonistic LILRB2 antibody (P_5G5) strongly enhanced systemic response to CpG challenge and enhanced phagocytic activities of macrophages (FIG. 6A, right panel).

The LILRB2 Antagonist Inhibits the Growth of Cancer Cells In Vivo.

Figure 6B:
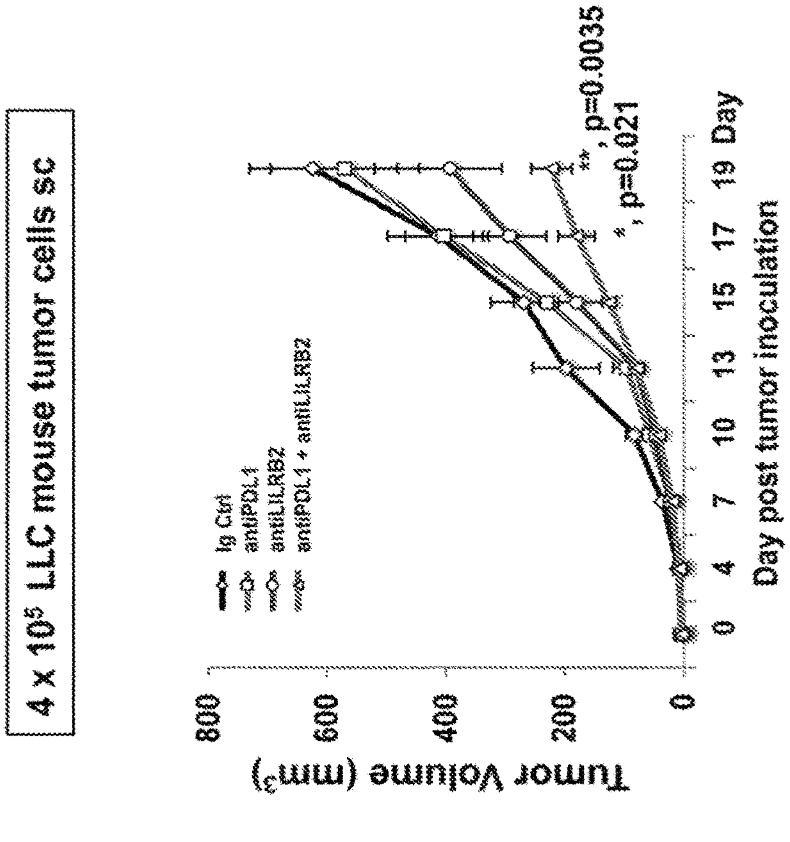
FIG. 6B: The tumor growth of mouse and human lung cancer cells were inhibited by antagonistic antiLILRB2 in tumor models.
Figure 6C:
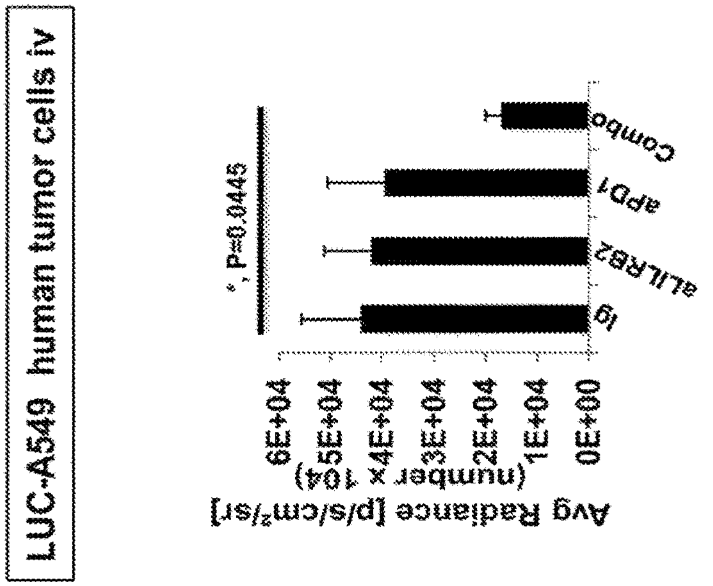
FIG. 6C: The tumor growth of mouse and human lung cancer cells were inhibited by antagonistic antiLILRB2 in tumor models.

The inventors further evaluated the anti-tumor effect of anti-LILRB2 mAb on LILRB2 transduced THP-1 leukemia cells in xenograft mouse models. We tested the anti-tumor effect of anti-LILRB2 mAb (clone P_5G5) with and without anti-PDL1 antibody treatment, and found that the antagonistic clone P_5G5 synergized anti-tumor effect of anti-PDL1 in vivo (FIG. 6B). Furthermore, the anti-tumor effect of LILRB2 antagonistic antibodies (P_5G5) inhibited the tumor growth of Luciferase-expressed-A549 in HLA-A2 matching humanized NCG mice model when combined with anti-PD-1 (FIG. 6C). These data suggest that LILRB2 antagonistic antibodies can promote myeloid differentiation and inhibit the tumor growth (FIG. 6C).

Example 8

Figures 7A, 7B, 7C:
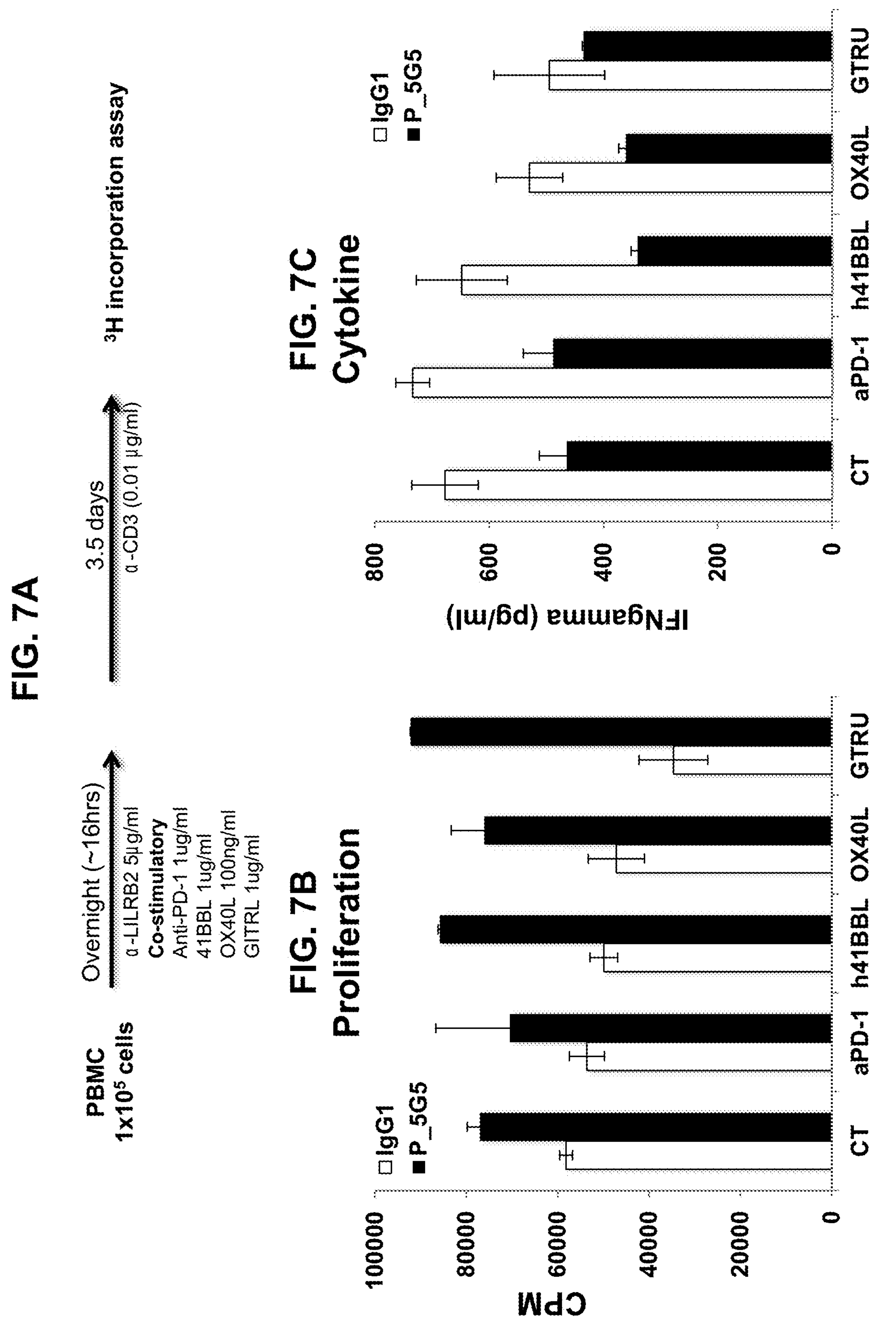
FIGS. 7A-7C: The synergistic effect of antiLILRB2 with co-stimulatory molecules.
Figure 8A:
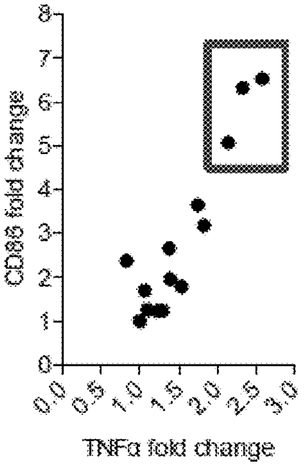
FIGS. 8A-FIG. 8E. Anti-LILRB2 antibodies enhance LPS response in primary human monocytes.
Figure 8B:
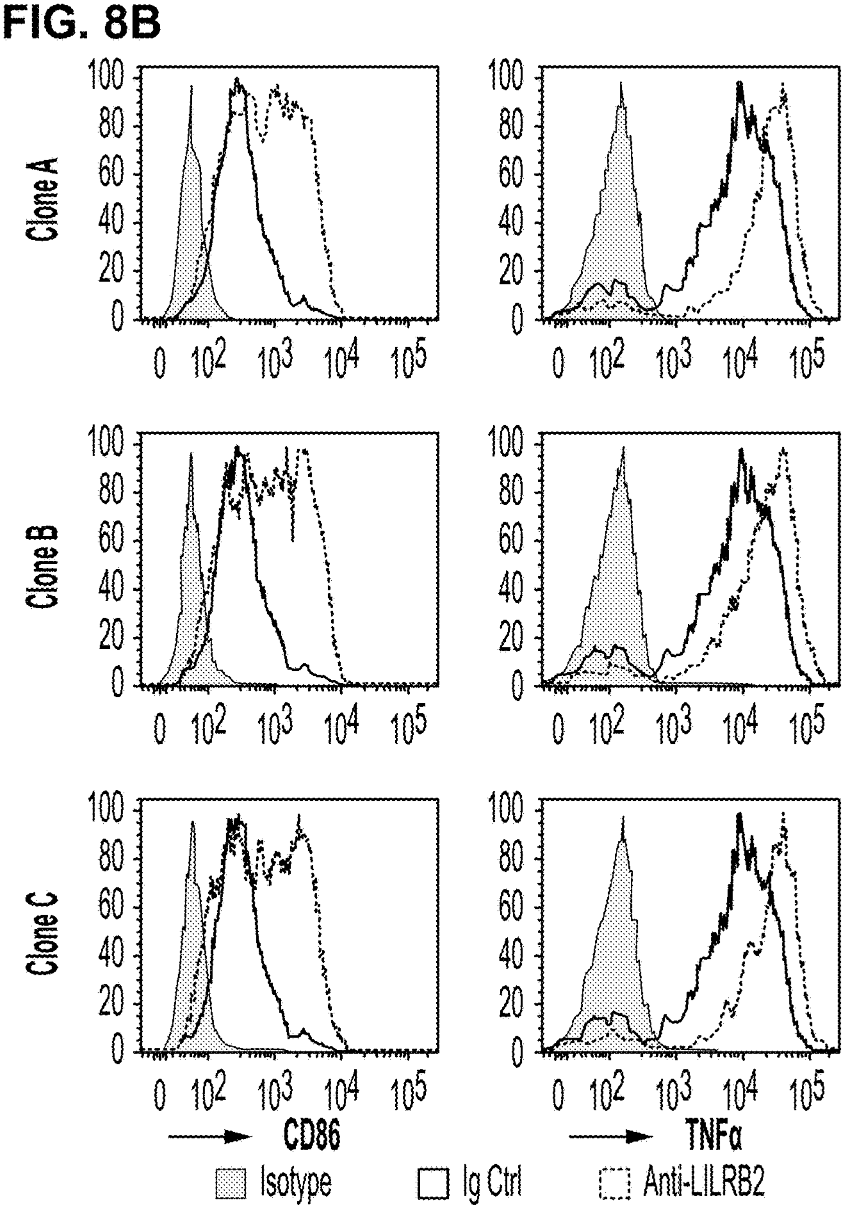
Figures 1, 8C:
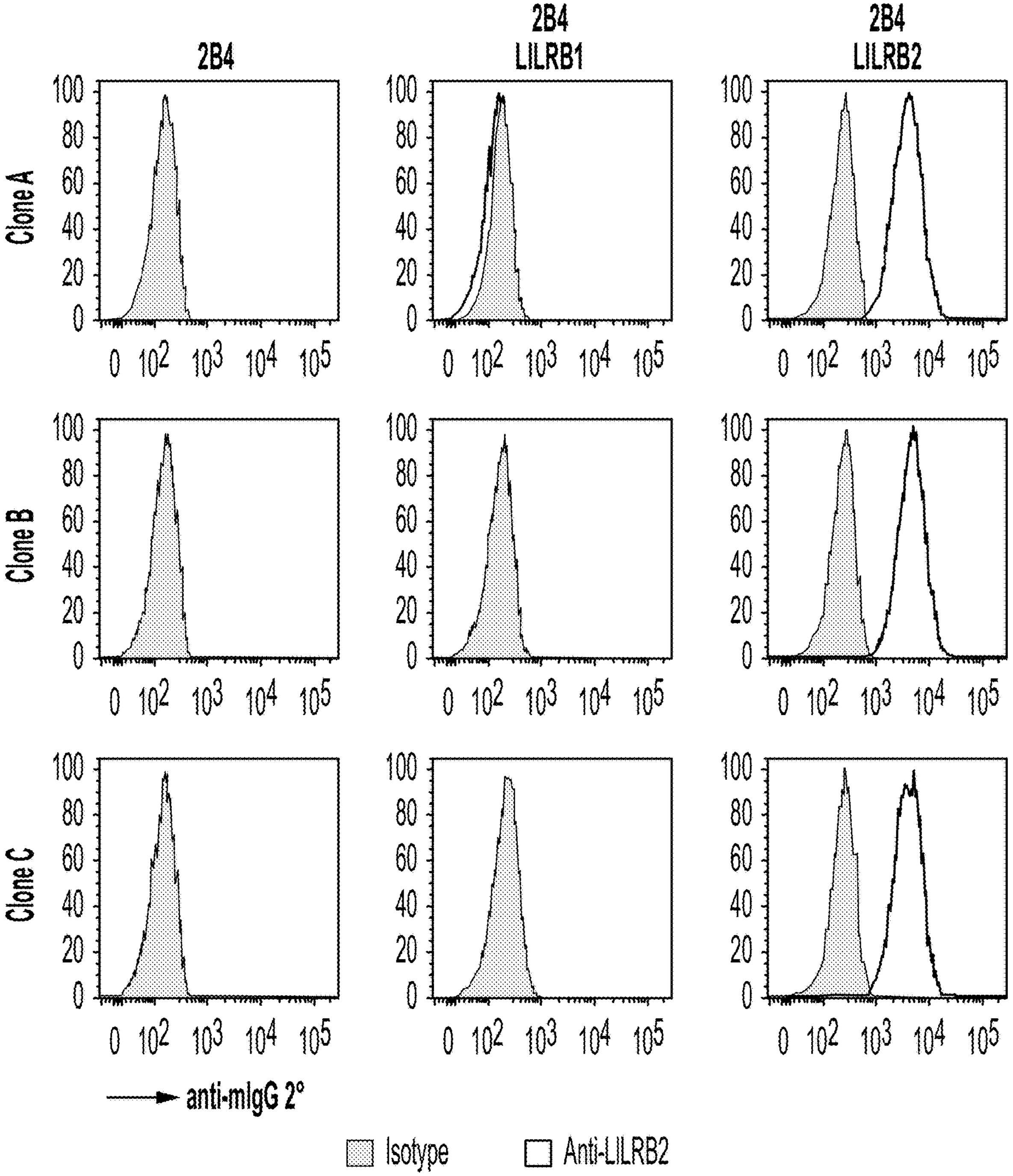
Figures 2, 8C:
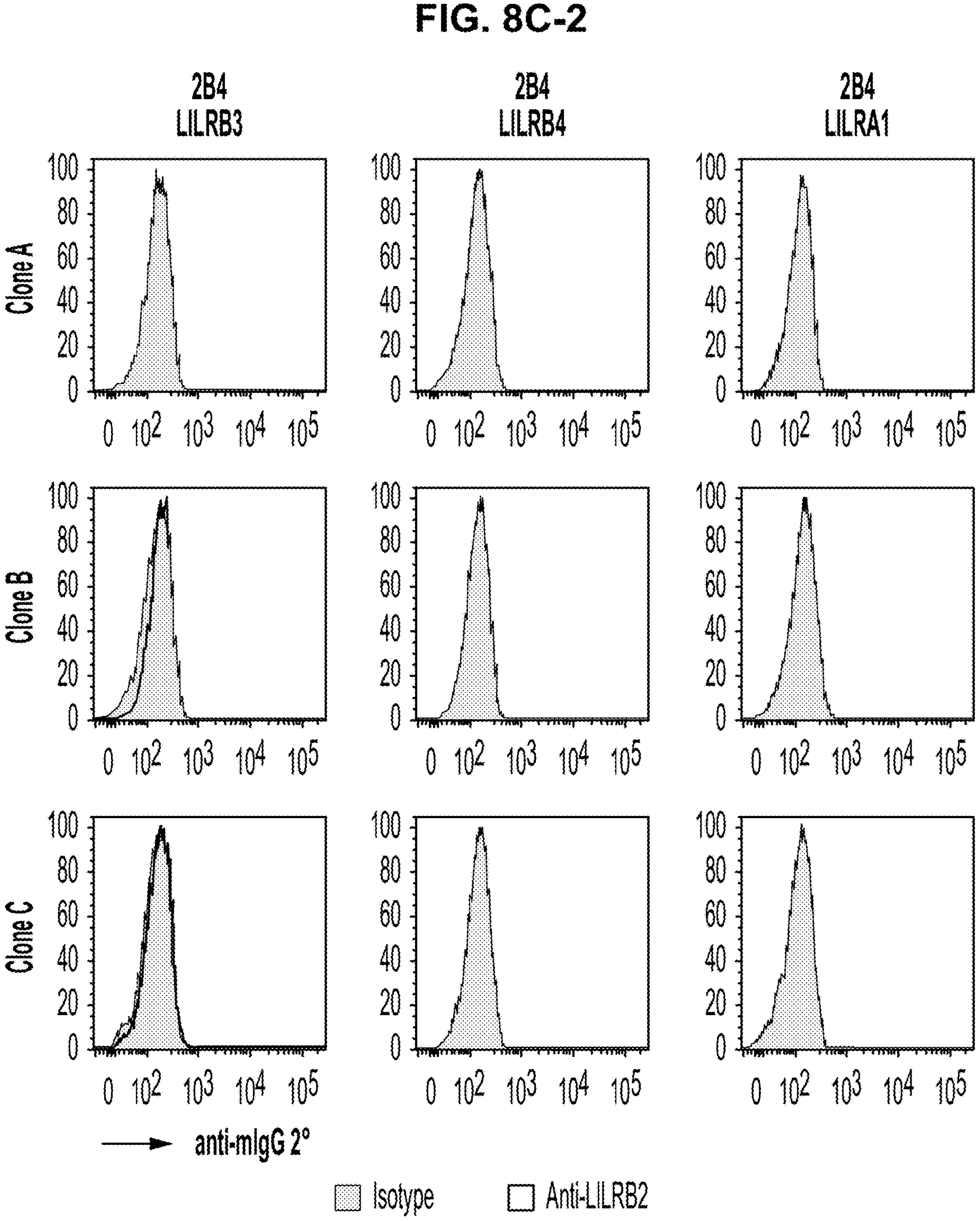
Figure 8D:
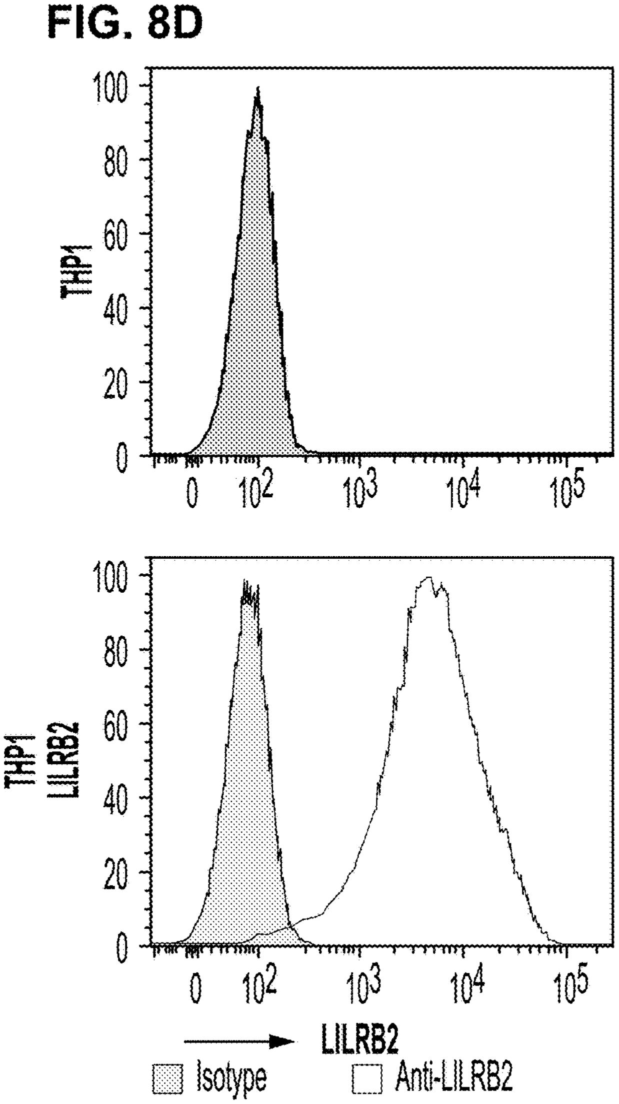
Figure 8E:
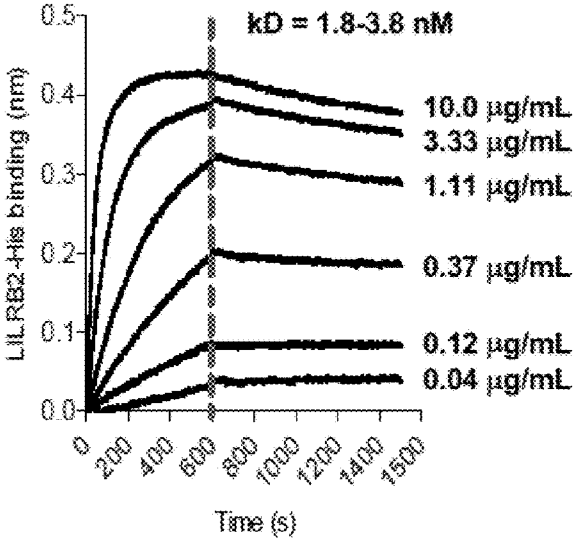

The Co-Stimulatory Effect of Anti-LILRB2 Antibody on Human PBMC Proliferation $1\times10^5$ total PBMC from healthy donors were cultured with stimulated with anti-LILRB2 Abs (5 μg/ml) in the presence of 1 μg/ml anti-PD-1 antibody, 1 μg/ml 4-1BBL, 100 ng/ml OX40L, or 1 μg/ml GITRL overnight (16 hours) and subsequently with a low dose of anti-CD3 (OKT3, 0.01 μg/ml) for 3 days (FIG. 7A). After 3 days of treatment, T cell proliferation was assessed by [$^3$H]-thymidine incorporation. Thymidine was added for the last 8 hours of culture followed by measurement on a scintillation counter. The effect on T cell proliferation (CPM) is shown in FIG. 7B. Supernatants were harvested for detection of interferon gamma production shown in FIG. 7C.

Example 9: Blocking Immunoinhibitory Receptor Lilrb2 Reprograms Tumor-Associated Myeloid Cells and Promotes Antitumor Immunity Introduction Macrophages not only mediate inflammation during infection but also suppress immunity during inflammation resolution (1) and promote immune escape within tumor microenvironments (2). The functional plasticity of macrophage phenotypes is largely influenced by the surrounding milieu. Viruses and bacteria activate toll-like receptor signaling to drive NFκB and favor macrophage release of iNOS, TNFα, and IL12 to support Th1 immunity while Th1-associated IFNγ activates STAT1 to support effector T cell responses. Conversely, humoral cytokines IL4/IL13 and IL10 secreted from tumor cells stimulate macrophages to release IL10, TGFβ, and Arginase 1. Simultaneous activation of STAT6, STAT3, and matrix proteases further support tissue remodeling and 7b2 immunity (3). Whether, and how, to target maturation pathways to control the plasticity of myeloid cell differentiation and macrophage phenotypes remain a challenging task for current cancer immunotherapies.

Among the myeloid receptors, paired-immunoglobulin-like receptor B (PIR-B) is the sole mouse receptor ortholog of human leukocyte immunoglobulin-like receptor B (LILRB) family (also known as ILT, LIR, and CD85) (4, 5). In B cells, Pirb deficiency results in increased BCR signaling and hyperactivity (6). Pirb-deficient macrophages similarly have increased proinflammatory cytokine release and exacerbated autoimmune diseases (7). PIR-B homeostatically suppresses immune activation by binding MHC I in cis and trans (8, 9). SHP1/2 phosphatases constitutively bind to the cytoplasmic domain of PIR-B and are hypothesized to be regulatory at steady state (10, 11). Our previous study demonstrated that PIR-B is a key regulator for maintaining the M2-like phenotype of tumor-infiltrating myeloid-derived suppressor cells (MDSC) (12). TLR and IFNγ signaling were magnified in Pirb-deficient MDSCs while IL4/IL13 and IL10 were suppressed. Mice with Pirb deficiency had reduced tumor burdens, enhanced anti-tumor responses, decreased Treg activation, and an infiltrating macrophage profile that resembled M1-like classical activation (12). Human LILRBs, similar to mouse PIR-B, bear immunoreceptor tyrosine-based inhibitory motifs (ITIM) that can attenuate signaling cascades generated from the crosslink-dependent activation of immunoreceptor tyrosine-based activating motifs (ITAM)-bearing receptors (13). However, less is known about how LILRBs regulate human myeloid cells and macrophage activation largely due to a lack of conservation between humans and mouse, with multiple LILRB family members in human instead of one PIR-B.

Expression of Lilrb1-5 is enriched in myeloid cell populations and appears to be primate-specific (14-16). LILRB3 and LILRB4 are orphan receptors (17, 18) and LILRB5 reportedly binds β2m-free heavy chains of HLA-B27 (19). LILRB1 and LILRB2 are the best-characterized receptors as both bind to classical and non-classical HLA-class I (17, 20) with a low binding affinity (Kd=14~45 μM for LILRB2) as well as to members of the angiopoietin-like protein family (21)(22). Furthermore, LILRB1 and LILRB2 may compete with CD8 for HLA-I binding to potentially modulate $CD8^+$ T cell responses (22). Activation of LILRB2 by viral expression of an HLA-B variant can promote myeloid cell tolerance and downregulate maturation and costimulatory molecule expression of dendritic cells (DC) (23). Several studies have shown that HLA-G-LILRB1/2 engagement increases IL4 and IL13, suppresses proinflammatory cytokine release, and promotes secretion of IL10 and TGFβ regulatory cytokines (24). Lower levels of LILRBs expression on DCs are correlated with enhanced antigen-presenting cell function (25). LILRB2 agonism has been shown to block DC $Ca^{2+}$-flux (17) and plays a crucial role in the tolerization of DC (26). Therefore, we hypothesized that targeting LILRB2 by antagonizing cell surface receptor-mediated activation may potentially alter the function of myeloid cells with immunosuppressive activities, i.e. MDSC or tumor-associated macrophages (TAM), toward a classically activated inflammatory macrophage phenotype.

The present study was designed to investigate whether LILRB2 is a valid and sufficient target for modulating myeloid cell functions. We generated LILRB2 specific monoclonal antibodies and found that a subset of LILRB2 antagonism altered AKT-dependent maturation of macrophages in response to MCSF, and enhanced NFκB and STAT1 activation in response to LPS/IFNγ stimuli. LILRB2 antagonism also rendered macrophages resistant to humoral cytokine-dependent STAT6 activation by IL4, relieved the suppressive effect of macrophages on T cell proliferation, and reprogrammed human macrophages from A549 lung tumor models and primary human non-small cell lung carcinoma (NSCLC). Furthermore, LILRB2 blockade changed the tumor microenvironment and promoted antitumor immunity when used in conjunction with anti-PDL1.

Our findings suggest that human LILRB2 is a critical homeostatic surface regulator for myeloid cell maturation with a great therapeutic value as a promising myeloid immune checkpoint target specifically aimed at myeloid cell functional determination. Blockade of LILRB2 can be used to reprogram TAM to improve the therapeutic outcome of cancer immune therapies through modulation of the tumor microenvironment.

Results

Figure 9A:
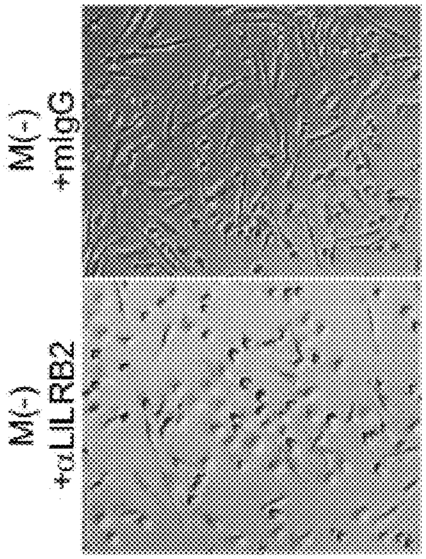
FIGS. 9A-FIG. 9I. LILRB2 antagonism generates inflammatory macrophages in the presence of MCSF.
Figure 9B:
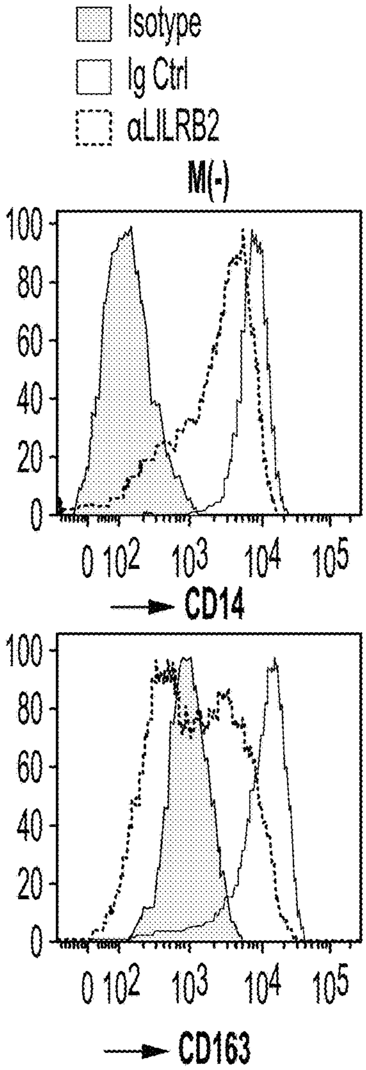
Figure 9C:
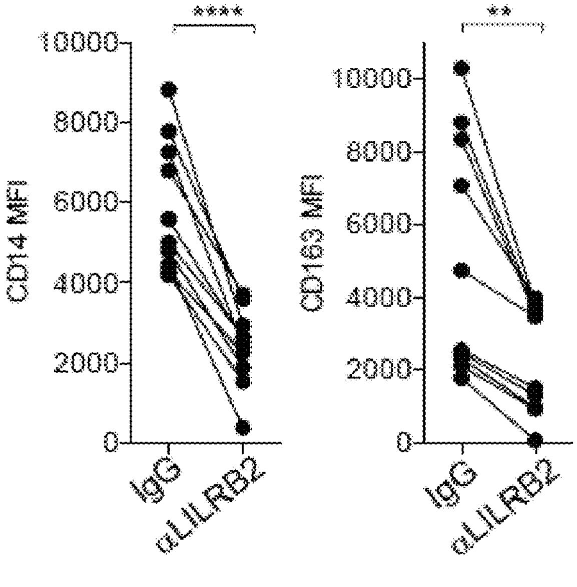
Figure 9D:
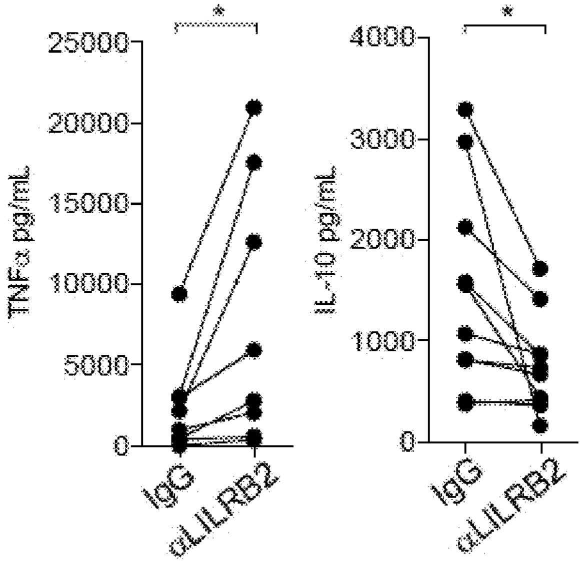
Figure 9E:
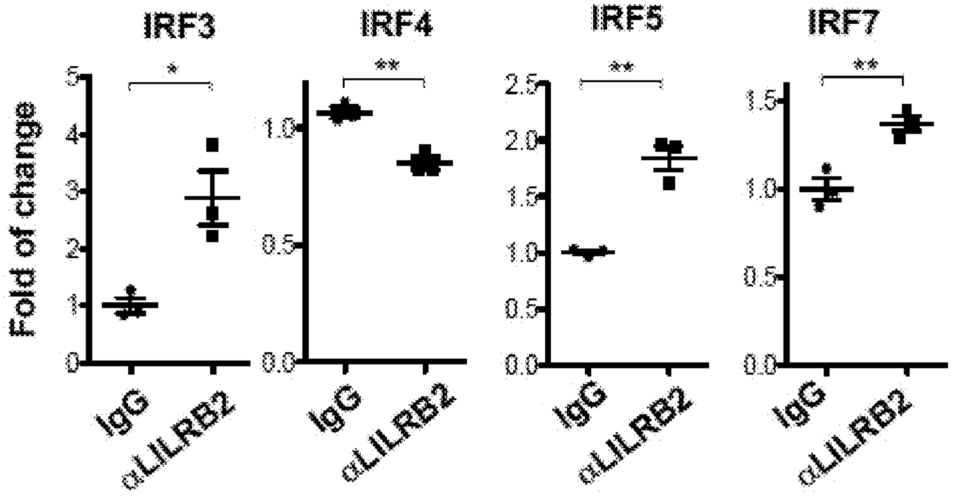
Figure 9F:
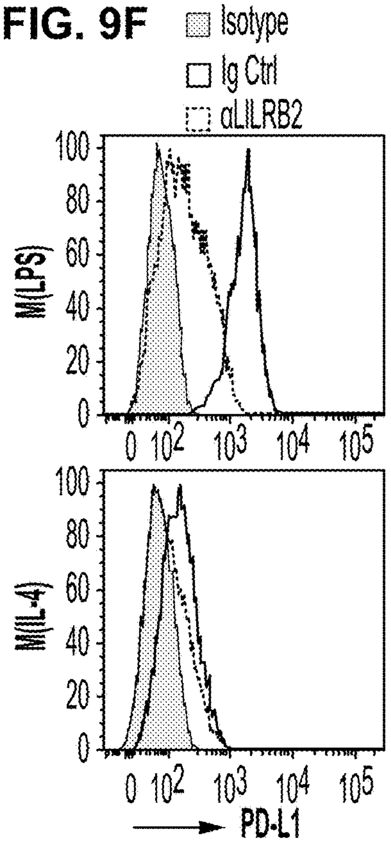
Figure 9G:
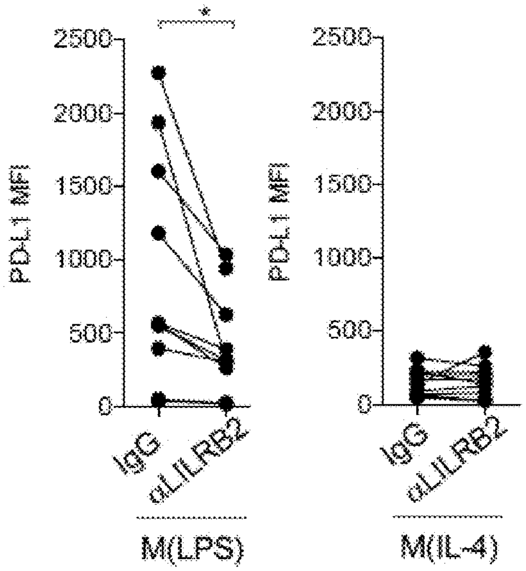
Figure 9H:
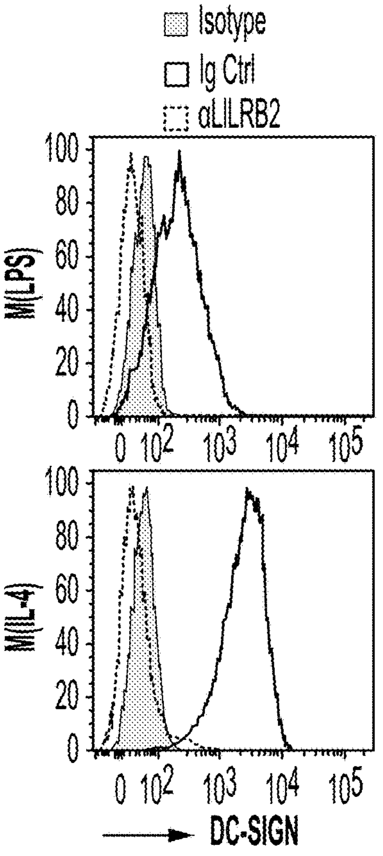
Figure 9I:
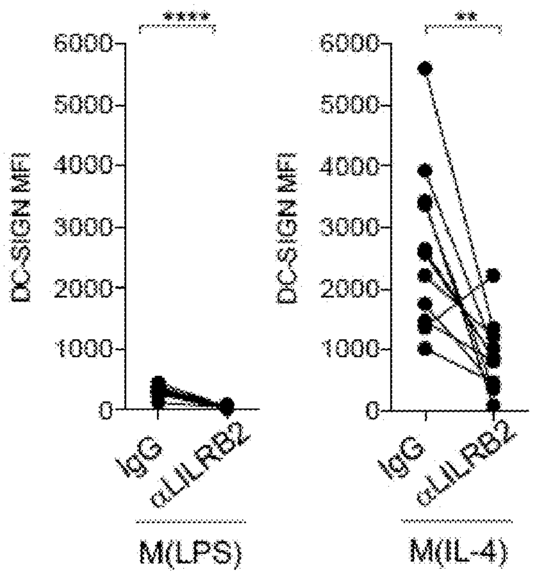
Figure 16A:
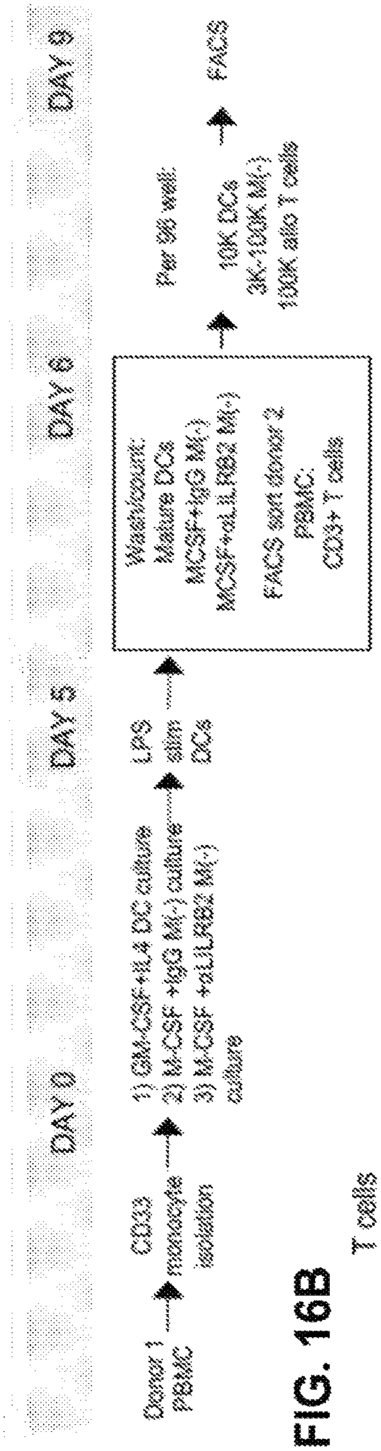
FIGS. 16A-16B. LILRB2 antagonism reduces macrophage-dependent inhibition on T cell proliferation.
Figure 16B:
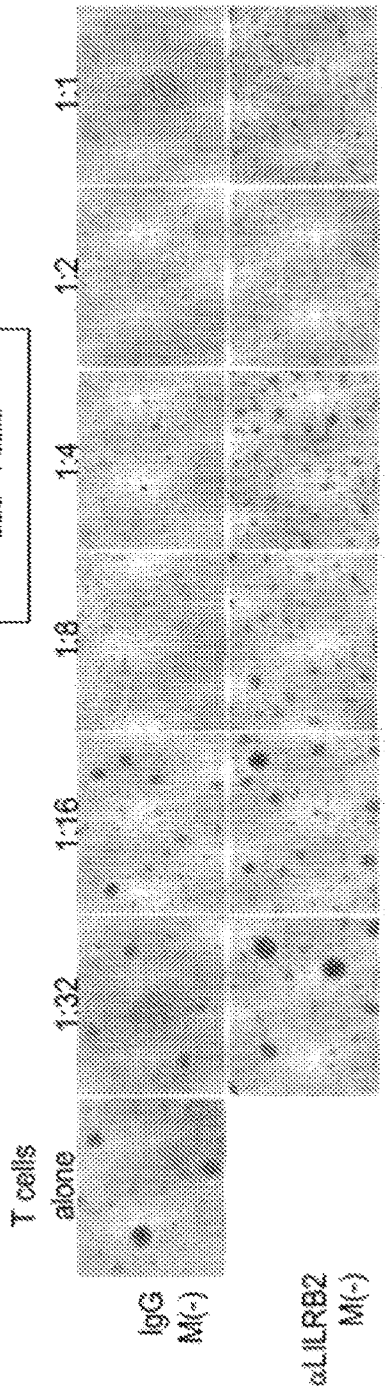

A subset of LILRB2 antibodies enhance activation of human monocytes In order to investigate the biological significance of LILRB2 on human macrophages, we developed anti-LILRB2 antibodies by immunizing mice with a Lilrb2 cDNA-encoding plasmid followed by boosting with LILRB2 vesicles or proteins. We screened hybridoma supernatants for LILRB binding by flow cytometry followed by peripheral blood mononuclear cell (PBMC)-based functional assays to assess whether clones could amplify monocyte activation. Several antibody clones could enhance CD86 and TNFα levels in the presence of LPS across multiple PBMC donors (FIG. 9A, FIG. 9B). Because members of the LILRB family share a high degree of homology, we tested for potential cross-reactivity by generating cell lines stably transduced with each receptor's extracellular domain (FIG. 16A). Cross-reactivity to LILRA1 was included since this receptor shares about 80% homology with the LILRB2 extracellular domain. FACS staining demonstrated that LILRB2 antibodies did not cross-react with related family members (FIG. 9C). Staining of PBMC was also restricted to the $CD33^+$ myeloid subset, specifically staining $CD14^+CD16^{hi}$ and $CD14^+CD16^{lo}$ monocyte populations (FIG. 16B). We identified LILRB2-specific antibodies that enhanced monocyte inflammatory potential in response to a low dose of LPS stimulus. We then determined the binding affinity of anti-LILRB2 against a THP1 human monocytic cell line that stably expresses the LILRB2 receptor (FIG. 9D). Biolayer interferometry is an optical technique that measures changes in molecule interactions on an immobilized probe. Using this approach, we measured the association and dissociation of immobilized anti-LILRB2 with LILRB2-His monomers at titrated concentrations (FIG. 9E). Dissociation of the complex was minimal at all LILRB2-His concentrations tested, and affinities were calculated in the range of 1.8-3.8 nM and were approximately 1000-fold stronger than endogenous HLA ligand binding (Kd=14~45 μM (22)).

LILRB2 Antagonism Alters MCSF-Dependent Maturation of Macrophages

Figure 10B:
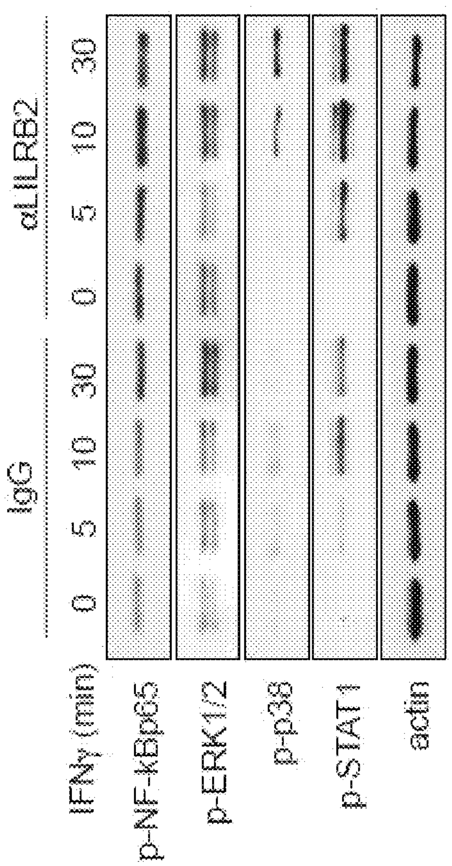
FIGS. 10A-FIG. 10I. LILRB2 antagonism favors NFκB/STAT1 inflammatory pathways.
Figure 10A:
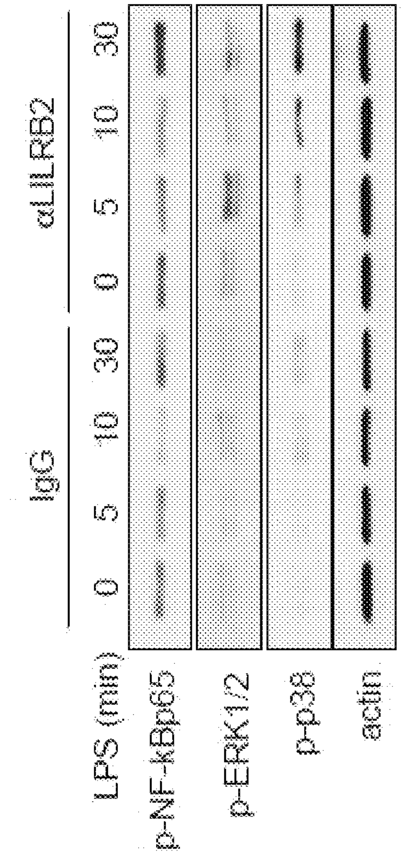

Because LILRB2 antagonists amplified monocyte activation in response to LPS, we investigated how LILRB2 blockade affects macrophage maturation. Studies in human monocyte-derived macrophages (MDM) have demonstrated different maturation phenotypes resulting from inflammatory cues (27, 28). We generated immature macrophages M(−) by treating $CD33^+$ monocytes from PBMCs of healthy donors with M-CSF for 5-7 days. While macrophages cultured in the presence of control Ig appeared elongated and loosely adherent, monocytes cultured in the presence of anti-LILRB2 appeared rounder and tightly adherent (FIG. 10A). Others have reported the positive effect of MCSF and IL10 on the spindle-like morphology and function of MCSF-derived human macrophages in vitro (29, 30). These observations suggest that LILRB2 antagonism may be interfering with typical MCSF-dependent maturation. We observed that both CD14 and CD163 expression were diminished in response to anti-LILRB2 across all human donors tested (FIG. 10B, FIG. 10C). CD14 has been shown to be upregulated by MCSF (27) and CD163 and is a scavenger receptor whose cell surface expression is correlated with anti-inflammatory responses and is an indicator of poor prognosis in a variety of cancers (31, 32). CD163 was also enhanced in the presence of M-CSF, IL6, IL10, and in response to glucocorticoids (33). To determine if macrophages display a differential response to LPS stimulation as was shown for monocytes, we stimulated immature macrophages overnight with LPS and measured TNFα and IL10 cytokine levels (FIG. 10D). We consistently observed increased TNFα and inhibited IL10 secretion across multiple donors. No detectable TNFα could be observed in macrophage cultures prior to LPS stimulation (data not shown) demonstrating that the increase of TNFα was specific to antibody functional activity.

IRF5 is induced by type I interferon and promotes inflammatory macrophage polarization (34), which is inhibited by IRF4. IRF4 is associated with alternative macrophage maturation, is induced by IL4, and negatively regulates TLR signaling and proinflammatory cytokines (35, 36). IRF3 is activated by TLR signaling and induces type I interferon-STAT1 signaling cascades (37) whereas IRF7 is reported to participate in the inflammatory microglial polarization switch (38). We observed that anti-LILRB2 upregulated IRF3, 5 and 7 but downregulated IRF4 during differentiation of immature macrophages (FIG. 10E), indicating that anti-LILRB2 potentially favors classical and inflammatory macrophage polarization. To rule out any contaminating endotoxin in LILRB antibody purification, we ensured endotoxin levels to be less than 0.005 EU per pg in all antibody batches.

To explore the effect of anti-LILRB2 on macrophage maturation pathways, we generated mature macrophages from MCSF cultured M(−) followed by 24-hour stimulation with LPS or IL4 to generate M(LPS) and M(IL4), respectively. Compared to M(−) and M(IL4), M(LPS) had markedly increased expression of PD-L1, consistent with literature reporting PD-L1 upregulation in response to TLR agonists (39).

Figure 10F:
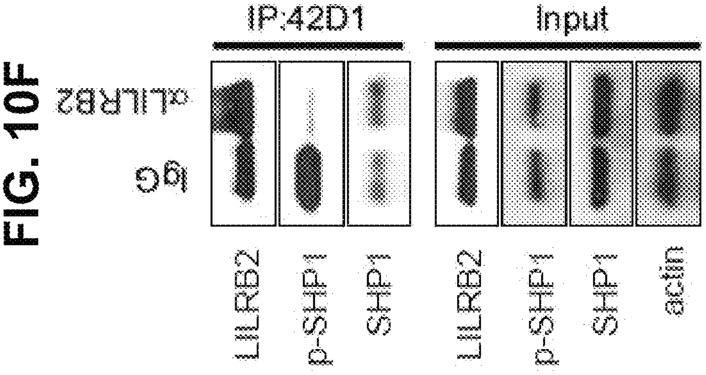
Figure 10E:
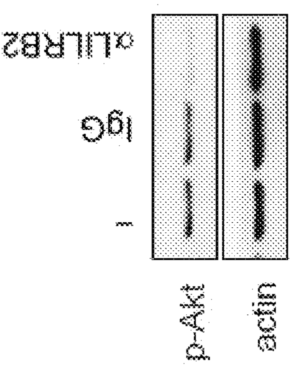
Figure 10C:
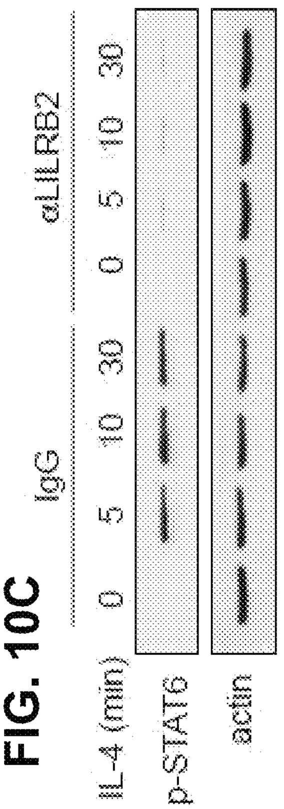
Figure 10D:
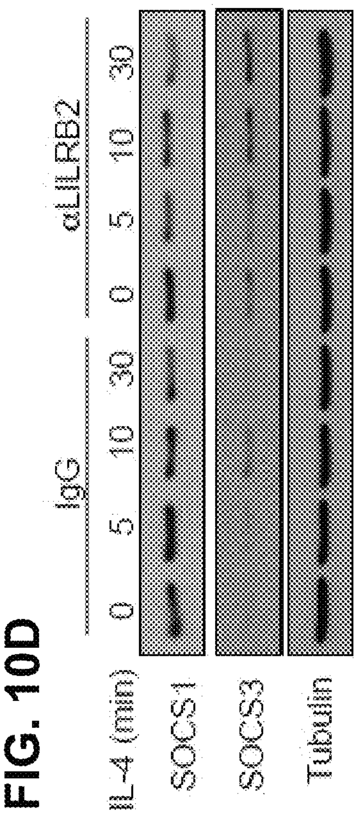
Figure 10I:
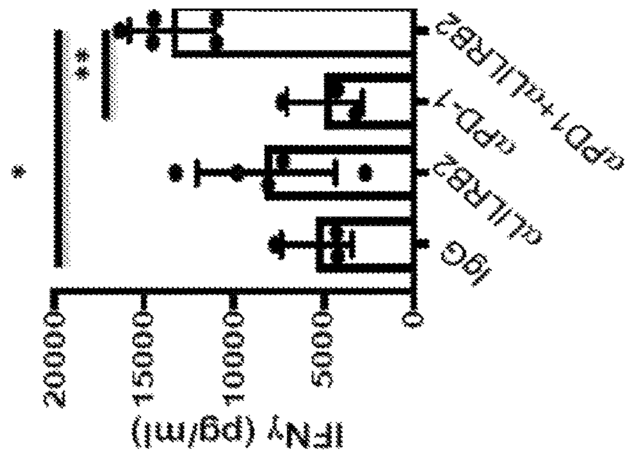
Figure 10H:
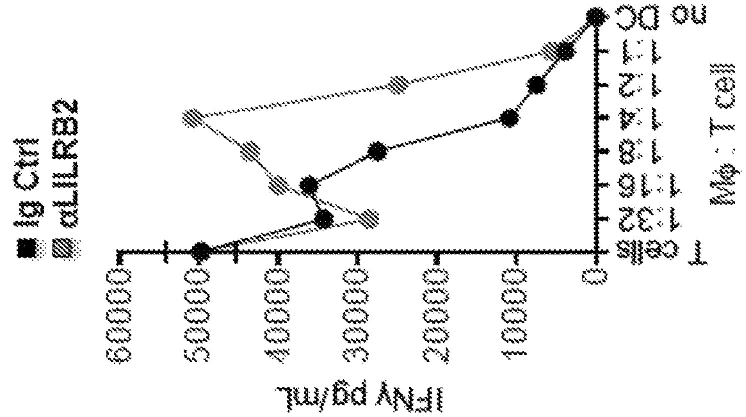
Figure 10G:
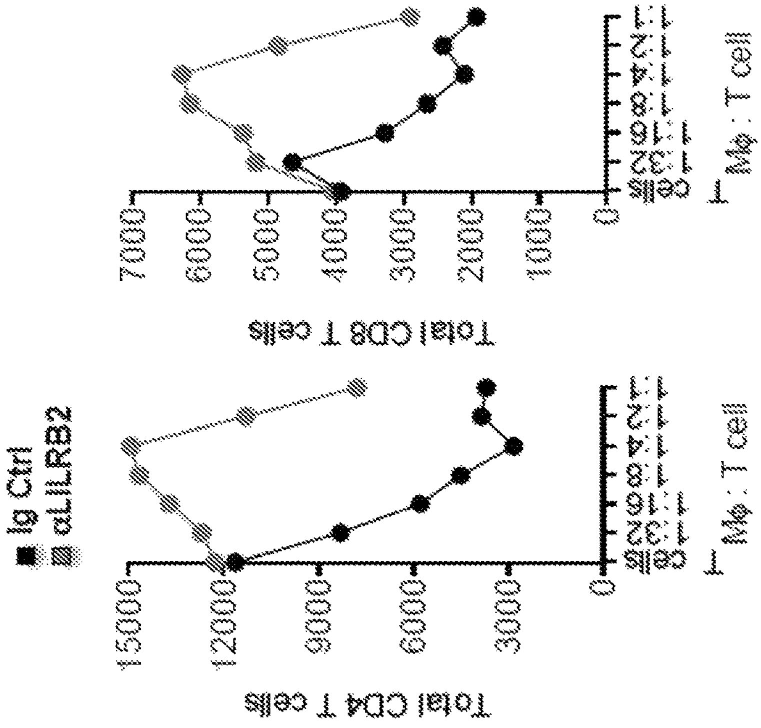

Surprisingly, we found that anti-LILRB2 treated M(LPS) significantly inhibited the induced expression of PD-L1 (FIG. 10F, FIG. 10G). PD-L1 expression on M(IL4) was negligible. These data suggest that LILRB2 antagonism may help prevent PD-L1 dependent suppression of effector T cells in inflammatory environments. We next investigated how anti-LILRB2 could affect macrophage maturation in response to the humoral cytokine IL4. We focused on macrophage DC-SIGN (CD209) since its expression is in part IL4-dependent (32), and it has been reported to be a well-accepted marker of M(IL4) macrophage maturation and immune tolerance (27, 40).

We found that DC-SIGN was induced at low levels in MCSF-derived M(−) and M(LPS), as has been previously reported in regulatory settings (41). In response to IL4 stimulation, M(IL4) express high levels of DC-SIGN. M(IL4) matured in the presence of anti-LILRB2 and showed significantly less induction of DC-SIGN expression and basal expression of DC-SIGN was found in M(LPS) (FIG. 10H, FIG. 10I). Collectively, the results from in vitro macrophage culture supported that LILRB2 antagonism sensitizes maturation in favor of classically activated phenotype.

LILRB2 Antagonism Favors Activation of NFκB/STAT1 and Inhibition of STAT6 Activation by IL4

Figure 11A:
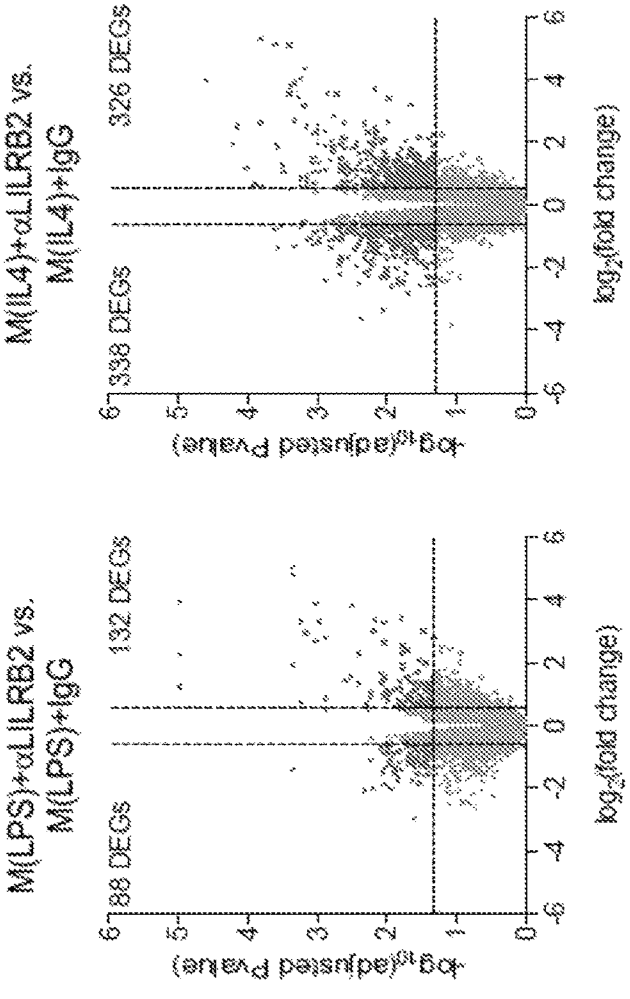
FIGS. 11A-FIG. 11D. LILRB2 blockade alters the macrophage transcriptome distinct from conventional M1 versus M2 phenotypes.
Figure 11B:
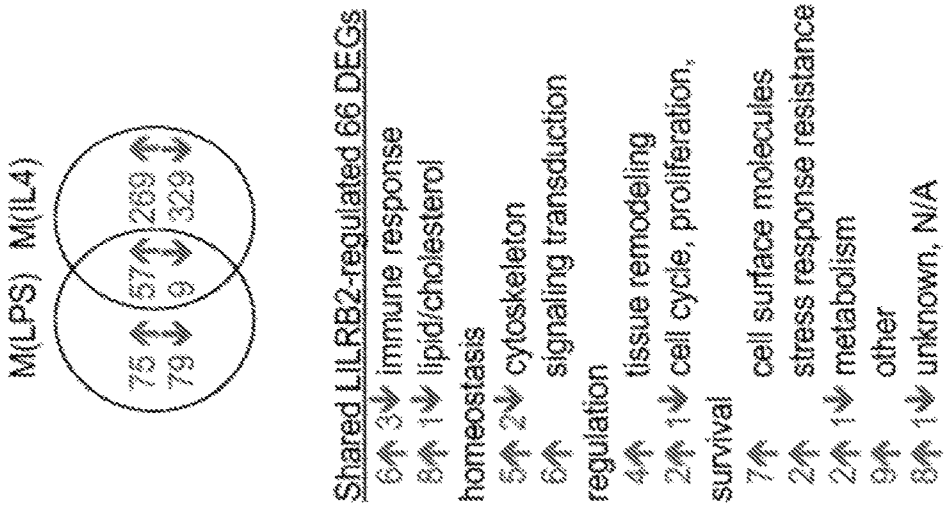
Figure 11C:
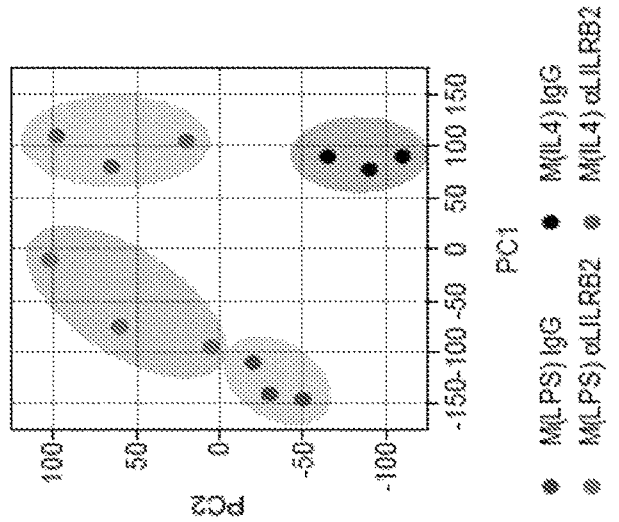
Figures 1, 11D:
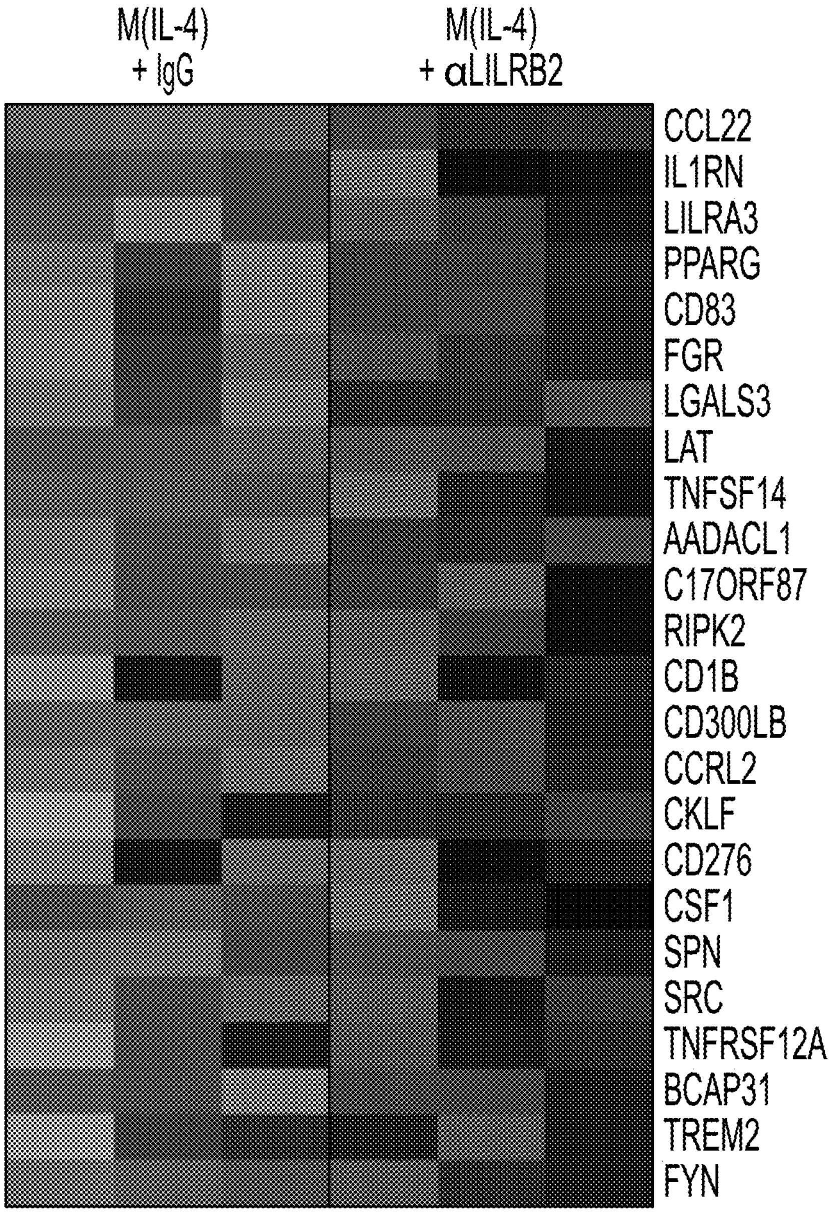
Figures 2, 11D:
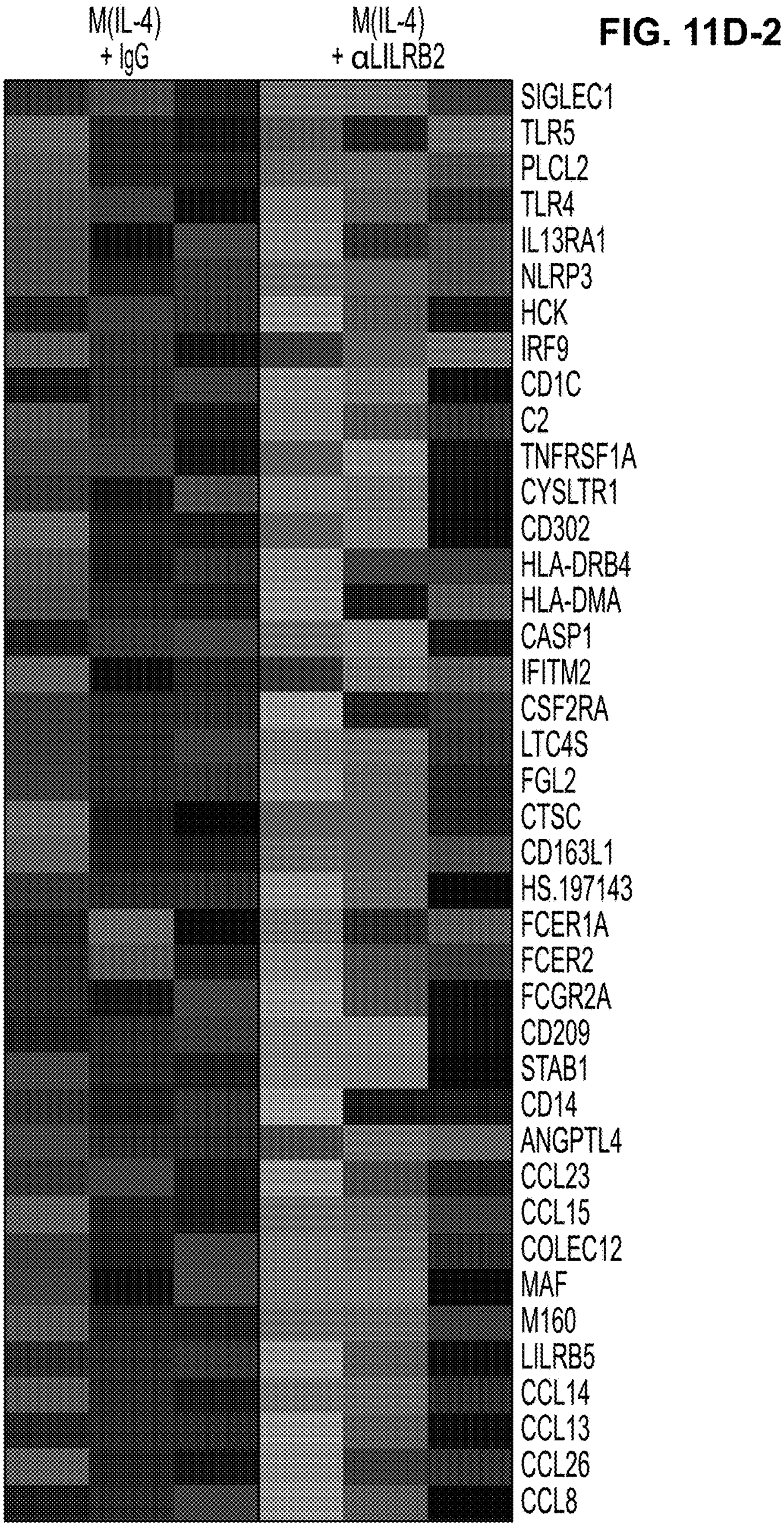

Groups describing macrophage maturation as M1-like (classically activated) versus M2-like (alternatively activated) largely characterize inflammatory phenotypes associated with NFκB/STAT1 activation and STAT6 activation, respectively (3). We, therefore, assessed if signaling patterns were regulated by LILRB2 antagonism. In response to LPS stimulation, anti-LILRB2-treated cells demonstrated increased NFκB, ERK1/2, and p38 activation (FIG. 11A). We found similar increases in NFκB, ERK1/2, and p38 phosphorylation as well as STAT1 phosphorylation in response to IFNγ (FIG. 11B). Because of reduced macrophage DC-SIGN expression in the presence of LILRB2 antagonism, we also determined if IL4 associated signaling was inhibited. In response to IL4 treatment, anti-LILRB2-treated cells showed strong inhibition of STAT6 phosphorylation (FIG. 11C), accompanied by an increased SOCS3 with no significant changes in SOCS1 expression (FIG. 11D). In addition to inflammatory cytokines, M-CSF drives proliferation and survival of macrophages that depends on PI3K/AKT activation (42, 43) and knockout models suggest important roles of AKT in determining maturation phenotype (44). We consistently observed diminished levels of AKT activation in anti-LILRB2 treated macrophages despite the presence of exogenous MCSF (FIG. 11E). Collectively, our data suggest that LILRB2 blockade increased sensitivity to inflammatory signaling cascades by inhibiting PI3K/AKT pathways downstream of MCSF.

LILRB receptors have been shown to constitutively recruit and activate SHP1 in macrophage populations (16). Co-immunoprecipitation experiments demonstrated that LILRB2-associated SHP1 phosphorylation was diminished in anti-LILRB2 treated macrophages (FIG. 11F). Thus, disruption of SHP1 activation downstream of LILRB2 may explain the increased sensitization of signaling cascades.

LILRB2 Antagonism Inhibits Myeloid-Dependent Suppression on Effector T Cells

Figures 1, 17A:
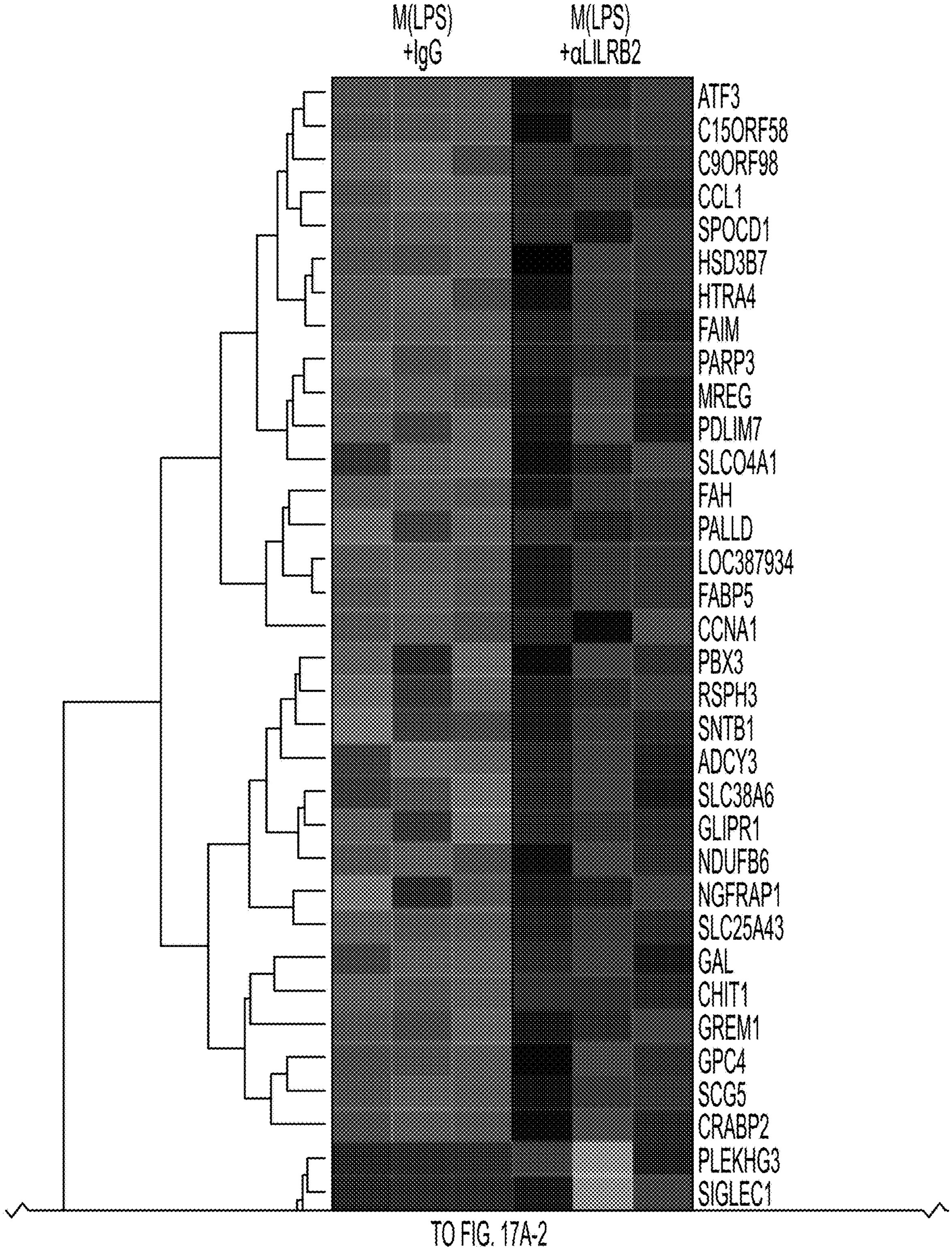
FIGS. 17A-17B. Differentially expressed genes of M(LPS) vs. M(IL4) macrophages.
Figures 2, 17A:
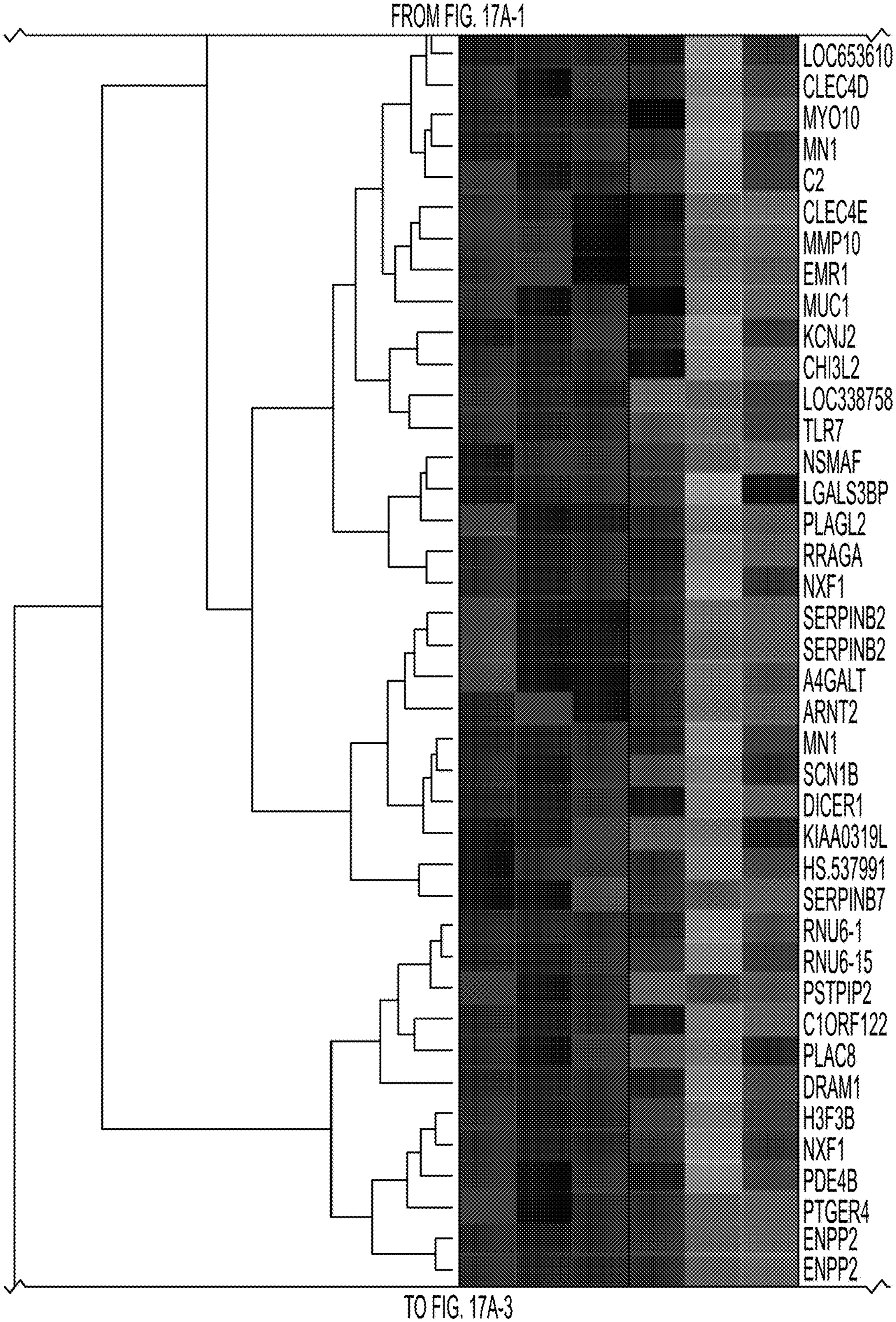
Figures 3, 17A:
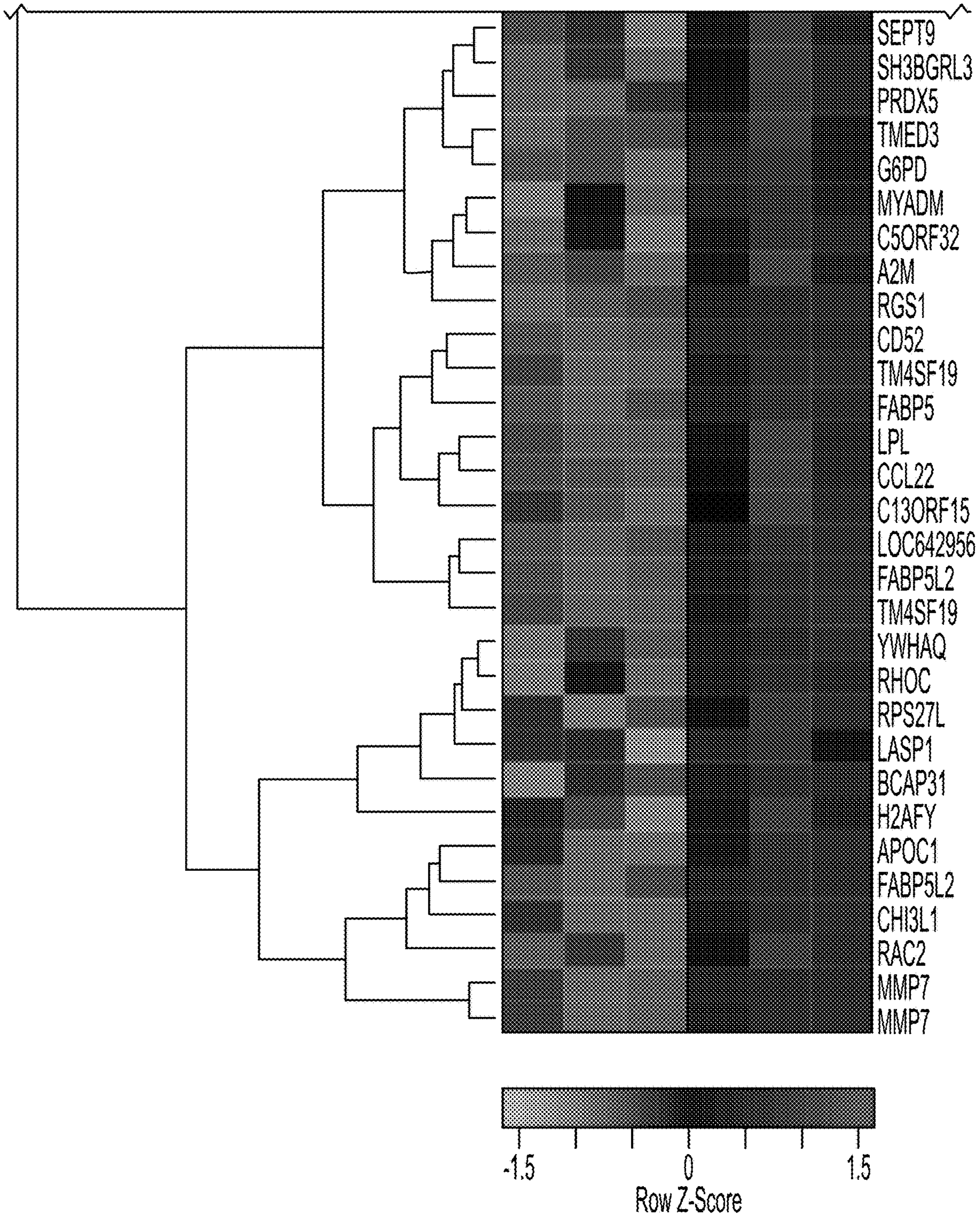
Figure 17B:
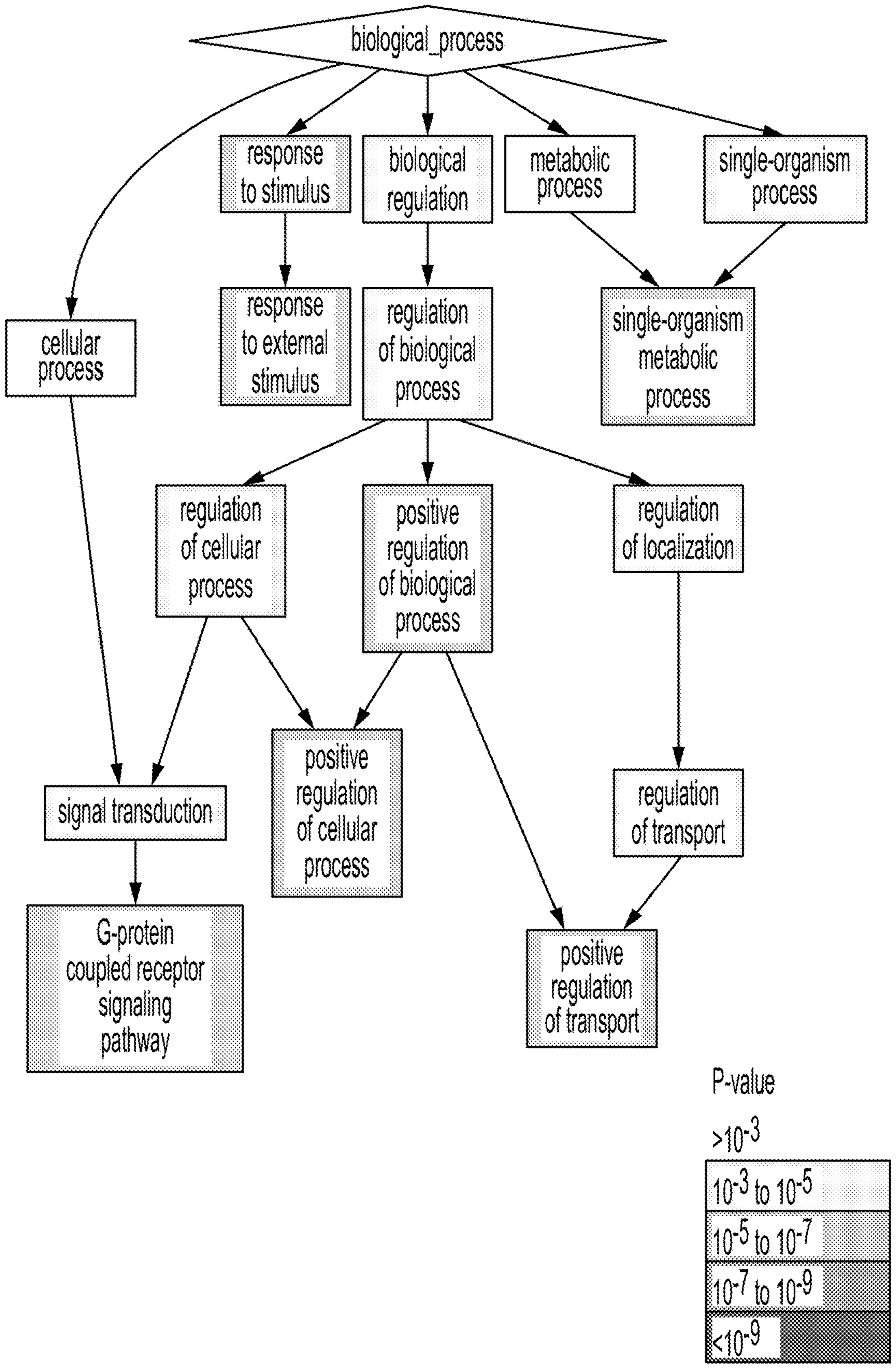

Since LILRB2 antagonism promoted inflammatory pathways supportive of Th1 adaptive immunity, we hypothesized that effector T cell responses would be improved in the presence of anti-LILRB2-matured macrophages. Macrophages and MDSC are known suppressors of effector T cell responses by using a variety of mechanisms including tryptophan catabolism by indoleamine 2,3-dioxygenase, PD-L1/L2 expression, and cytokine-dependent regulatory T cell conversion. To test the suppressive nature of anti-LILRB2-matured macrophages in native adaptive T cell responses, we performed one-way mixed lymphocyte reactions (MLR). After three days, clonal populations of outgrowing alloantigen-specific T cells were observed (FIG. 17A, FIG. 17B). Total numbers of CD4 and CD8 T cells were determined by FACS. The macrophages generated in the presence of anti-LILRB2 showed restored CD4/CD8 T cell numbers (FIG. 11G) and IFNγ secretion (FIG. 11H) indicating anti-LILRB2 diminished suppressive capacity as compared to IgG-treated macrophages. In PBMC cultures stimulated with a low dose of OKT3, anti-LILRB2 significantly synergized with PD-1 blockade to enhance effector T cell secretion of IFNγ (FIG. 11I). Altogether, we demonstrated that LILRB2 antagonism induced a macrophage phenotype that enhances adaptive Th1 effector T cell responses.

Figures 12A, 12B:
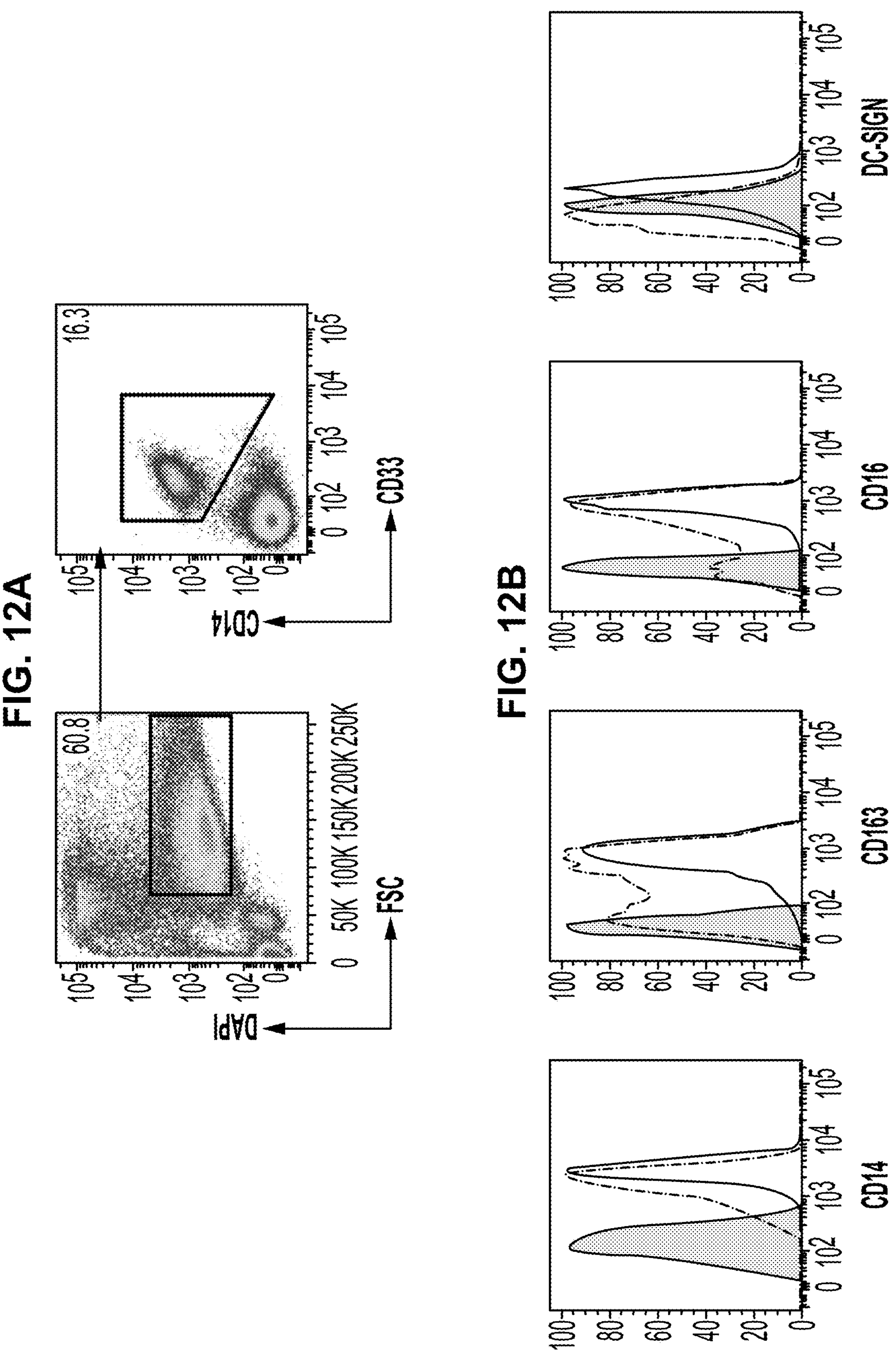
FIGS. 12A-FIG. 12G. LILRB2 blockade reprograms lung tumor-associated macrophage maturation in vitro and in vivo.
Figure 12C:
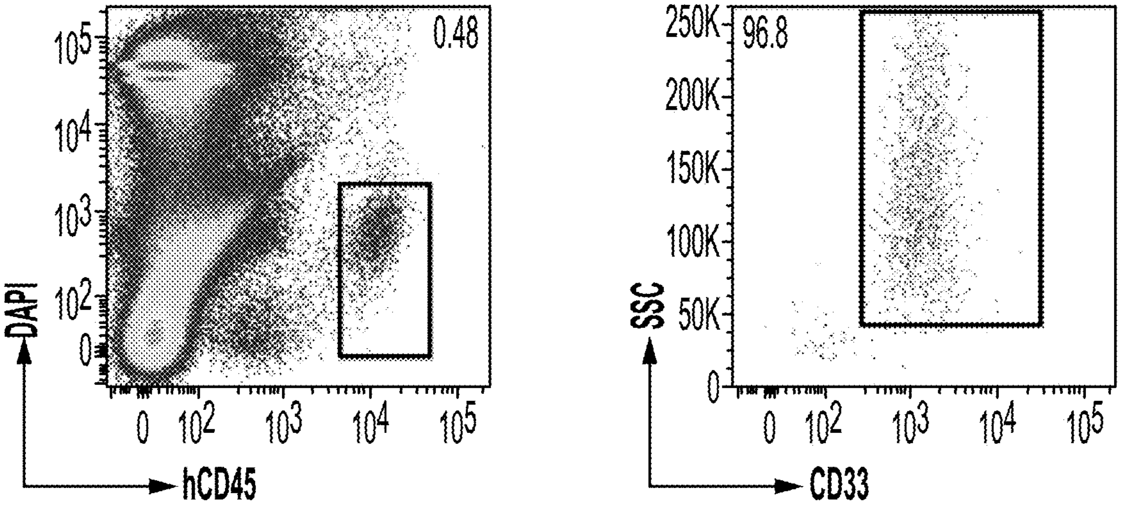
Figure 18A:
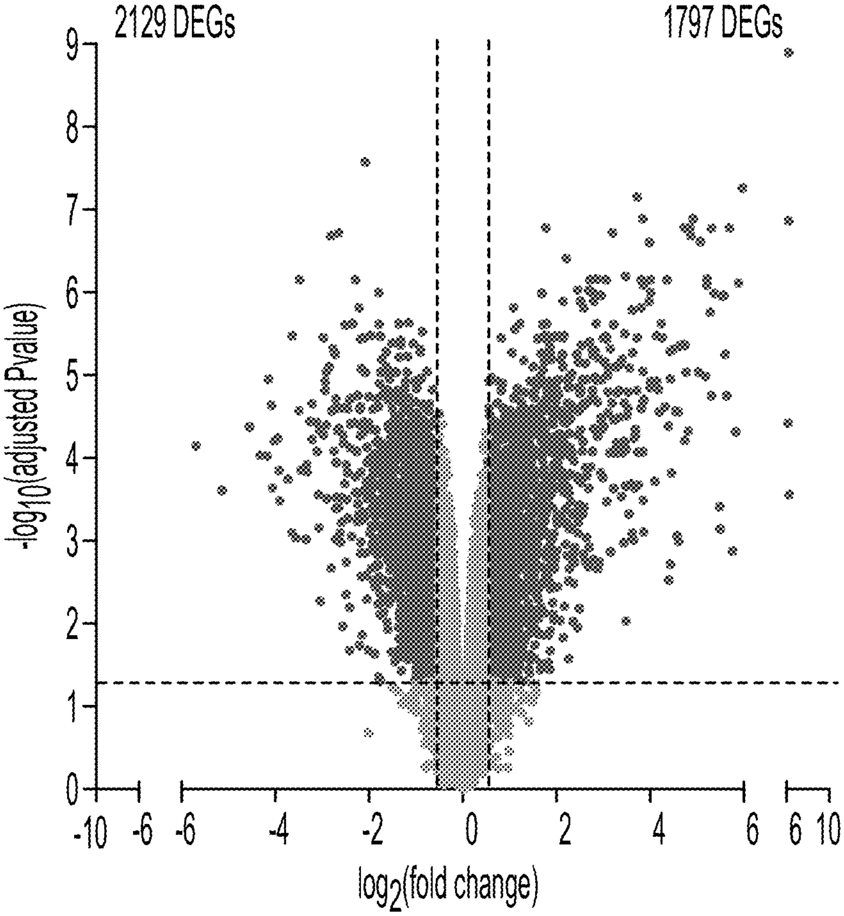
FIGS. 18A-18E. Differentially expressed genes from monocyte-derived macrophages in the context of LILRB2 antagonism.
Figures 1, 18B:
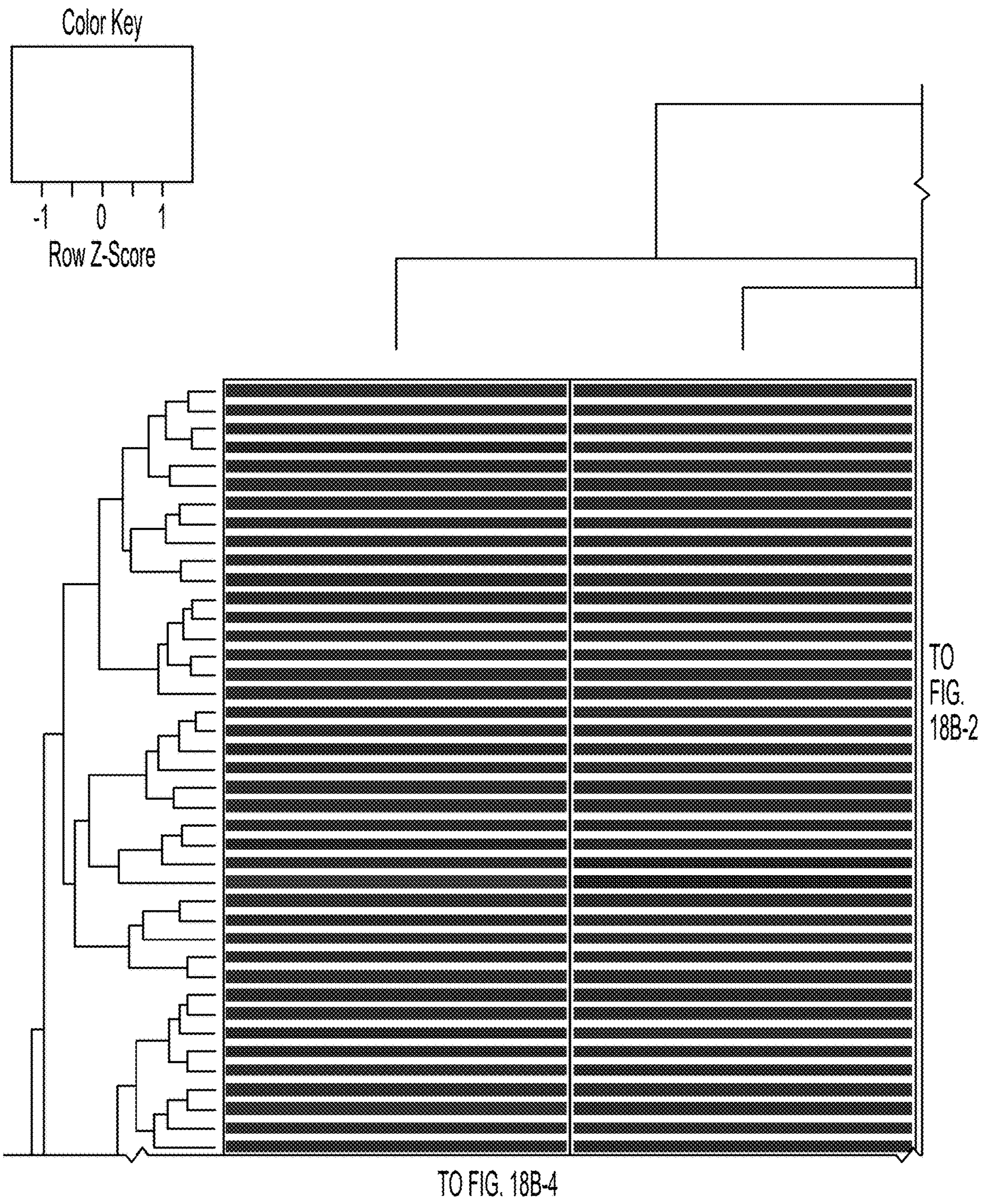
Figures 2, 18B:
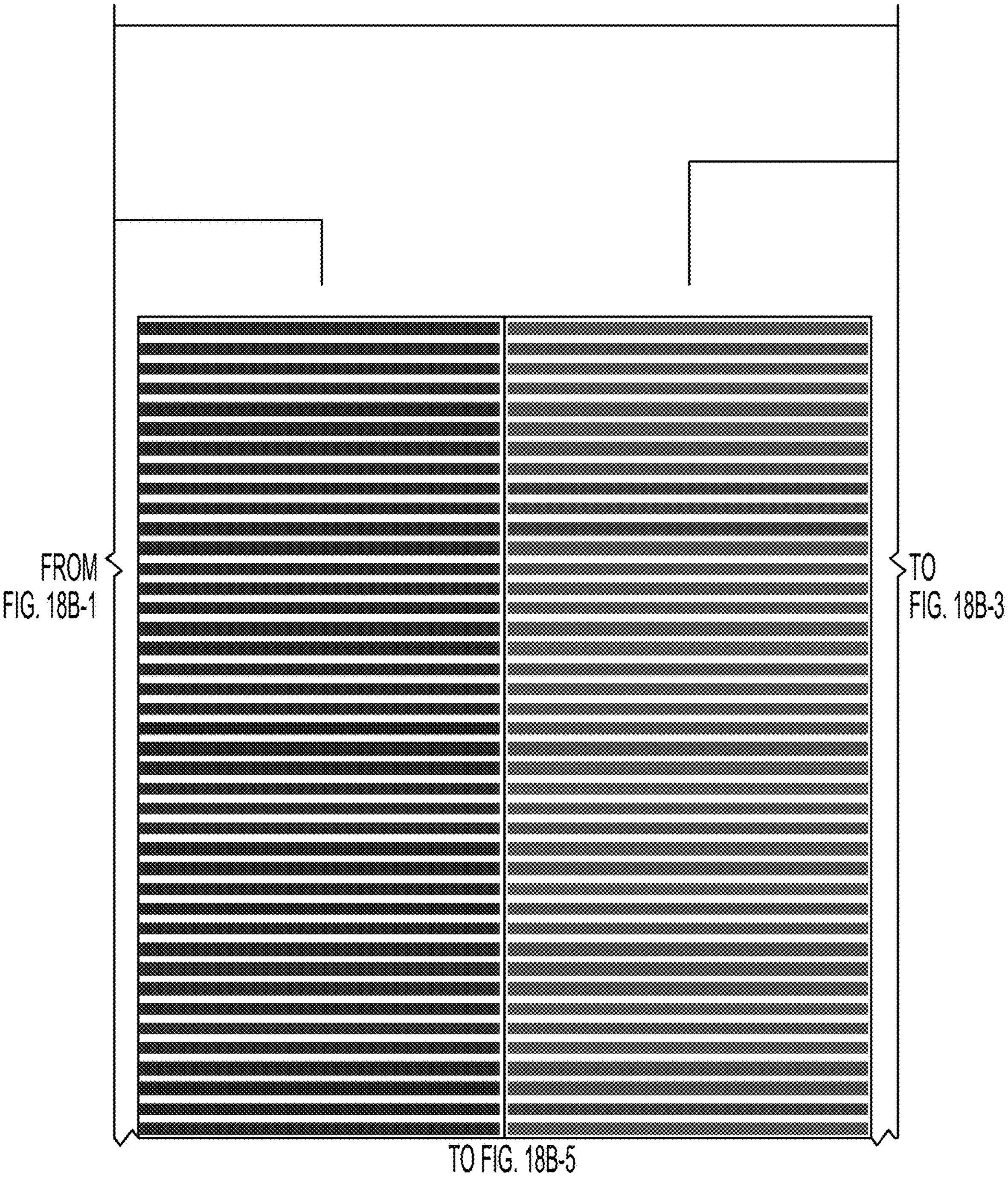
Figures 3, 18B:
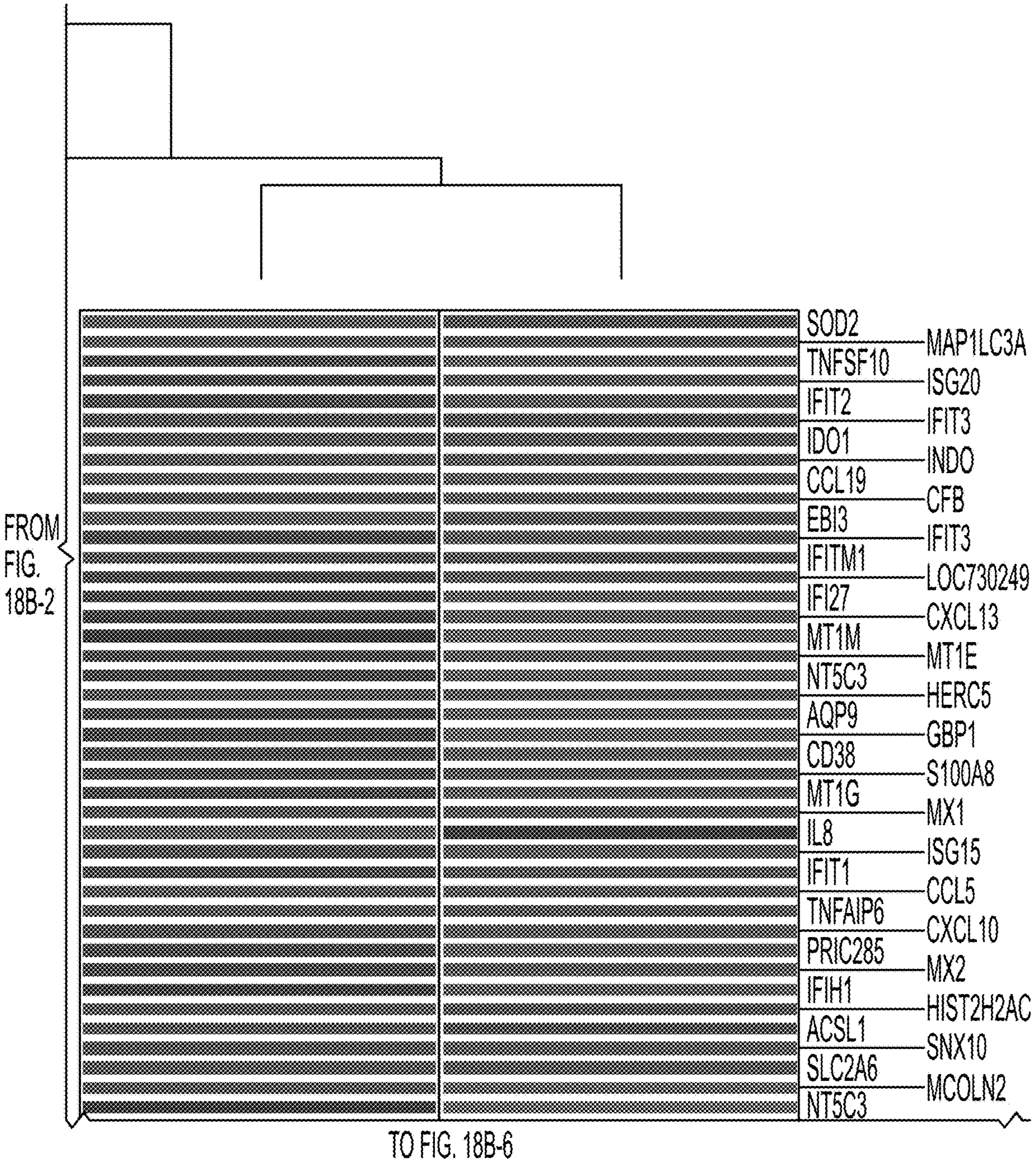
Figures 4, 18B:
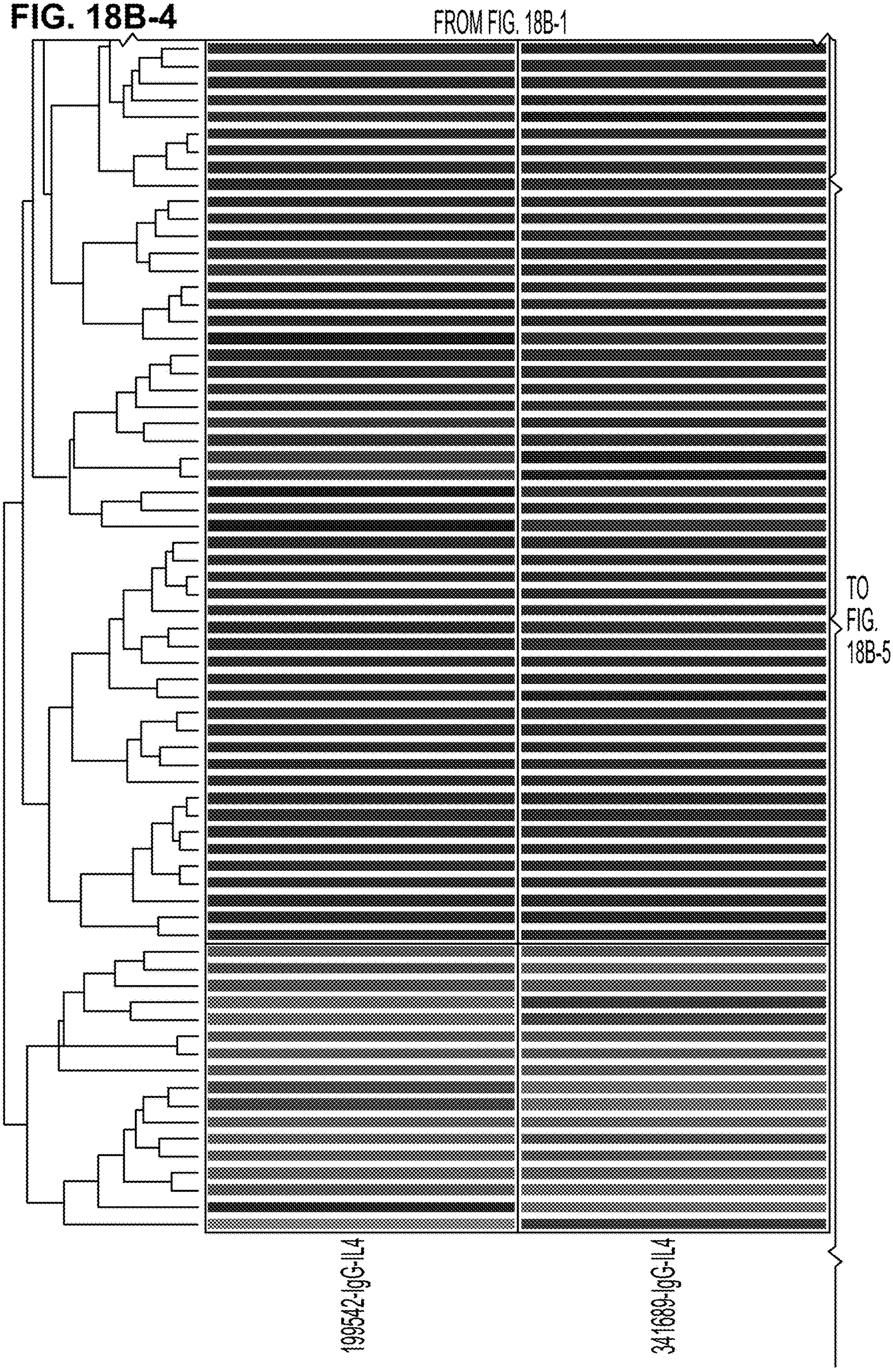
Figures 5, 18B:
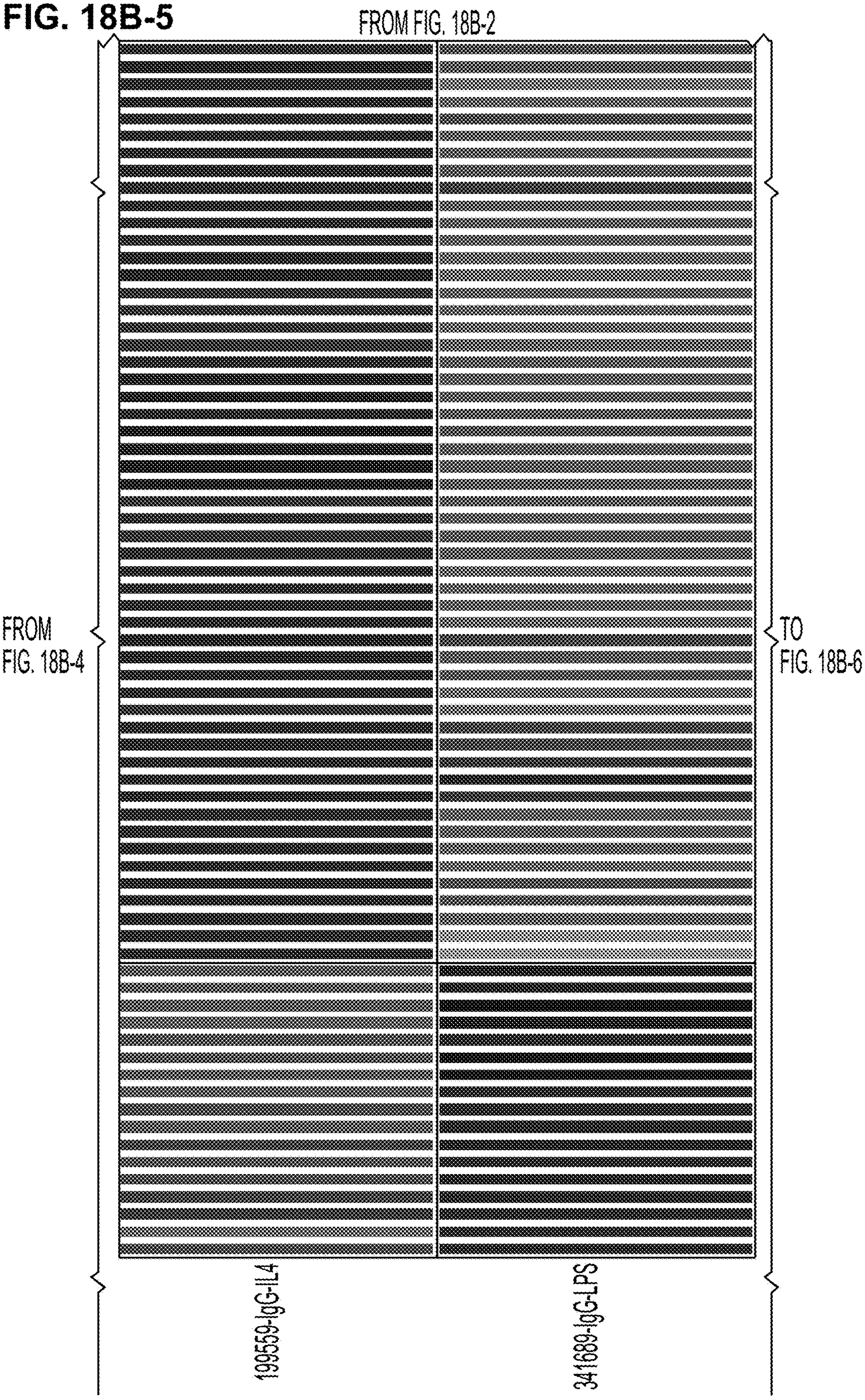
Figures 6, 18B:
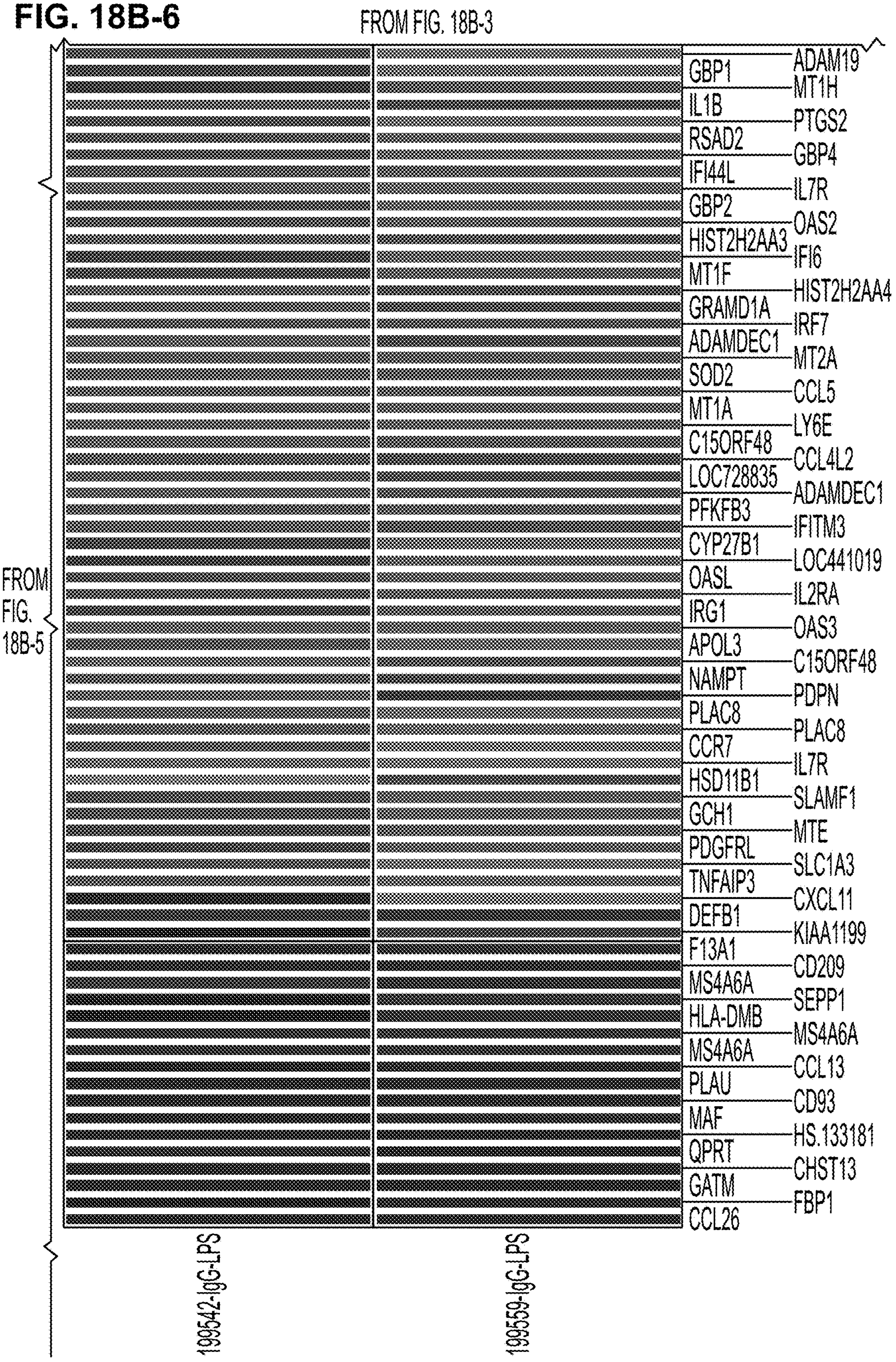
Figures 1, 18C:
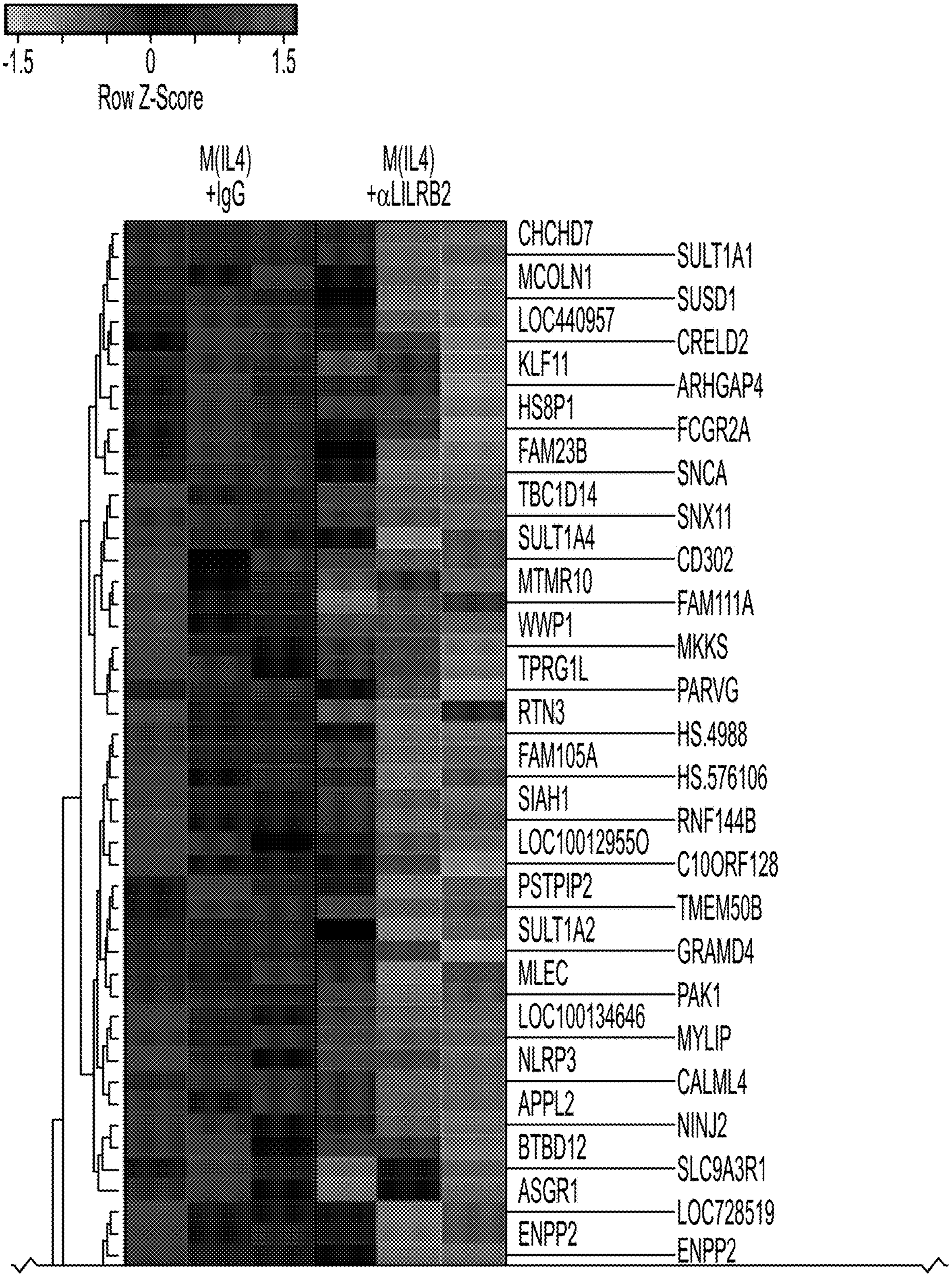
Figures 2, 18C:
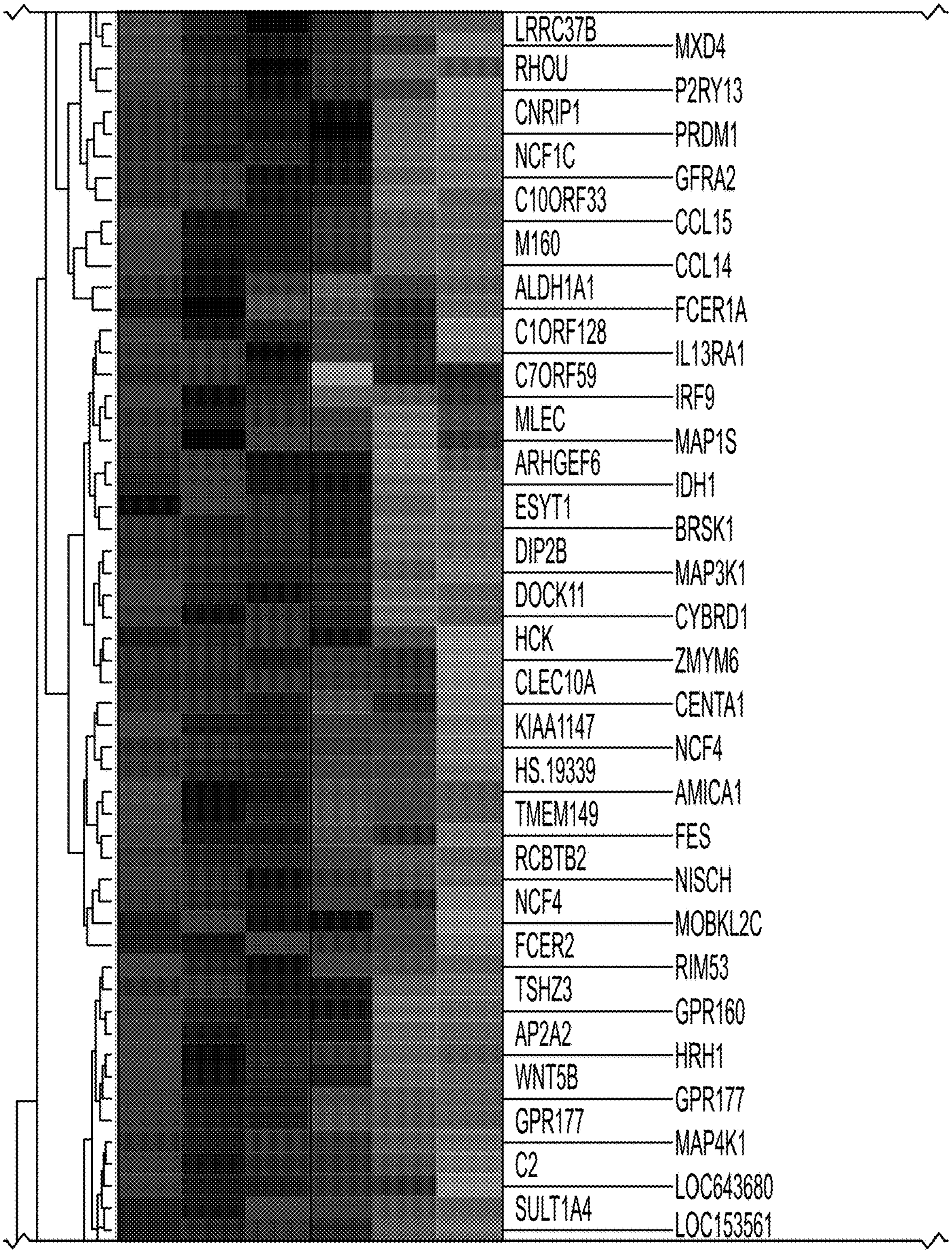
Figures 3, 18C:
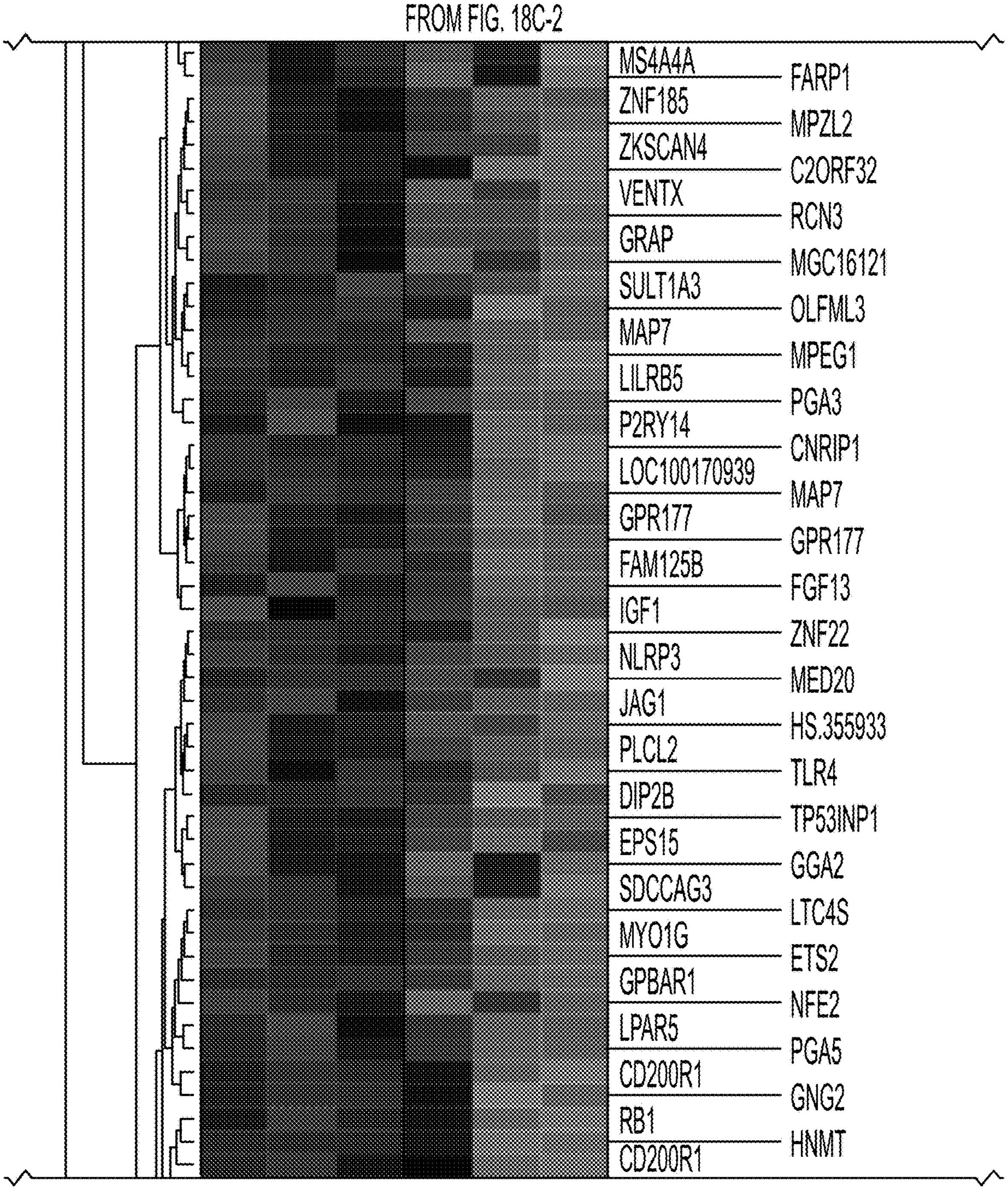
Figures 4, 18C:
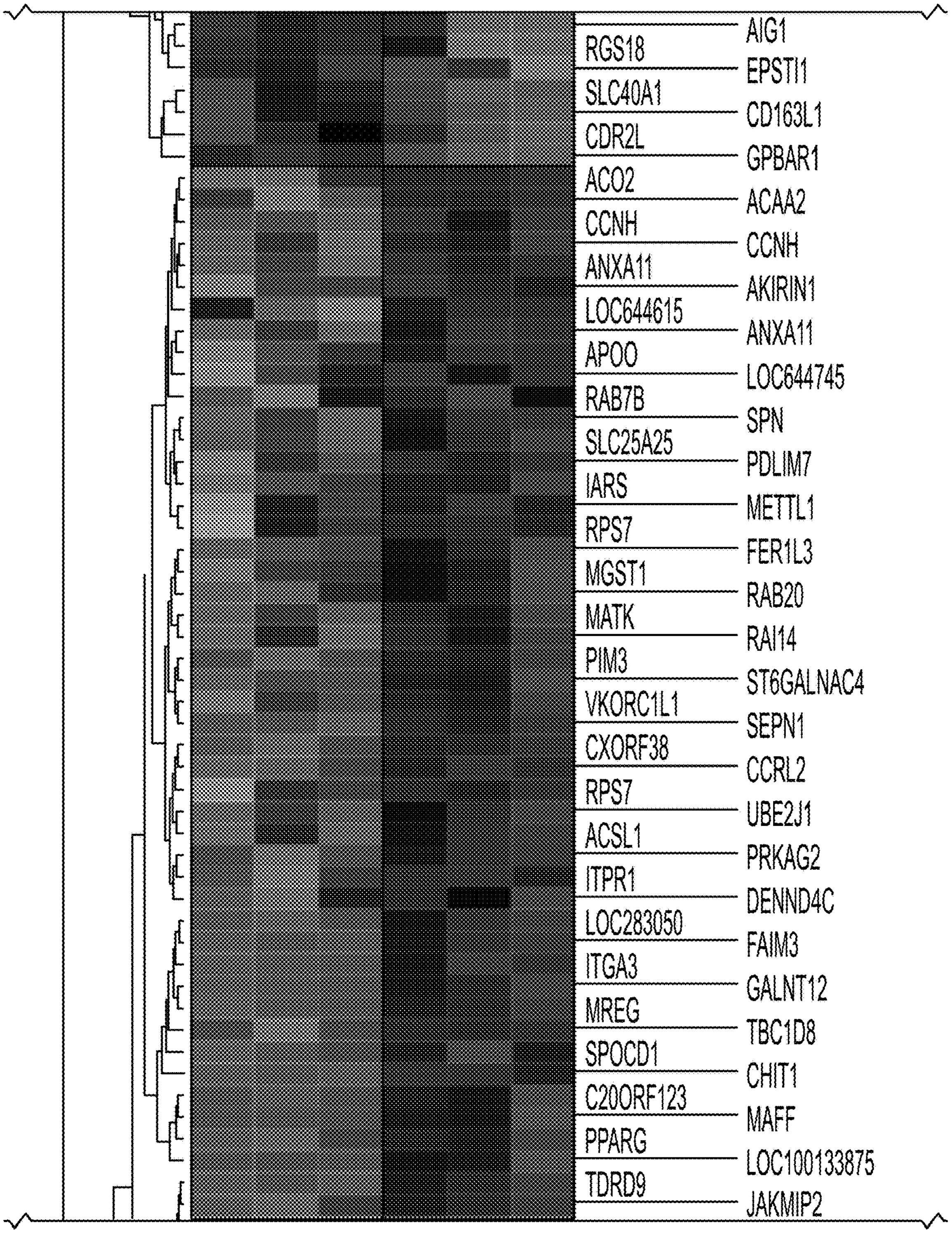
Figures 5, 18C:
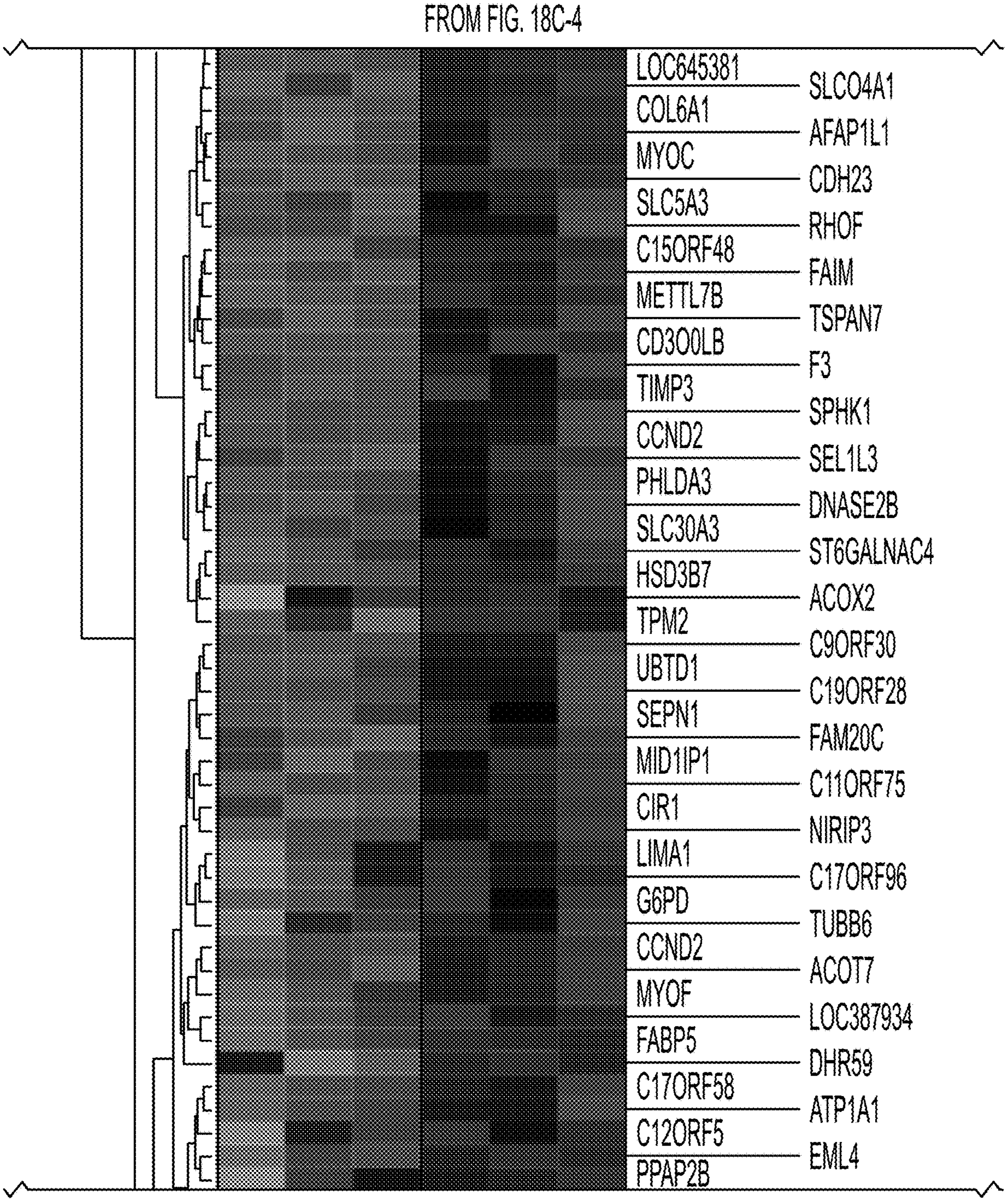
Figures 6, 18C:
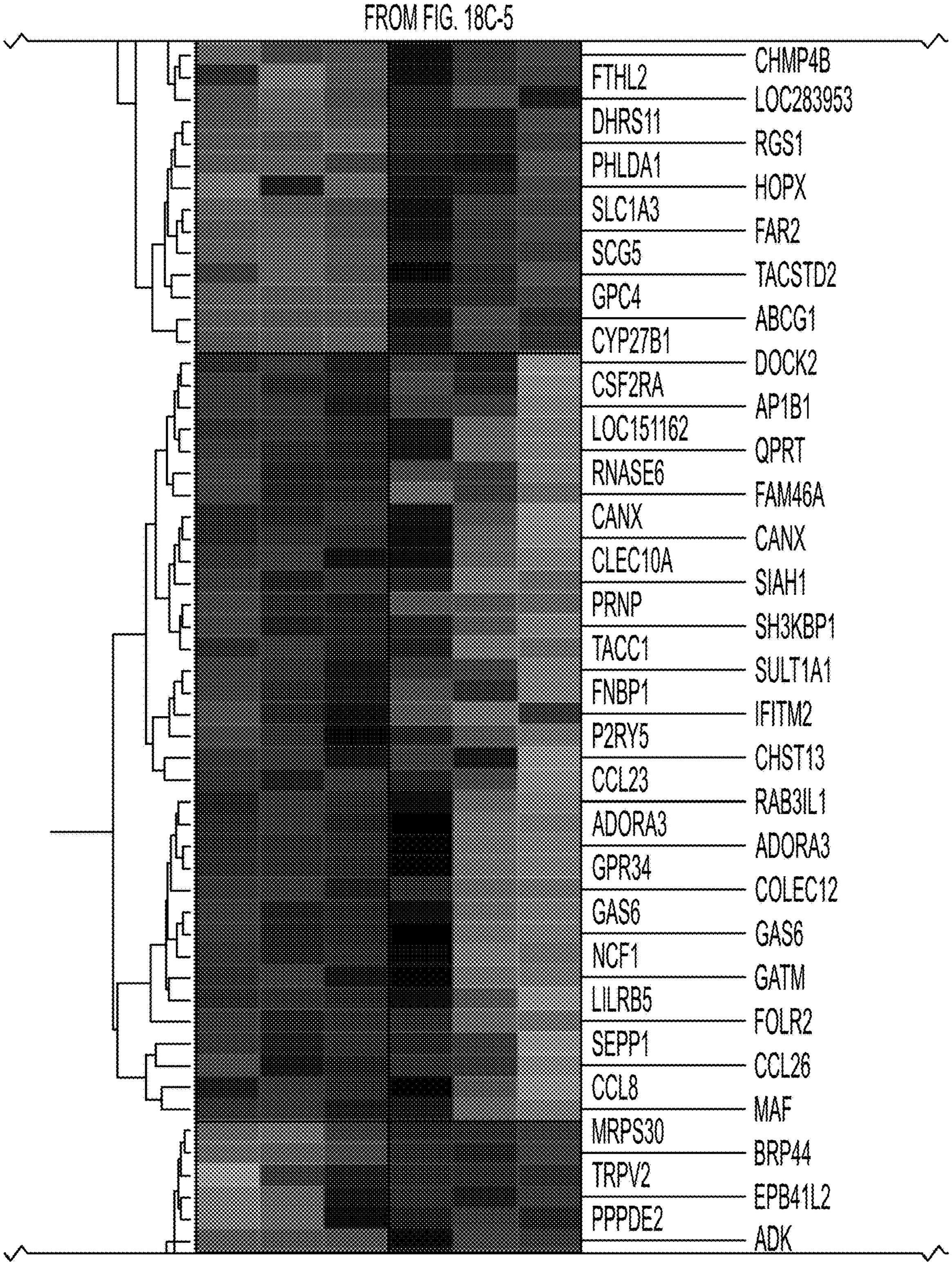
Figures 7, 18C:
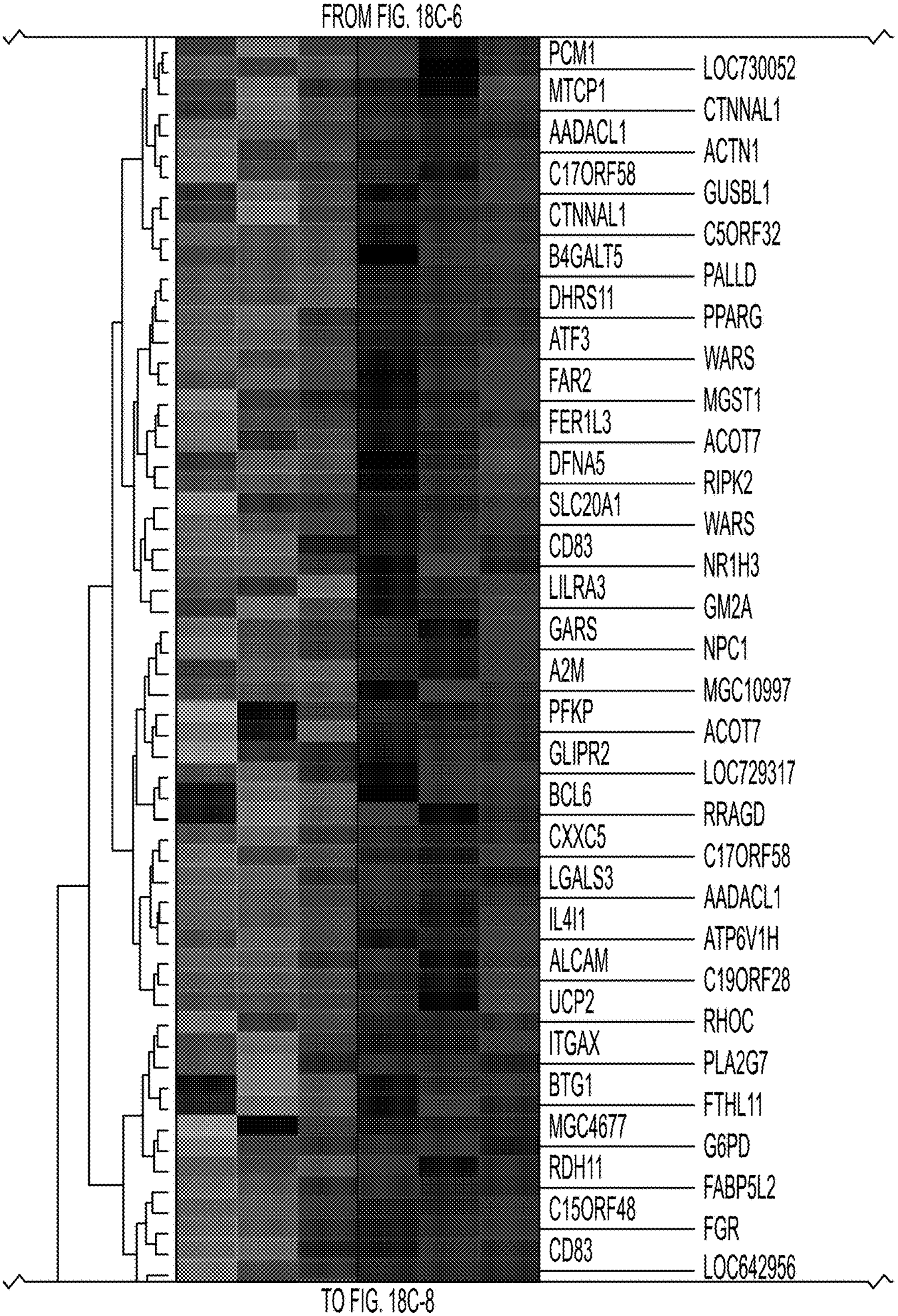
Figures 8, 18C:
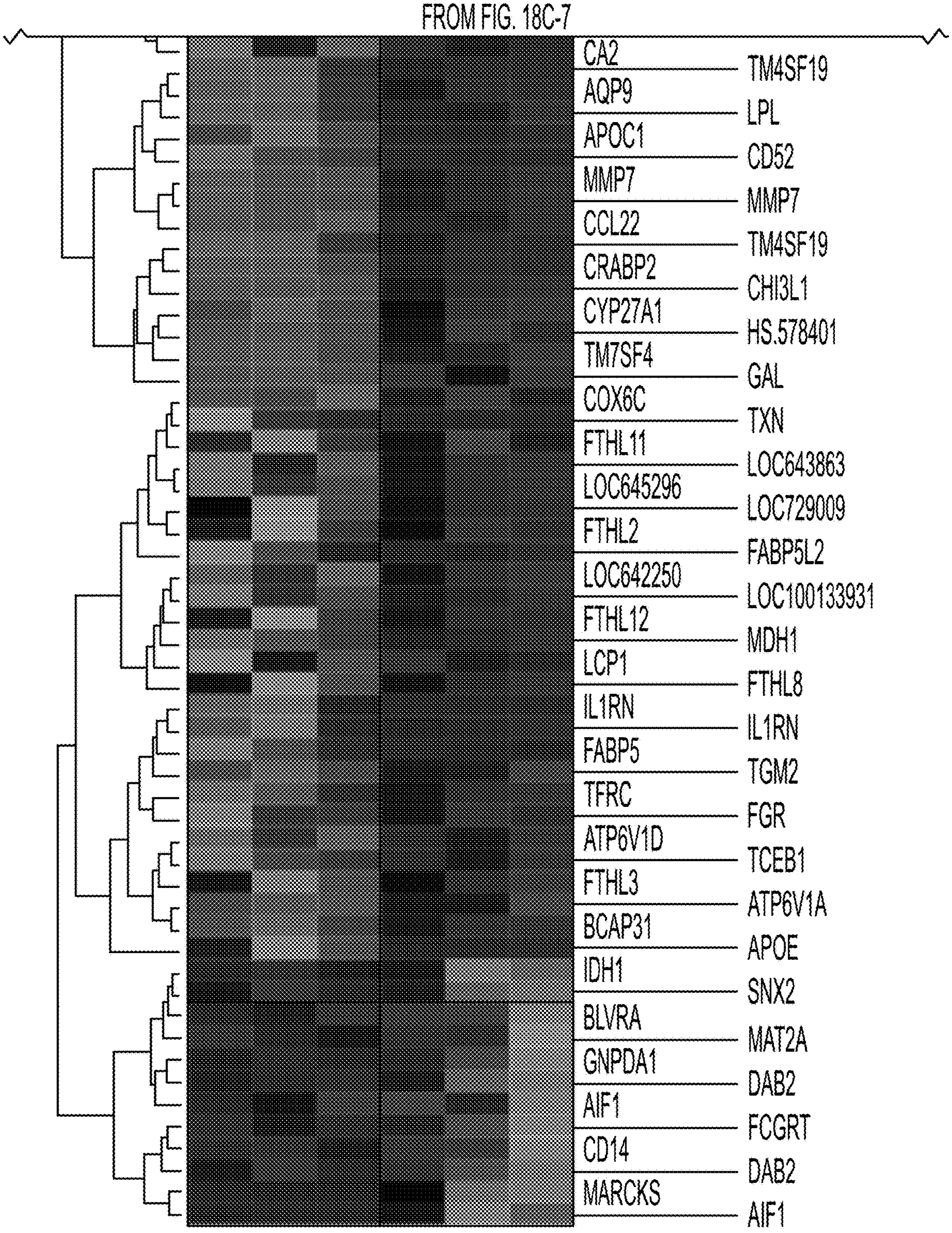
Figures 1, 18D:
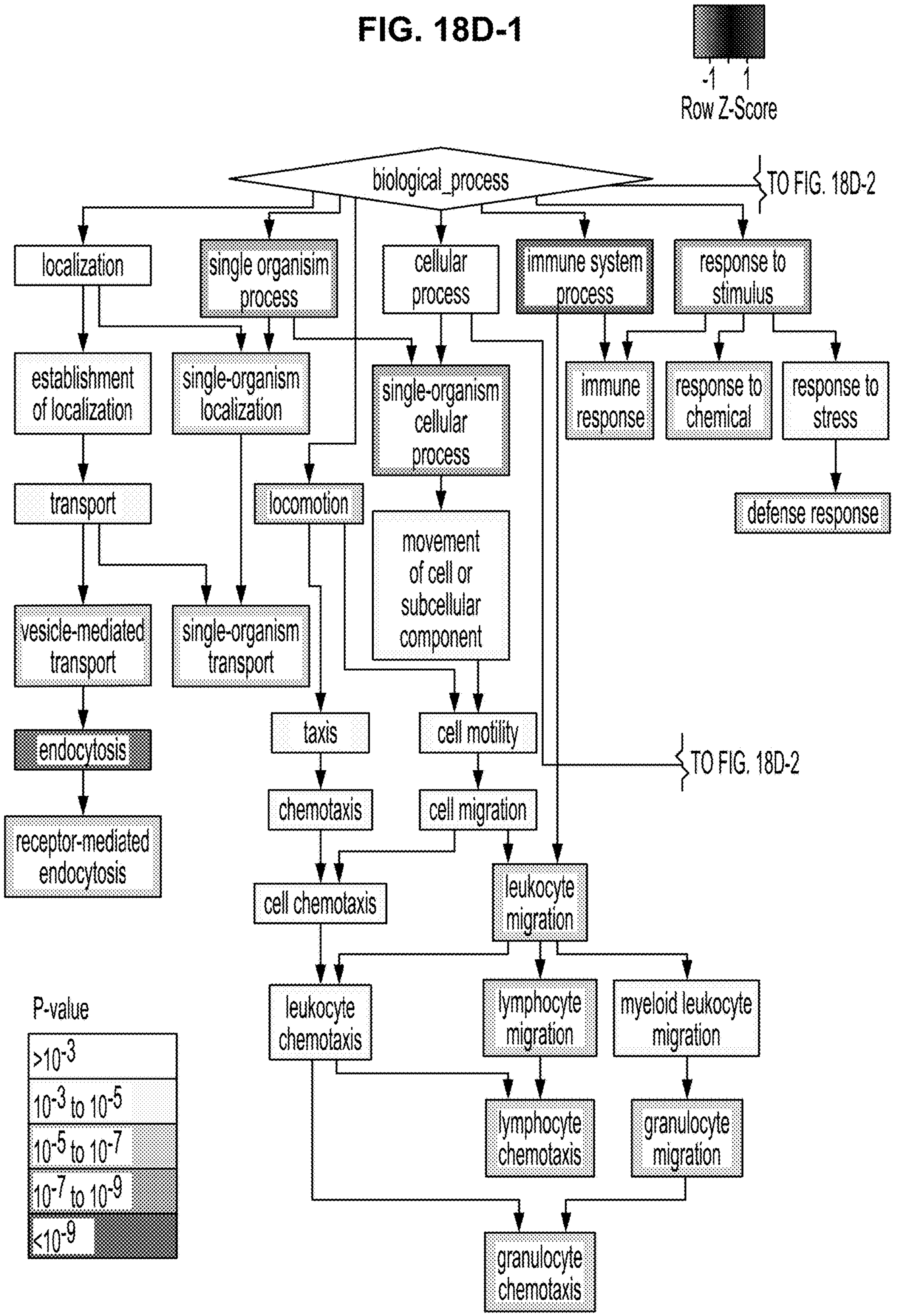
Figures 2, 18D:
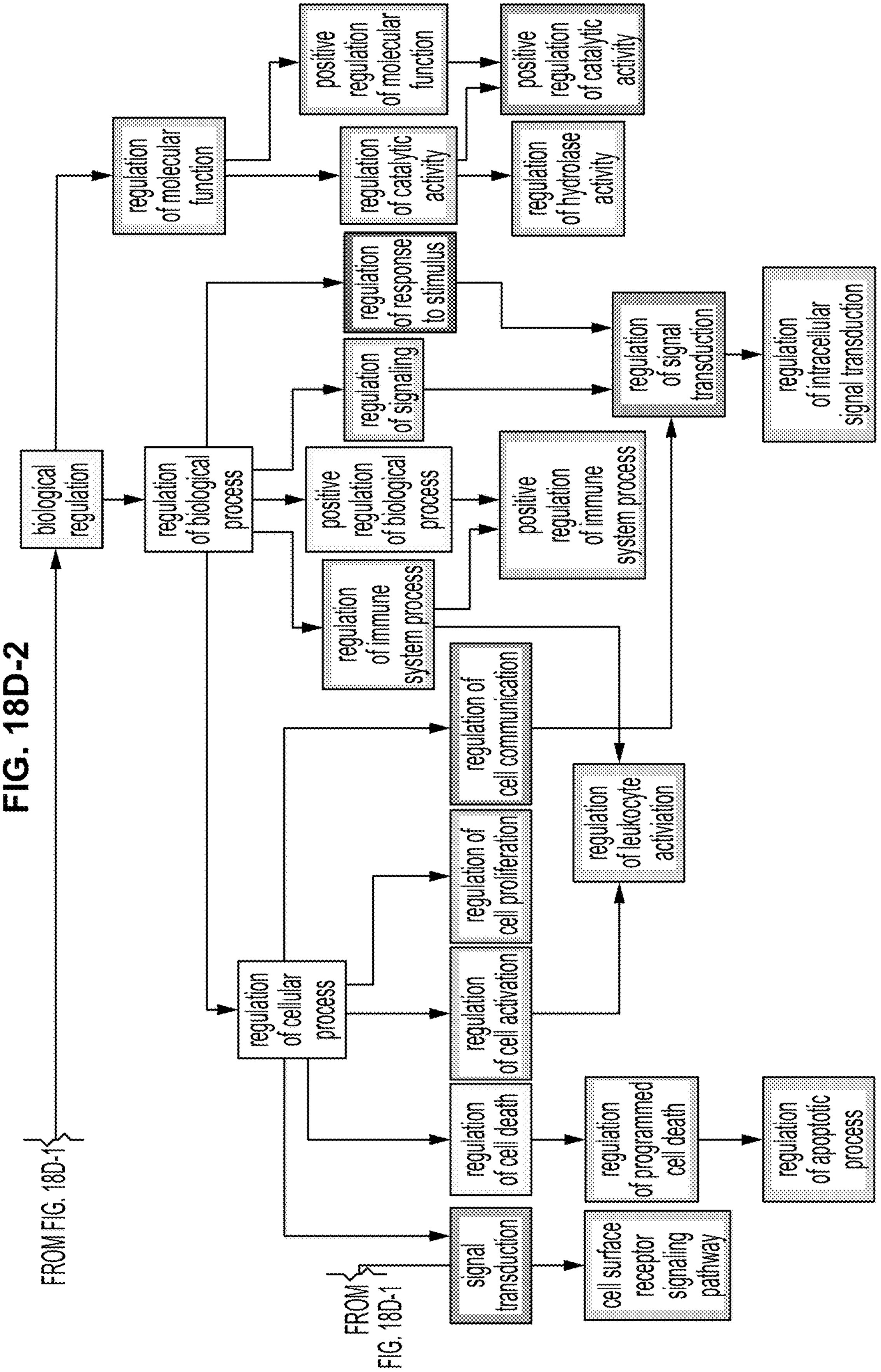
Figure 18E:
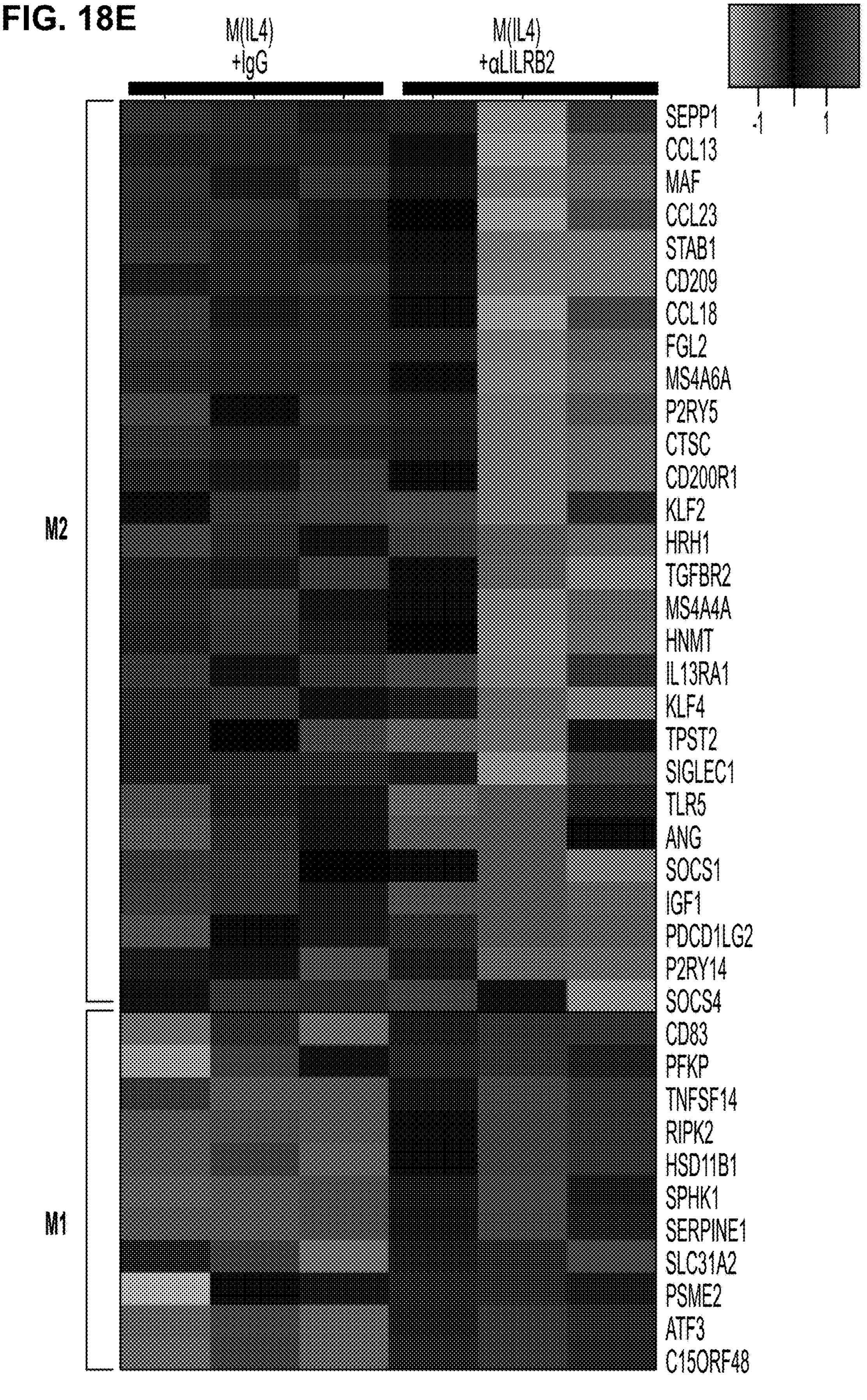

LILRB2 Blockade Alters M(IL4) Immune, Migratory, and Vesicle Trafficking Pathways Transcriptome studies can provide additional insight into the maturation and phenotypic changes of macrophages. Early microarray studies comparing M(LPS) and M(IL4) populations have defined markers and pathway networks associated with M1 vs. M2-like functional phenotypes (27). Using the same experimental conditions in the context of anti-LILRB2, we performed Illumina microarray analysis to determine how LILRB2 blockade may affect transcriptional networks in M(LPS) and M(IL4). Comparison of M(LPS) and M(IL4) IgG-treated transcriptomes identified 3,926 differentially expressed genes (DEGs) (FIG. 18A, FIG. 18B) with significant overlap between the top 100 and those originally described by Mantovani (27). Anti-LILRB2 versus IgG treatment of M(LPS) yielded 220 DEGs whereas the same treatments in M(IL4) yielded 664 DEGs (FIG. 12A). The changes in 66 DEGs were conserved between anti-LILRB2 treated M(LPS) and M(IL4) (FIG. 12B). Collectively, these data demonstrate that LILRB2 antagonism results in substantially more transcriptional changes under conditions of IL4 maturation versus LPS maturation, and the 66 conserved DEGs indicate that LILRB2 antagonist-specific gene alterations are independent of cytokine-induced maturation. Genes regulating immune function, lipid/cholesterol homeostasis, and cytoskeletal homeostasis were most prominent. In both M(LPS) and M(IL4), LILRB2 blockade upregulated LILRA3 transcript, a secreted LILR family member that may further compete with other LILR family members. Anti-LILRB2 increased Ccl22, FGR, and Trem2 transcription as well as M1-associated Sphk1 transcription but decreased Siglec1, PLC decoy messenger Plcl2, and complement protein C2 transcription as well as M2-associated Klf2 transcripts. Principle component analysis of M(LPS) and M(IL4) in response to IgG or anti-LILRB2 suggests that LILRB2 blockade generates unique macrophage phenotypes that are dissimilar from each other (FIG. 12C).

Figures 12D, 12E, 12F, 12G:
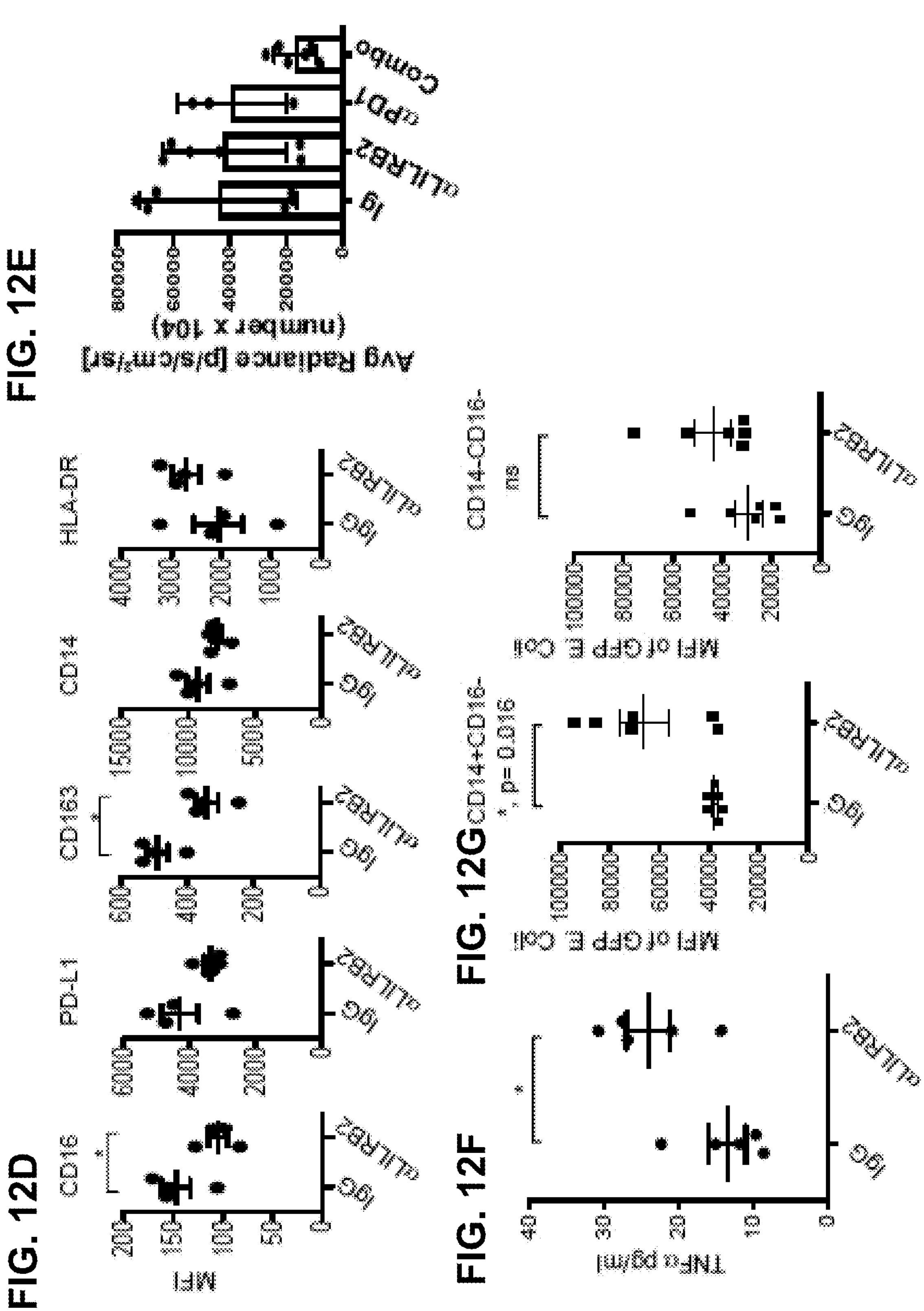
Figure 19:
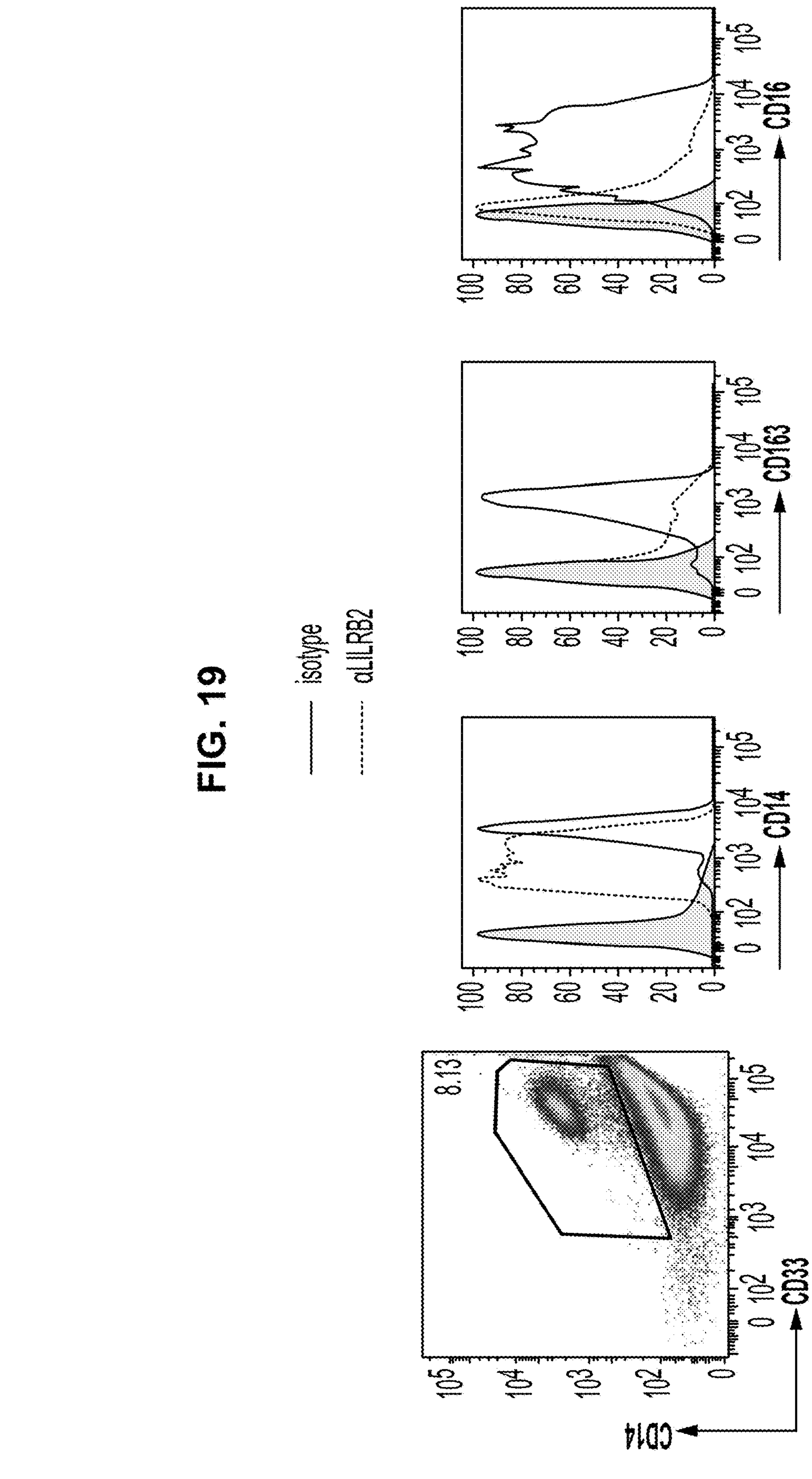
FIG. 19. LILRB2 blockade reprograms breast tumor-associated macrophage maturation.

The finding that LILRB2 blockade has a more significant impact on M(IL4) versus M(LPS) global transcription suggests that LILRB2 may be more important for maintaining immune homeostasis in the steady state or M2-like macrophages versus M1-like macrophages. We applied gene ontology analysis using the GOrilla platform (45, 46) to provide a functional interpretation of the raw data. M(LPS) DEGs were associated with G-coupled protein receptor signaling, transport, and other cellular processes. In M(IL4), LILRB2 blockade significantly altered genes associated with immune function, as well as cell migration/motility, lipid metabolism, apoptosis/proliferation, and increased enzymatic remodeling/activity (FIG. 19C, FIG. 19D), however, no clear association with immune function was noted in LPS stimulation (FIG. 19A, FIG. 19B). In response to anti-LILRB2, M(IL4) genes associated with immune function were properly regulated (FIG. 12D). Interestingly, CD83, Light, Ripk2, and Tweakr transcripts implicated in enhanced adaptive immunity and co-stimulation were upregulated. Consistent with previous reports (27, 47), M1-associated genes were upregulated, including Pfkp, Sphk1, Slc31a2, Serpine1, Hsd11b etc. (FIG. 19E). Sphingosine kinase 1 (Sphk1) is associated with obese adipose tissue macrophages from high-fat diet and ob/ob mice (48). Compared to M1-associated genes, more M2-associated genes were downregulated by anti-LILRB2 including Il13rα1, CD302, Fgl2, cathepsin C, CD163L1, Dc-sign (CD209), Maf, Ccl13, Ccl23, Stab1 and Tlr5 (FIG. 12D). LILRB2 blockade suppressed MAF in M(IL4), an important regulator of the macrophage enhancer landscape and M2-associated gene expression (49). Other M2-associated genes were also downregulated, including Klf2/Klf4, Tgfbr2, Ms4a6a, Alox15 etc. (FIG. 19E). The biological role of these molecules in M1/M2 differentiation remains to be elucidated. Notably, in addition to increased Lilra3 levels, M(IL4) treated with anti-LILRB2 showed significant inhibition of Lilrb5 and Angpt14 transcript. Chemokine transcript levels were also strongly inhibited, e.g. Ccl8, Ccl26, Ccl13, Ccl14, Ccl15, and Ccl23. We also observed that LILRB2 blockade suppressed LPS-induced dual-specific PTPs (DSPs), Dusp10 (MKP-5, JNK and p38 pathway-associated phosphatase) (50) and Dusp22 (JSP-1, JNK pathway-associated phosphatase) (51), which mediates negative feedback control of the inflammatory response.

In summary, our transcriptome-wide analyses demonstrated that LILRB2 blockade results in phenotypic changes in macrophage maturation that include immune, as well as metabolic, sorting, and cytoskeletal changes.

Figure 13A:
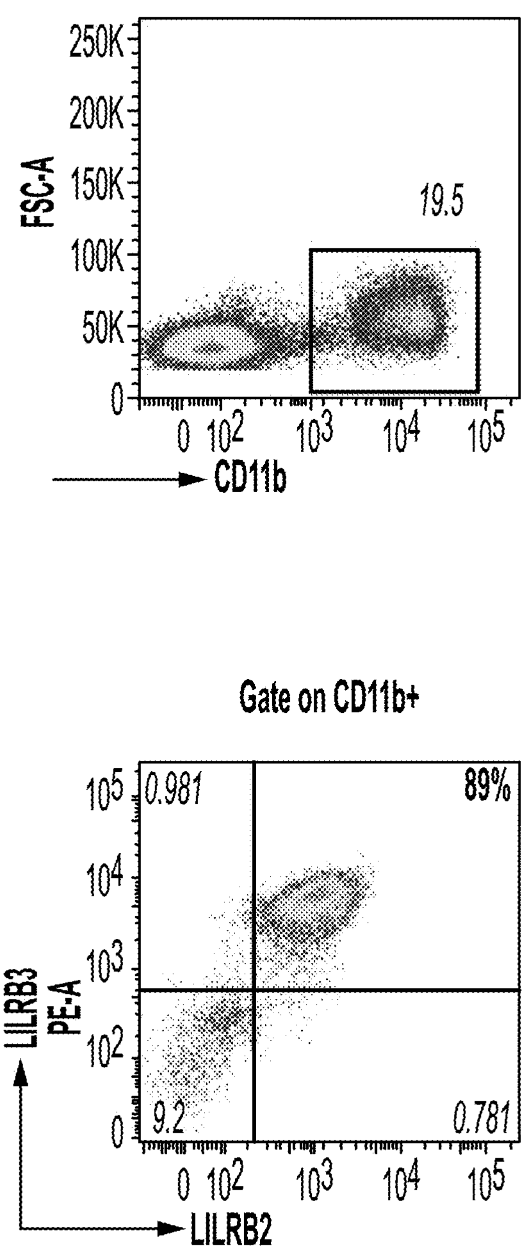
FIGS. 13A-FIG. 13G. Anti-tumor effect of LILRB2 blockade in LILRB2 transgenic mice in LLC tumor model.
Figure 13B:
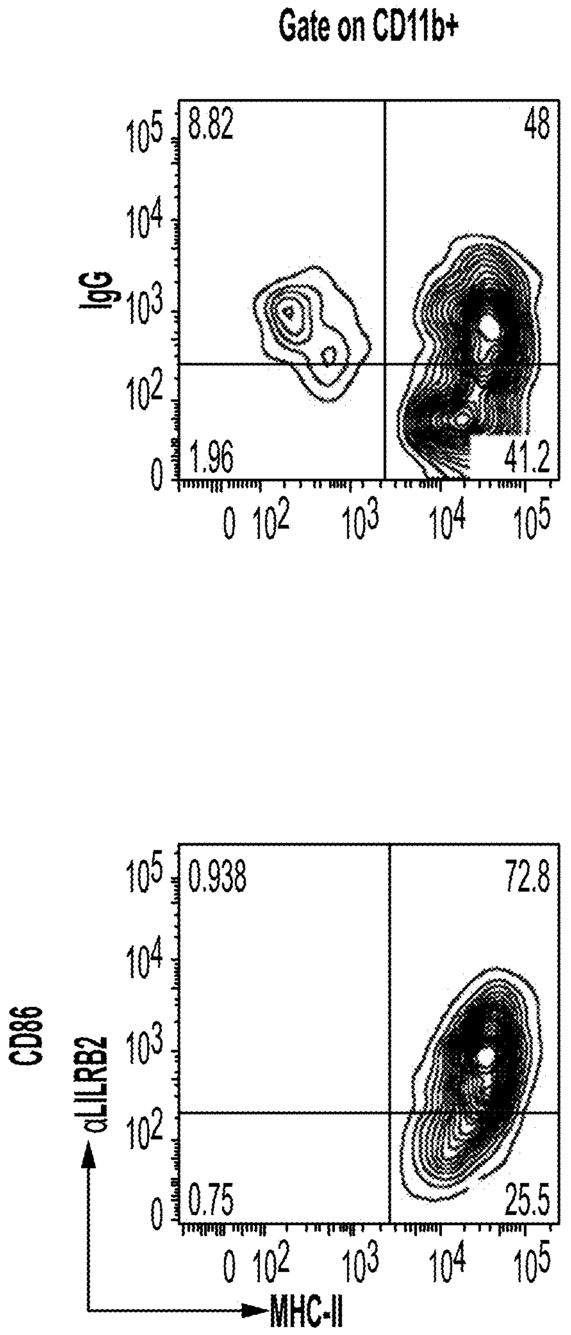
Figure 13C:
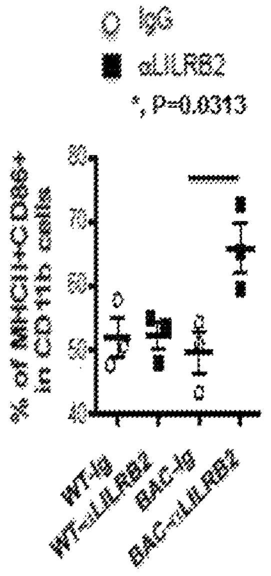
Figure 13D:
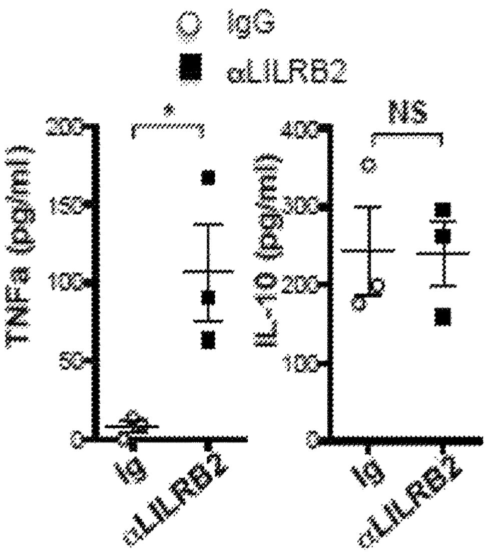
Figure 13E:
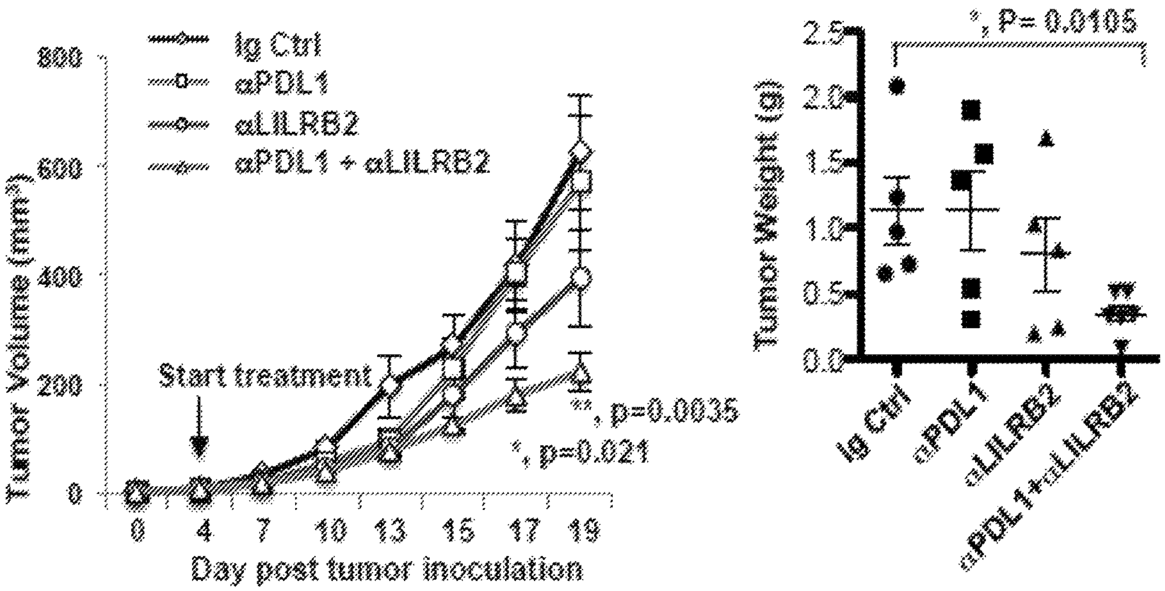
Figure 20A:
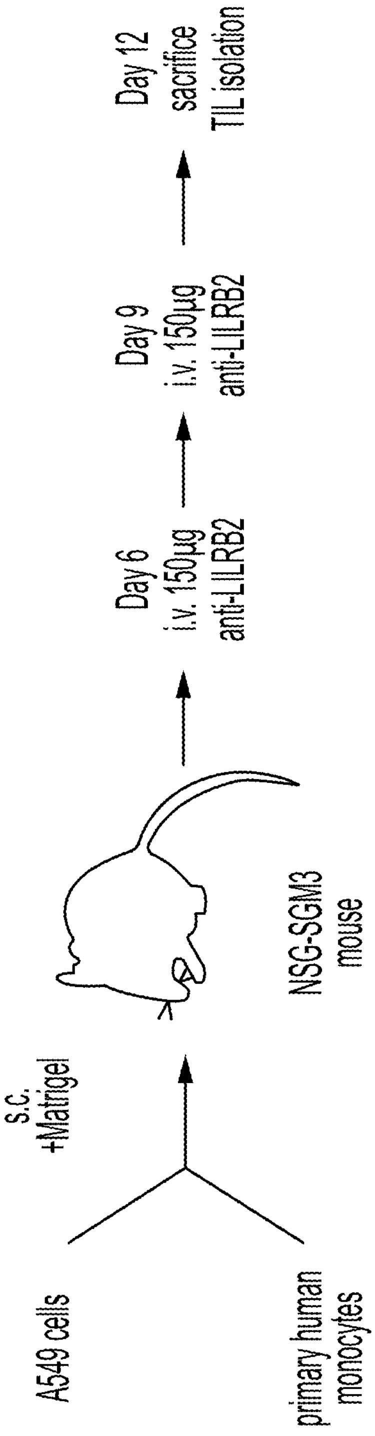
FIGS. 20A-20D. A549 lung cancer xenograft models and the generation humanized MISTRG mice.
Figures 1, 20B:
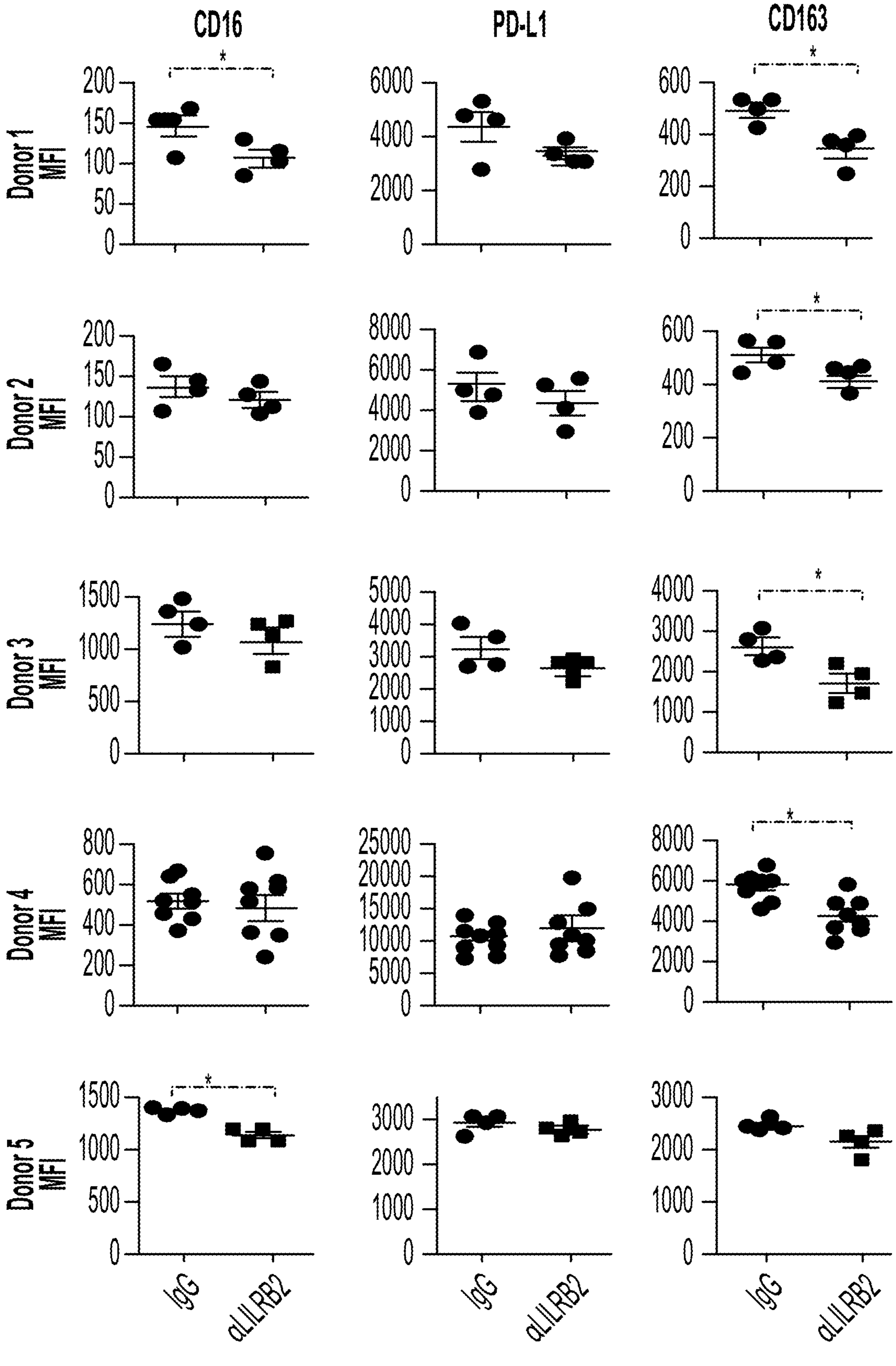
Figures 2, 20B:
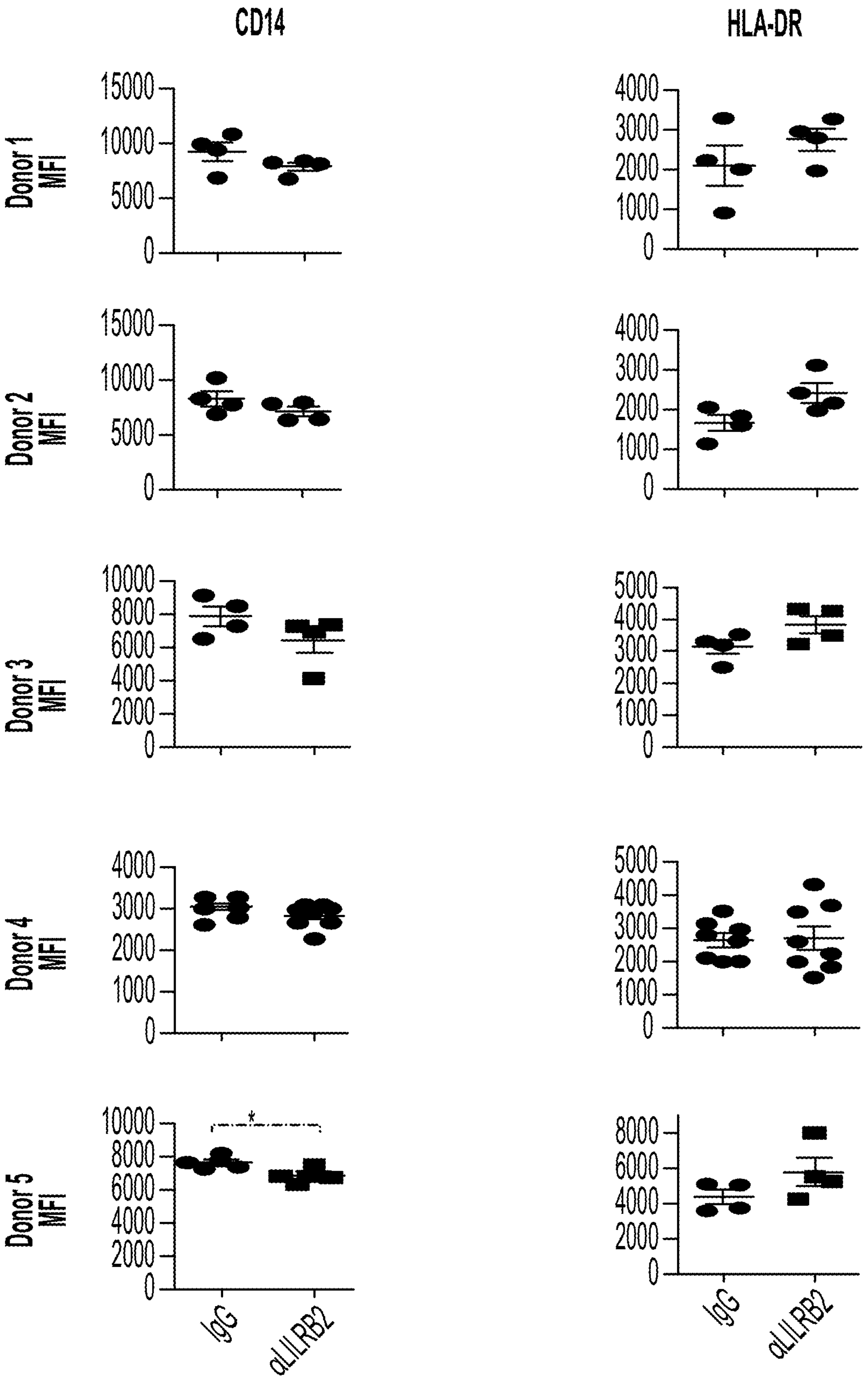
Figures 20C, 20D:
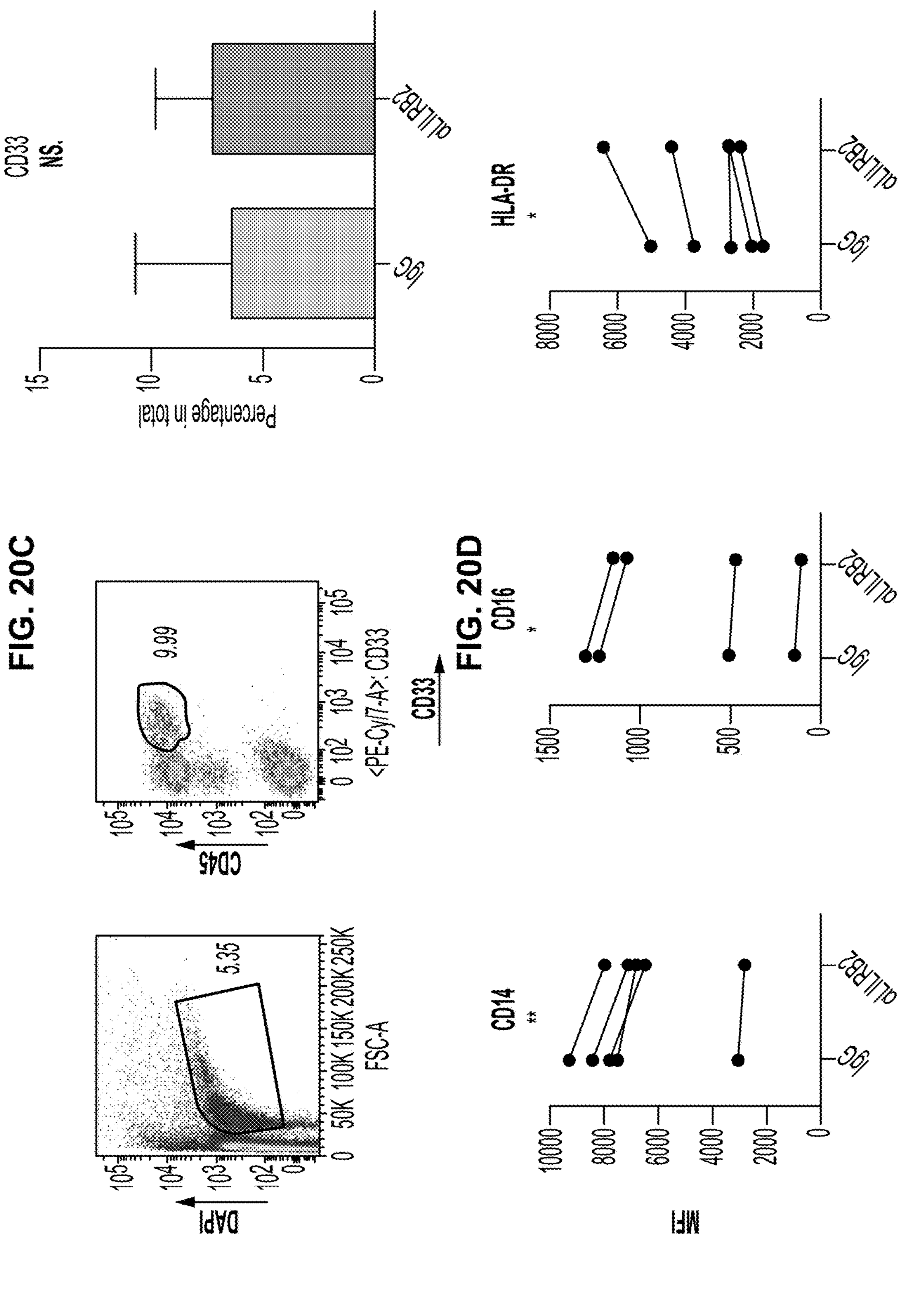
Figure 21:
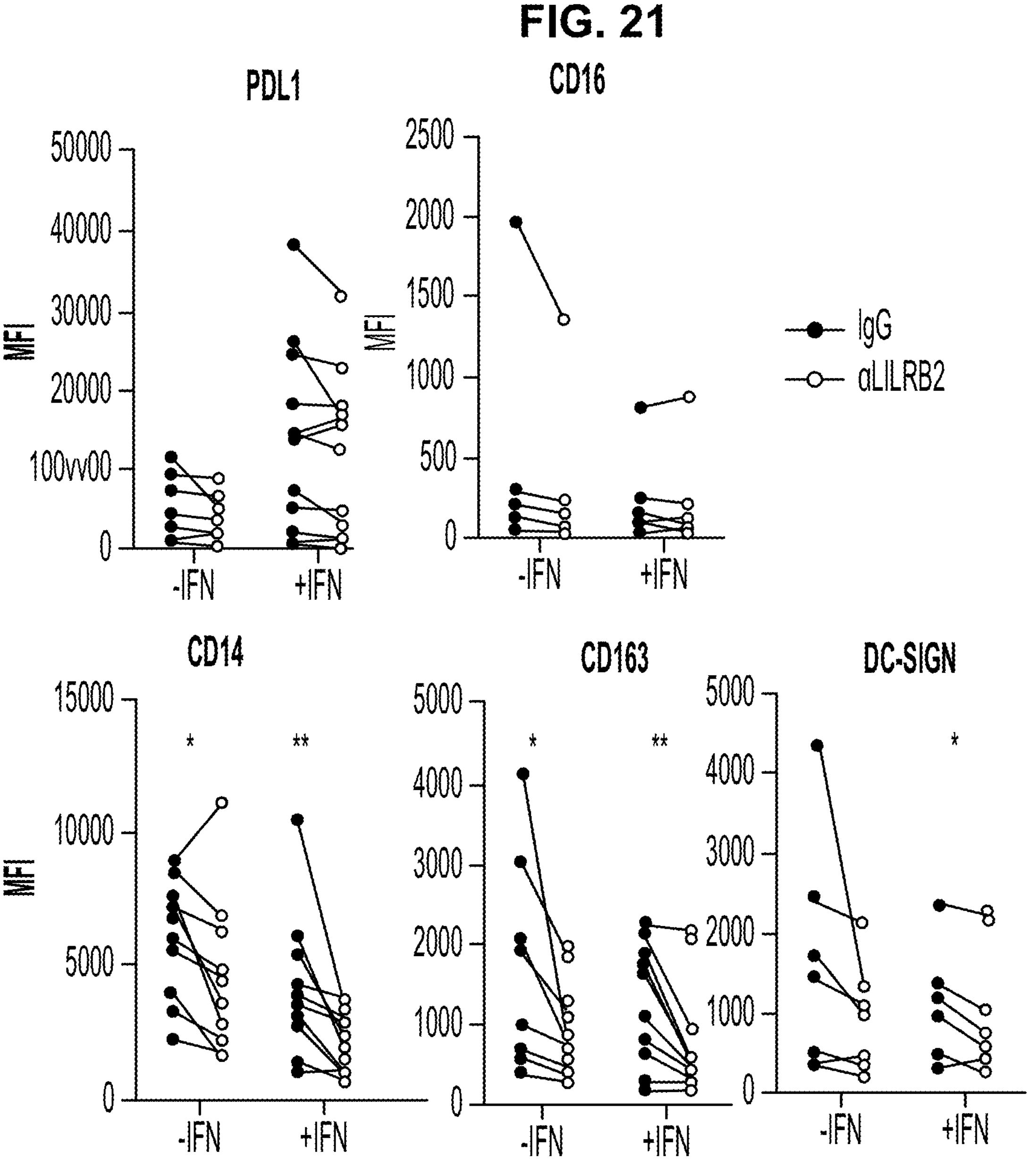
FIG. 21. Lung cancer patient-derived tumor infiltrating myeloid cells respond to LILRB2 blockade.
Figure 22A:
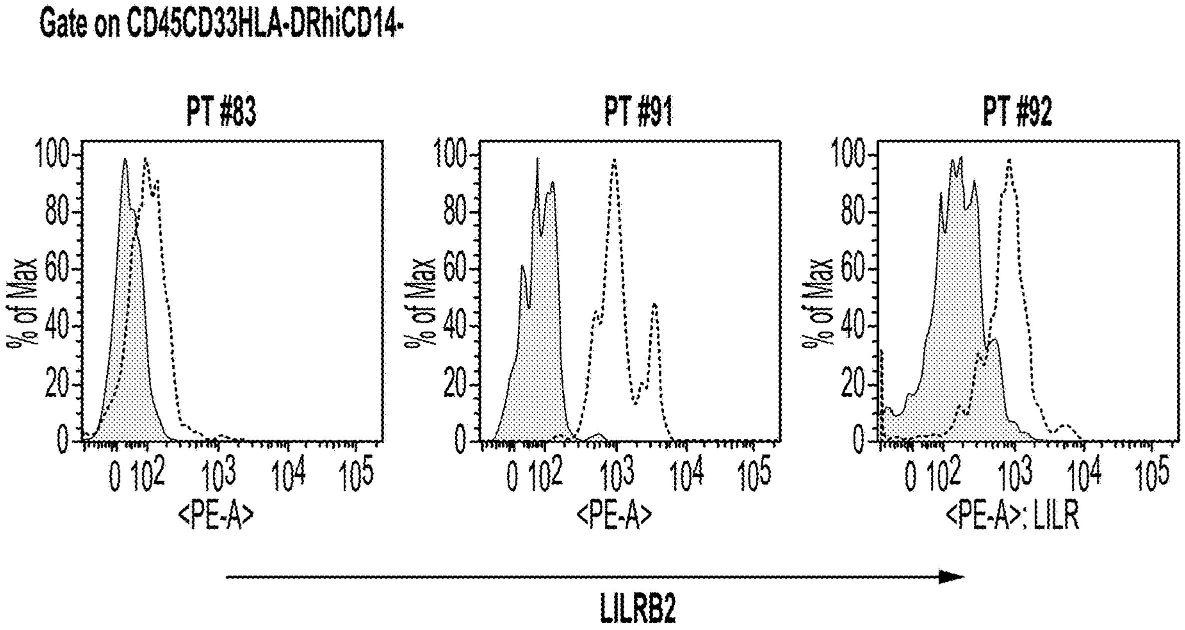
FIGS. 22A-22B. LILRB2 expression on CD45+CD33+ HLADRhiCD14-dendritic cells in tumor infiltrated lymphocytes and CD14+monocyte-differentiated dendritic cells.
Figure 22B:
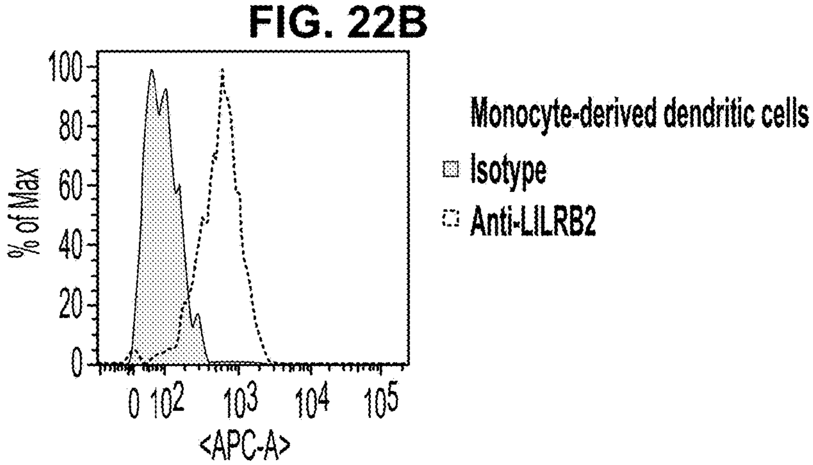

LILRB2 Blockade can Alter Tumor Cell-Induced Macrophage Maturation and Promote Antitumor Immunity We determined if LILRB2 blockade could alter the macrophage phenotype in the presence of tumor-derived factors and the tumor microenvironment. Some tumor cells are sufficient to promote the autocrine production of M-CSF by monocytes in a process dependent on tumor cell-derived IL6 (52). We hypothesized that co-culture of tumor cells with human monocytes would be sufficient to generate macrophages. Gating on $CD33^{+}CD14^{+}$ cells, we reproduced the finding that A549 NSCLC cells were sufficient to generate macrophages whose profile resembled macrophages derived from M-CSF cultures (FIG. 13A). We further observed that A549-derived macrophages cultured in the presence of LILRB2 antagonist had decreased levels of CD14, CD163, CD16 and DC-SIGN (FIG. 13B), consistent with our observations on MCSF primary macrophage cultures (FIG. 10). Similar to A549 NSCLC cells, LILRB2 antagonist exerted a similar impact on Hs578T breast cancer cell-derived macrophages (FIG. 20A, FIG. 20B). We next assessed if A549 cells could generate primary human macrophages when co-injected subcutaneously in immunodeficient NSG-SGM3 mice and whether LILRB2 blockade could similarly reprogram macrophages in vivo (FIG. 21). FACS gating on human CD45+CD33+cells identified human myeloid cells from tumor single-cell suspensions (FIG. 13C). FACS analysis of immune markers showed that specific reductions in CD163 were reproducibly detected in four out of total five donors (FIG. 21B). Furthermore, changes in other markers, including CD14, CD16 and PD-L1 were variable across donors in response to αLILRB2. FIG. 13D showed the representative data from one donor, while combined data from all five donors for CD14, HLADR and CD16 is presented in FIG. 21D. CD14 and CD16 were significantly down-regulated while HLA-DR was upregulated following anti-LILRB2 treatment across multiple mice and multiple human monocyte donors by using paired comparative analysis (FIG. 21D) HLA-A2 matched humanized NCG mice were used for in vivo experiments in order to trace long-term anti-tumor responses by LILRB2 blockade together with anti-PD-1 treatment, using an A549 (HLA-A2+) xenograft model with luciferase-expressing A549 (LUC-A549) cells. The results showed that the anti-LILRB2 and anti-PD-1 combination substantially decreased LUC-A549 tumor burden (FIG. 13E). To assess the effect of anti-LILRB2 on promoting M1 phenotypes of human macrophages in vivo, we generated a humanized mouse model using human $CD34^{+}$ cord blood stem cell-engrafted MISTRG mice to study in vivo responses of human macrophages.

Figure 13F:
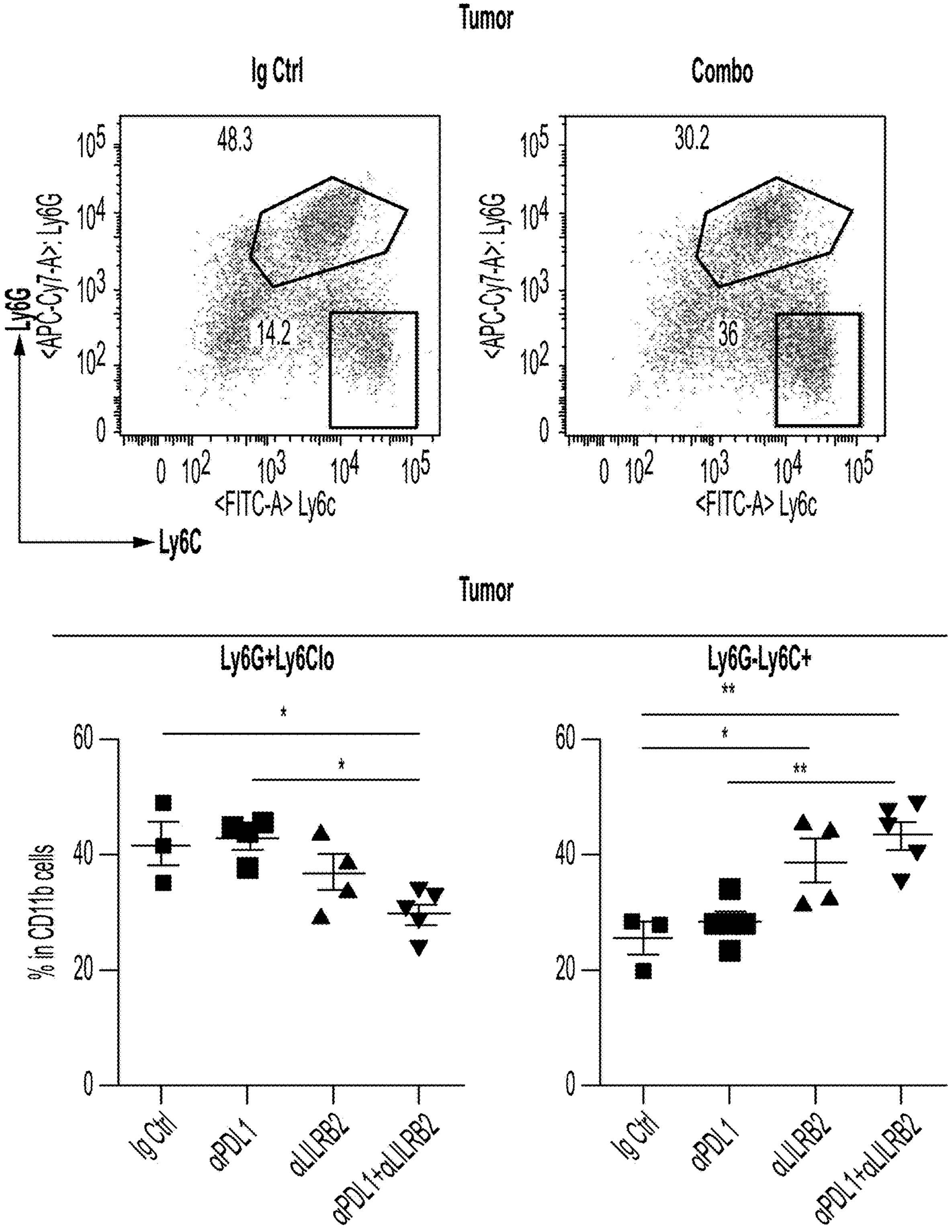
Figure 13G:
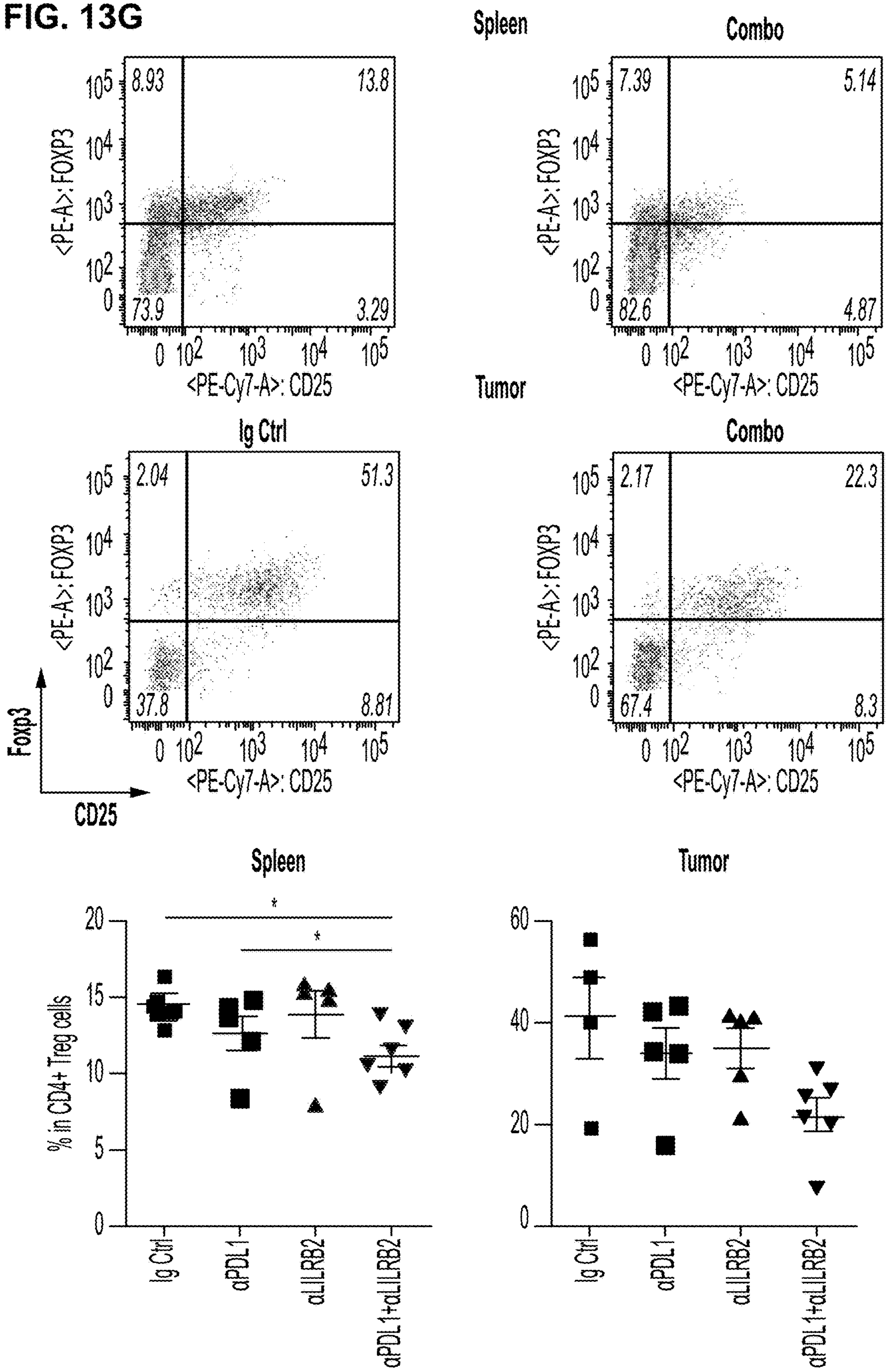

MISTRG mice support xenogenic human hematopoietic development due to humanized knock-in alleles ($M\text{-}CSF^{h}$, $IL3/GM\text{-}CSF^{h}$ and $TPO^{h}$) important for innate immune cell development that enable the full recapitulation of human myeloid development and function in the mouse. Similar human $CD33^{+}$ cell engraftment rates were observed between experimental groups (FIG. 21C). The humanized mice were treated with CpG and TNFα concentration in serum was measured. Interestingly, approximately two-fold higher human TNFα levels were found in mice treated with anti-LILRB2 vs. control Ig (FIG. 13F). The effect of LILRB2 on phagocytosis in this humanized mouse model was tested using GFP expressing *Escherichia coli*. Anti-LILRB2 significantly increased the phagocytic activity of $CD14^+CD16^-$ monocytes on GFP-expressing *Escherichia coli* when compared with the control Ig treated group (FIG. 13G).

Taken together, our data indicate that anti-LILRB2 can reprogram human macrophages in vivo to enhance anti-tumor responses in a xenograft human lung cancer model, a systemic response to CpG challenge and phagocytic activities of macrophages in humanized MISTRG mice. The overall results indicate that antagonistic LILRB2 antibody can modulate macrophage function to an M1-associated phenotype and further enhance pro-inflammatory responses in vivo.

LILRB2 Blockade can Enhance Antitumor Responses and Decrease MDSC and Treg Populations in Syngeneic Lewis Lung Carcinoma (LLC)-Bearing Mice.

Figure 14A:
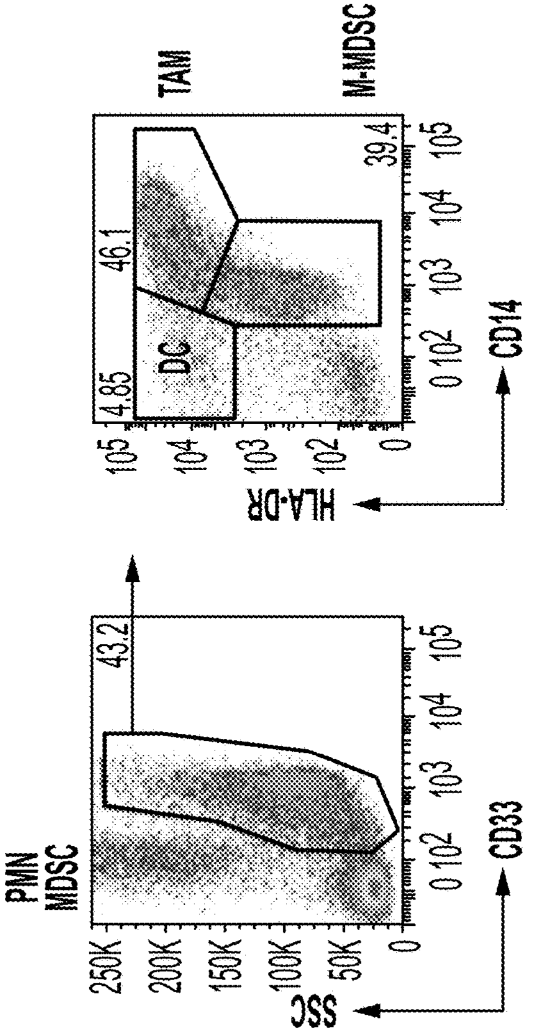
FIGS. 14A-FIG. 14F. Lung cancer patient-derived tumor-infiltrating myeloid cells respond to LILRB2 blockade.
Figure 14B:
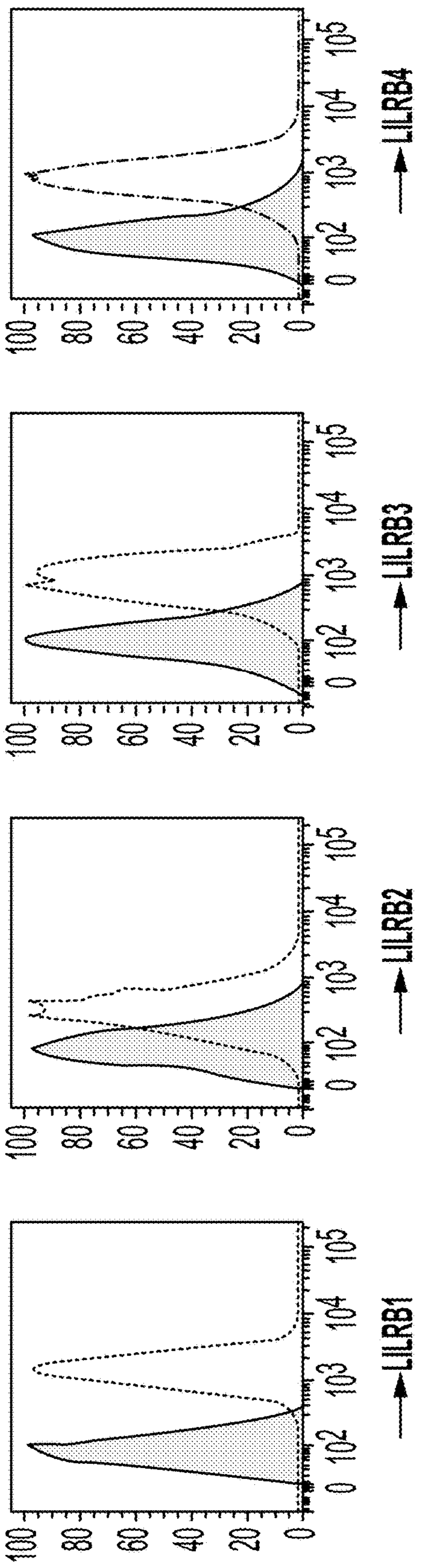
Figure 14D:
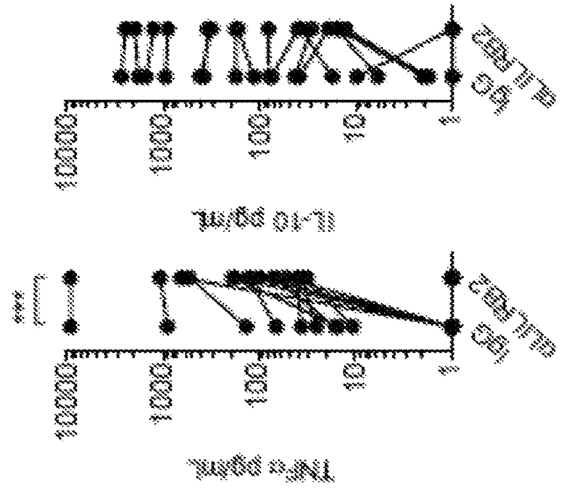
Figure 14C:
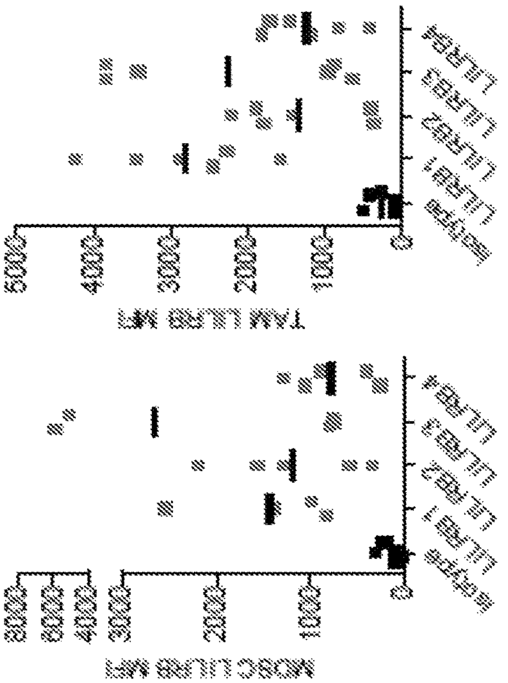
Figure 14E:
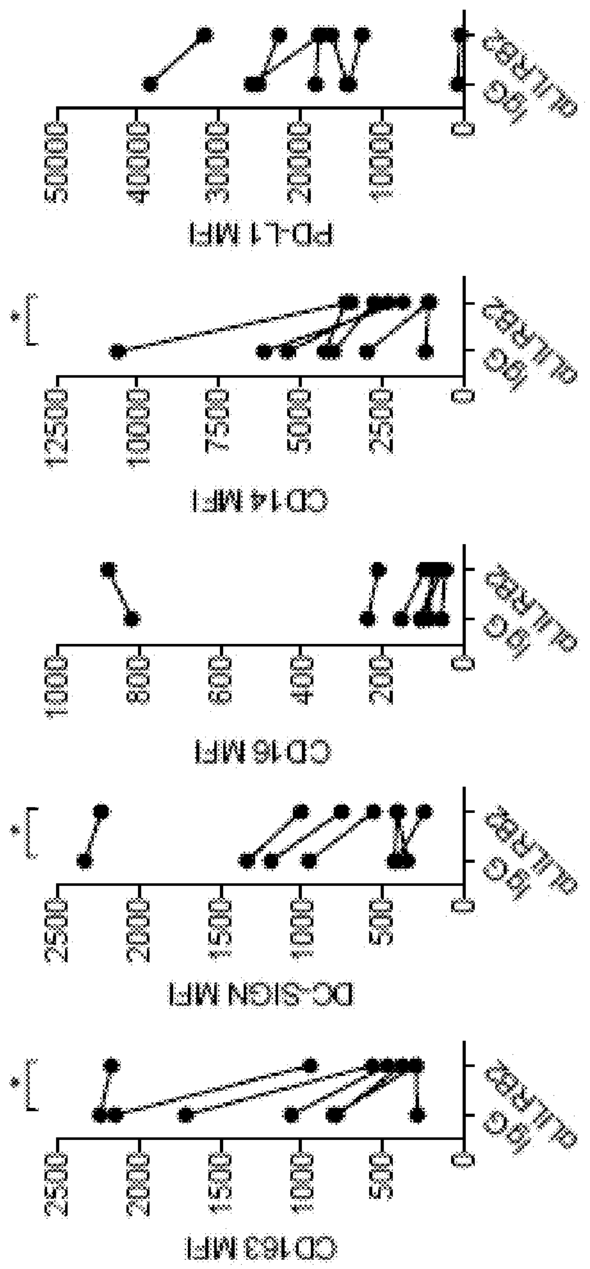
Figure 14F:
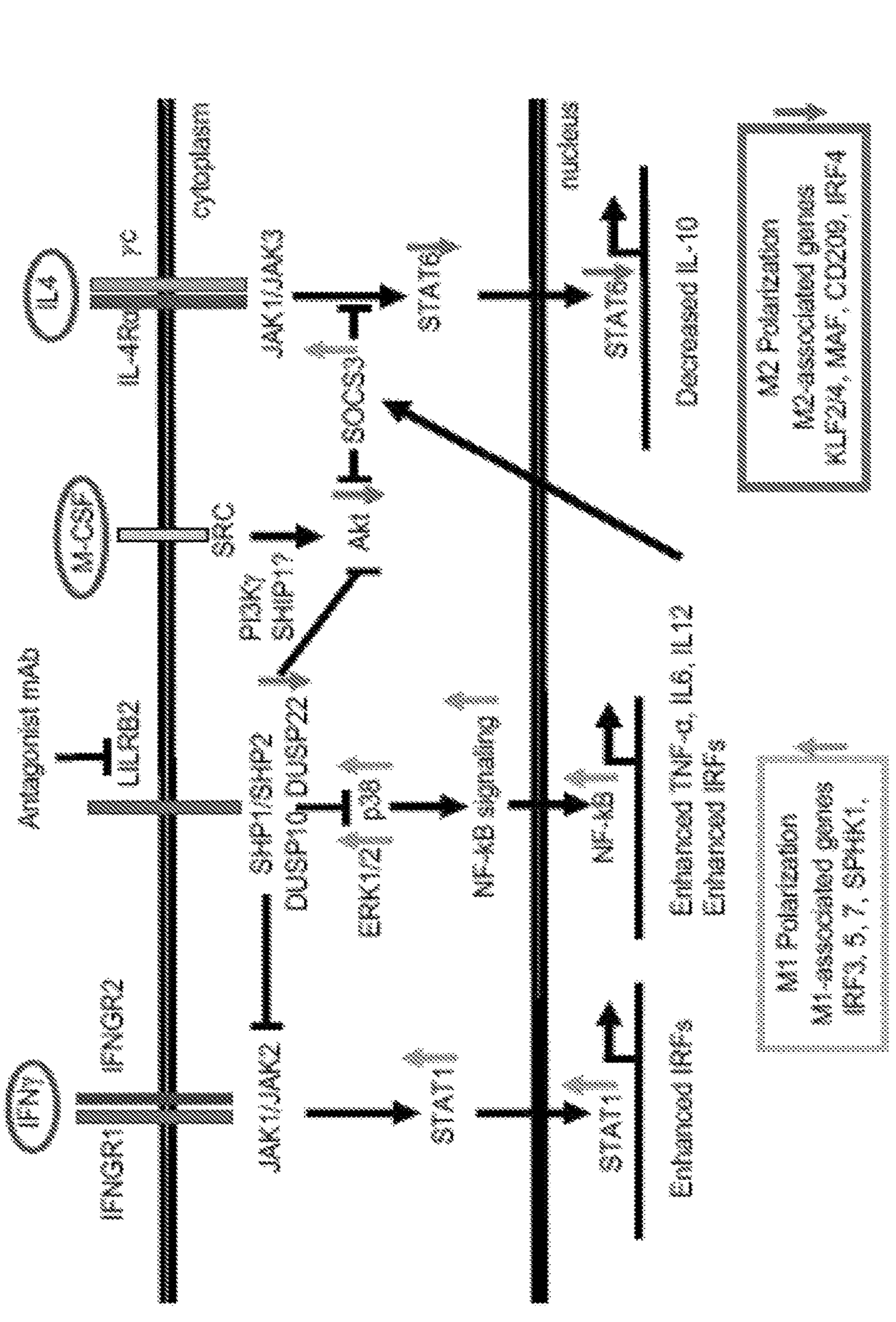

Since LILRB2 is only expressed on human, not mouse cells, and exhibits very low homology to the mouse Pirb gene, our antibody did not crossreact in the mouse system. Therefore, we employed BAC DNA injection to develop LILRB2 transgenic mice. These mice highly expressed LILRB2/3 on $CD11b^+$ cells in the peripheral blood (FIG. 14A), and anti-LILRB2 treatment increased the $CD86^+$ $MHCII^+$ population (FIG. 14B, FIG. 14C) as well as TNFα secretion in response to LPS stimulation in vitro (FIG. 14D). We evaluated whether LILRB2 blockade alone or in combination with anti-PD-L1 treatment could inhibit tumor progression and modulate the tumor microenvironment in a Lewis lung carcinoma model. PD-L1 blockade had no effect on tumor growth while LILRB2 blockade showed moderate anti-tumor effect. Blockade of both PD-L1 and LILRB2 led to significantly reduced tumor size and weight in LLC-tumor bearing mice (FIG. 14E). Furthermore, the combination of anti-LILRB2 and anti-PD-L1 significantly decreased the granulocytic Ly6G+Ly6Cint MDSC population but increased monocytic Ly6G-Ly6Chi MDSC in tumor tissues (FIG. 14F). When anti-LILRB2 was combined with anti-PD-L1 treatment, the $CD4^+CD25^+Foxp3^+$ Treg populations in spleen and tumor-infiltrated lymphocytes were both substantially decreased (FIG. 14G). Overall, LILRB2 blockade significantly decreased MDSC and Treg populations and enhanced the therapeutic efficacy of anti-PD-L1 treatment in vivo.

Primary Tumor-Associated Macrophages Respond to LILRB2 Blockade Ex Vivo

Figure 15A:
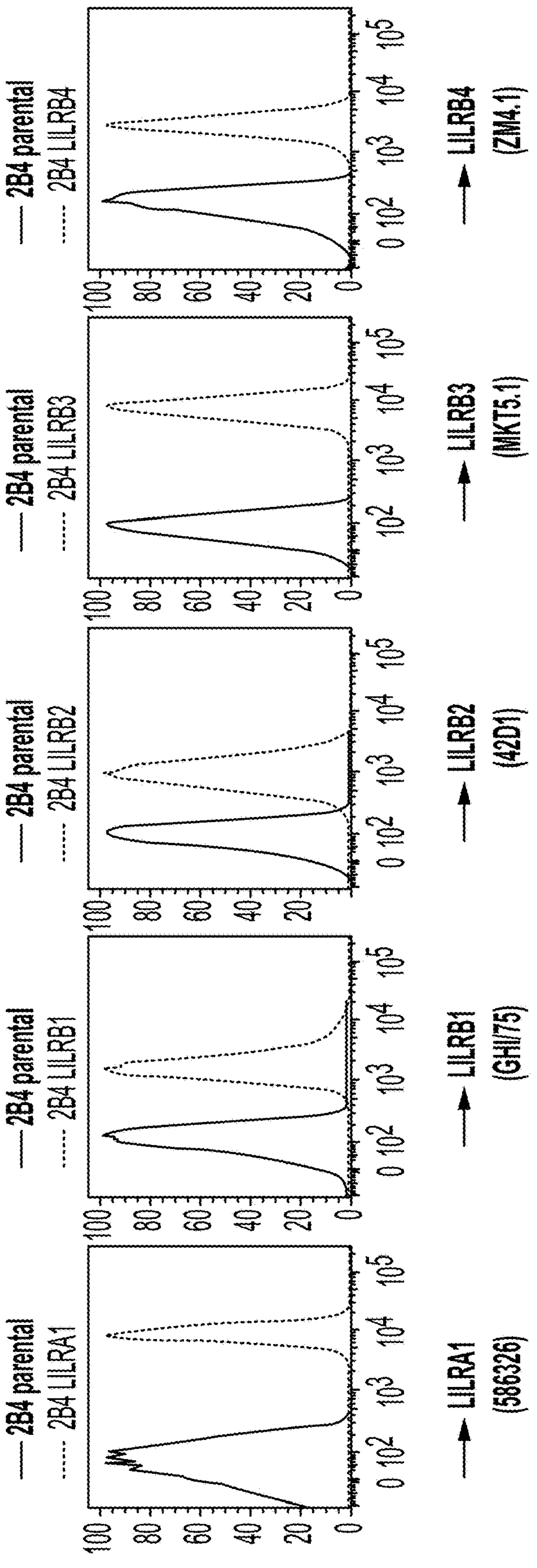
FIGS. 15A-15B. LILRB and LILRA1 detection on transduced cell lines and PBMC.
Figure 15B:
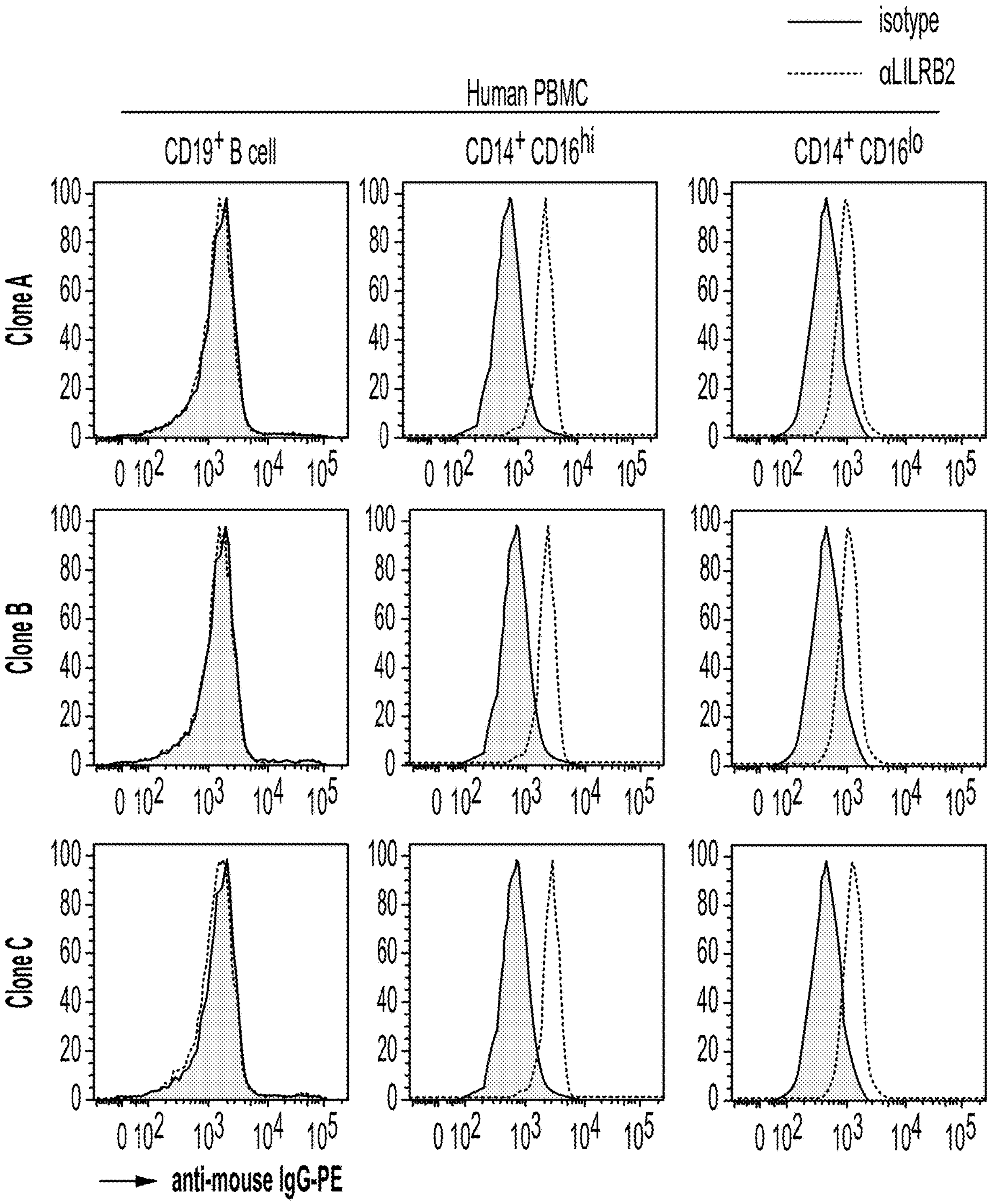
Figures 1, 23A:
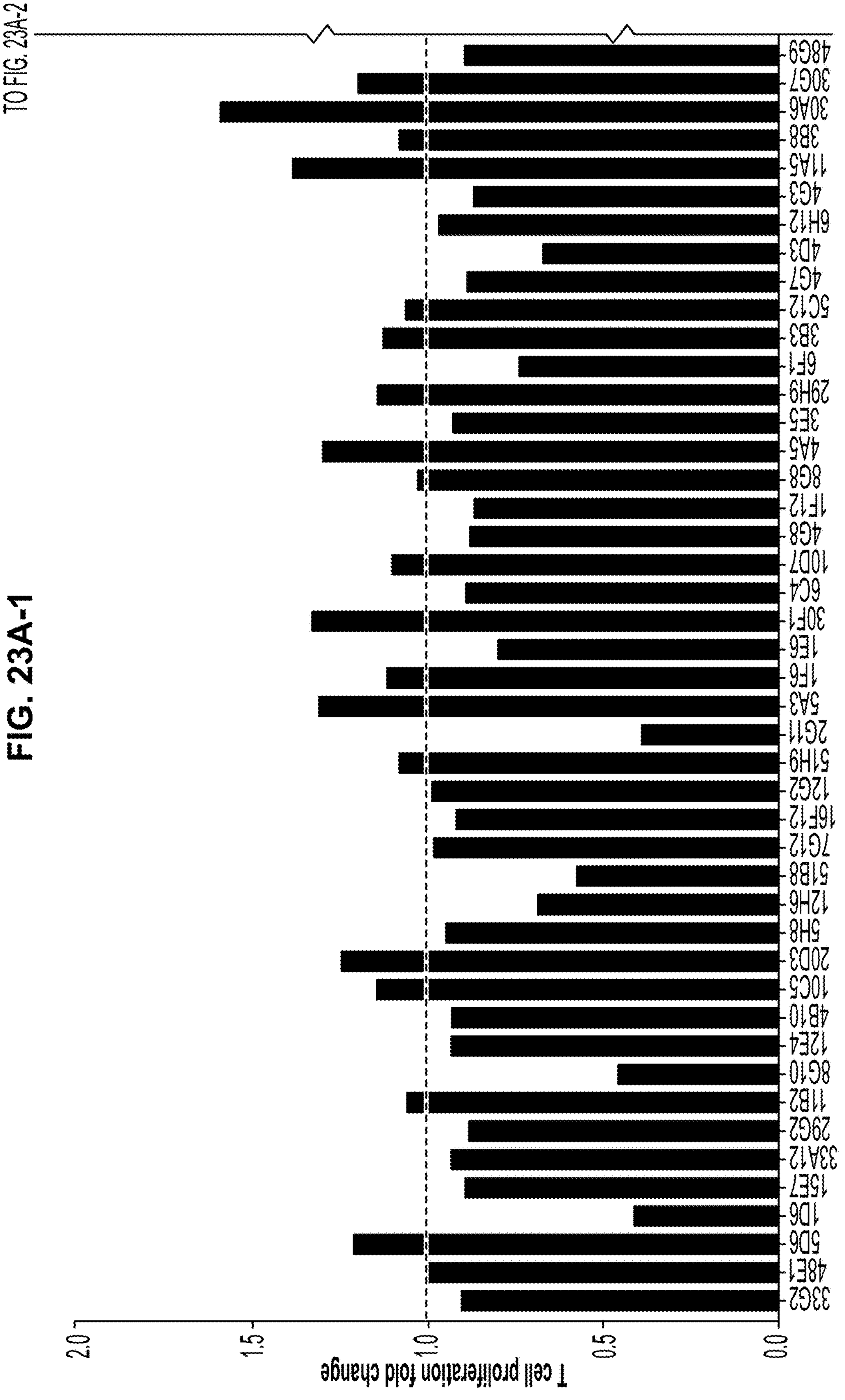
FIGS. 23A-23C are graphs showing OKT3-mediated T cell proliferation (CPM) following stimulation of PBMC from healthy donors. PBMC were cultured with LILRB2 antibodies overnight (16 hours) and stimulated with a low dose (0.01 μg/ml) anti-CD3 (OKT3) for 3 days. After 3 days of treatment, [$^3$H]-thymidine was added for the last 8 hours of culture followed by measurement on a scintillation counter. Clone ranking based on TNF alpha from FIG. 1A is presented. The relative fold change in T-cell proliferation (CPM) is presented in FIG. 23A. T-cell proliferation is shown in FIG. 23B. The overall difference in T-cell proliferation from FIG. 23B is presented in FIG. 23C.
Figures 2, 23A:
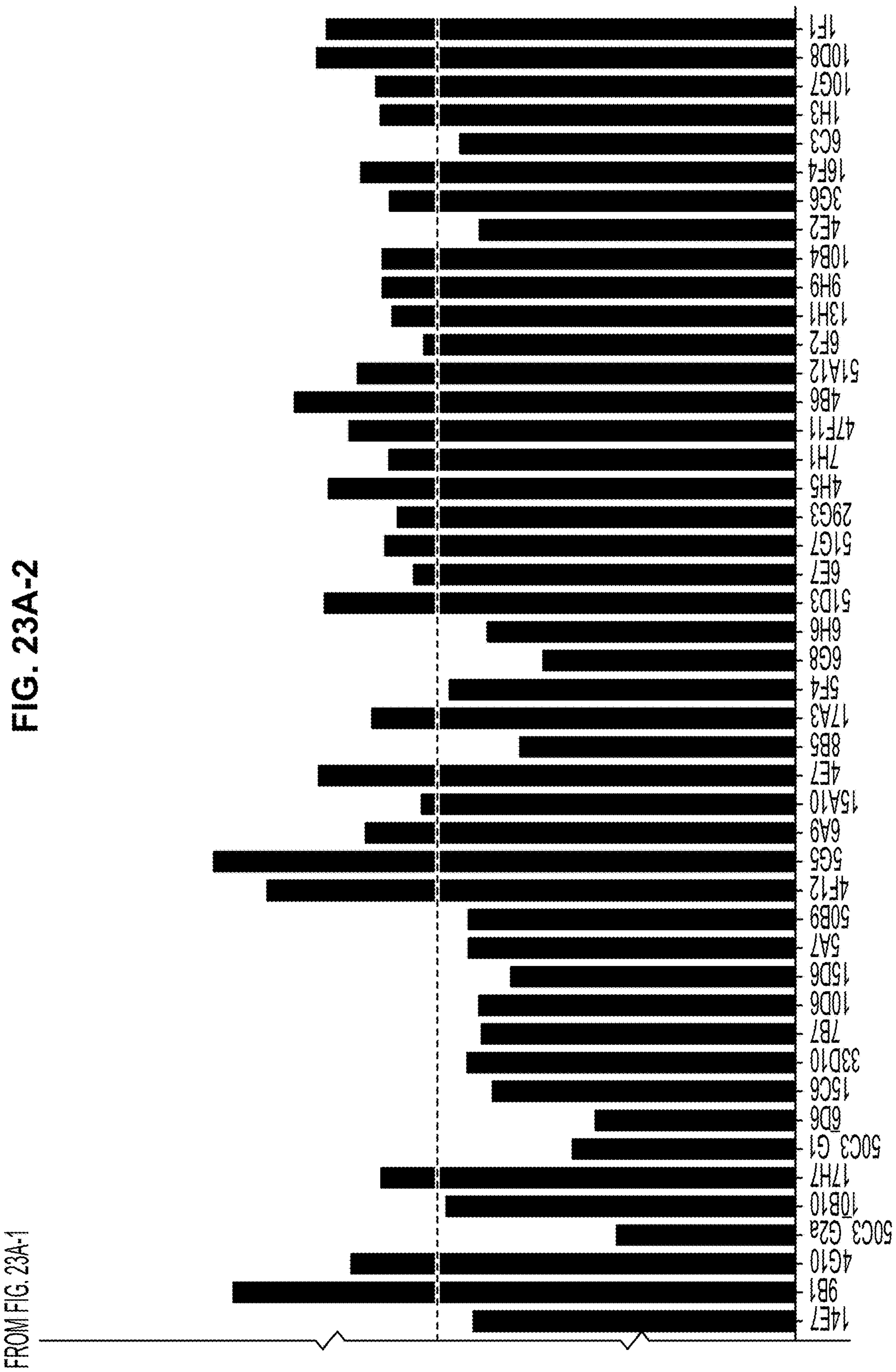
Figures 1, 23B:
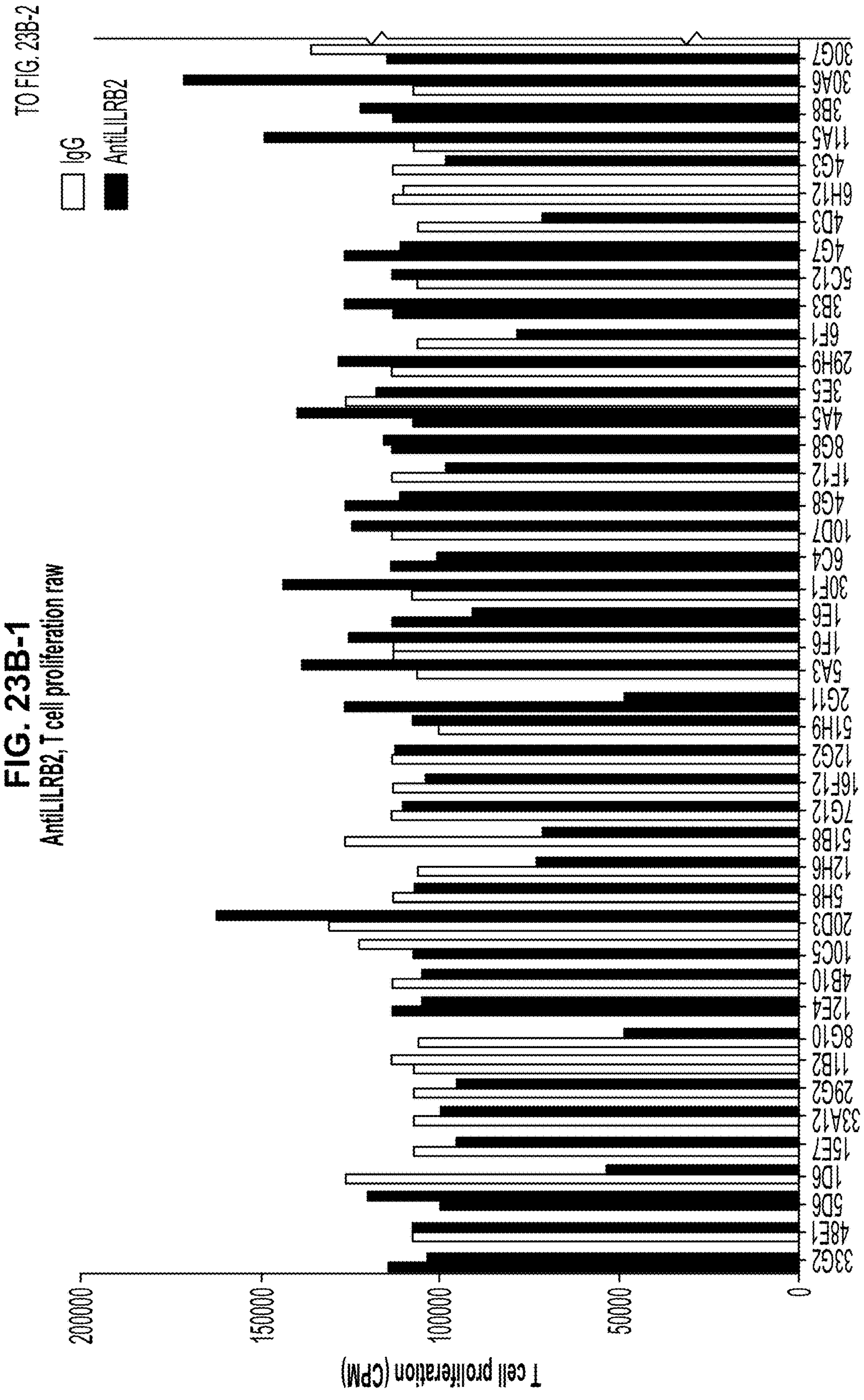
Figures 2, 23B:
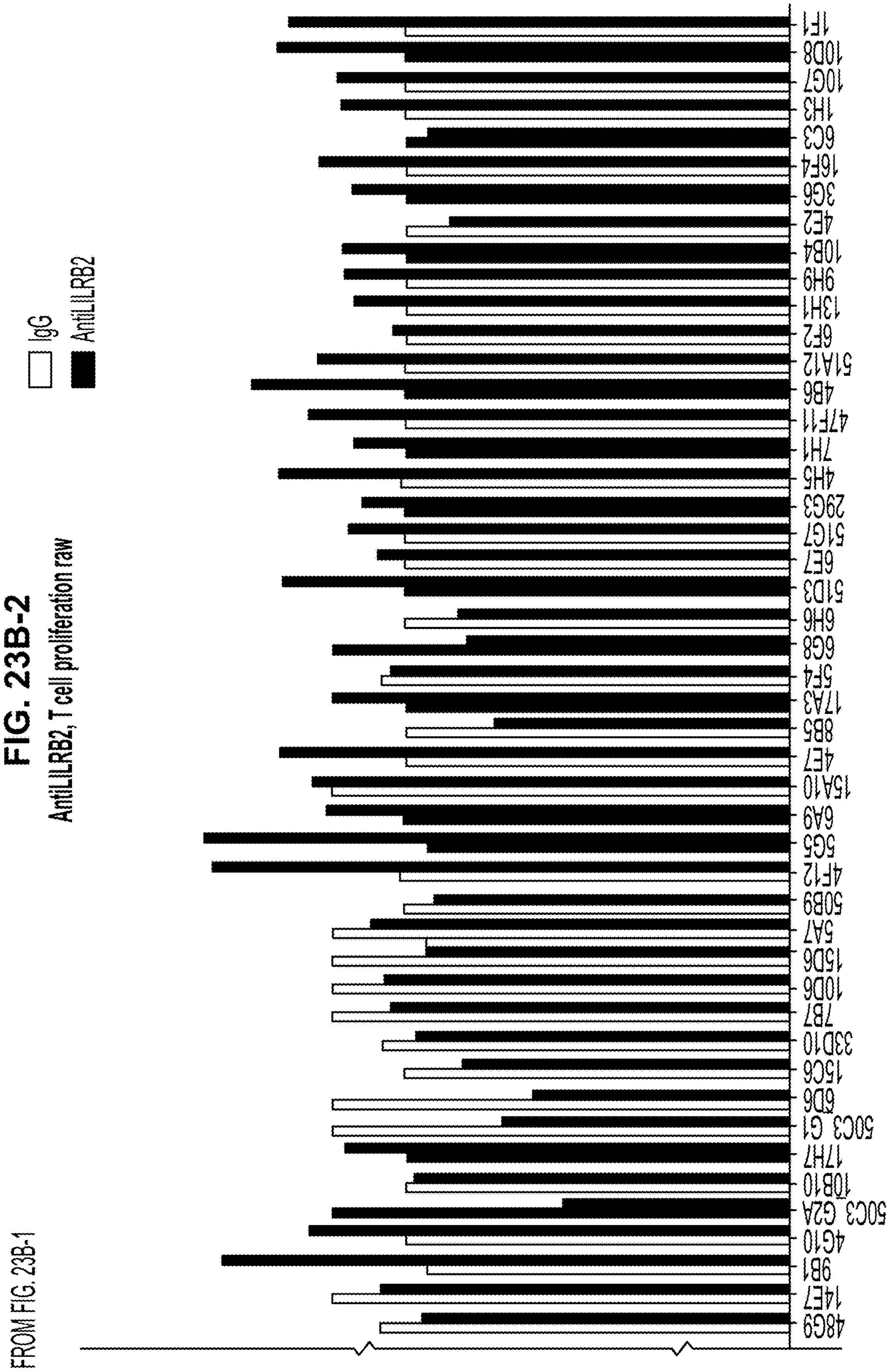

We next determined if LILRB2 blockade could reprogram isolated primary tumor-associated macrophages ex vivo. Single cell suspensions of collagenase-digested tumor tissues were used to isolate tumor-infiltrating leukocytes. By gating on DAPI-negative live cells and human CD45, we could identify infiltrating tumor associated macrophages (TAM) and MDSC based on CD33, CD14, and HLA-DR gating (FIG. 15A). Staining for LILRB family members revealed variable, but a ubiquitous expression of LILRB1, LILRB2, LILRB3, and LILRB4 among MDSC and TAM populations (FIG. 15B, FIG. 15C) while dendritic cells isolated from cancer patients' tumor tissues or derived from healthy donor PBMC expressed LILRB2 (FIG. 23A, FIG. 23B). To investigate if tumor-infiltrating myeloid populations could respond to LILRB2 blockade, we stimulated tumor infiltrating leukocytes ex vivo for 48 hours with M-CSF in the presence or absence of IFNγ or anti-LILRB2. Monocytes from most patients showed enhanced TNFα release with the treatment of anti-LILRB2 (FIG. 15D). Analyses of cell surface markers CD163, DC-SIGN, and CD14 showed significantly diminished expression in response to LILRB2 blockade. Although a trend of decreased CD16 and PD-L1 expression was observed, it was not statistically significant (FIG. 15E). These experiments were only 48 hours in duration and inclusive of total leukocyte populations found in the tumor. Nevertheless, our ex vivo data demonstrate that tumor-associated macrophages from patient biopsies express a wide range of LILRB family members and are responsive to LILRB2 antagonism.

Discussion

Our study demonstrates that antagonism of LILRB2 by specific monoclonal antibodies is sufficient to enhance inflammatory responses in monocytes and directly alters downstream macrophage maturation phenotypes. We observed constitutive activation of SHP-1 downstream of LILRB2 that was abrogated upon LILRB2 blockade. MCSF monocyte-derived macrophages matured in the presence of LILRB2 antagonism showed increased sensitivity to LPS and IFNγ stimuli as indicated by enhanced STAT1, ERK, and NFκB phosphorylation, but were resistant to IL4 stimulation as shown by reduced STAT6 phosphorylation and DC-SIGN expression along with increased SOCS3. Interestingly, LILRB2 blockade itself augmented NFκB and ERK1/2 phosphorylation and decreased AKT phosphorylation, implying that LILRB2 antagonism alone is sufficient to moderately drive MCSF monocyte-derived macrophages toward an M1 lineage. Nevertheless, LILRB2 antagonism suppressed an M2-associated and IL4-driven gene cluster while promoting those associated with an M1 phenotype. We proposed a LILRB2 mediated signal regulation model (FIG. 15F) in which LILRB2 blockade can suppress SHP1/2 phosphorylation and lead to an Ml program through restored activation of ERK (53) and p38 by suppression of SHP1/DUSPs-mediated direct or indirect dephosphorylation (ERK at Y204 and p38 at Y182), leading to further activation of NFκB. Consistent with literature (54), downregulation of SHP1/SHP2 recruitment/activation led to removal of a suppressor of JAK-STAT1 signaling and thus enhanced the IFN-induced signaling cascade (55). On the other hand, LILRB2 antagonism inhibited STAT6 phosphorylation by increasing SOCS3, which has been reported to suppress IL4/STAT6 signaling (56). The induction of SOCS3 could result from the anti-LILRB2-mediated release of proinflammatory cytokines (IL6 and IL12) through activation of MAPK/NFκB cascades (57, 58). Phosphorylation of AKT was significantly inhibited by LILRB2 blockade, which could be due to potential inhibition of: 1) SOCS3 (59, 60) or, 2) PI3-kinase γ or SHIP-1—two molecules that have been identified as key regulators for the macrophage switch between immune stimulation and suppression (61, 62).

We have previously shown that adoptive transfer of Pirb deficient MDSCs decreases tumor burden and lung metastases. Modulating macrophage function represents an attractive approach to cancer immunotherapy since a body of literature has shown that TAM are often a major component of the tumor microenvironment that contributes to tumor immune evasion (2). TAM targeted therapeutics focusing on macrophage depletion highlight the clinical benefit in reducing tumor burden in mouse models (63). However, CSF1R inhibitors can enhance circulating levels of pro-tumor granulocytic MDSC while withdrawal of CCL2 neutralization treatment can accelerate monocyte rebound to tumors (64, 65). Consequently, enhanced metastases and worse outcome are observed in several mouse models of breast cancer upon treatment cessation. TAM and M2-like macrophages appear to share functional similarities (66). Immunotherapies that reprogram TAM to support adaptive anti-tumor immunity offer an alternative strategy that avoids the potential pitfalls associated with TAM depletion (67). LILRB2 blockade appeared to alter the tumor-dependent maturation of macrophages similar to what was observed with MDM cultures. Furthermore, we demonstrated enhanced acute TNFα release and increased phagocytic capabilities in response to LILRB2 antibody treatment in xenograft humanized mice. Patient biopsies from NSCLC showed significant infiltration of MDSC and TAM populations. These primary MDSC/TAMs expressed high levels of LILRB proteins and were capable of undergoing the macrophage phenotype switch in the presence of LILRB2 blockade in ex vivo studies. LILRB2 appeared to be a critical negative regulator in both primary monocyte-derived macrophages as well as TAM populations harvested from patients. We also observed that anti-LILRB2 significantly decreased $Ly6G^{+}Ly6C^{int}$ granulocytic MDSC in both spleen and tumor tissues in an immune competent syngeneic LILRB transgenic mouse model.

Most importantly, LILRB2 antagonism substantially enhanced the efficacy of an immune checkpoint inhibitor, anti-PD-1, in a PBMC humanized NCG mouse model bearing human lung cancer cells, A549 (FIG. 13E). We further confirmed the effect of LILRB2 blockade in an immunocompetent syngeneic Lilrb2/3 BAC transgenic mouse model (FIG. 14E). It is important to note that anti-PD-L 1 treatment alone showed a limited antitumor effect in LLC-tumor bearing immune-competent mice (68, 69). We found that LILRB2 antagonism suppressed LPS-induced CD274 (PD-L1) expression in activated monocytes from healthy donors (FIG. 10) and that blockade of both LILRB2 and PD-L1 potentiated a strong host antitumor immunity against LLC tumors in LILRB2 transgenic mice. Concomitantly, we observed significant decreases in granulocytic MDSC and Treg in tumor-bearing mice treated with anti-LILRB2 and anti-PD-L1. The unexpected increase in monocytic MDSC did not compromise the efficacy of anti-PD-L1, suggesting that LILRB2 antagonism converted monocytic MDSC into a non-suppressive and immunostimulatory phenotype, similar to that of Pirb deficient MDSC (12) and macrophages in the presence of LILRB2 blockade (FIG. 13).

Several pathways have been shown to be involved in M2 polarization, including mTOR-semaphorin 6D (Sema6D)-peroxisome proliferator receptor γ (PPARγ) (70), PI3Kγ-mTOR (62) and TSC-mTOR pathways (71, 72). Targeting these pathways can potentially provide high therapeutic values in immune-oncology.

Our transcriptome data indicated that LILRB2 blockade markedly down-regulated multiple gene targets involved in M2-like maturation while genes associated with enhanced adaptive immunity and co-stimulation were upregulated. Our study highlighted that antagonism of LILRB2 inhibited both AKT activation and IL4 signaling, which may interfere with Sema6D/PI3Kγ/mTOR signaling pathways. This suggests that antagonism of LILRB2 may have broader impacts on reversing immunosuppressive function of tumor-associated macrophages to enhance the efficacy of immune checkpoint inhibitors. Our data provided strong evidence that LILRB2 antagonism could be a promising approach for reprogramming TAM in the tumor microenvironment, thereby enhancing adaptive anti-tumor immunity.

Materials and Methods

Animals

NSG-SGM3 (Stock No. 013062) and MISTRG mice (Stock No. 017712) were purchased from Jackson Laboratory (Bar Harbor, ME). NCG mice (Stock No. 572) were purchased from Charles River Laboratories (Wilmington, MA). All animal experiments were conducted in accordance with the animal guidelines of the Icahn School of Medicine at Mount Sinai and the Houston Methodist Research Institute.

Cell Lines

Lilrb1-4 and Lilra1 expressing 2B4 reporter cells were generated by transfection with plasmids carrying corresponding Lilr-Fc fusion genes followed by selection by GS/MAS systems and maintained in Dulbecco's modified Eagle's medium (DMEM, Corning Cellgro, Manassas, VA) containing 10% fetal bovine serum (FBS, Atlantic Biologicals, Atlantic, GA)+100 nM penicillin/streptomycin (Life Technologies). THP-1 cells, a pro-monocytic cell line, were cultured in RPMI 1640 (Corning Cellgro, Manassas, VA) supplemented with 10% FBS, 0.1 mM non-essential amino acids (Gibco), 1 mM sodium pyruvate. THP-1 and human alveolar adenocarcinoma A549 cell lines were purchased from the American Type Culture Collection (Manassas, VA). LILRB2+THP-1 cells were generated by retroviral transfection with full-length LILRB2 plasmid.

Flow Cytometric Analysis and Generation of Anti-LILRB2 Hybridoma

Commercial anti-LILRB2 antibodies, clone 42D1 and clone 287219 were purchased from Biolegend (San Diego, CA) and eBioscience (San Diego, CA), respectively. Anti-LILRB1 (clone GHI/75), anti-LILRB3 (clone MKT5.1) and anti-LILRB4 (clone ZM4.1) antibodies were from Biolegend. Anti-LILRA1 (clone 586326) antibody was from Novus Biologicals (Littleton, CO). Human anti-CD4-FITC (Clone RPA-T4), anti-CD8-PE (Clone HIT8a), anti-CD16-FITC (Clone CB16), anti-DC-SIGN-PE (Clone eB-h209), anti-CD163-APC (Clone GHI/61), anti-PD-L1-PerCP-Cy5.5 (Clone MIH1), anti-CD33-PE-Cy7 (clone WM-53), anti-CD14-APC-Cy7 (Clone 61D3), anti-CD45-PE (clone 2D1) and anti-HLA-DR-FITC (clone LN3) were purchased from eBioscience or Biolegend. Mouse anti-CD11b-PerCP (clone M1/70), anti-CD8a-eFluor 780 (clone 53-6.7), anti-CD4-FOXP3 (clone FJK-16S), anti-CD4-FITC (clone GK1.5), anti-CD25-PE-Cy7 (clone PC61.5), anti-MHCII-PE-Cy7 (clone M5/114.15.2), anti-Ly6G-APC-Cy7 (clone 1A8) and anti-CD25-PE-Cy7 (clone PC61.5) were purchased from eBioscience or Biolegend. Anti-Ly6C-FITC (clone AL-21) and anti-mouse arginase 1-APC (clone IC5868F) were purchased from BD Biosciences (Franklin Lakes, NJ) and R&D Systems (Minneapolis, MN), respectively.

We generated anti-LILRB2 antibodies by immunizing with Lilrb2 DNA followed by boosting once with LILRB2 vesicle or protein. Outgrowing fused hybridoma clones were expanded in vitro and supernatants were screened by using FACS on 2B4 LILRB2 expressing cells labeled with goat polyclonal anti-mouse IgG secondary antibody (Biolegend). The 2B4 cell is a generous gift from Dr. Hisashi Arase, Research Institute for Microbial Diseases, Osaka University, Japan.

For functional screening of anti-LILRB2 antibodies, PBMC were incubated with 20 μl of antibody-containing supernatants for 48 hours. LPS (50 ng/ml, Sigma-Aldrich, St. Louis, MO) and GolgiPlug (BD Biosciences) were added at last 4 hours of cell culture. The cells were harvested for surface CD86 (anti-CD86-Alexa Fluor 488, clone IT2.2, Biolegend) and intracellular TNFα (anti-TNFα-PE-Cy7, clone MAB11, Biolegend) per the manufacturer's instructions (GolgiPlug Kit, BD Biosciences). In flow cytometric analyses, dead cells were excluded by DAPI (Sigma-Aldrich) staining.

In vitro studies were performed with antibody 1H3; in vivo studies were performed with antibody 5G5.

Biolayer Interferometry Binding Assay

Real-time binding assays between LILRB2-His (Sino Biologicals, Wayne, PA) and anti-LILRB2 antibodies were performed using biolayer interferometry on an Octet Red system (Fortebio, Menlo Park, CA, USA). This system monitors interference of light reflected from the surface of a fiber optic sensor to measure the thickness of molecules bound to the sensor surface. Anti-LILRB2 antibody (10 μg/mL) was coupled to kinetics grade Protein G/mouse IgG high binding biosensors (Fortebio). Sensors coated with Anti-LILRB2 antibody were allowed to bind to LILRB2-His in PBS with 0.1% (v/v) Tween-20 and 10% DMSO at increasing concentrations. Binding kinetics were calculated using the Octet Red software package, which determined the best fit for the observed binding curves and calculated the association rate constants. LILRB2-His was dissociated by incubating the sensors in PBS with 0.1% Tween-20 and 10% DMSO. Best fit dissociation curves were determined, and the dissociation rate constants were calculated. Binding affinities (kD) were calculated as the kinetic dissociation rate constant divided by the kinetic association rate constant.

Antibody Purification and Endotoxin Test

Clonal hybridoma cells were cultured in ClonaCell-HY Medium A (StemCell Technologies) followed by adaptation to serum-free conditions using Hybridoma-SFM (ThermoFisher Scientific). Hybridoma cells were expanded in 50 mL of Hybridoma SFM for 2 weeks or until medium was exhausted. Antibody-containing supernatant was harvested by centrifugation (800 g, 10 mins) and concentrated using Amicon Ultra-15 centrifugal filter concentrators with a nominal molecular weight limit of 100 kDa. Concentrated supernatants were then purified using Nab Protein A/G Spin Kit (Thermo Fisher Scientific, Waltham, MA) according to manufacturer's instructions. Purified antibody was desalted using Zeba™ Spin Desalting Columns, 7K MWCO (Thermo Fisher Scientific). Purified antibodies were further concentrated by centrifugal filter (Thermo Fisher Scientific), if needed. Endotoxin levels in purified antibodies were determined by Pierce™ LAL Chromogenic Endotoxin Quantitation Kit (Thermo Fisher Scientific) according to manufacturer's protocol.

Generation and Differentiation of Human Monocyte-Derived Macrophages

Buffy coats from healthy donors were purchased from the New York Blood Center. PBMC were isolated by using a LymphoPrep (StemCell #07851). $CD33^+$ monocytes were purified from healthy PBMC donors using $CD33^+$ magnetic beads (Miltenyi Biotech, Cat. No. 130-045-501) and treated with IgG or anti-LILRB2 (1 μg/mL) in the presence of M-CSF (50 ng/ml) (PeproTech: 300-25) for 5 days. After 5-day culture, immature macrophages were obtained for flow analysis or further stimulated with LPS (50 ng/ml) or IL4 (25 ng/ml) for 16-24 hours. The supernatants were collected and TNFα and IL10 production was determined by ELISA (eBioscience).

A549 xenograft model in NSG-SGM3 immuno-deficient mice $3\times10^6$ A549 cells and $CD33^+$ myeloid cells from healthy donors were suspended in 50% Matrigel (Corning, Cat: 356231) and subcutaneously co-inoculated into NSG-SGM3 mice (Jackson Laboratories, No: 013062). Each mouse received two subcutaneous A549/$CD33^+$ implants in the right and left flank (Day 0). Anti-RB2 antibody and corresponding Ig controls were injected intravenously on day 6 and day 9 (150 μg/mice). The tumors were measured and dissected for analysis on day 12. Tumor-infiltrating lymphocytes were purified as previously described for flow cytometric analysis of MI/M2 differentiation.

Luciferase-Expressing A549 (LUC-A549) Xenograft Model in HLA-A2+PBMC Humanized NCG Mice Human luciferase-A549 cancer cells (LUC-A549, from GenTarget, Inc.) ($2\times10^6$ cells) were intravenously injected into NCG immuno-deficient mice on day 0. Human HLA-A2+PBMC ($1\times10^7$ cells) were purified and intravenously injected into test mice together with anti-LILRB2 on day 3 and day 13. Anti-LILRB2 and IgG (200 μg/mice) were given once every three days for a total of 8 injections. Anti-PD-1 (Nivolumab) was given once per week (200 μg/mice) for a total of 3 injections. Subsequently, the LUC-A549 tumor-bearing mice were monitored for bioluminescent imaging of luciferase activity using the IVIS Spectrum In Vivo Imaging System and Living Image software (Perkin Elmer, Inc.). Prior to imaging, 250 μl luciferin (at 15 mg/ml; PerkinElmer, Waltham, MA) was administered intraperitoneally. Afterward, the mice were anesthetized by isoflurane inhalation and imaged. Tumor progression was quantified by bioluminescence signals (Avg Radiance [p/s/$cm^2$/sr]) from the lungs 25 days after tumor inoculation.

Generation of Bacterial Artificial Chromosome (BAC) Transgenic Mice

BAC clones for both the human Lilrb2 and Lilrb3 genes were isolated from a human BAC library (BACPAK Resources Center). BAC DNA was purified by NucleoBond Xtra Midi EF Kit. The identity of BAC DNA was confirmed via PCR for our gene of interest (Lilrb2), then microinjected into embryonic stem (ES) cells. Germline transmission of the targeted allele was confirmed by PCR and flow cytometry.

Lewis Lung Carcinoma (LLC)-Tumor Model in Lilrb2 Transgenic Mice.

Lewis lung carcinoma (LLC) tumor cells ($4\times10^5$ cells) were subcutaneously injected into LILRB2 B6 transgenic mice. Antibody treatments were started when tumors reached 2 mm×2 mm. Anti-LILRB2 (200 μg/mouse) treatment was started on day 4 after tumor inoculation for a total of 6 injections. Anti-PD-L1 (200 μg/mouse) treatment was started with the second injection of Anti-LILRB2 for a total of 5 injections. The tumors were dissected for analysis on day 21. Splenocytes and tumor-infiltrating lymphocytes were purified for flow cytometric analysis on MDSC and Treg populations.

Phagocytosis of GFP-Expressing *E. coli* Ex Vivo.

Humanized MISTRG mice were screened by assessing human $CD33^+$ cell engraftment and equally distributed between human IgG control and anti-LILRB2 groups. The test mice were intraperitoneally injected with anti-LILRB2 Ab (150 μg/mouse) for 48 hours. Peripheral blood cells were isolated and incubated with *E. coli* expressing GFP at the ratio of $2\times10^8$ *E. Coli* per $1\times10^7$ peripheral blood cells for 4 h at 37° C. Duplicates per mouse were performed. After the incubation, the cells were washed with PBS and analyzed by gating on viable CD45+CD33+CD14+ population.

CpG Challenge Experiment

MISTRG newborns received a low-dose of radiation (150 rad) then were intrahepatically injected with $5\times10^4$ $CD34^+$ human stem cells from cord blood (StemCell Technologies, Cat. 70008) as previously described (73). After 8 weeks, the mice were checked for engraftment of $CD45^+$ and $CD33^+$ population in the peripheral blood. The naïve humanized MISTRG mice were intravenously injected with IgG control or anti-LILRB2 antibodies (150 μg/mouse) for two days, and then intraperitoneally challenged with 5 nmol CpG (Cat:

ODN1668; Invivogen, San Diego, CA). After 2 hours, serum was collected and analyzed using ELISA for TNFα levels.

Western Blot and Co-Immunoprecipitation.

LILRB2-transduced THP-1 cells were treated with 1 μg/ml IgG or anti-LILRB2 for 24 h followed by acute stimulation with 50 ng/ml LPS, 20 ng/ml IFNγ, or 20 ng/ml IL4 for 5, 10, 30 minutes. The cells were lysed using cell lysis reagent (Sigma-Aldrich). Protein samples were separated on 8% sodium dodecyl sulfate (SDS)-polyacrylamide gels and transferred to PVDF membranes. The membranes were blocked in 4% skim milk solution, incubated with an appropriate antibody, and subsequently incubated with a secondary antibody conjugated to horseradish peroxidase. The antibodies for p-STAT1, p-ERK1/2, p-p38, p-NF-κBp65, p-STAT6, SOCS1, SOCS3, p-Akt, SHP-1 and p-SHP-1 were purchased from Cell Signaling Technology (Beverly, MA), and the antibody for actin was purchased from Santa Cruz Biotechnology (Dallas, TX). The immunoreactive bands were visualized with the ECL system (Thermo Scientific). For immunoprecipitation, LILRB2$^+$ THP-1 cells were treated with IgG or anti-LILRB2 for 24 h and 0.1 mM Na3VO4 (Sigma-Aldrich) for the last hour. The cells were lysed using cell lysis buffer including 1 mM Na3VO4 and 25 mM alpha-glycerophosphate. Dynabeads protein G (Life Technologies, Carlsbad, CA) was used for pull-down. The pull-down samples were subjected to immunoblot assay and probed by anti-LILRB2, anti-SHP-1, and anti-p-SHP-1.

Human Multiple-Lymphocyte Reactions (MLR) Assay

Mature dendritic cells for use as stimulator cells were generated by culturing sorted CD14$^+$ monocytes in the presence of human GM-CSF (50 ng/ml) (PeproTech, Rocky Hill, NJ) for 5 days followed by LPS stimulation. IgG or anti-LILRB2-treated mature macrophages were generated as previously described. Allogeneic T cells as responder cells were purified from unrelated healthy donors and co-cultured with mature dendritic cells and titrated ratios of macrophages for 72 hours (FIG. 17A). No antibody was present in the culture for the duration of the MLR. Cells and supernatants from MLRs were analyzed for CD4 and CD8 T cell number by FACS and IFNγ secretion by ELISA.

Transcriptome Analysis

IgG- or anti-LILRB2-treated monocyte-derived macrophages from three healthy donors were subjected to microarray analysis. RNA was hybridized to Human HT-12 v4 Expression BeadChips (Illumina) and Illumina HiScan was used for scanning. Raw intensity data were processed using Genome Studio (version 2011.1) Gene Expression Module (version 1.9.0) and further processed using the lumi R package from Bioconductor. The data were adjusted for background signal before exporting from BeadStudio and underwent VST transformation and quantile normalization. Probes with no expression were removed. Differential gene expression analysis was performed using the limma R package, and significantly differentially expressed genes were identified based on a fold change of ≥1.5 and a p-value of <0.05 with Benjamini & Hochberg false-discovery rate correction. Heatmaps of differentially expressed genes were created using the plots R package, and unsupervised hierarchical clustering was performed based on Euclidean distance. Expression values were z-score normalized, and high and low expression are shown as red and green, respectively, with intermediate expression as white. Principal component analysis was performed using the prcomp function in R. The accession number for the microarray data is GSE117340.

Reverse Transcriptase-Polymerase Chain Reaction (RT-PCR)

RT-PCR was performed on total RNA prepared by the Tri Reagent Method. Two μg of RNA was used for cDNA synthesis using M-MLV reverse transcriptase (Promega, Madison, WI) and oligo (dT) 18 (Thermo Scientific). Indicated below are the sequences of 5' and 3' primers used for each of the tested genes, respectively. IRF3, Forward: 5'AGGTCCACAGTATTCTCCAGG (SEQ ID NO:366); Reverse: 5'AGGTCCACAGTATTCTCCAGG (SEQ ID NO:367); IRF4, Forward: 5'GCTGATCGACCAGATCGACAG (SEQ ID NO:368); Reverse: 5' CGGUTGTAGTCCTGCTTGC (SEQ ID NO:369); IRF5, Forward: 5' GGGCTTCAATGGGTCAACG (SEQ ID NO:370); Reverse: 5' GCCTTCGGTGTATITCCCTG (SEQ ID NO:371); IRF7, Forward: 5'CCCAGCAGGTAGCATCCC (SEQ ID NO:372); Reverse: 5'GCAGCAGTCCTCCGTGTAG (SEQ ID NO:373).

Isolation of Infiltrating Leukocytes from Human Lung Cancer Tissue

Eleven fresh lung cancer samples, including NSCLC and mesothelioma, were obtained from the Lung and Esophageal Surgery Institute, Mount Sinai Medical Center. This study involving human tissues was approved by the Institutional Review Board of the Icahn School of Medicine at Mount Sinai and was conducted in accordance with federal and institutional guidelines. Tumor samples were digested with Collagenase D 2 mg/ml (Sigma-Aldrich) for 30-45 min at 37° C. The tissue lysates were then filtered through a 40 μM cell strainer and the flow-through washed with PBS at 400×g for 5 minutes twice to pellet tumor cells. Lung cancer or mesothelioma-derived infiltrating lymphocytes (TIL) were isolated by density gradient medium, Lymphoprep (Stemcell Technologies, Cat: 07801). 100K to 200K TIL were cultured with 50 ng/mL MCSF (PeproTech) in the presence or absence of 50 ng/mL IFNγ (PeproTech), LPS (Sigma-Aldrich) and IgG or anti-LILRB2 at 1 μg/ml for two days. Cells and supernatants were subjected to flow cytometric analysis and TNFα/IL 10 production by ELISA, respectively.

Statistics

All data are presented as the means f standard deviation. Data were compared using two-tailed Student's t-test. Paired t-test was used to compare results from the same treatments from different healthy donors or cancer patients. All analyses were conducted using Prism and SPSS. Data were considered statistically significant at a value of $p<0.05$.

Study Approval

All animal procedures were approved by the IACUC in Center for Comparative Medicine and Surgery of Mount Sinai School of Medicine and in Comparative Medicine of Houston Methodist Research Institute.

REFERENCES

1. Ortega-Gomez A, Perretti M, and Soehnlein O. Resolution of inflammation: an integrated view. EMBO Mol Med. 2013; 5(5):661-74.
2. Noy R, and Pollard J W. Tumor-associated macrophages: from mechanisms to therapy. Immunity. 2014; 41(1):49-61.
3. Martinez F O, and Gordon S. The M1 and M2 paradigm of macrophage activation: time for reassessment. F1000prime reports. 2014; 6:13.
4. van der Touw W, Chen H M, Pan P Y, and Chen S H. LILRB receptor-mediated regulation of myeloid cell maturation and function. Cancer Immunol Immunother. 2017; 66(8):1079-87.

5. Zhang J, Mai S, Chen H M, Kang K, Li X C, Chen S H, et al. Leukocyte immunoglobulin-like receptors in human diseases: an overview of their distribution, function, and potential application for immunotherapies. J Leukoc Biol. 2017; 102(2):351-60.
6. Ujike A, Takeda K, Nakamura A, Ebihara S, Akiyama K, and Takai T. Impaired dendritic cell maturation and increased T(H)2 responses in PIR-B(−/−) mice. Nat Immunol. 2002; 3(6):542-8.
7. Munitz A, Cole E T, Beichler A, Groschwitz K, Ahrens R, Steinbrecher K, et al. Paired immunoglobulin-like receptor B (PIR-B) negatively regulates macrophage activation in experimental colitis. Gastroenterology. 2010; 139(2): 530-41.
8. Endo S, Sakamoto Y, Kobayashi E, Nakamura A, and Takai T. Regulation of cytotoxic T lymphocyte triggering by PIR-B on dendritic cells. Proceedings of the National Academy of Sciences of the United States of America. 2008; 105(38):14515-20.
9. Takai T. Paired immunoglobulin-like receptors and their MHC class I recognition. Immunology. 2005; 115(4):433-40.
10. Ho L H, Uehara T, Chen C C, Kubagawa H, and Cooper M D. Constitutive tyrosine phosphorylation of the inhibitory paired Ig-like receptor PIR-B. Proc Natl Acad Sci USA. 1999; 96(26):15086-90.
11. Maeda A, Kurosaki M, Ono M, Takai T, and Kurosaki T. Requirement of SH2-containing protein tyrosine phosphatases SHP-1 and SHP-2 for paired immunoglobulin-like receptor B (PIR-B)-mediated inhibitory signal. J Exp Med. 1998; 187(8):1355-60.
12. Ma G, Pan P Y, Eisenstein S, Divino C M, Lowell C A, Takai T, et al. Paired immunoglobin-like receptor-B regulates the suppressive function and fate of myeloid-derived suppressor cells. Immunity. 2011; 34(3):385-95.
13. Ravetch J V, and Lanier L L. Immune inhibitory receptors. Science. 2000; 290(5489):84-9.
14. Bashirova A A, Apps R, Vince N, Mochalova Y, Yu X G, and Carrington M. Diversity of the human LILRB3/A6 locus encoding a myeloid inhibitory and activating receptor pair. Immunogenetics. 2014; 66(1):1-8.
15. Slukvin, I I, Grendell R L, Rao D S, Hughes A L, and Golos T G. Cloning of rhesus monkey LILRs. Tissue Antigens. 2006; 67(4):331-7.
16. Mori Y, Tsuji S, Inui M, Sakamoto Y, Endo S, Ito Y, et al. Inhibitory immunoglobulin-like receptors LILRB and PIR-B negatively regulate osteoclast development. Journal of immunology. 2008; 181(7):4742-51.
17. Colonna M, Samaridis J, Cella M, Angman L, Allen R L, O'Callaghan C A, et al. Human myelomonocytic cells express an inhibitory receptor for classical and nonclassical MHC class I molecules. Journal of immunology. 1998; 160(7):3096-100.
18. Cheng H, Mohammed F, Nam G, Chen Y, Qi J, Gamer L I, et al. Crystal structure of leukocyte Ig-like receptor LILRB4 (ILT3/LIR-5/CD85k): a myeloid inhibitory receptor involved in immune tolerance. The Journal of biological chemistry. 2011; 286(20):18013-25.
19. Zhang Z, Hatano H, Shaw J, Olde Nordkamp M, Jiang G, Li D, et al. The Leukocyte Immunoglobulin-Like Receptor Family Member LILRB5 Binds to HLA-Class I Heavy Chains. PLoS One. 2015; 10(6):e0129063.
20. Jones D C, Kosmoliaptsis V, Apps R, Lapaque N, Smith I, Kono A, et al. HLA class I allelic sequence and conformation regulate leukocyte Ig-like receptor binding. Journal of immunology. 2011; 186(5):2990-7.
21. Zheng J, Umikawa M, Cui C, Li J, Chen X, Zhang C, et al. Inhibitory receptors bind ANGPTLs and support blood stem cells and leukaemia development. Nature. 2012; 485(7400):656-60.
22. Shiroishi M, Tsumoto K, Amano K, Shirakihara Y, Colonna M, Braud V M, et al. Human inhibitory receptors Ig-like transcript 2 (ILT2) and ILT4 compete with CD8 for MHC class I binding and bind preferentially to HLA-G. Proceedings of the National Academy of Sciences of the United States of America. 2003; 100(15):8856-61.
23. Lichterfeld M, Kavanagh D G, Williams K L, Moza B, Mui S K, Miura T, et al. A viral CTL escape mutation leading to immunoglobulin-like transcript 4-mediated functional inhibition of myelomonocytic cells. J Exp Med. 2007; 204(12):2813-24.
24. Shakhawat A, Shaikly V, Elzatma E, Mavrakos E, Jabeen A, and Fernandez N. Interaction between HLA-G and monocyte/macrophages in human pregnancy. J Reprod Immunol. 2010; 85(1):40-6.
25. Banchereau J, Zurawski S, Thompson-Snipes L, Blanck J P, Clayton S, Munk A, et al. Immunoglobulin-like transcript receptors on human dermal CD14+dendritic cells act as a CD8-antagonist to control cytotoxic T cell priming. Proceedings of the National Academy of Sciences of the United States of America. 2012; 109(46): 18885-90.
26. Chang C C, Ciubotariu R, Manavalan J S, Yuan J, Colovai Al, Piazza F, et al. Tolerization of dendritic cells by T(S) cells: the crucial role of inhibitory receptors ILT3 and ILT4. Nat Immunol. 2002; 3(3):237-43.
27. Martinez F O, Gordon S, Locati M, and Mantovani A. Transcriptional profiling of the human monocyte-to-macrophage differentiation and polarization: new molecules and patterns of gene expression. Journal of immunology. 2006; 177(10):7303-11.
28. Murray P J, Allen J E, Biswas S K, Fisher E A, Gilroy D W, Goerdt S, et al. Macrophage activation and polarization: nomenclature and experimental guidelines. Immunity. 2014; 41(1):14-20.
29. Hashimoto S, Yamada M, Motoyoshi K, and Akagawa K S. Enhancement of macrophage colony-stimulating factor-induced growth and differentiation of human monocytes by interleukin-10. Blood. 1997; 89(1):315-21.
30. Hashimoto S, Suzuki T, Dong H Y, Yamazaki N, and Matsushima K. Serial analysis of gene expression in human monocytes and macrophages. Blood. 1999; 94(3): 837-44.
31. Ino Y, Yamazaki-Itoh R, Shimada K, Iwasaki M, Kosuge T, Kanai Y, et al. Immune cell infiltration as an indicator of the immune microenvironment of pancreatic cancer. British journal of cancer. 2013; 108(4):914-23.
32. Zaki M A, Wada N, Ikeda J, Shibayama H, Hashimoto K, Yamagami T, et al. Prognostic implication of types of tumor-associated macrophages in Hodgkin lymphoma. Virchows Archiv: an international journal of pathology. 2011; 459(4):361-6.
33. Etzerodt A, and Moestrup S K. CD163 and inflammation: biological, diagnostic, and therapeutic aspects. Antioxidants & redox signaling. 2013; 18(17):2352-63.
34. Krausgruber T, Blazek K, Smallie T, Alzabin S, Lockstone H, Sahgal N, et al. IRF5 promotes inflammatory macrophage polarization and TH1-TH17 responses. Nat Immunol. 2011; 12(3):231-8.
35. Zhao G N, Jiang D S, and Li H. Interferon regulatory factors: at the crossroads of immunity, metabolism, and disease. Biochim Biophys Acta. 2015; 1852(2):365-78.

36. Negishi H, Ohba Y, Yanai H, Takaoka A, Honma K, Yui K, et al. Negative regulation of Toll-like-receptor signaling by IRF-4. Proc Natl Acad Sci USA. 2005; 102(44): 15989-94.

37. Fleetwood A J, Dinh H, Cook A D, Hertzog P J, and Hamilton J A. GM-CSF- and M-CSF-dependent macrophage phenotypes display differential dependence on type I interferon signaling. J Leukoc Biol. 2009; 86(2):411-21.

38. Tanaka T, Murakami K, Bando Y, and Yoshida S. Interferon regulatory factor 7 participates in the M1-like microglial polarization switch. Glia. 2015; 63(4):595-610.

39. Rodriguez-Garcia M, Porichis F, de Jong O G, Levi K, Diefenbach T J, Lifson J D, et al. Expression of PD-L1 and PD-L2 on human macrophages is up-regulated by HIV-1 and differentially modulated by IL-10. Journal of leukocyte biology. 2011; 89(4):507-15.

40. Conde P, Rodriguez M, van der Touw W, Jimenez A, Burns M, Miller J, et al. DC-SIGN(+) Macrophages Control the Induction of Transplantation Tolerance. Immunity. 2015; 42(6):1143-58.

41. Dominguez-Soto A, Sierra-Filardi E, Puig-Kroger A, Perez-Maceda B, Gomez-Aguado F, Corcuera M T, et al. Dendritic cell-specific ICAM-3-grabbing nonintegrin expression on M2-polarized and tumor-associated macrophages is macrophage-CSF dependent and enhanced by tumor-derived IL-6 and IL-10. Journal of immunology. 2011; 186(4):2192-200.

42. Smith J L, Schaffner A E, Hofmeister J K, Hartman M, Wei G, Forsthoefel D, et al. ets-2 is a target for an akt (Protein kinase B)/jun N-terminal kinase signaling pathway in macrophages of motheaten-viable mutant mice. Molecular and cellular biology. 2000; 20(21):8026-34.

43. Kelley T W, Graham M M, Doseff A I, Pomerantz R W, Lau S M, Ostrowski M C, et al. Macrophage colony-stimulating factor promotes cell survival through Akt/protein kinase B. The Journal of biological chemistry. 1999; 274(37):26393-8.

44. Arranz A, Doxaki C, Vergadi E, Martinez de la Torre Y, Vaporidi K, Lagoudaki E D, et al. Akt1 and Akt2 protein kinases differentially contribute to macrophage polarization. Proceedings of the National Academy of Sciences of the United States of America. 2012; 109(24):9517-22.

45. Eden E, Navon R, Steinfeld I, Lipson D, and Yakhini Z. GOrilla: a tool for discovery and visualization of enriched GO terms in ranked gene lists. BMC bioinformatics. 2009; 10:48.

46. Eden E, Lipson D, Yogev S, and Yakhini Z. Discovering motifs in ranked lists of DNA sequences. PLoS computational biology. 2007; 3(3):e39.

47. de las Casas-Engel M, Dominguez-Soto A, Sierra-Filardi E, Bragado R, Nieto C, Puig-Kroger A, et al. Serotonin skews human macrophage polarization through HTR2B and HTR7. J Immunol. 2013; 190(5):2301-10.

48. Gabriel T L, Mirzaian M, Hooibrink B, Ottenhoff R, van Roomen C, Aerts J, et al. Induction of Sphk1 activity in obese adipose tissue macrophages promotes survival. PLoS One. 2017; 12(7):e0182075.

49. Kang K, Park S H, Chen J, Qiao Y, Giannopoulou E, Berg K, et al. Interferon-gamma Represses M2 Gene Expression in Human Macrophages by Disassembling Enhancers Bound by the Transcription Factor MAF. Immunity. 2017; 47(2):235-50 e4.

50. Tanoue T, Moriguchi T, and Nishida E. Molecular cloning and characterization of a novel dual specificity phosphatase, MKP-5. J Biol Chem. 1999; 274(28):19949-56.

51. Li J P, Yang C Y, Chuang H C, Lan J L, Chen D Y, Chen Y M, et al. The phosphatase JKAP/DUSP22 inhibits T-cell receptor signalling and autoimmunity by inactivating Lck. Nat Commun. 2014; 5:3618.

52. Chomarat P, Banchereau J, Davoust J, and Palucka A K. IL-6 switches the differentiation of monocytes from dendritic cells to macrophages. Nature immunology. 2000; 1(6):510-4.

53. Nakata K, Suzuki Y, Inoue T, Ra C, Yakura H, and Mizuno K. Deficiency of SHP1 leads to sustained and increased ERK activation in mast cells, thereby inhibiting IL-3-dependent proliferation and cell death. Mol Immunol. 2011; 48(4):472-80.

54. Blanchette J, Abu-Dayyeh I, Hassani K, Whitcombe L, and Olivier M. Regulation of macrophage nitric oxide production by the protein tyrosine phosphatase Src homology 2 domain phosphotyrosine phosphatase 1 (SHP-1). Immunology. 2009; 127(1):123-33.

55. Bohmer F D, and Friedrich K. Protein tyrosine phosphatases as wardens of STAT signaling. JAKSTAT. 2014; 3(1):e28087.

56. Hebenstreit D, Luft P, Schmiedlechner A, Duschl A, and Horejs-Hoeck J. SOCS-1 and SOCS-3 inhibit IL-4 and IL-13 induced activation of Eotaxin-3/CCL26 gene expression in HEK293 cells. Mol Immunol. 2005; 42(3): 295-303.

57. Carow B, and Rottenberg M E. SOCS3, a Major Regulator of Infection and Inflammation. Front Immunol. 2014; 5:58.

58. White C A, and Nicola N A. SOCS3: An essential physiological inhibitor of signaling by interleukin-6 and G-CSF family cytokines. JAKSTAT. 2013; 2(4):e25045.

59. Zhang L, Du J, Hu Z, Han G, Delafontaine P, Garcia G, et al. IL-6 and serum amyloid A synergy mediates angiotensin II-induced muscle wasting. J Am Soc Nephrol. 2009; 20(3):604-12.

60. Gordon P, Okai B, Hoare J I, Erwig L P, and Wilson H M. SOCS3 is a modulator of human macrophage phagocytosis. J Leukoc Biol. 2016; 100(4):771-80.

61. Rauh M J, Sly L M, Kalesnikoff J, Hughes M R, Cao L P, Lam V, et al. The role of SHIP1 in macrophage programming and activation. Biochem Soc Trans. 2004; 32(Pt 5):785-8.

62. Kaneda M M, Messer K S, Ralainirina N, Li H, Leem C J, Gorjestani S, et al. PI3Kgamma is a molecular switch that controls immune suppression. Nature. 2016; 539 (7629):437-42.

63. Ries C H, Cannarile M A, Hoves S, Benz J, Wartha K, Runza V, et al. Targeting tumor-associated macrophages with anti-CSF-1R antibody reveals a strategy for cancer therapy. Cancer Cell. 2014; 25(6):846-59.

64. Bonapace L, Coissieux M M, Wyckoff J, Mertz K D, Varga Z, Junt T, et al. Cessation of CCL2 inhibition accelerates breast cancer metastasis by promoting angiogenesis. Nature. 2014; 515(7525):130-3.

65. Swierczak A, Cook A D, Lenzo J C, Restall C M, Doherty J P, Anderson R L, et al. The promotion of breast cancer metastasis caused by inhibition of CSF-1R/CSF-1 signaling is blocked by targeting the G-CSF receptor. Cancer immunology research. 2014; 2(8):765-76.

66. Mantovani A, Sozzani S, Locati M, Allavena P, and Sica A. Macrophage polarization: tumor-associated macrophages as a paradigm for polarized M2 mononuclear phagocytes. Trends in immunology. 2002; 23(11):549-55.

67. Mantovani A, and Allavena P. The interaction of anti-cancer therapies with tumor-associated macrophages. The Journal of experimental medicine. 2015; 212(4):435-45.

68. Li H Y, McSharry M, Bullock B, Nguyen T T, Kwak J, Poczobutt J M, et al. The Tumor Microenvironment Regulates Sensitivity of Murine Lung Tumors to PD-1/PD-L1 Antibody Blockade. Cancer Immunol Res. 2017; 5(9):767-77.

69. Lin H, Wei S, Hurt E M, Green M D, Zhao L, Vatan L, et al. Host expression of PD-L1 determines efficacy of PD-L1 pathway blockade-mediated tumor regression. J Clin Invest. 2018; 128(4):1708.

70. Kang S, Nakanishi Y, Kioi Y, Okuzaki D, Kimura T, Takamatsu H, et al. Semaphorin 6D reverse signaling controls macrophage lipid metabolism and anti-inflammatory polarization. Nat Immunol. 2018; 19(6):561-70.

71. Wilson J L, and Weichhart T. TORching a semaphore for alternative macrophage activation. Nat Immunol. 2018; 19(6):512-4.

72. Byles V, Covarrubias A J, Ben-Sahra I, Lamming D W, Sabatini D M, Manning B D, et al. The TSC-mTOR pathway regulates macrophage polarization. Nat Commun. 2013; 4:2834.

73. Rongvaux A, Willinger T, Martinek J, Strowig T, Gearty S V, Teichmann L L, et al. Development and function of human innate immune cells in a humanized mouse model. Nat Biotechnol. 2014; 32(4):364-72. abc

Figures 1, 23C:
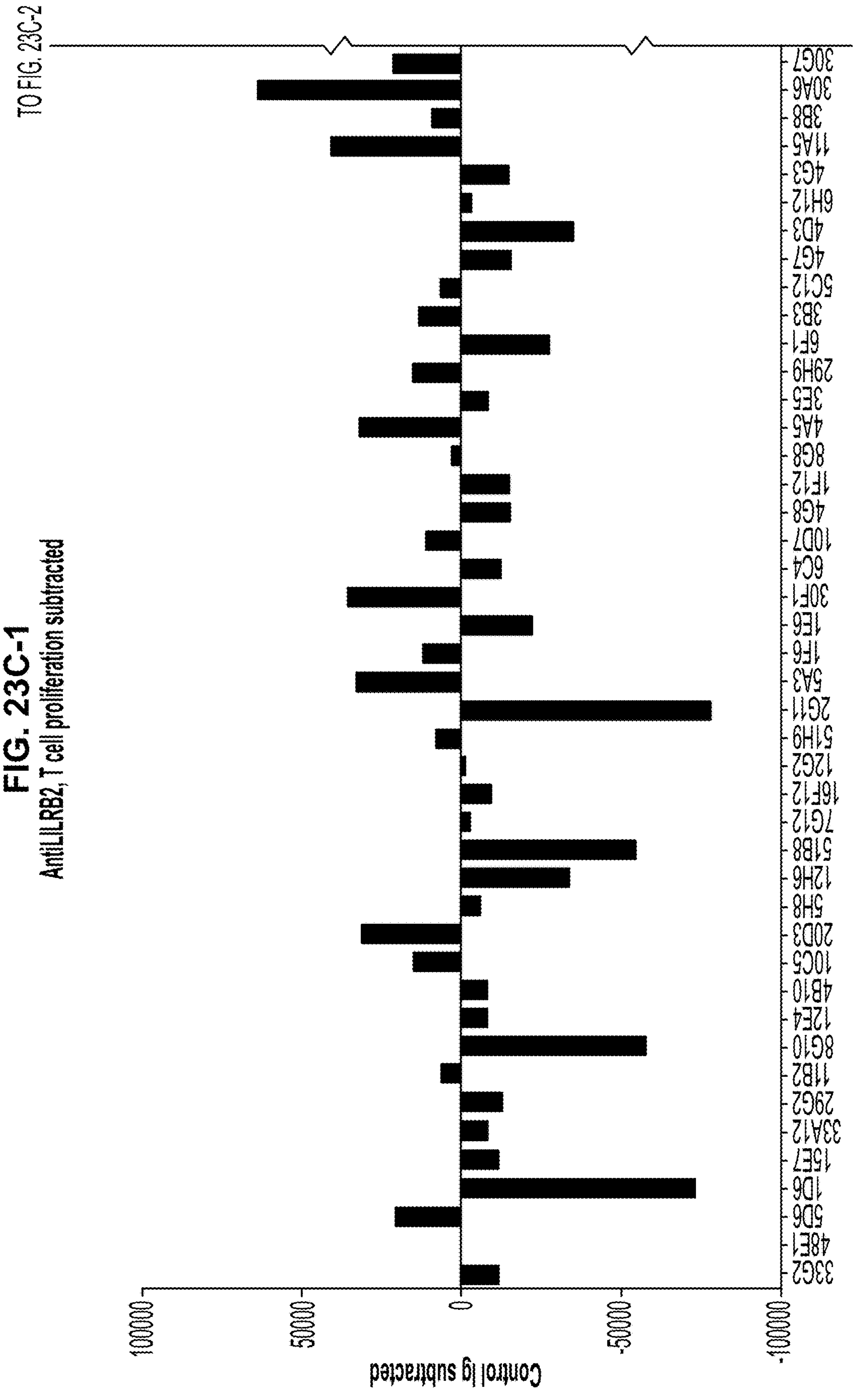
Figures 2, 23C:
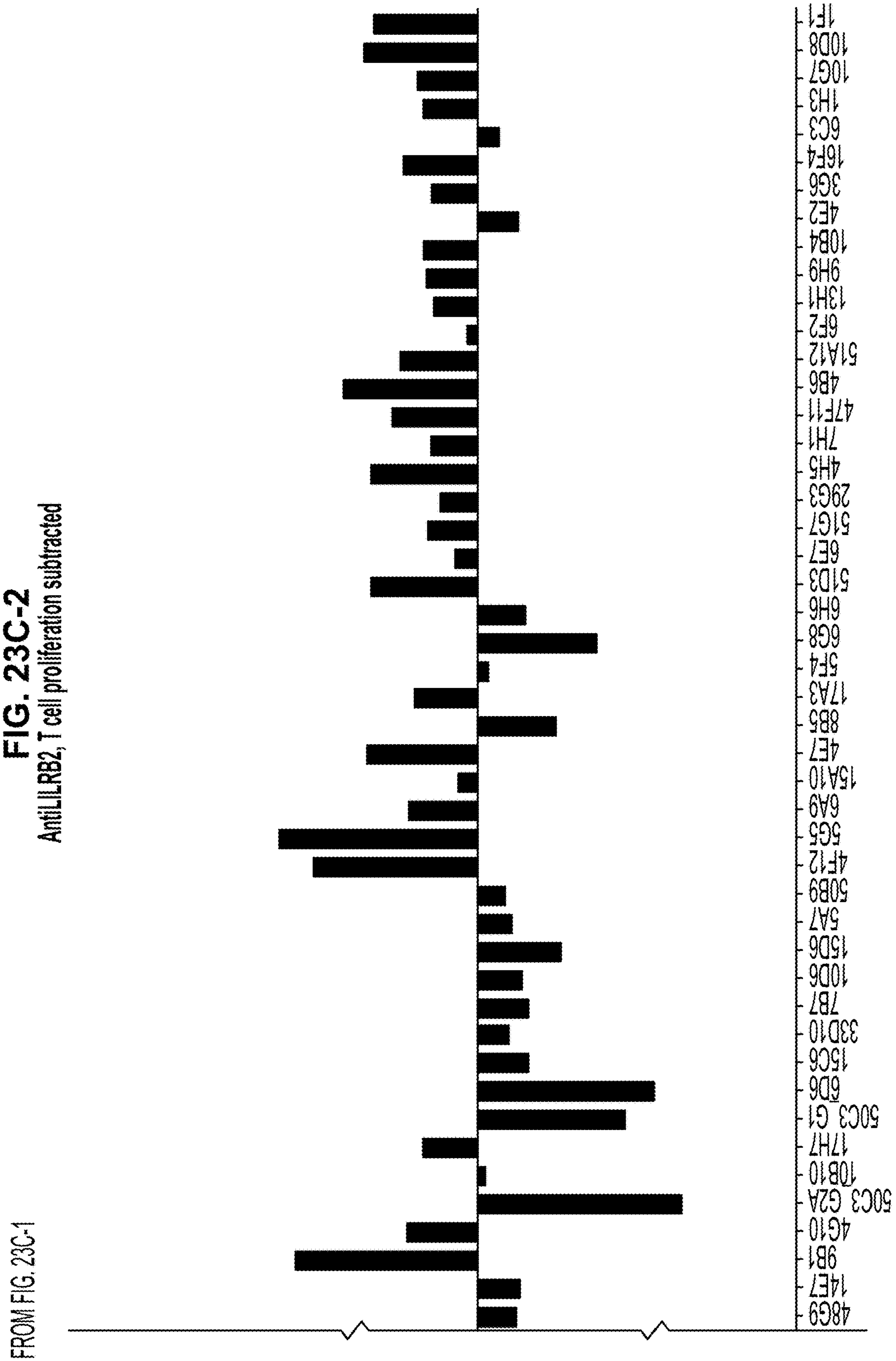

Example 10: Anti-LILRB2 Antibodies Modulate IFN Gamma Release In Vitro and Inhibited Allogeneic T Cell Proliferation In Vitro FIGS. 23A-23C are graphs showing OKT3-mediated T cell proliferation (CPM) following stimulation of PBMC from healthy donors. PBMC were cultured with LILRB2 antibodies overnight (16 hours) and stimulated with a low dose (0.01 μg/ml) anti-CD3 (OKT3) for 3 days. After 3 days of treatment, [3H]-thymidine was added for the last 8 hours of culture followed by measurement on a scintillation counter. Clone ranking based on TNF alpha from FIG. 1A is presented. The relative fold change in T-cell proliferation (CPM) is presented in FIG. 23A. T-cell proliferation is shown in FIG. 23B. The overall difference in T-cell proliferation from FIG. 23B is presented in FIG. 23C.

Figures 1, 23D:
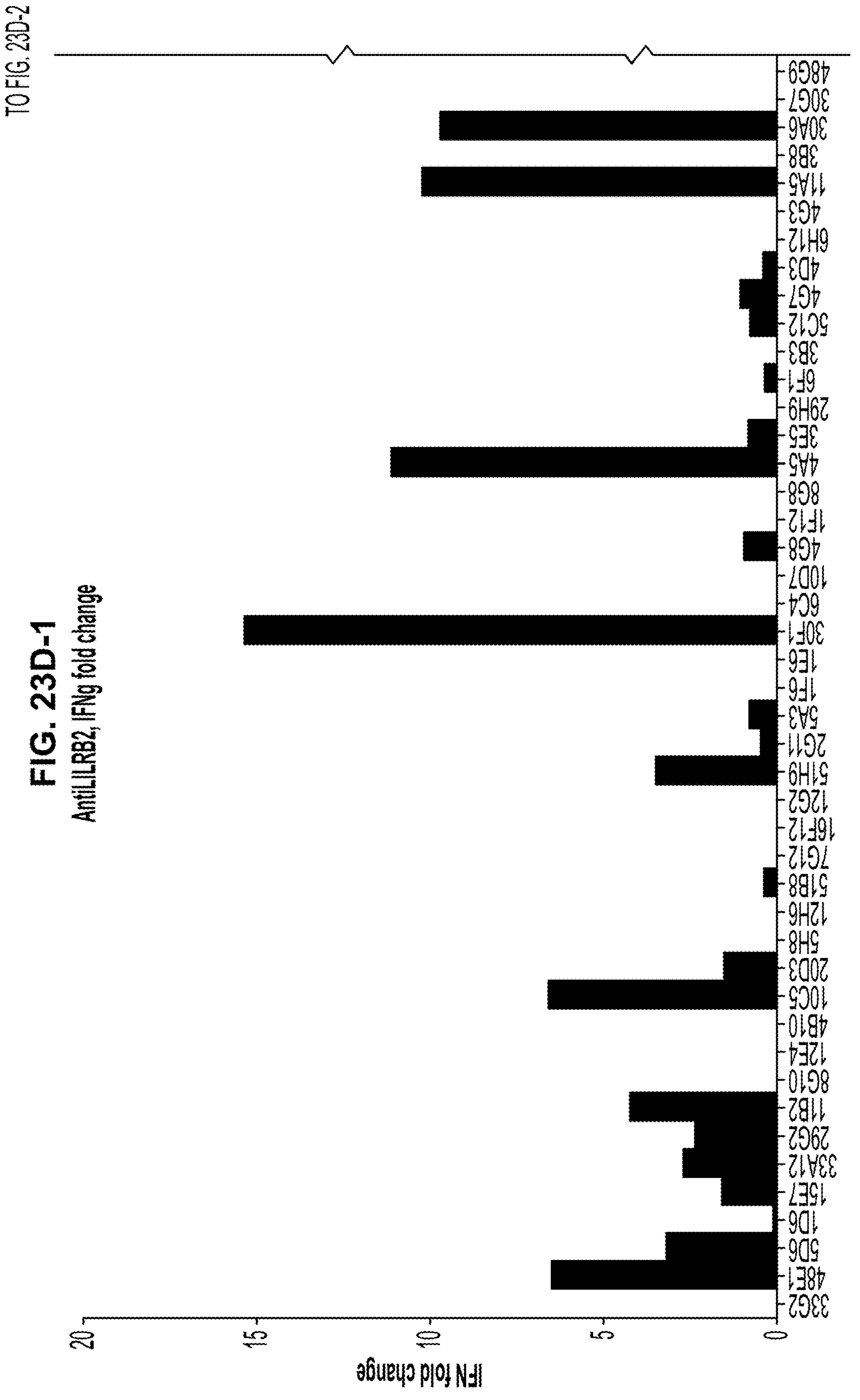
FIGS. 23D-23F are graphs showing the IFN-γ production from PBMCs obtained from healthy donors. PBMCs were cultured with LILRB2 antibodies overnight (16 hours) and stimulated with a low dose (0.01 μg/ml) anti-CD3 (OKT3) for 3 days. Supernatants were collected and IFN-γ production was measured by ELISA. Clone ranking based on TNF alpha from FIG. 1A is presented. The relative fold change in IFN-γ production release is presented in FIG. 23D. The secretion of IL-10 is shown in FIG. 23E. The overall difference in IL-10 concentrations from FIG. 23E is presented in FIG. 23F.
Figures 2, 23D:
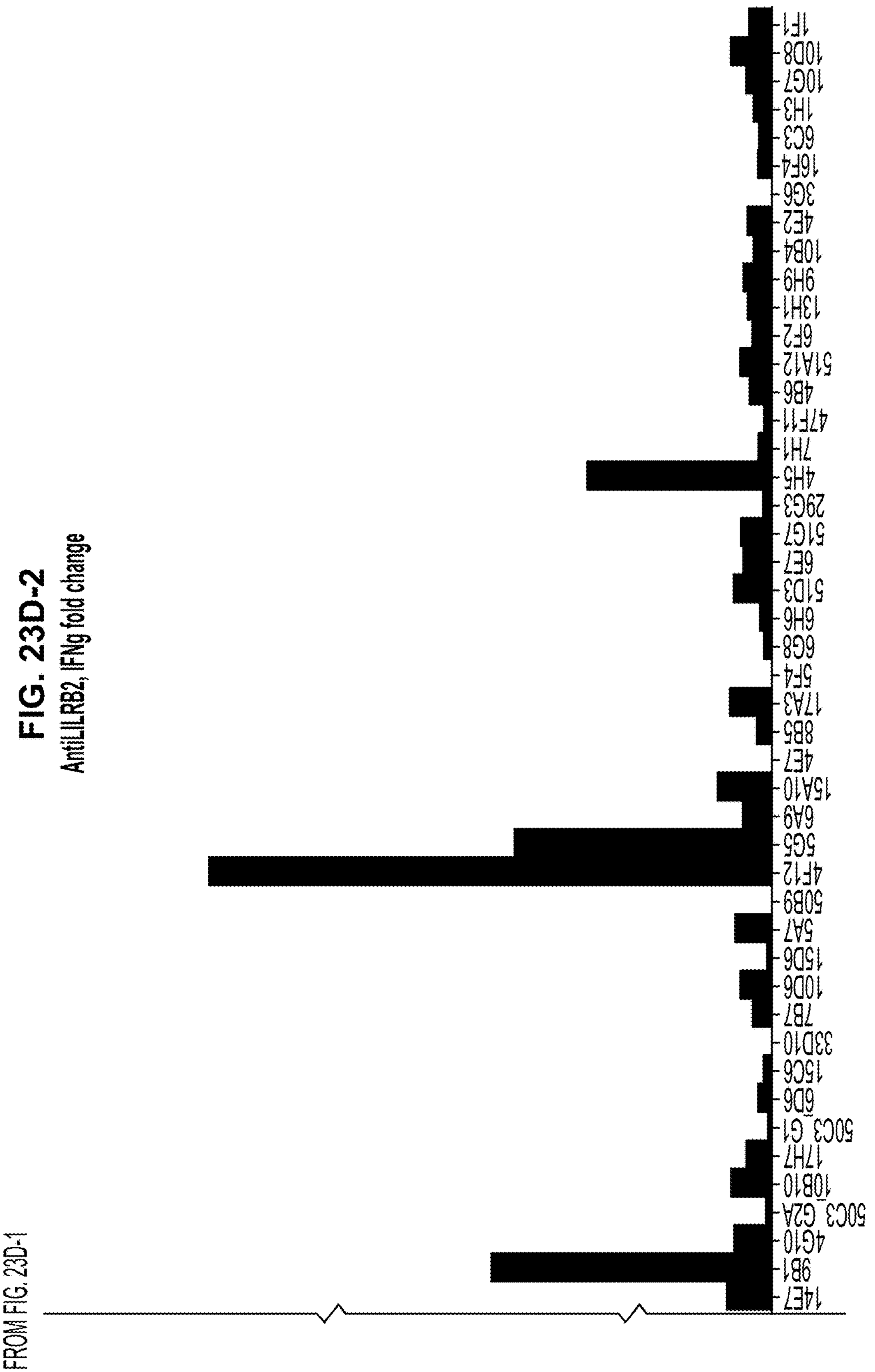
Figures 1, 23E:
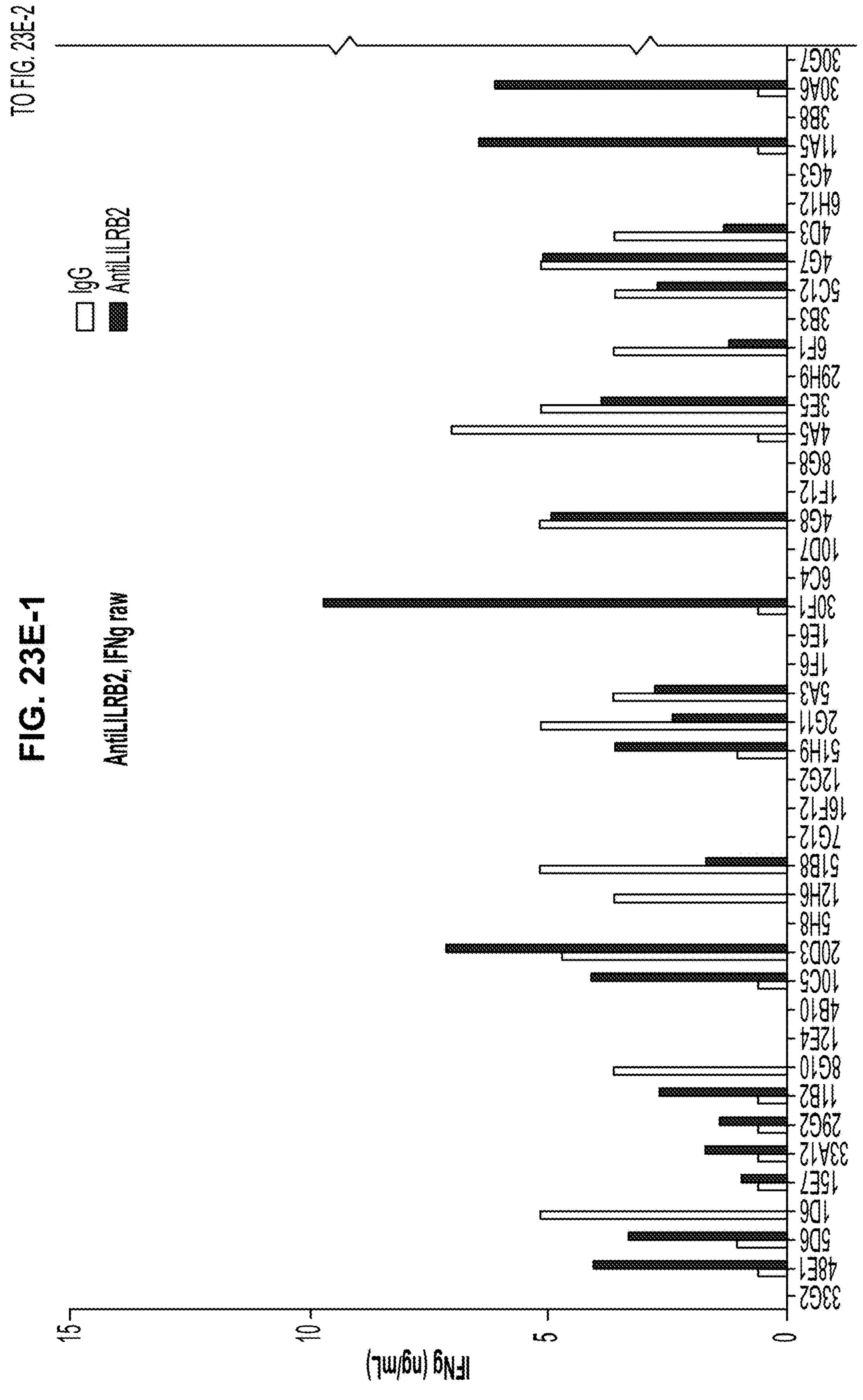
Figures 2, 23E:
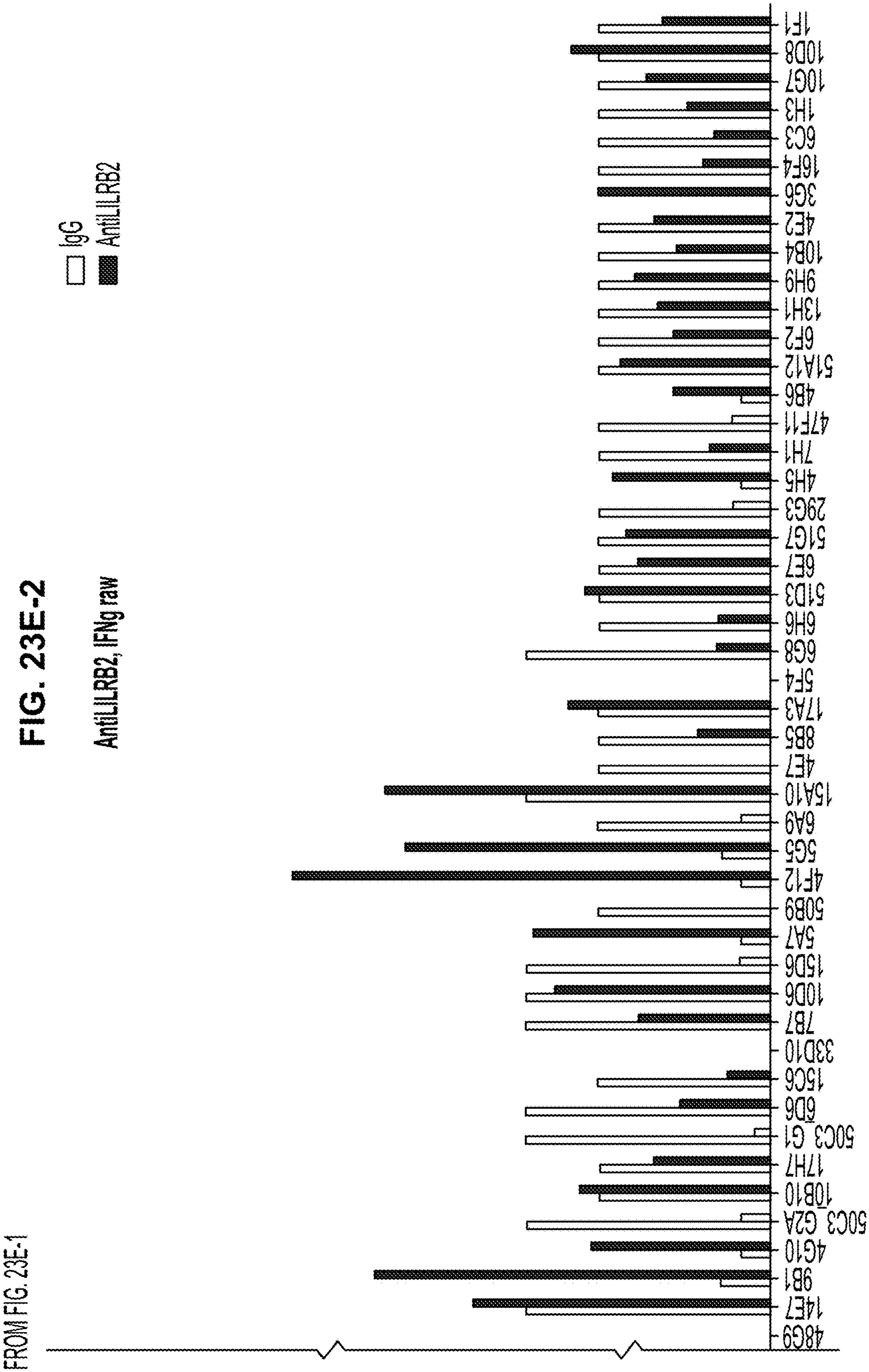
Figures 1, 23F:
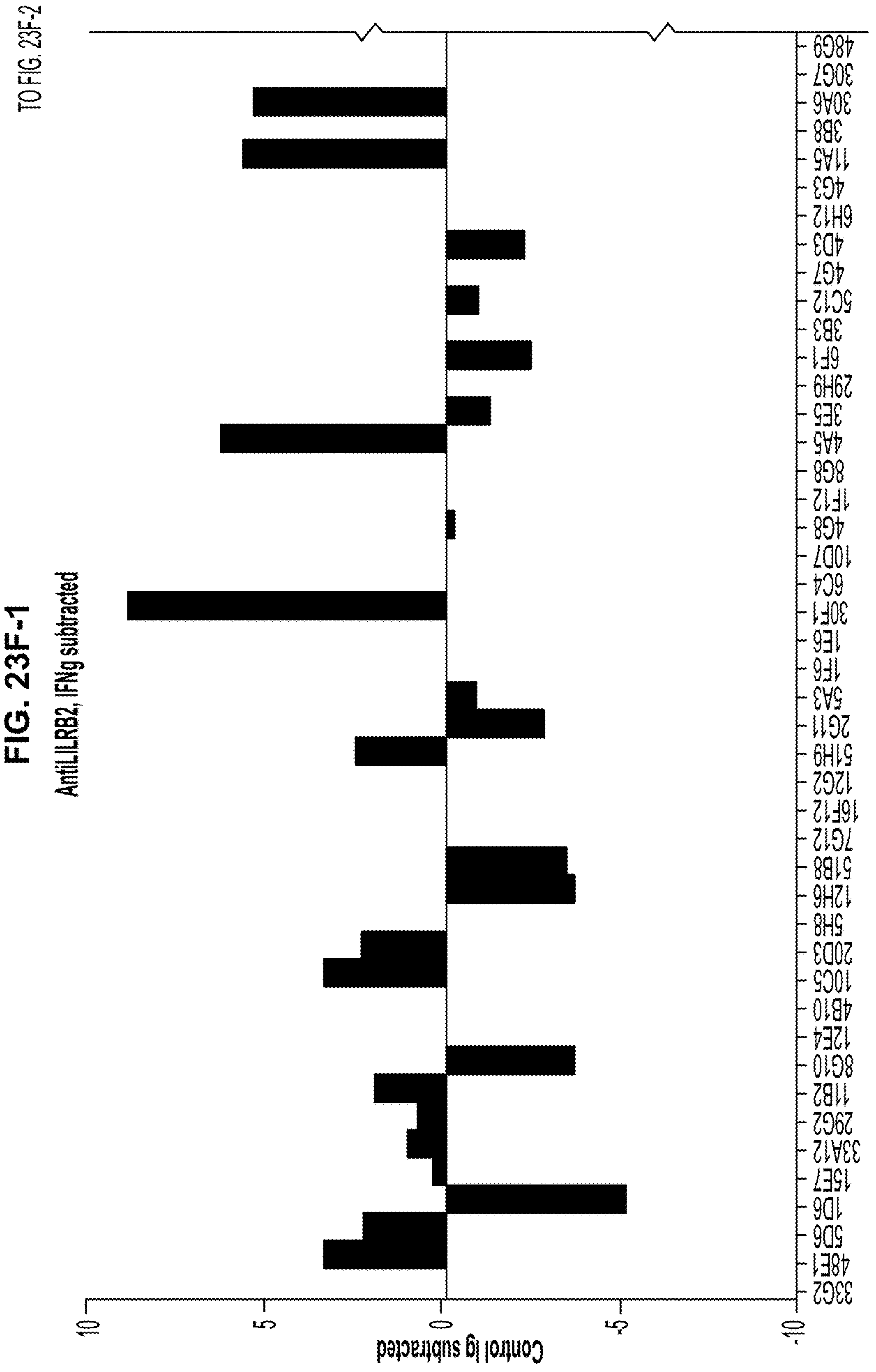
Figures 2, 23F:
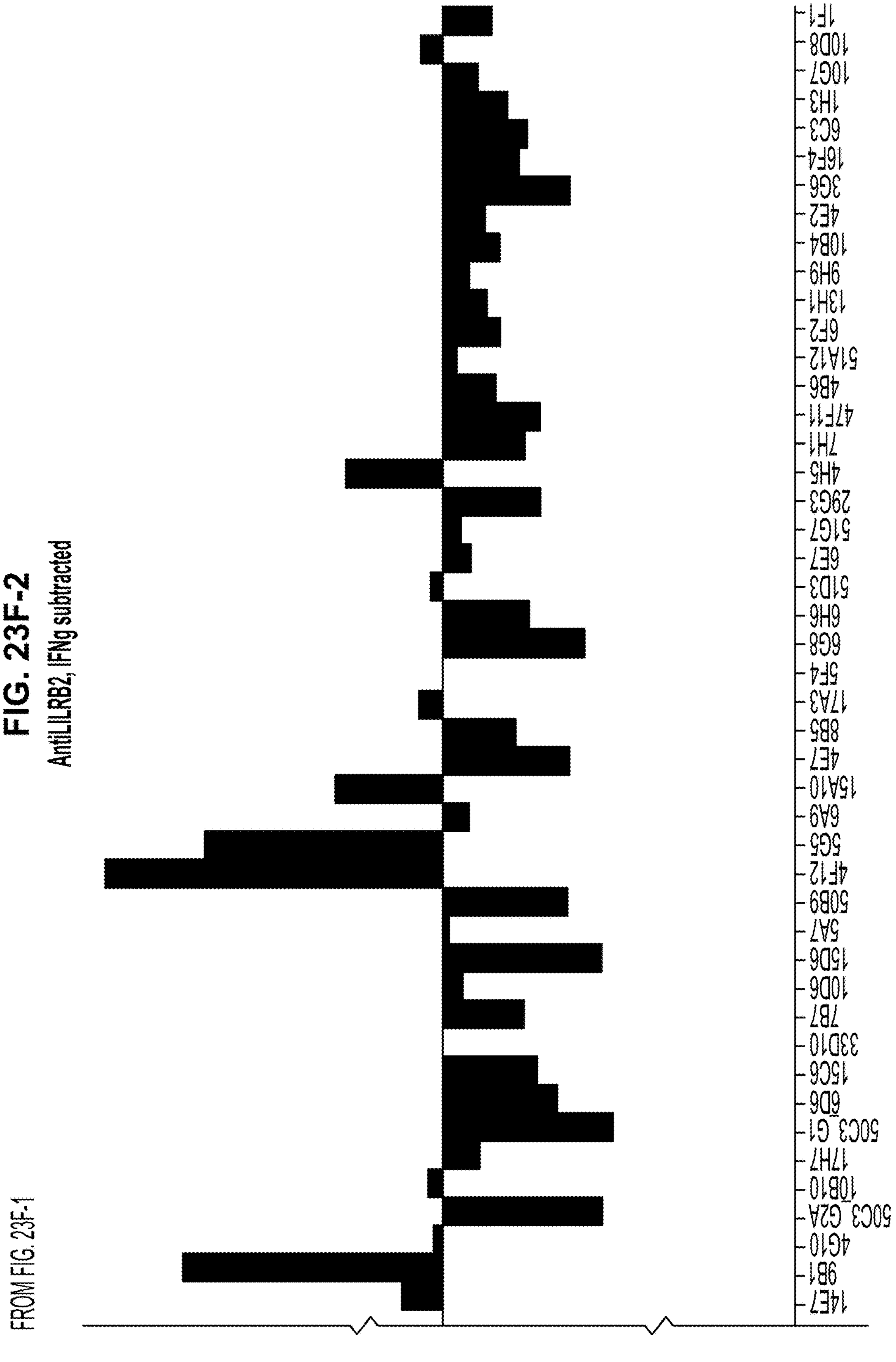
Figure 23H:
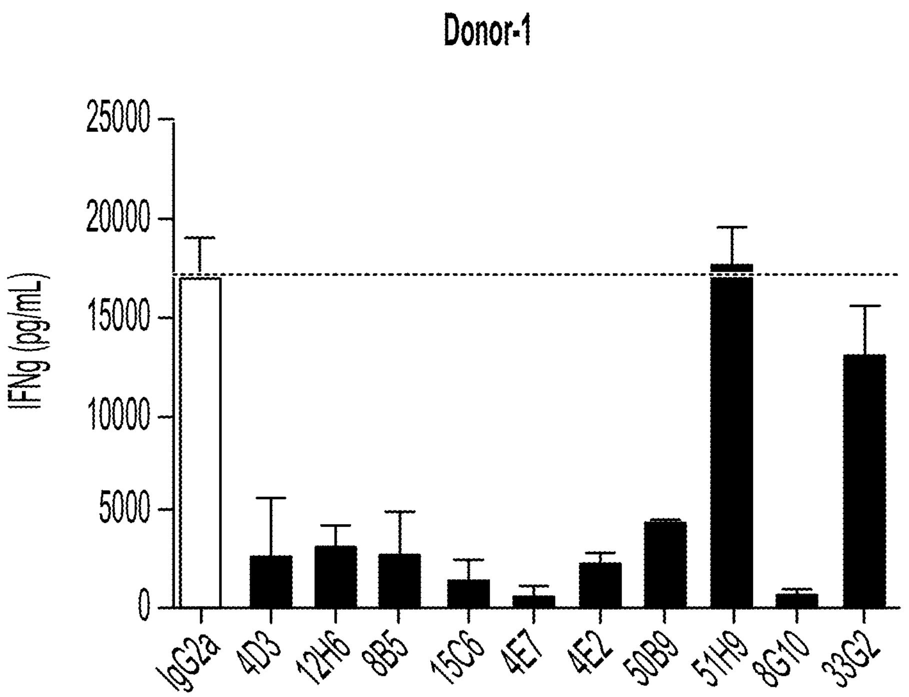
FIG. 23H shows the suppression of T cell IFN-γ production upon treatment with anti-LILRB2 agonist antibodies.
Figure 1:
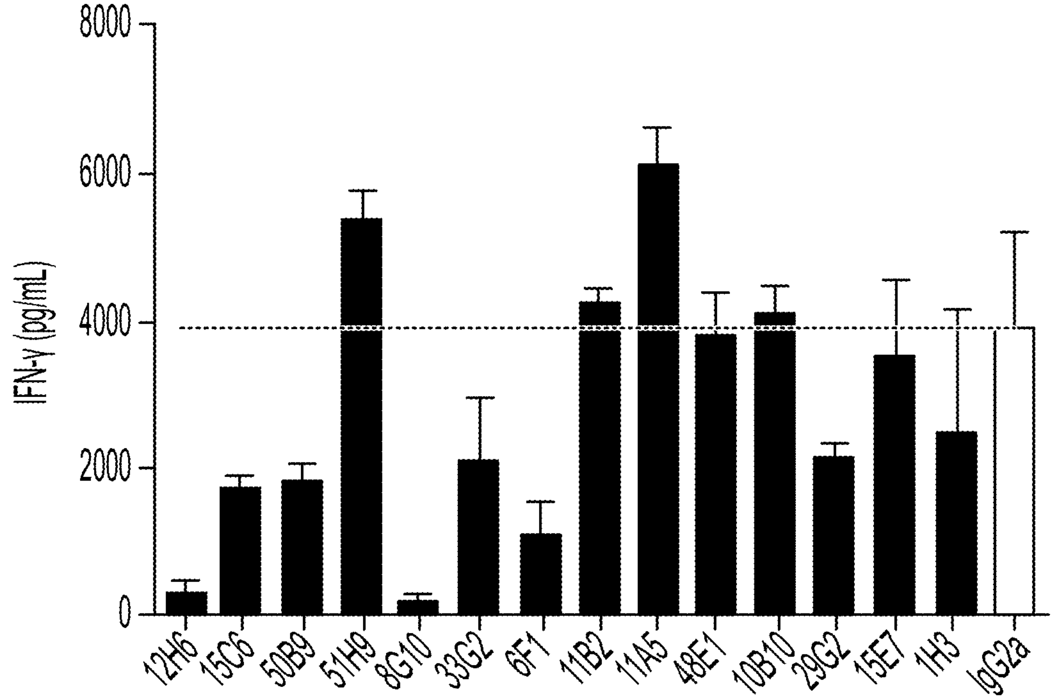
Figures 2, 23H:
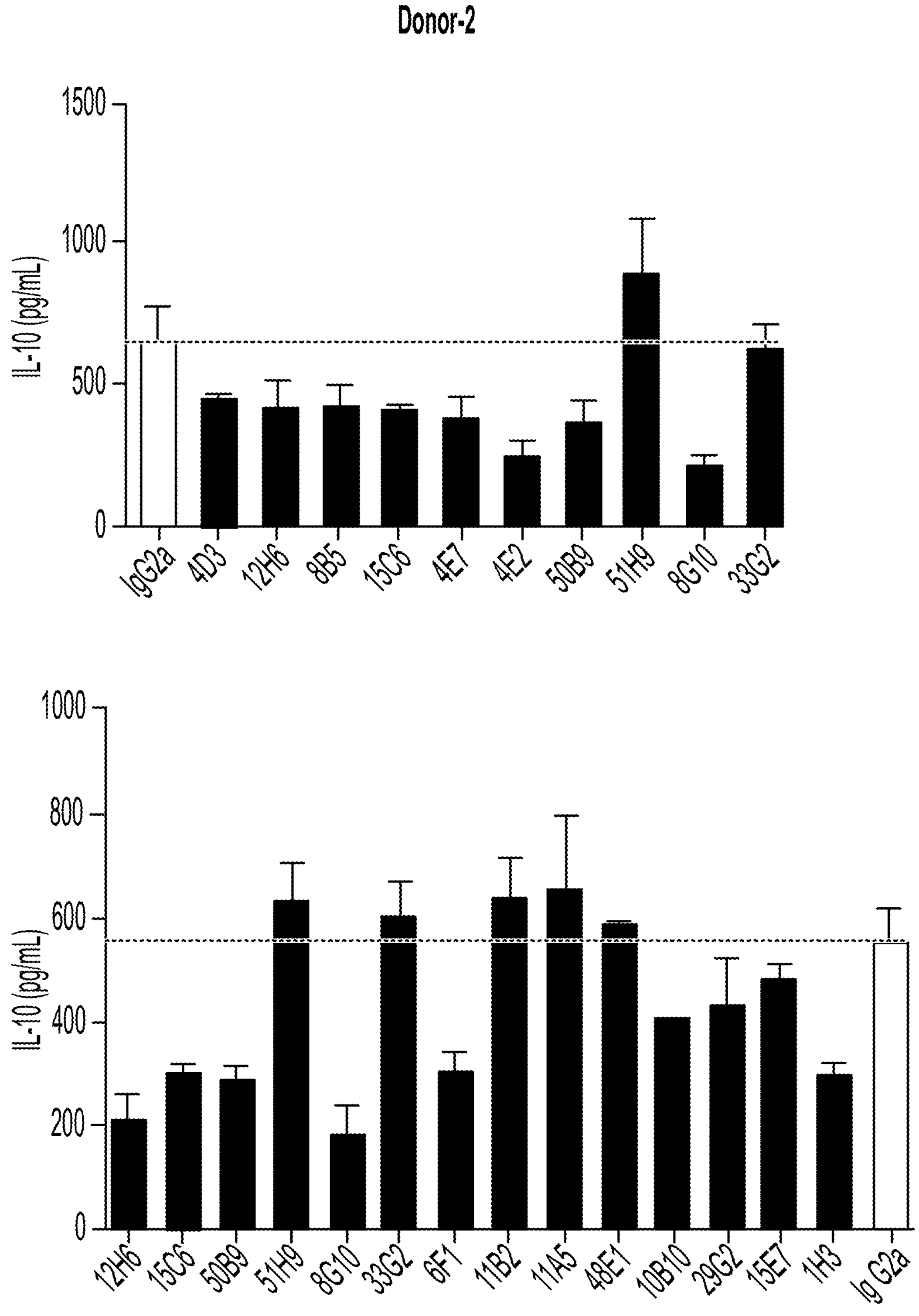

FIGS. 23D-23F are graphs showing the IFN-γ production from PBMCs obtained from healthy donors. PBMCs were cultured with LILRB2 antibodies overnight (16 hours) and stimulated with a low dose (0.01 μg/ml) anti-CD3 (OKT3) for 3 days. Supernatants were collected and IFN-γ production was measured by ELISA. Clone ranking based on TNF alpha from FIG. 1A is presented. The relative fold change in IFN-γ production release is presented in FIG. 23D. The secretion of IL-10 is shown in FIG. 23E. The overall difference in IL-10 concentrations from FIG. 23E is presented in FIG. 23F.

The ability of the agonist antibodies to cross-react with the LILRA family was tested. As shown in FIG. 23G, each of the anti-LILRB2 agonist antibodies tested cross-reacted with the LILRA1 family.

FIG. 23G shows the suppression of T cell IFN-γ production upon treatment with anti-LILRB2 agonist antibodies.

Figure 23I:
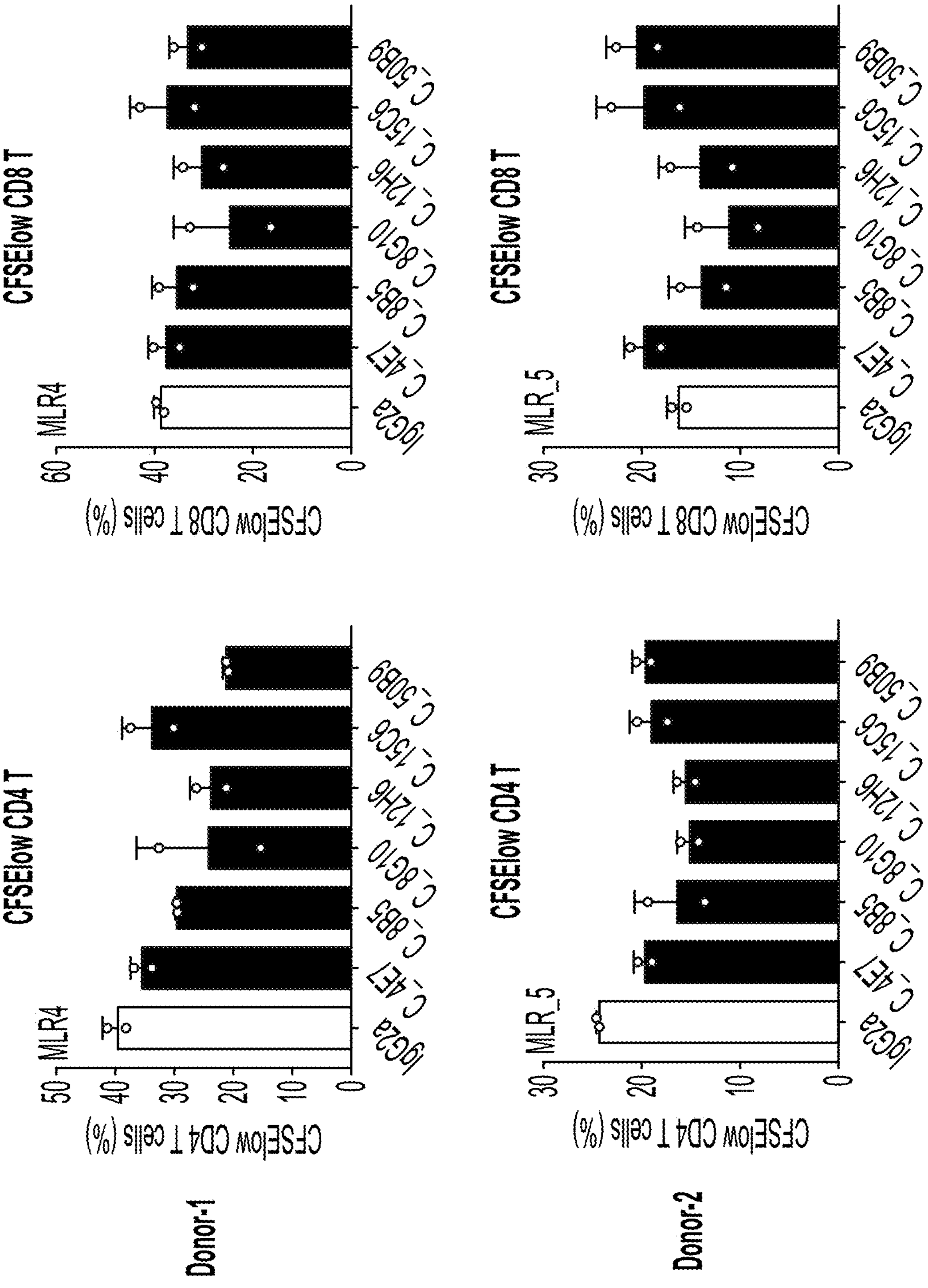
FIG. 23I shows suppression of the MLR reaction by the anti-LILRB2 agonist antibodies.

FIG. 23I shows suppression of the MLR reaction by the anti-LILRB2 agonist antibodies.

Example 11: Anti-LILRB2 CAR T-Cells

Figure 24:
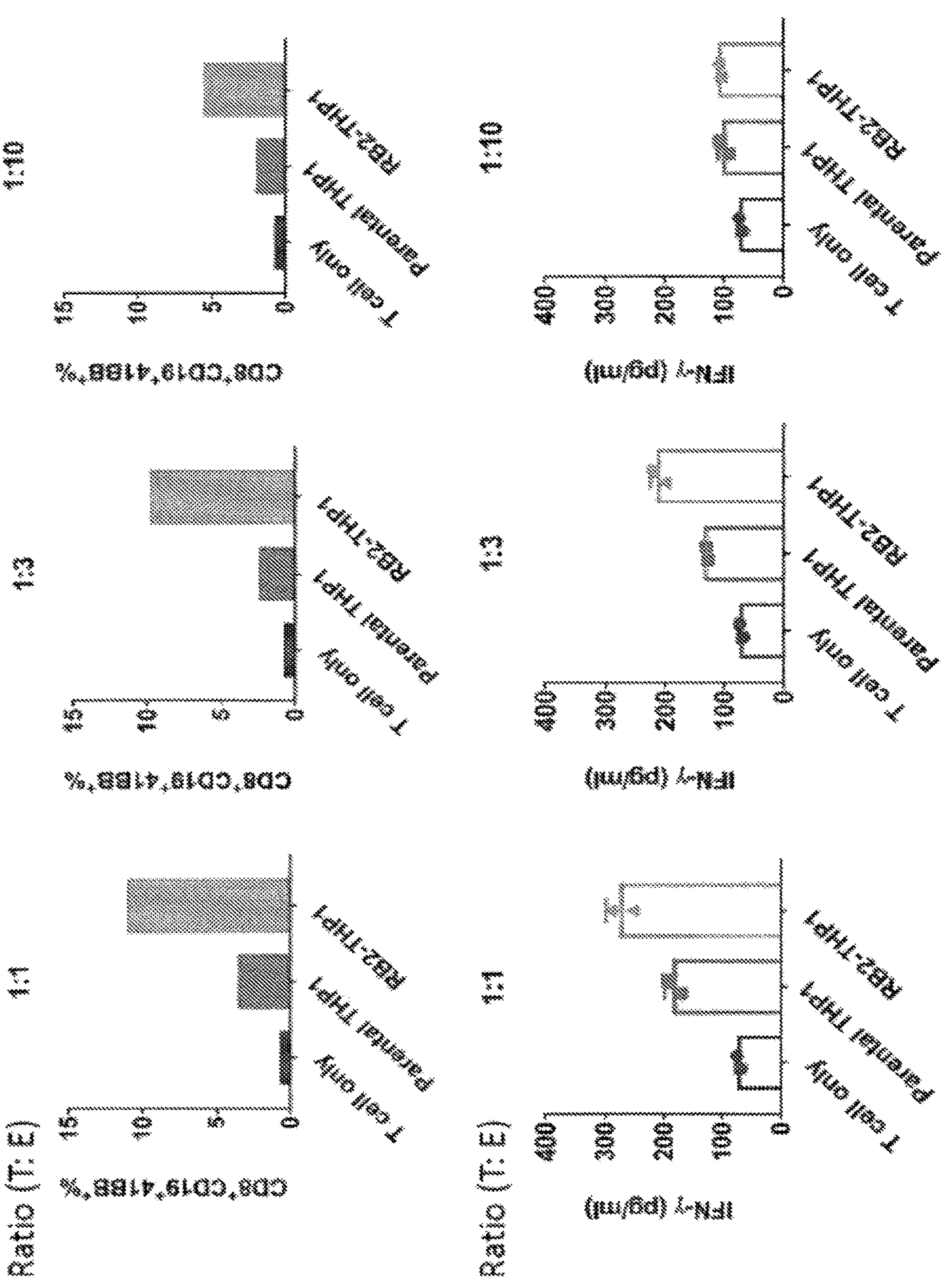
FIG. 24: Anti-LILRB2 CAR-T cells demonstrate specific activation and cytokine release when stimulated by LILRB2+leukemia cells, e.g., THP-1. Using Anti-LILRB2-CAR-T short form vector (upper panel): Anti-LILRB2 CAR-T cells displayed activation specificity to target LILRB2 proteins. The anti-LILRB2 CAR-T cells were co-cultured with LILRB2-expressing THP1 cells or parental THP1 cells for 24 hours at target: effector ranging from 1:1 to 1:10. CAR-T cell activation was determined by detection of 41BB expression using flow cytometry. T cells without transduction were used as control. Lower panel: Anti-LILRB2 CAR-T cells displayed cytokine release specificity to target LILRB2 proteins. Supernatant was collected after 24-hour co-culture of anti-LILRB2 CAR-T cells with LILRB2-expressing THP1 cells or parental THP1 cells at target: effector ranging from 1:1 to 1:10. Cytokine release was assayed for interferon γ (IFNγ) by ELISA. T cells without transduction were used as control.

LILRB2 CARs were generated using the 1H3 Fab region. FIG. 24 shows that anti-LILRB2 CAR-T cells demonstrated specific activation and cytokine release when stimulated by LILRB2+leukemia cells, e.g., THP-1. Using Anti-LILRB2-CAR-T short form vector (FIG. 24, upper panel), anti-LILRB2 CAR-T cells displayed activation specificity to target LILRB2 proteins. The anti-LILRB2 CAR-T cells were co-cultured with LILRB2-expressing THP1 cells or parental THP1 cells for 24 hours at a target:effector (T:E) ratio ranging from 1:1 to 1:10. CAR-T cell activation was determined by detection of 41BB expression using flow cytometry. T cells without transduction were used as control. FIG. 24, lower panel: Anti-LILRB2 CAR-T cells displayed cytokine release specificity to target LILRB2 proteins. Supernatant was collected after a 24-hour co-culture of anti-LILRB2 CAR-T cells with LILRB2-expressing THP1 cells or parental THP1 cells at a target:effector (T:E) ranging from 1:1 to 1:10. Cytokine release was assayed for interferon γ (IFNγ) by ELISA. T cells without transduction were used as control.

Figure 25:
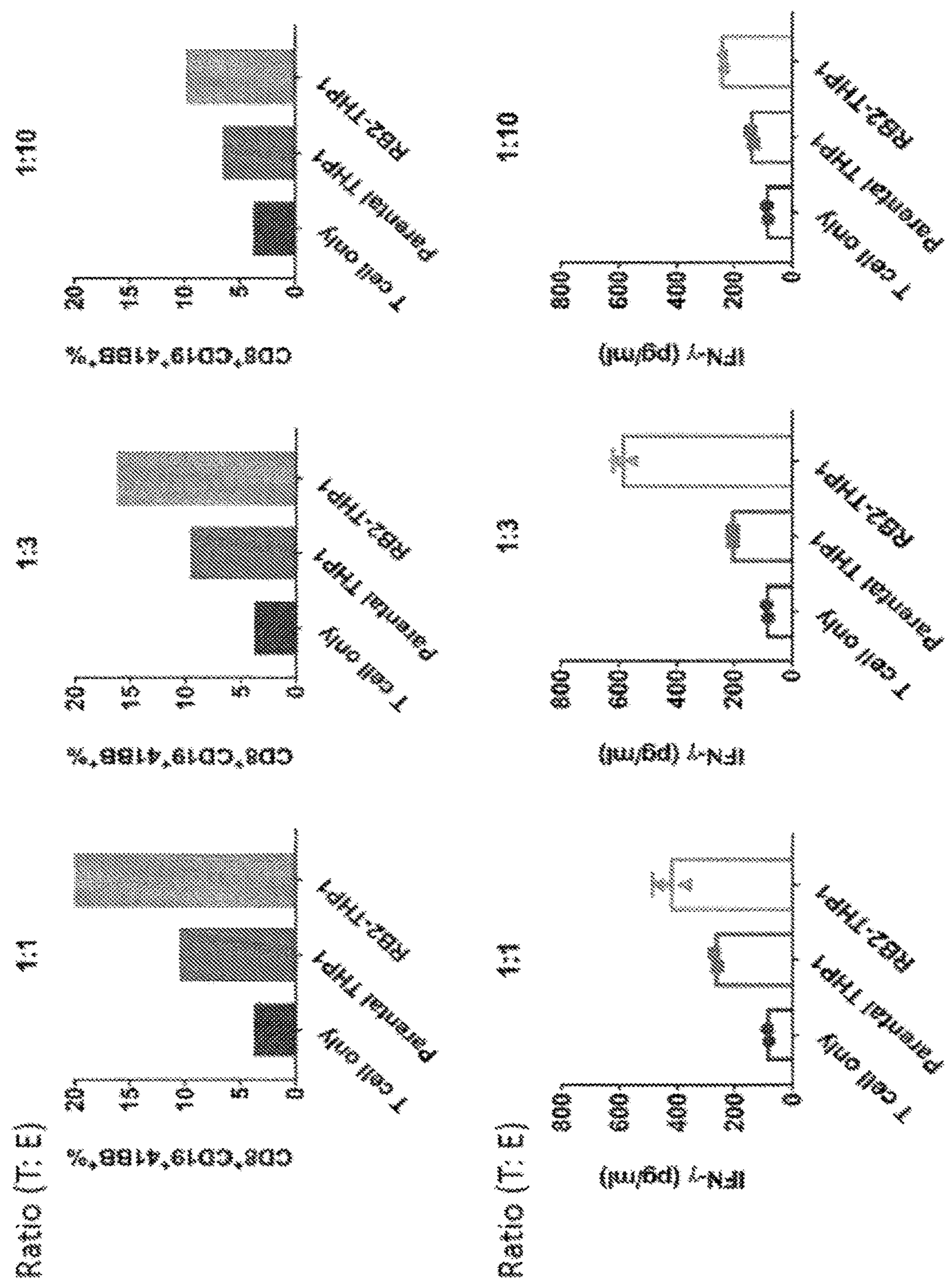
FIG. 25: Anti-LILRB2 CAR-T cells demonstrate specific activation and cytokine release when stimulated by LILRB2+leukemia cells. Anti-LILRB2-CAR-T long form vector (upper panel): Anti-LILRB2 CAR-T cells displayed activation specificity to target LILRB2 proteins. The anti-LILRB2 CAR-T cells were co-cultured with LILRB2-expressing THP1 cells or parental THP1 cells for 24 hours at target: effector ranging from 1:1 to 1:10. CAR-T cell activation was determined by detection of 41BB expression using flow cytometry. T cells without transduction were used as control. Lower panel: Anti-LILRB2 CAR-T cells displayed cytokine release specificity to target LILRB2 proteins. Supernatant was collected after 24-hour co-culture of anti-LILRB2 CAR-T cells with LILRB2-expressing THP1 cells or parental THP1 cells at target: effector ranging from 1:1 to 1:10. Cytokine release was assayed for interferon γ (IFNγ) by ELISA. T cells without transduction were used as control.

FIG. 25 shows that anti-LILRB2 CAR-T cells demonstrated specific activation and cytokine release when stimulated by LILRB2+leukemia cells. Using anti-LILRB2-CAR-T long form vector (FIG. 25, upper panel), anti-LILRB2 CAR-T cells displayed activation specificity to target LILRB2 proteins. The anti-LILRB2 CAR-T cells were co-cultured with LILRB2-expressing THP1 cells or parental THP1 cells for 24 hours at a target:effector ratio ranging from 1:1 to 1:10. CAR-T cell activation was determined by detection of 41BB expression using flow cytometry. T cells without transduction were used as control. FIG. 25, lower panel shows that Anti-LILRB2 CAR-T cells displayed cytokine release specificity to target LILRB2 proteins. Supernatant was collected after a 24-hour co-culture of anti-LILRB2 CAR-T cells with LILRB2-expressing THP1 cells or parental THP1 cells at target:effector ratio ranging from 1:1 to 1:10. Cytokine release was assayed for interferon γ (IFNγ) by ELISA. T cells without transduction were used as control.

Figure 26:
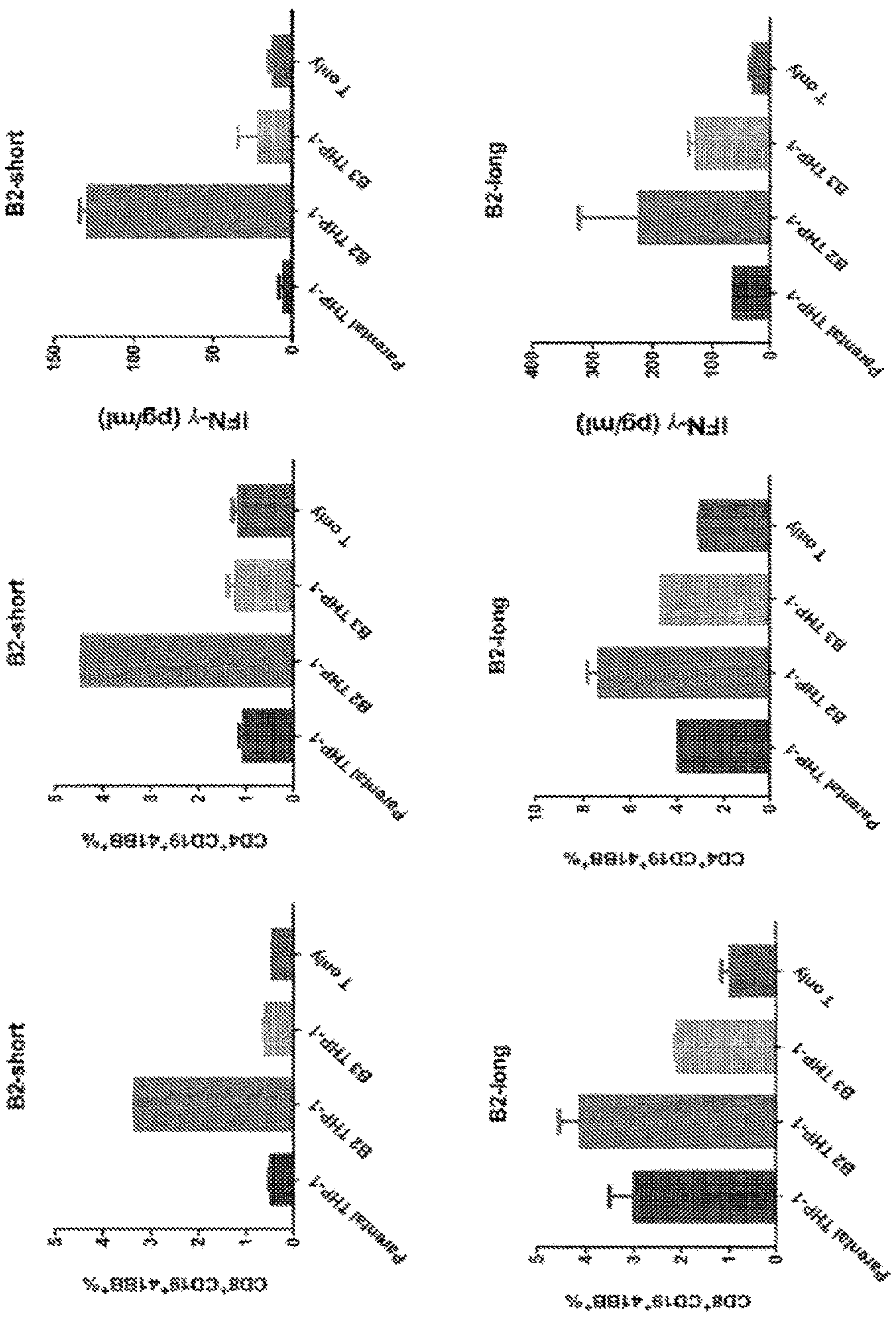
FIG. 26. Anti-LILRB2 CAR-T cells demonstrate binding specificity to target LILRB2. Anti-LILRB2 CAR-T cells, both short (upper panel) and long (lower panel) form, were co-cultured with LILRB2-expressing THP1 cells, LILRB3-expressing THP1 cells or parental THP1 cells for 24 hours. CAR-T cell activation was determined by detection of 41BB expression using flow cytometry. T cells without transduction were used as control.

FIG. 26 shows that anti-LILRB2 CAR-T cells demonstrated binding specificity to target LILRB2. Anti-LILRB2 CAR-T cells, both short (FIG. 26, upper panel) and long (FIG. 26, lower panel) form, were co-cultured with LILRB2-expressing THP1 cells, LILRB3-expressing THP1 cells, or parental THP1 cells for 24 hours. CAR-T cell activation was determined by detection of 41BB expression using flow cytometry. T cells without transduction were used as control.

Figure 27:
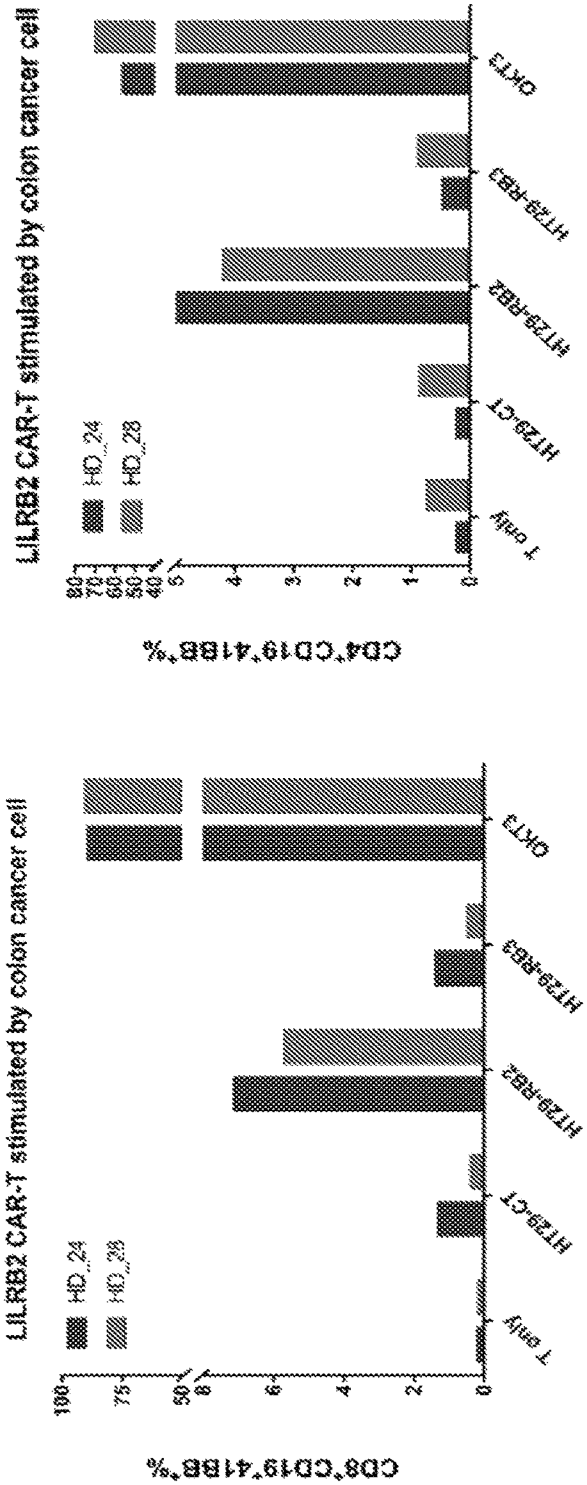
FIG. 27: Anti-LILRB2 CAR-T cells demonstrate binding specificity to target LILRB2 protein in HT29 colon cancer cells. Anti-LILRB2 CAR-T cells were co-cultured with LILRB2-, LILRB3-expressing HT29 cells or HT29 control cells for 24 hours. CAR-T cell activation was determined by detection of activation markers on 41BB expression using flow cytometry. CAR-T cells stimulated with OKT3 were used as positive control for CAR-T cell activation. T cells without transduction were used as control.

FIG. 27 shows that anti-LILRB2 CAR-T cells demonstrated binding specificity to target LILRB2 protein in HT29 colon cancer cells. Anti-LILRB2 CAR-T cells were co-cultured with LILRB2-, LILRB3-expressing HT29 cells, or HT29 control cells for 24 hours. CAR-T cell activation was determined by detection of activation markers on 41BB expression using flow cytometry. CAR-T cells stimulated with OKT3 were used as positive control for CAR-T cell activation. T cells without transduction were used as control.

Figure 28:
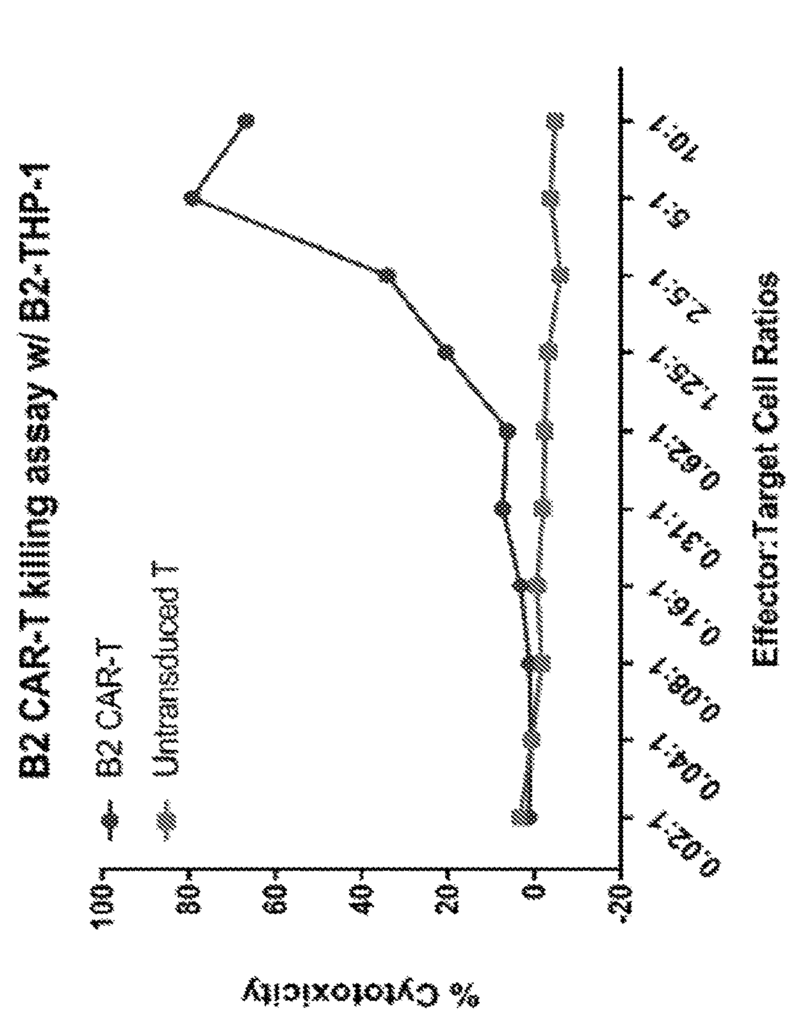
FIG. 28: Anti-LILRB2 CAR-T cells display efficient cytotoxicity against LILRB2-expressing leukemia cells in vitro. LILRB2-expressing leukemia cells (B2-THP1) were co-cultured with anti-LILRB2 CAR-T or untransduced T cells at effector: target ranging from 0.02:1 to 10:1. Supernatant was collected after 7 hours co-culture and cytotoxicity was determined by detection of LDH release.

FIG. 28 shows that Anti-LILRB2 CAR-T cells displayed efficient cytotoxicity against LILRB2-expressing leukemia cells in vitro. LILRB2-expressing leukemia cells (B2-THP1) were co-cultured with anti-LILRB2 CAR-T (left bars) or untransduced T cells (riht bars) at effector:target ranging from 0.02:1 to 10:1.

Supernatant was collected after 7 hours of co-culture and cytotoxicity was determined by detection of LDH release.

Figure 29:
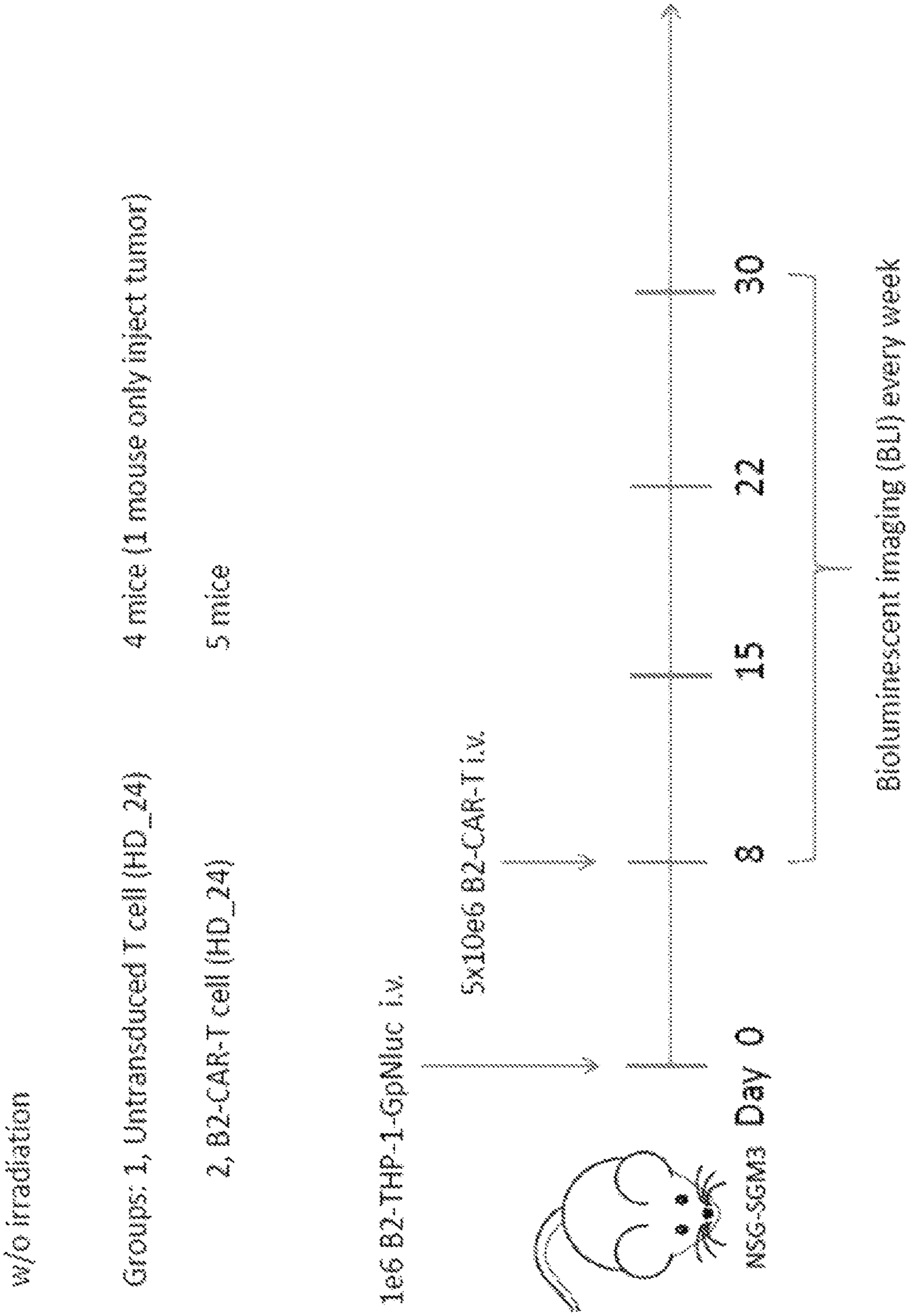
FIG. 29: Experimental design for demonstration the efficacy of the anti-LILRB2 CAR-T cells in the THP1-LILRB2 xenografn mouse model. NSG-SGM3 mice were injected with LILRB2-expressing THP1 cells on day 0, and treated with untransduced T cells (control) or anti-LILRB2 CAR-T cells on day 8, 15, 22 and 30. Bioluminescent images were taken weekly.

FIG. 29 shows the experimental design for demonstration the efficacy of the anti-LILRB2 CAR-T cells in the THP1-LILRB2 xenograft mouse model. NSG-SGM3 mice were injected with LILRB2-expressing THP1 cells on day 0, and treated with untransduced T cells (control) or anti-LILRB2 CAR-T cells on day 8, 15, 22 and 30. Bioluminescent images were taken weekly.

Figure 30:
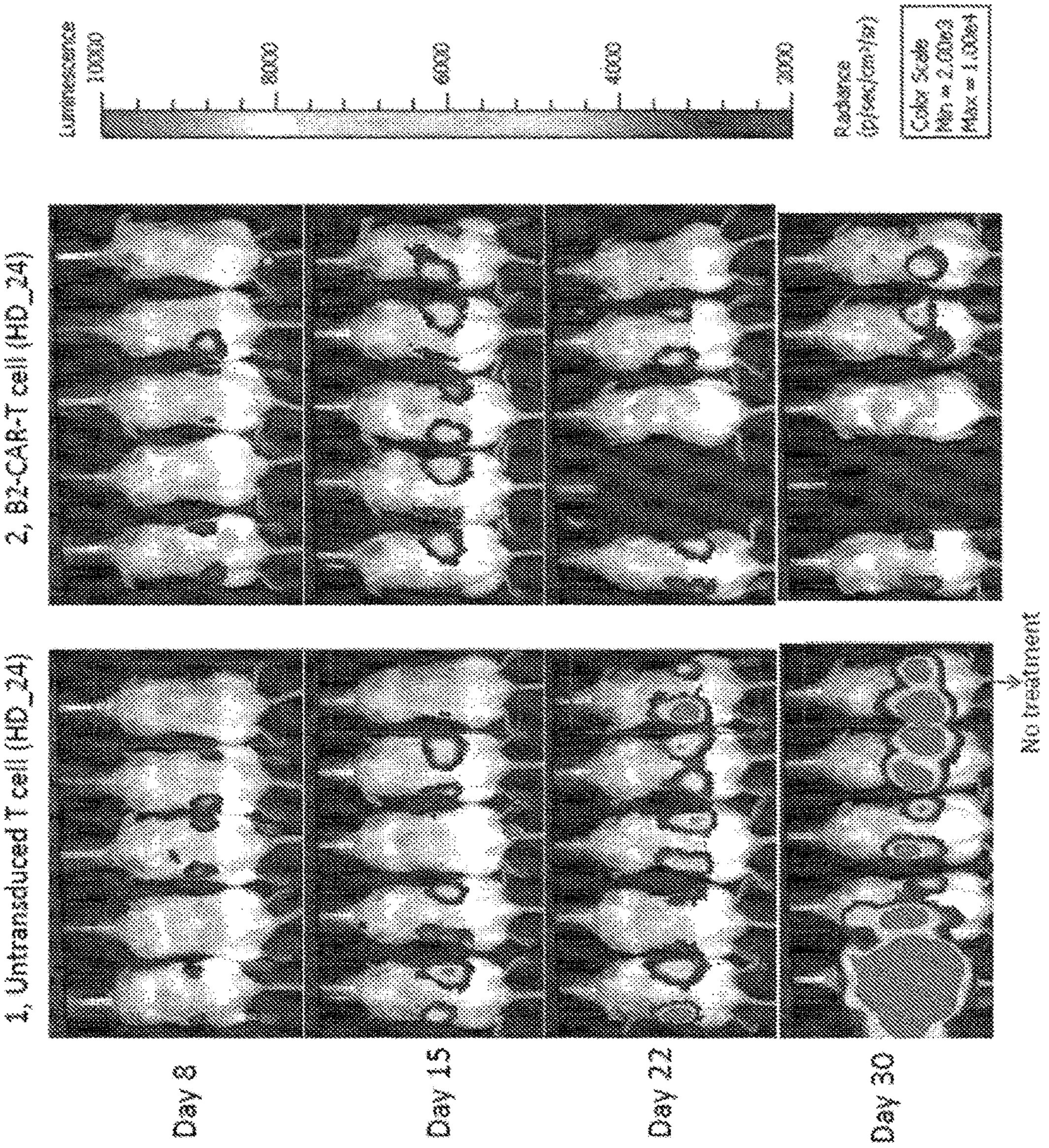
FIGS. 30-33: Anti-LILRB2 CAR-T cells reduced leukemia burden in the THP1-LILRB2 xenograft mouse model. NSG-SGM3 mice were injected with LILRB2-expressing THP1 cells on day 0, and treated with untransduced T cells (control) or anti-LILRB2 CAR-T cells on day 8, 15, 22 and 30. Bioluminescent images (BLI) were taken weekly.
Figure 31:
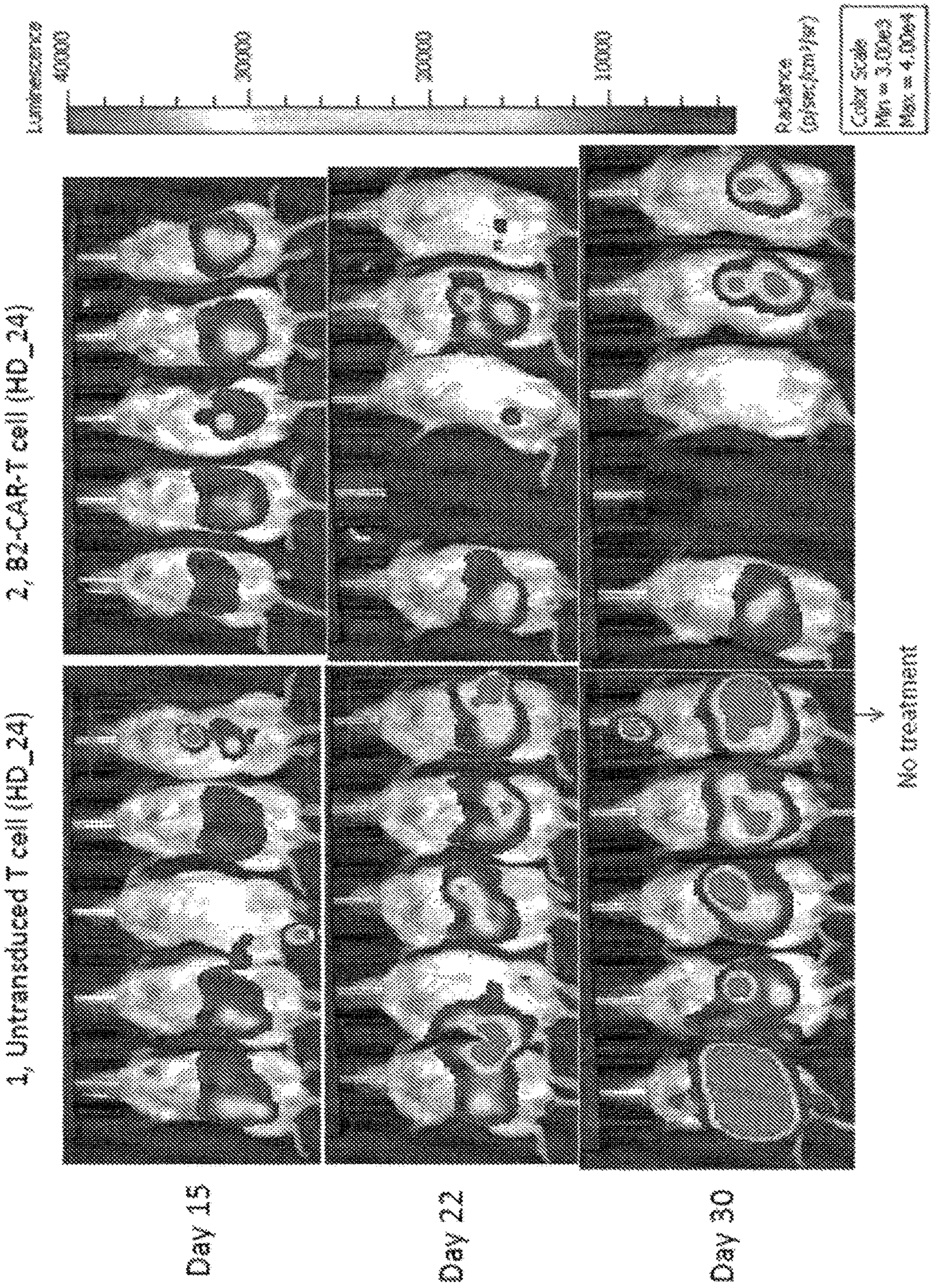

FIGS. 30-33 show that anti-LILRB2 CAR-T cells reduced leukemia burden in the THP1-LILRB2 xenograft mouse model. NSG-SGM3 mice were injected with LILRB2-expressing THP1 cells on day 0, and treated with untransduced T cells (control) or anti-LILRB2 CAR-T cells on day 8, 15, 22 and 30. Bioluminescent images (BLI) were taken weekly. FIG. 30 shows weekly BLI of mice treated with untransduced T cells (left) or anti-LILRB2-CAR-T cells (right); images were taken from the back of mice. FIG. 31 shows weekly BLI of mice treated with untransduced T cells (left) or anti-LILRB2-CAR-T cells (right); images were taken from the abdomen.

Figure 32:
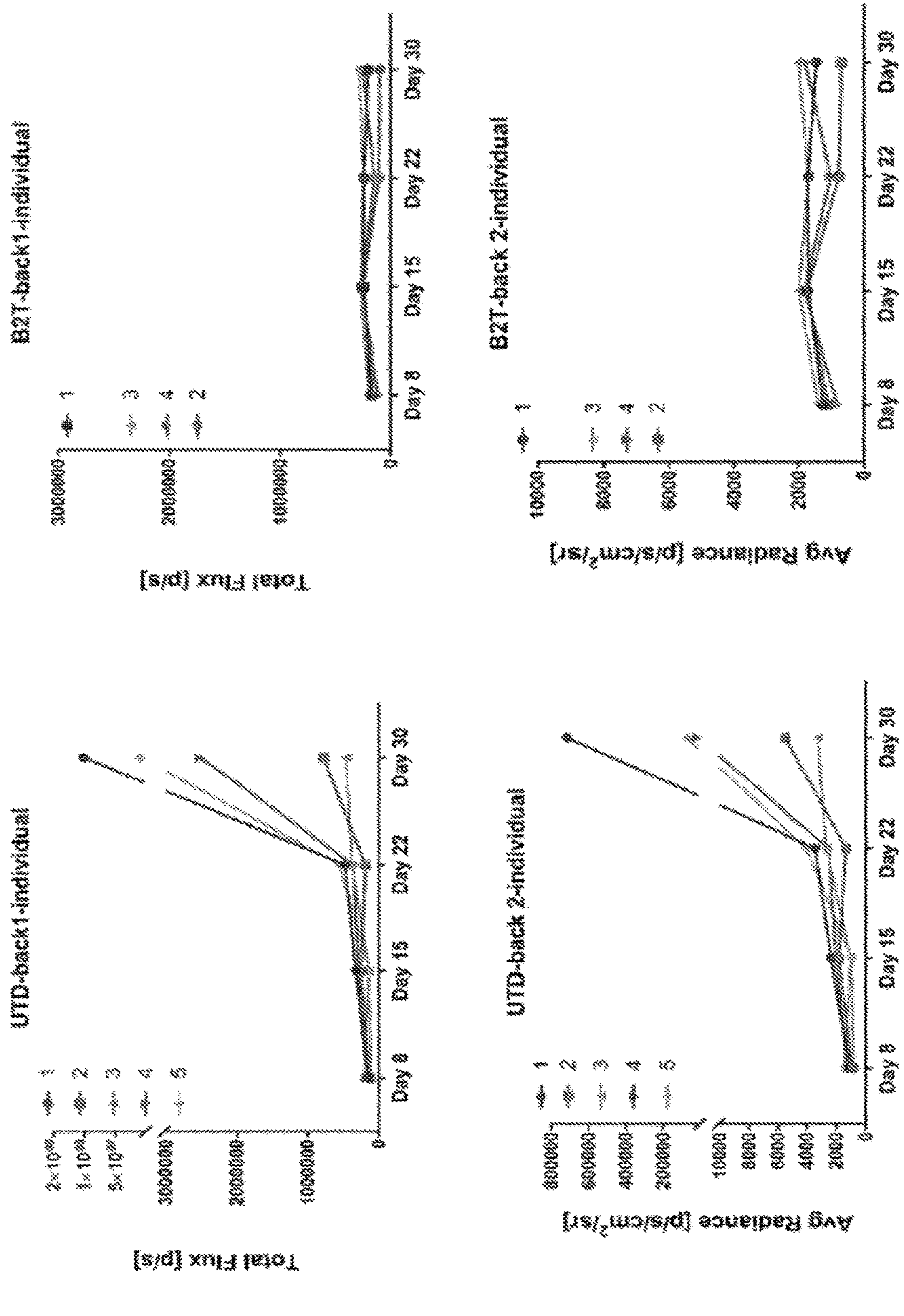

FIG. 32 shows plots of total flux (p/s) as a function of time; each shape represents an individual mouse in the treatment group. FIG. 32 demonstrates that anti-LILRB2 CAR-T cells (right) decreased leukemia burden as compared to the control T cell-treated (left) mice.

Figure 33:
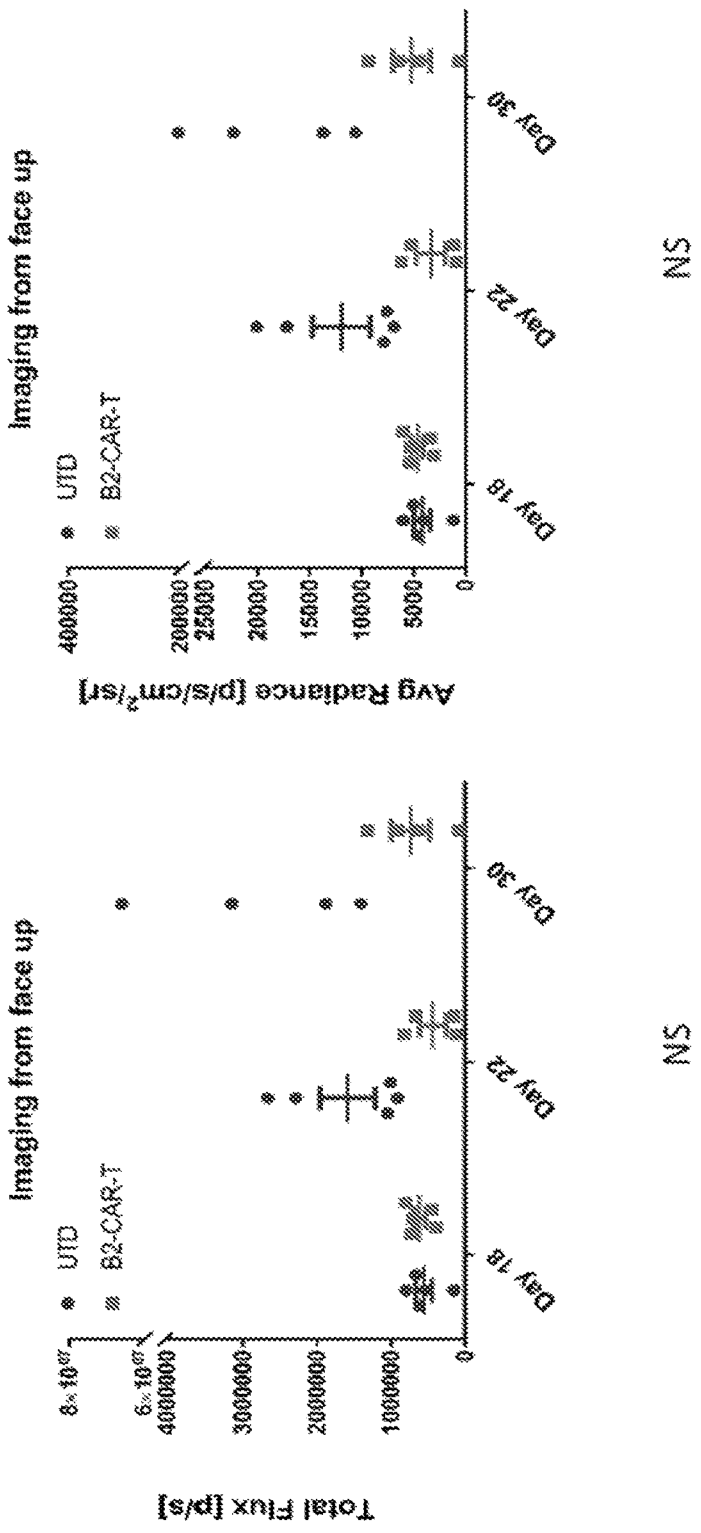

FIG. 33 shows the quantification results of leukemia burden in total flux (left panel) and average radiance (right panel). Mice treated with anti-LILRB2 CAR-T cells (squares) showed decrease of the tumor burden compared to the untransduced T cell-treated mice (circles).

Example 12: Anti-LILRB4 CAR-T Cells

Figure 34:
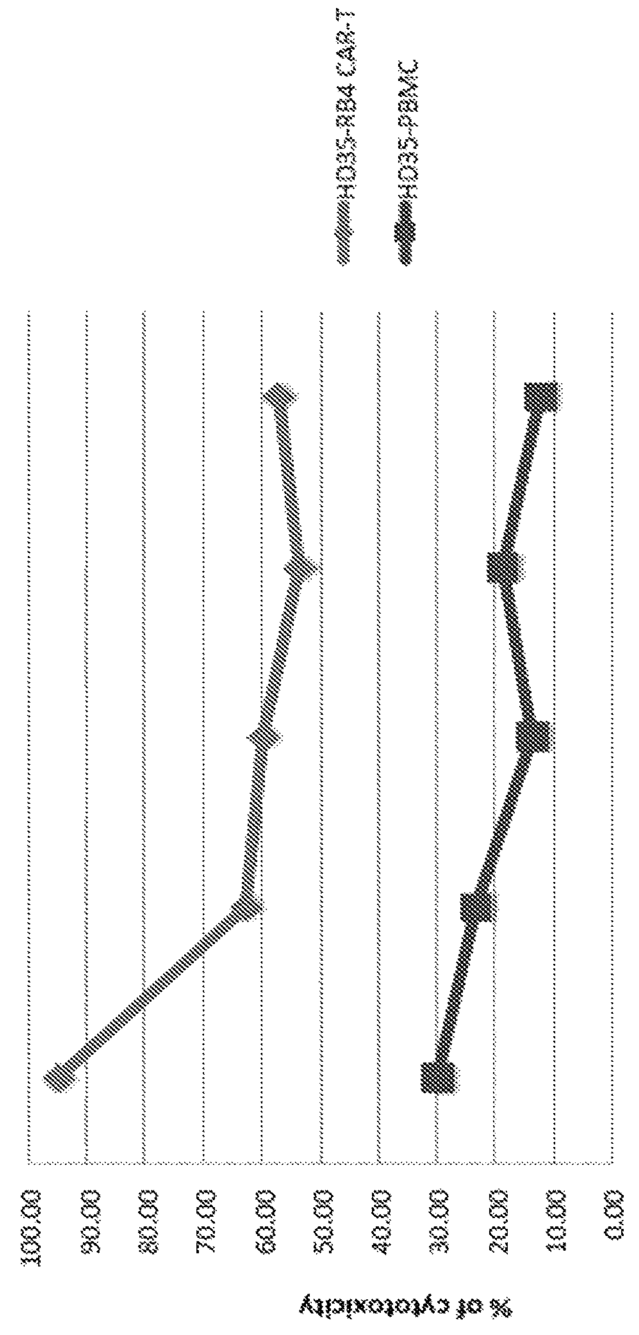
FIG. 34: Anti-LILRB4 CAR-T cells demonstrated cytotoxicity against LILRB4 protein expressing human AML cells.

Anti-LILRB4 CAR-T cells were generated. FIG. 34 shows that anti-LILRB4 CAR-T cells demonstrated cytotoxicity against LILRB4 protein expressing human AML cells.

Figure 35A:
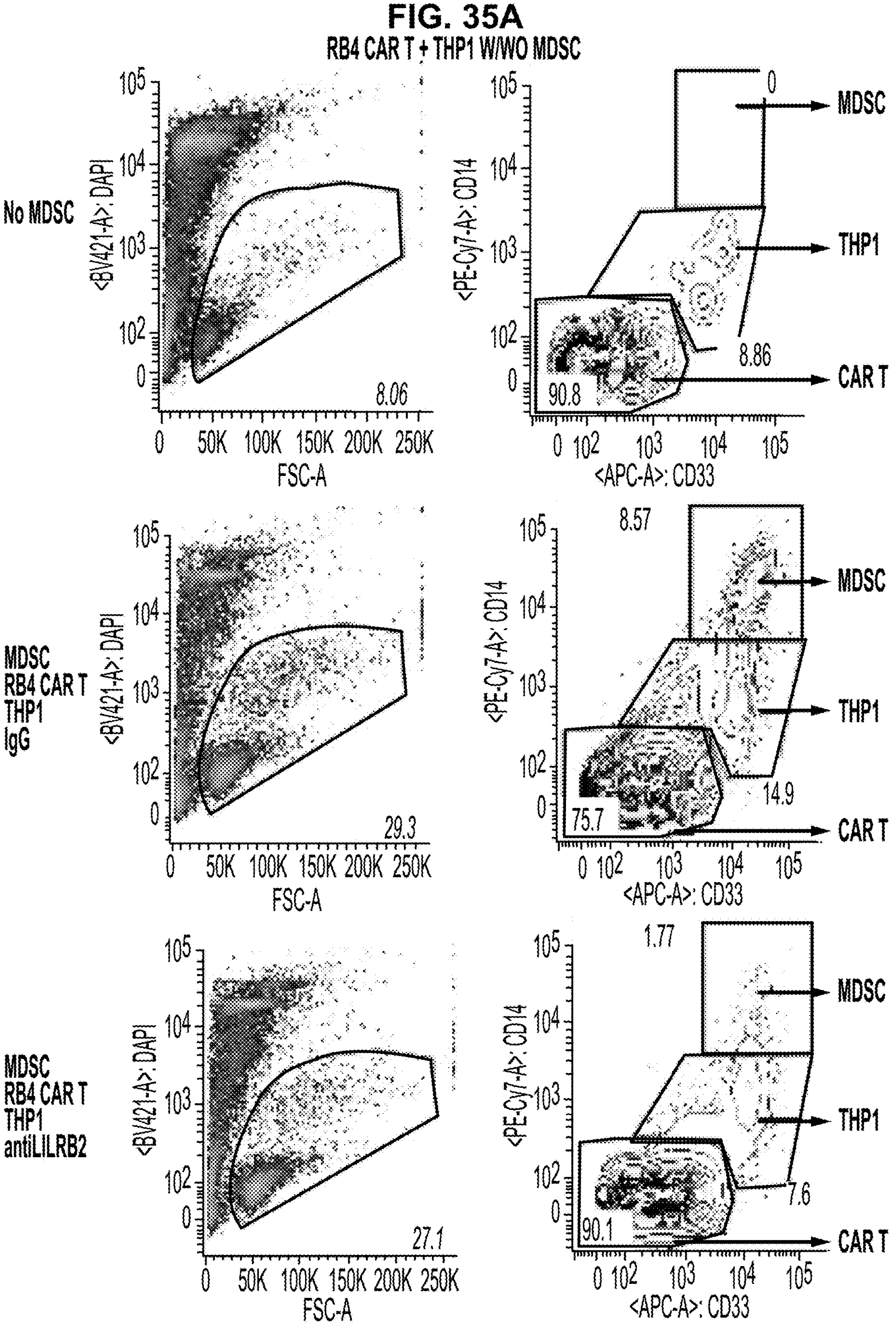
FIGS. 35A-35B: Antagonistic anti-LILRB2 abrogates MDSC-mediated inhibition of CAR-T T cell proliferation.
Figure 35B:
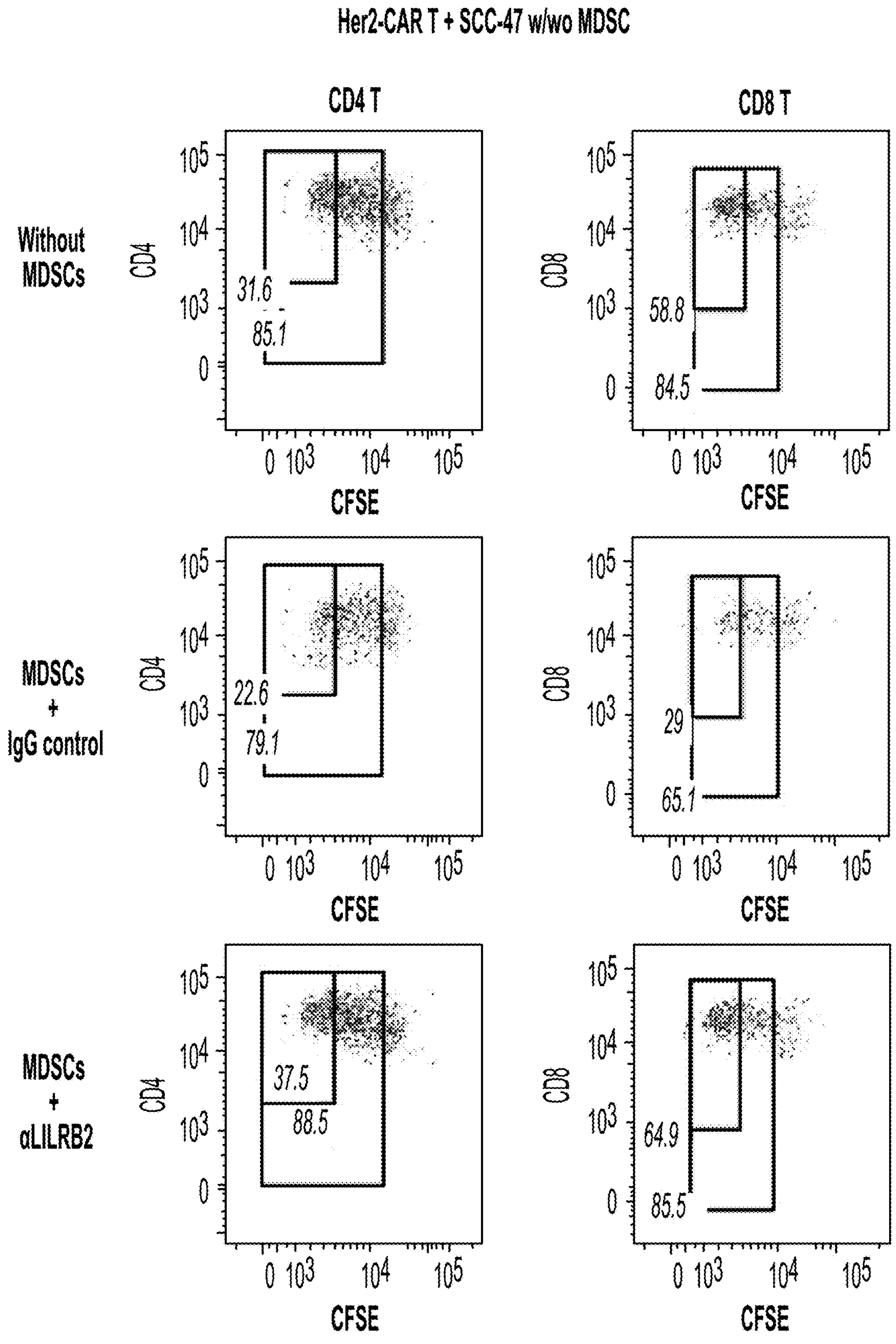

Example 13: Anti-LILRB2 Ab Abrogates MDSCs-Mediated Suppression of CAR-T Cells Given the strong functional activities of Anti-LILRB2 on macrophages maturation, we investigated whether anti-LILRB2 (antibody 20D3 with human IgG4) could abolish MDSCs-mediated suppression of CAR-T cells proliferation. We generated in vitro-cultured monocyte-derived MDSCs and co-cultured with CAR-T cells in presence of target tumor cells. MDCSs significantly suppressed CAR-T cell proliferation induced by target tumor cells, i.e., AML (THP-1) (FIG. 35A) or Her-2 positive head and neck solid cancer (SCC-47) (FIG. 35B). Notably, anti-LILRB2 antibody abrogated MDSCs-mediated suppression, reinvigorated both CD4 and CD8 T cells proliferation (FIG. 35B) and enhanced the CAR-T mediated killing effect on tumor cells as well as MDSC that are LILRB2 positive (FIG. 35A). The result suggests that anti-LILRB2 can overcome MDSCs-mediated suppression and enhance CAR-T cell proliferation.

TABLE 3

| | | FACS binding | | | | | | | | | Myeloid cell-TNFa | | | Myeloid cell-IL10 | | |
|---|---|---|---|---|---|---|---|---|---|---|---|---|---|---|---|---|
| Clone | Isotype | B1 | B2 | B3 | B4 | A1 | A2 | A4 | A5 | A6 | IgG | Avg | Δ | IgG | Avg | Δ |
| 10B10 | G2a, k | — | X | — | — | — | — | — | — | — | 482.80 | 1756.65 | 3.64 | 413.48 | 276.63 | 0.67 |
| 10B4 | G2a, k | — | X | — | — | — | — | — | — | — | 482.80 | 4345.88 | 9.00 | 413.48 | 299.24 | 0.72 |
| 10C5 | G2b, k | — | X | — | — | — | — | — | — | — | 817.41 | 1392.89 | 1.70 | 433.35 | 296.91 | 0.69 |
| 10D6 | G2a, k | — | X | — | — | | | | | | 561.40 | 2332.00 | 4.15 | 567.70 | 820.60 | 1.45 |
| 10D7 | G2a, k | — | X | — | — | | | | | | 813.02 | 1995.07 | 2.45 | 1123.81 | 353.28 | 0.31 |
| 10D8 | G2a, k | — | X | — | — | — | — | — | — | — | 482.80 | 5743.12 | 11.90 | 413.48 | 296.48 | 0.72 |
| 10G7 | G2a, k | — | X | — | — | | | | | | 482.80 | 5263.61 | 10.90 | 413.48 | 312.88 | 0.76 |
| 11A5 | G2b, k | — | X | — | — | X | — | x/? | — | — | 817.41 | 2434.68 | 2.98 | 433.35 | 356.58 | 0.82 |
| 11B2 | G2b, k | — | X | — | — | X | — | — | — | — | 817.41 | 1133.93 | 1.39 | 433.35 | 492.05 | 1.14 |
| 12E4 | G2a, k | — | X | — | — | | | | | | 813.02 | 1236.69 | 1.52 | 1123.81 | 961.73 | 0.86 |
| 12G2 | G2a, k | — | X | — | — | — | — | — | — | — | 813.02 | 1680.01 | 2.07 | 1123.81 | 522.16 | 0.46 |
| 12H6 | G2a, k | — | X | — | — | X | — | — | — | — | 482.80 | 885.28 | 1.83 | 413.48 | 369.40 | 0.89 |
| 13H1 | G2a, k | X | X | — | — | x | x/? | — | — | — | 482.80 | 4195.15 | 8.69 | 413.48 | 268.98 | 0.65 |
| 14E7 | G2a, k, ? | — | X | — | — | — | — | — | — | — | 561.40 | 1801.00 | 3.21 | 567.70 | 1027.00 | 1.81 |
| 15A10 | G1, k | — | X | — | — | — | — | — | — | — | 561.40 | 2685.00 | 4.78 | 567.70 | 448.10 | 0.79 |
| 15C6 | G2a, k | — | X | — | — | X | — | — | — | — | 482.80 | 1861.93 | 3.86 | 413.48 | 358.84 | 0.87 |
| 15D6 | G2a, k | — | X | — | — | — | — | — | — | — | 561.40 | 2387.00 | 4.25 | 567.70 | 693.70 | 1.22 |
| 15E7 | G2b, k | — | X | — | — | — | — | — | — | — | 817.41 | 872.05 | 1.07 | 433.35 | 489.79 | 1.13 |
| 16F12 | G2a, k | X | X | — | — | X | X | — | — | — | 813.02 | 1670.93 | 2.06 | 1123.81 | 630.11 | 0.56 |
| 16F4 | G2a, k | — | X | — | — | — | — | — | — | — | 482.80 | 4742.78 | 9.82 | 413.48 | 213.63 | 0.52 |
| 17A3 | G2a, k | — | X | — | — | — | — | — | — | — | 482.80 | 2436.22 | 5.05 | 413.48 | 237.80 | 0.58 |
| 17H7 | G2a, k | — | X | — | — | — | — | — | — | — | 482.80 | 1773.18 | 3.67 | 413.48 | 287.85 | 0.70 |
| 1D6 | G2a, k | — | X | — | — | — | — | — | — | — | 561.40 | 585.70 | 1.04 | 567.70 | 716.70 | 1.26 |
| 1E6 | G2a, k | — | X | — | — | X | x/? | — | — | — | 813.02 | 1838.71 | 2.26 | 1123.81 | 487.98 | 0.43 |
| 1F1 | G2a, k | — | X | — | — | — | — | — | — | — | 482.80 | 6496.72 | 13.46 | 413.48 | 232.86 | 0.56 |
| 1F12 | G2a, k | — | X | — | — | | | | | | 813.02 | 2074.23 | 2.55 | 1123.81 | 446.17 | 0.40 |
| 1F6 | G2a, k | — | X | — | — | — | — | — | — | — | 813.02 | 1764.14 | 2.17 | 1123.81 | 558.71 | 0.50 |
| 1H3 | G2a, k | — | X | — | — | — | — | — | — | — | 482.80 | 5245.71 | 10.87 | 413.48 | 269.43 | 0.65 |
| 20D3 | IgG2b | — | X | — | — | — | — | — | — | — | 2101.58 | 3641.99 | 1.73 | 282.98 | 231.05 | 0.82 |
| 29G2 | G2b, k | — | X | — | — | — | — | — | — | — | 817.41 | 989.45 | 1.21 | 433.35 | 503.60 | 1.16 |
| 29G3 | G2a, k | — | X | — | — | — | — | — | — | — | 482.80 | 3309.24 | 6.85 | 413.48 | 228.30 | 0.55 |
| 29H9 | G2a, k | — | X | — | — | — | — | — | — | — | 813.02 | 2154.31 | 2.65 | 1123.81 | 398.85 | 0.35 |
| 2G11 | G2a, k | — | X | — | — | — | — | — | — | — | 561.40 | 1185.00 | 2.11 | 567.70 | 1067.00 | 1.88 |

TABLE 3-continued

| | | FACS binding | | | | | | | | | Myeloid cell-TNFa | | | Myeloid cell-IL10 | | |
|---|---|---|---|---|---|---|---|---|---|---|---|---|---|---|---|---|
| Clone | Isotype | B1 | B2 | B3 | B4 | A1 | A2 | A4 | A5 | A6 | IgG | Avg | Δ | IgG | Avg | Δ |
| 30A6 | G2b, k | — | X | — | — | — | — | — | — | — | 817.41 | 2560.22 | 3.13 | 433.35 | 260.67 | 0.60 |
| 30F1 | G2a, k | — | X | — | — | — | — | — | — | — | 817.41 | 1854.20 | 2.27 | 433.35 | 342.65 | 0.79 |
| 30G7 | G2b, k | — | X | — | — | —/? | —/? | —/? | —/? | —/? | 976.54 | 3109.61 | 3.18 | 1035.09 | 258.67 | 0.25 |
| 33A12 | G2b, k | — | X | — | — | x | x | x | — | x/? | 817.41 | 889.75 | 1.09 | 433.35 | 464.51 | 1.07 |
| 33D10 | G2a, k | — | X | — | — | | | | | | 813.02 | 3267.64 | 4.02 | 1123.81 | 331.76 | 0.30 |
| 33G2 | G2b, 3, k? | — | X | — | — | — | — | — | — | — | 976.54 | 296.92 | 0.30 | 1035.09 | 1101.19 | 1.06 |
| 3B3 | G2a, k | — | X | — | — | | | | | | 813.02 | 2202.77 | 2.71 | 1123.81 | 659.47 | 0.59 |
| 3B8 | G2a, k | — | X | — | — | | | | | | 813.02 | 2471.43 | 3.04 | 1123.81 | 402.58 | 0.36 |
| 3E5 | M, k | — | X | — | — | — | — | — | — | — | 561.40 | 1485.00 | 2.65 | 567.70 | 1038.00 | 1.83 |
| 3G6 | G2a, k | — | X | — | — | — | — | — | — | — | 482.80 | 4585.53 | 9.50 | 413.48 | 259.95 | 0.63 |
| 47F11 | G2a, k | — | X | — | — | — | — | — | — | — | 482.80 | 3761.06 | 7.79 | 413.48 | 240.53 | 0.58 |
| 48E1 | G2b, k | — | X | — | — | — | — | — | — | — | 817.41 | 602.54 | 0.74 | 433.35 | 560.13 | 1.29 |
| 48G9 | G2a, k | — | X | — | — | | | | | | 813.02 | 2594.50 | 3.19 | 1123.81 | 302.35 | 0.27 |
| 4A5 | G2b, k | — | X | — | — | — | — | — | — | — | 817.41 | 2108.83 | 2.58 | 433.35 | 368.97 | 0.85 |
| 4B10 | G2a, k | — | X | — | — | | | | | | 813.02 | 1236.69 | 1.52 | 1123.81 | 961.73 | 0.86 |
| 4B6 | G2a, k | — | X | — | — | x/? | — | — | — | x/? | 482.80 | 3955.50 | 8.19 | 413.48 | 353.42 | 0.85 |
| 4D3 | G2a, k | — | X | — | — | X | — | — | — | — | 482.80 | 1354.86 | 2.81 | 413.48 | 423.34 | 1.02 |
| 4E2 | G2a, k | — | X | — | — | X | — | x/? | — | x/? | 482.80 | 4501.37 | 9.32 | 413.48 | 201.55 | 0.49 |
| 4E7 | G2a, k | — | X | — | — | x | — | — | — | — | 482.80 | 2354.80 | 4.88 | 413.48 | 379.16 | 0.92 |
| 4F12 | IgG1 and IgG2b? | — | X | — | — | + | — | — | — | — | 817.41 | 3770.11 | 4.61 | 433.35 | 195.83 | 0.45 |
| 4G10 | G2a, k | — | X | — | — | x | x | — | x | x | 482.80 | 1652.42 | 3.42 | 413.48 | 227.89 | 0.55 |
| 4G3 | G2a, k | — | X | — | — | | | | | | 813.02 | 2378.22 | 2.93 | 1123.81 | 514.67 | 0.46 |
| 4G7 | G2a, k | — | X | — | — | — | — | — | — | — | 561.40 | 1556.00 | 2.77 | 567.70 | 656.90 | 1.16 |
| 4G8 | G2a, k | — | X | — | — | — | — | — | — | — | 561.40 | 1406.00 | 2.50 | 567.70 | 783.80 | 1.38 |
| 4H5 | G2b, k | — | X | — | — | X | X | — | — | — | 817.41 | 5685.82 | 6.96 | 433.35 | 217.50 | 0.50 |
| 50B9 | G2a, k | — | X | — | — | X | — | x/? | — | — | 482.80 | 2116.66 | 4.38 | 413.48 | 292.91 | 0.71 |
| 50C3_G1 | G1, k | — | X | — | — | — | — | — | — | — | 561.40 | 2100.00 | 3.74 | 567.70 | 673.50 | 1.19 |
| 50C3_G2a | G2a, k | — | X | — | — | — | — | — | — | — | 561.40 | 1997.00 | 3.56 | 567.70 | 637.60 | 1.12 |
| 51A12 | G2a, k | — | X | — | — | — | — | — | — | — | 482.80 | 4162.42 | 8.62 | 413.48 | 308.13 | 0.75 |
| 51B8 | G2a, k | X | X | X | X | | | | | | 561.40 | 1071.00 | 1.91 | 567.70 | 1059.00 | 1.87 |
| 51D3 | G2a, k | — | X | — | — | — | — | — | — | — | 482.80 | 2852.88 | 5.91 | 413.48 | 243.84 | 0.59 |
| 51G7 | G2a, k | — | X | — | — | — | — | — | — | — | 482.80 | 3286.09 | 6.81 | 413.48 | 273.18 | 0.66 |
| 51H9 | G1, k | — | X | — | — | x | — | — | — | — | 1139.96 | 2391.57 | 2.10 | 523.21 | 424.20 | 0.81 |
| 5A3 | G2a, k | — | X | — | — | X | — | — | — | — | 482.80 | 1035.96 | 2.15 | 413.48 | 262.21 | 0.63 |
| 5A7 | G2a, b, k ?? | — | X | — | — | — | — | — | — | — | 561.40 | 2458.00 | 4.38 | 567.70 | 960.40 | 1.69 |
| 5C12 | G2a, k | — | X | — | — | x | x | — | — | — | 482.80 | 1329.87 | 2.75 | 413.48 | 164.67 | 0.40 |
| 5D6 | G3, k | — | X | — | — | X | — | — | — | — | 1139.96 | 898.80 | 0.79 | 523.21 | 416.64 | 0.80 |
| 5F4 | G2a, k | — | X | — | — | | | | | | 813.02 | 4245.69 | 5.22 | 1123.81 | 182.38 | 0.16 |
| 5G5 | IgG1 | — | X | — | — | — | — | — | — | — | 1139.96 | 5371.09 | 4.71 | 523.21 | 233.48 | 0.45 |
| 5H8 | G3, k | — | X | — | — | — | — | — | — | — | 813.02 | 1411.79 | 1.74 | 1123.81 | 614.59 | 0.55 |
| 6A9 | G2a, k | — | X | — | — | — | — | — | — | — | 482.80 | 2300.54 | 4.77 | 413.48 | 206.67 | 0.50 |
| 6C3 | G2a, k | — | X | — | — | — | — | — | — | — | 482.80 | 4858.34 | 10.06 | 413.48 | 253.63 | 0.61 |
| 6C4 | G2a, k | — | X | — | — | | | | | | 813.02 | 1987.00 | 2.44 | 1123.81 | 300.62 | 0.27 |
| 6D6 | G2a, k | — | X | — | — | — | — | — | — | — | 561.40 | 2136.00 | 3.80 | 567.70 | 1025.00 | 1.81 |
| 6E7 | G2a, k | — | X | — | — | x | x | — | — | — | 482.80 | 3266.69 | 6.77 | 413.48 | 174.15 | 0.42 |
| 6F1 | G2a, k | — | X | — | — | X | — | — | — | — | 482.80 | 1285.41 | 2.66 | 413.48 | 490.22 | 1.19 |
| 6F2 | G2a, k | — | X | — | — | — | — | — | — | — | 482.80 | 4185.57 | 8.67 | 413.48 | 193.35 | 0.47 |
| 6G8 | G2a, k | — | X | — | — | — | — | — | — | — | 561.40 | 2980.00 | 5.31 | 567.70 | 789.30 | 1.39 |
| 6H12 | G2a, k | — | X | — | — | — | — | — | — | — | 813.02 | 2289.15 | 2.82 | 1123.81 | 341.30 | 0.30 |
| 6H6 | G2a, k | — | X | — | — | X | — | — | — | — | 482.80 | 2743.76 | 5.68 | 413.48 | 279.22 | 0.68 |
| 7B7 | G2a, k | — | X | — | — | — | — | — | — | — | 561.40 | 2308.00 | 4.11 | 567.70 | 940.10 | 1.66 |
| 7G12 | G2a, k | — | X | — | — | | | | | | 813.02 | 1649.30 | 2.03 | 1123.81 | 349.26 | 0.31 |
| 7H1 | G2a, k | — | X | — | — | — | X | — | — | — | 482.80 | 3693.24 | 7.65 | 413.48 | 262.66 | 0.64 |
| 8B5 | G2a, k | — | X | — | — | x | — | — | — | — | 482.80 | 2393.23 | 4.96 | 413.48 | 282.67 | 0.68 |
| 8G10 | G2a, k | — | X | — | — | | | | | | 482.80 | 710.01 | 1.47 | 413.48 | 441.90 | 1.07 |
| 8G8 | G2a, k | — | X | — | — | | | | | | 813.02 | 2083.08 | 2.56 | 1123.81 | 373.07 | 0.33 |
| 9B1 | G1, k | — | X | — | — | x | — | +/− | — | — | 1139.96 | 3837.93 | 3.37 | 523.21 | 329.04 | 0.63 |
| 9H9 | G2a, k | — | X | — | — | — | — | — | — | — | 482.80 | 4202.10 | 8.70 | 413.48 | 264.12 | 0.64 |
| 6H2 | G2a, k | — | X | — | — | | | | | | | | | | | |
| 11E5 | G2a, k | — | X | — | — | | | | | | | | | | | |

TABLE 4

| | | FACS binding | | | | | | | | | T cell proliferation | | | IFNgamma | | |
|---|---|---|---|---|---|---|---|---|---|---|---|---|---|---|---|---|
| Clone | Isotype | B1 | B2 | B3 | B4 | A1 | A2 | A4 | A5 | A6 | IgG | Avg | Δ | IgG | Avg | Δ |
| 10B10 | G2a, k | — | X | — | — | — | — | — | — | — | 106489.00 | 104360.00 | 0.98 | 3.63 | 4.00 | 1.10 |
| 10B4 | G2a, k | — | X | — | — | — | — | — | — | — | 106489.00 | 123972.00 | 1.16 | 3.63 | 1.97 | 0.54 |
| 10C5 | G2b, k | — | X | — | — | — | — | — | — | — | 107803.00 | 123191.00 | 1.14 | 0.63 | 4.12 | 6.53 |
| 10D6 | G2a, k | — | X | — | — | | | | | | 126503.00 | 112588.00 | 0.89 | 5172.00 | 4570.00 | 0.88 |
| 10D7 | G2a, k | — | X | — | — | | | | | | 113425.50 | 125098.50 | 1.10 | | | |
| 10D8 | G2a, k | — | X | — | — | — | — | — | — | — | 106489.00 | 142671.50 | 1.34 | 3.63 | 4.23 | 1.16 |

TABLE 4-continued

| | | FACS binding | | | | | | | | | T cell proliferation | | | IFNgamma | | |
|---|---|---|---|---|---|---|---|---|---|---|---|---|---|---|---|---|
| Clone | Isotype | B1 | B2 | B3 | B4 | A1 | A2 | A4 | A5 | A6 | IgG | Avg | Δ | IgG | Avg | Δ |
| 10G7 | G2a, k | — | X | — | — | | | | | | 106489.00 | 125522.50 | 1.18 | 3.63 | 2.63 | 0.72 |
| 11A5 | G2b, k | — | X | — | — | X | — | x/? | — | — | 107803.00 | 148998.00 | 1.38 | 0.63 | 6.45 | 10.21 |
| 11B2 | G2b, k | — | X | — | — | X | — | — | — | — | 107803.00 | 114218.00 | 1.06 | 0.63 | 2.65 | 4.20 |
| 12E4 | G2a, k | — | X | — | — | | | | | | 113425.50 | 105493.50 | 0.93 | | | |
| 12G2 | G2a, k | — | X | — | — | — | — | — | — | — | 113425.50 | 112442.50 | 0.99 | | | |
| 12H6 | G2a, k | — | X | — | — | X | — | — | — | — | 106489.00 | 73176.50 | 0.69 | 3.63 | 0.00 | 0.00 |
| 13H1 | G2a, k | X | X | — | — | x | x/? | — | — | — | 106489.00 | 120671.00 | 1.13 | 3.63 | 2.40 | 0.66 |
| 14E7 | G2a, k, ? | — | X | — | — | — | — | — | — | — | 126503.00 | 113440.00 | 0.90 | 5172.00 | 6306.00 | 1.22 |
| 15A10 | G1, k | — | X | — | — | — | — | — | — | — | 126503.00 | 132608.00 | 1.05 | 5172.00 | 8137.00 | 1.57 |
| 15C6 | G2a, k | — | X | — | — | X | — | — | — | — | 106489.00 | 90458.00 | 0.85 | 3.63 | 0.94 | 0.26 |
| 15D6 | G2a, k | — | X | — | — | — | — | — | — | — | 126503.00 | 100627.00 | 0.80 | 5172.00 | 648.20 | 0.13 |
| 15E7 | G2b, k | — | X | — | — | — | — | — | — | — | 107803.00 | 96047.50 | 0.89 | 0.63 | 0.98 | 1.54 |
| 16F12 | G2a, k | X | X | — | — | X | x | — | — | — | 113425.50 | 104224.00 | 0.92 | | | |
| 16F4 | G2a, k | — | X | — | — | — | — | — | — | — | 106489.00 | 130284.00 | 1.22 | 3.63 | 1.44 | 0.40 |
| 17A3 | G2a, k | — | X | — | — | — | — | — | — | — | 106489.00 | 126518.50 | 1.19 | 3.63 | 4.30 | 1.19 |
| 17H7 | G2a, k | — | X | — | — | — | — | — | — | — | 106489.00 | 123802.00 | 1.16 | 3.63 | 2.49 | 0.69 |
| 1D6 | G2a, k | — | X | — | — | — | — | — | — | — | 126503.00 | 53300.00 | 0.42 | 5172.00 | 65.33 | 0.01 |
| 1E6 | G2a, k | — | X | — | — | X | x/? | — | — | — | 113425.50 | 91294.50 | 0.80 | | | |
| 1F1 | G2a, k | — | X | — | — | — | — | — | — | — | 106489.00 | 139162.00 | 1.31 | 3.63 | 2.28 | 0.63 |
| 1F12 | G2a, k | — | X | — | — | | | | | | 113425.50 | 98269.50 | 0.87 | | | |
| 1F6 | G2a, k | — | X | — | — | — | — | — | — | — | 113425.50 | 125797.50 | 1.11 | | | |
| 1H3 | G2a, k | — | X | — | — | — | — | — | — | — | 106489.00 | 123972.00 | 1.16 | 3.63 | 1.76 | 0.49 |
| 20D3 | IgG2b | — | X | — | — | — | — | — | — | — | 131103.50 | 162378.50 | 1.24 | 4.74 | 7.13 | 1.50 |
| 29G2 | G2b, k | — | X | — | — | — | — | — | — | — | 107803.00 | 95307.00 | 0.88 | 0.63 | 1.44 | 2.28 |
| 29G3 | G2a, k | — | X | — | — | — | — | — | — | — | 106489.00 | 118189.00 | 1.11 | 3.63 | 0.83 | 0.23 |
| 29H9 | G2a, k | — | X | — | — | — | — | — | — | — | 113425.50 | 128979.50 | 1.14 | | | |
| 2G11 | G2a, k | — | X | — | — | — | — | — | — | — | 126503.00 | 48714.00 | 0.39 | 5172.00 | 2428.00 | 0.47 |
| 30A6 | G2b, k | — | X | — | — | — | — | — | — | — | 107803.00 | 171924.50 | 1.59 | 0.63 | 6.11 | 9.68 |
| 30F1 | G2a, k | — | X | — | — | — | — | — | — | — | 107803.00 | 143620.00 | 1.33 | 0.63 | 9.69 | 15.36 |
| 30G7 | G2b, k | — | X | — | — | —/? | —/? | —/? | —/? | —/? | 114800.00 | 136601.50 | 1.19 | | | |
| 33A12 | G2b, k | — | X | — | — | x | x | x | — | x/? | 107803.00 | 99787.00 | 0.93 | 0.63 | 1.71 | 2.70 |
| 33D10 | G2a, k | — | X | — | — | | | | | | 113425.50 | 104015.00 | 0.92 | | | |
| 33G2 | G2b, 3, k? | — | X | — | — | — | — | — | — | — | 114800.00 | 103238.50 | 0.90 | | | |
| 3B3 | G2a, k | — | X | — | — | | | | | | 113425.50 | 127069.50 | 1.12 | | | |
| 3B8 | G2a, k | — | X | — | — | | | | | | 113425.50 | 122720.50 | 1.08 | | | |
| 3E5 | M, k | — | X | — | — | — | — | — | — | — | 126503.00 | 118181.00 | 0.93 | 5172.00 | 3917.00 | 0.76 |
| 3G6 | G2a, k | — | X | — | — | — | — | — | — | — | 106489.00 | 121175.50 | 1.14 | 3.63 | 0.00 | 0.00 |
| 47F11 | G2a, k | — | X | — | — | — | — | — | — | — | 106489.00 | 133442.50 | 1.25 | 3.63 | 0.84 | 0.23 |
| 48E1 | G2b, k | — | X | — | — | — | — | — | — | — | 107803.00 | 107667.00 | 1.00 | 0.63 | 4.07 | 6.45 |
| 48G9 | G2a, k | — | X | — | — | | | | | | 113425.50 | 101328.50 | 0.89 | | | |
| 4A5 | G2b, k | — | X | — | — | — | — | — | — | — | 107803.00 | 139982.50 | 1.30 | 0.63 | 7.01 | 11.10 |
| 4B10 | G2a, k | — | X | — | — | | | | | | 113425.50 | 105493.50 | 0.93 | | | |
| 4B6 | G2a, k | — | X | — | — | x/? | — | — | — | x/? | 106489.00 | 148998.00 | 1.40 | 3.63 | 2.10 | 0.58 |
| 4D3 | G2a, k | — | X | — | — | X | — | — | — | — | 106489.00 | 71567.50 | 0.67 | 3.63 | 1.32 | 0.36 |
| 4E2 | G2a, k | — | X | — | — | X | — | x/? | — | x/? | 106489.00 | 93836.00 | 0.88 | 3.63 | 2.44 | 0.67 |
| 4E7 | G2a, k | — | X | — | — | x | — | — | — | — | 106489.00 | 141627.50 | 1.33 | 3.63 | 0.00 | 0.00 |
| 4F12 | IgG1 and IgG2b? | — | X | — | — | + | — | — | — | — | 107803.00 | 159582.00 | 1.48 | 0.63 | 10.12 | 16.03 |
| 4G10 | G2a, k | — | X | — | — | x | x | — | x | x | 106489.00 | 133442.50 | 1.25 | 3.63 | 3.81 | 1.05 |
| 4G3 | G2a, k | — | X | — | — | | | | | | 113425.50 | 98490.00 | 0.87 | | | |
| 4G7 | G2a, k | — | X | — | — | — | — | — | — | — | 126503.00 | 111154.00 | 0.88 | 5172.00 | 5134.00 | 0.99 |
| 4G8 | G2a, k | — | X | — | — | — | — | — | — | — | 126503.00 | 111120.00 | 0.88 | 5172.00 | 4950.00 | 0.96 |
| 4H5 | G2b, k | — | X | — | — | X | X | — | — | — | 107803.00 | 141627.50 | 1.31 | 0.63 | 3.33 | 5.28 |
| 50B9 | G2a, k | — | X | — | — | X | — | x/? | — | — | 106489.00 | 98028.00 | 0.92 | 3.63 | 0.04 | 0.01 |
| 50C3_G1 | G1, k | — | X | — | — | — | — | — | — | — | 126503.00 | 79836.00 | 0.63 | 5172.00 | 331.40 | 0.06 |
| 50C3_G2a | G2a, k | — | X | — | — | — | — | — | — | — | 126503.00 | 63009.00 | 0.50 | 5172.00 | 635.50 | 0.12 |
| 51A12 | G2a, k | — | X | — | — | — | — | — | — | — | 106489.00 | 131185.50 | 1.23 | 3.63 | 3.24 | 0.89 |
| 51B8 | G2a, k | X | X | X | X | | | | | | 126503.00 | 71578.00 | 0.57 | 5172.00 | 1706.00 | 0.33 |
| 51D3 | G2a, k | — | X | — | — | — | — | — | — | — | 106489.00 | 140367.50 | 1.32 | 3.63 | 3.91 | 1.08 |
| 51G7 | G2a, k | — | X | — | — | — | — | — | — | — | 106489.00 | 122392.50 | 1.15 | 3.63 | 3.07 | 0.85 |
| 51H9 | G1, k | — | X | — | — | x | — | — | — | — | 99683.00 | 107844.00 | 1.08 | 1.05 | 3.60 | 3.43 |
| 5A3 | G2a, k | — | X | — | — | X | — | — | — | — | 106489.00 | 139162.00 | 1.31 | 3.63 | 2.77 | 0.76 |
| 5A7 | G2a, b, k ?? | — | X | — | — | — | — | — | — | — | 126503.00 | 116098.00 | 0.92 | 5172.00 | 5001.00 | 0.97 |
| 5C12 | G2a, k | — | X | — | — | x | x | — | — | — | 106489.00 | 113368.50 | 1.06 | 3.63 | 2.71 | 0.75 |
| 5D6 | G3, k | — | X | — | — | X | — | — | — | — | 99683.00 | 120671.00 | 1.21 | 1.05 | 3.37 | 3.21 |
| 5F4 | G2a, k | — | X | — | — | | | | | | 113425.50 | 110364.00 | 0.97 | | | |
| 5G5 | IgG1 | — | X | — | — | — | — | — | — | — | 99683.00 | 162405.00 | 1.63 | 1.05 | 7.74 | 7.37 |
| 5H8 | G3, k | — | X | — | — | — | — | — | — | — | 113425.50 | 107355.00 | 0.95 | | | |
| 6A9 | G2a, k | — | X | — | — | — | — | — | — | — | 106489.00 | 128158.00 | 1.20 | 3.63 | 2.91 | 0.80 |
| 6C3 | G2a, k | — | X | — | — | — | — | — | — | — | 106489.00 | 99787.00 | 0.94 | 3.63 | 1.22 | 0.34 |
| 6C4 | G2a, k | — | X | — | — | | | | | | 113425.50 | 100940.50 | 0.89 | | | |
| 6D6 | G2a, k | — | X | — | — | — | — | — | — | — | 126503.00 | 70838.00 | 0.56 | 5172.00 | 1884.00 | 0.36 |
| 6E7 | G2a, k | — | X | — | — | x | x | — | — | — | 106489.00 | 114218.00 | 1.07 | 3.63 | 2.82 | 0.78 |
| 6F1 | G2a, k | — | X | — | — | X | — | — | — | — | 106489.00 | 78905.00 | 0.74 | 3.63 | 1.18 | 0.33 |
| 6F2 | G2a, k | — | X | — | — | — | — | — | — | — | 106489.00 | 110255.00 | 1.04 | 3.63 | 2.02 | 0.56 |
| 6G8 | G2a, k | — | X | — | — | — | — | — | — | — | 126503.00 | 89225.00 | 0.71 | 5172.00 | 1174.00 | 0.23 |

TABLE 4-continued

| | | FACS binding | | | | | | | | | T cell proliferation | | | IFNgamma | | |
|---|---|---|---|---|---|---|---|---|---|---|---|---|---|---|---|---|
| Clone | Isotype | B1 | B2 | B3 | B4 | A1 | A2 | A4 | A5 | A6 | IgG | Avg | Δ | IgG | Avg | Δ |
| 6H12 | G2a, k | — | X | — | — | — | — | — | — | — | 113425.50 | 110522.00 | 0.97 | | | |
| 6H6 | G2a, k | — | X | — | — | X | — | — | — | — | 106489.00 | 91760.00 | 0.86 | 3.63 | 1.14 | 0.31 |
| 7B7 | G2a, k | — | X | — | — | — | — | — | — | — | 126503.00 | 110702.00 | 0.88 | 5172.00 | 2809.00 | 0.54 |
| 7G12 | G2a, k | — | X | — | — | | | | | | 113425.50 | 110685.50 | 0.98 | | | |
| 7H1 | G2a, k | — | X | — | — | — | X | — | — | — | 106489.00 | 121175.50 | 1.14 | 3.63 | 1.31 | 0.36 |
| 8B5 | G2a, k | — | X | — | — | x | — | — | — | — | 106489.00 | 81691.00 | 0.77 | 3.63 | 1.57 | 0.43 |
| 8G10 | G2a, k | — | X | — | — | | | | | | 106489.00 | 48406.50 | 0.45 | 3.63 | 0.00 | 0.00 |
| 8G8 | G2a, k | — | X | — | — | | | | | | 113425.50 | 116319.00 | 1.03 | | | |
| 9B1 | G1, k | — | X | — | — | x | — | +/− | — | — | 99683.00 | 157553.00 | 1.58 | 1.05 | 8.39 | 7.99 |
| 9H9 | G2a, k | — | X | — | — | — | — | — | — | — | 106489.00 | 123150.00 | 1.16 | 3.63 | 2.90 | 0.80 |
| 6H2 | G2a, k | — | X | — | — | | | | | | | | | | | |
| 11E5 | G2a, k | — | X | — | — | | | | | | | | | | | |

TABLE 5

| | Kappa chain sequence | | |
|---|---|---|---|
| Clones | CDR1 | CDR2 | CDR3 Junc. |
| 1F1 | QDIVKN (SEQ ID NO: 1) | YAT (SEQ ID NO: 35) | CLQFYEFPLTF (SEQ ID NO: 50) |
| 10D8 | QSVDNYGYSY (SEQ ID NO: 2) | AAS (SEQ ID NO: 36) | CQHIKEDTFSF (SEQ ID NO: 51) |
| 10G7 | QSVDYDGDSY (SEQ ID NO: 3) | AAS (SEQ ID NO: 36) | CQQSNEDPFTF (SEQ ID NO: 52) |
| 1H3 | QSIGTS (SEQ ID NO: 4) | IAS (SEQ ID NO: 37) | CQQSNGWPLTF (SEQ ID NO: 53) |
| 6C3 | QSIGTS (SEQ ID NO: 4) | FAS (SEQ ID NO: 38) | CQQSNGWPLTF (SEQ ID NO: 53) |
| 16F4 | QSVDYDGDSY (SEQ ID NO: 3) | AAS (SEQ ID NO: 36) | CQQSNEDPFTF (SEQ ID NO: 52) |
| 3G6 | QSVDYDGDSY (SEQ ID NO: 3) | AAS (SEQ ID NO: 36) | CQQSNEDPFTF (SEQ ID NO: 52) |
| 4E2 | QDMNTA (SEQ ID NO: 5) | SAS (SEQ ID NO: 39) | CQQHYS TLPTF (SEQ ID NO: 54) |
| 9H9 | QSVDYDGDSY (SEQ ID NO: 3) | AAS (SEQ ID NO: 36) | CQQSNEDPFTF (SEQ ID NO: 52) |
| 13H1 | QNINVW (SEQ ID NO: 6) | KAS (SEQ ID NO: 40) | CQQGQSYPLTF (SEQ ID NO: 55) |
| 6F2 | QSVDYDGDSY (SEQ ID NO: 3) | AAS (SEQ ID NO: 36) | CQQSNEDTFTF (SEQ ID NO: 56) |
| 51A12 | QSIGTS (SEQ ID NO: 4) | FAS (SEQ ID NO: 38) | CQQSNSWPLTF (SEQ ID NO: 57) |
| 4B6 | QSVDYDGDSY (SEQ ID NO: 3) | AAS (SEQ ID NO: 36) | CQQSNEDPFTF (SEQ ID NO: 52) |
| 47F11 | QSIGTS (SEQ ID NO: 4) | FAS (SEQ ID NO: 38) | CQQSNSWPLTF (SEQ ID NO: 57) |
| 7H1 | RTLVRL (SEQ ID NO: 8) | YAT (SEQ ID NO: 35) | CLHFYEFPLEF (SEQ ID NO: 58) |
| 4H5 | QDIVKN (SEQ ID NO: 1) | YAT (SEQ ID NO: 35) | CLQFYEFPLTF (SEQ ID NO: 50) |
| 29G3 | KSVSISGYSY (SEQ ID NO: 9) | LAS (SEQ ID NO: 42) | CQHSRELPFTF (SEQ ID NO: 59) |
| 51G7 | QSIGTS (SEQ ID NO: 4) | FAS (SEQ ID NO: 38) | CQQSNSWPLTF (SEQ ID NO: 57) |

TABLE 5-continued

| | | | |
|---|---|---|---|
| 6E7 | QSLVNSYGITY (SEQ ID NO: 10) | GIS (SEQ ID NO: 43) | CLQGTHQPWTF (SEQ ID NO: 60) |
| 51D3 | QSIGTS (SEQ ID NO: 4) | FAS (SEQ ID NO: 38) | CQQSNSWPLTF (SEQ ID NO: 57) |
| 6H6 | SSVSSSC (SEQ ID NO: 11) | STS (SEQ ID NO: 44) | CQQYKWLPITF (SEQ ID NO: 61) |
| 17A3 | ENIYSN (SEQ ID NO: 12) | AAT (SEQ ID NO: 49) | CQHFWDIPYTF (SEQ ID NO: 62) |
| 8B5 | QDIVNY (SEQ ID NO: 13) | YTS (SEQ ID NO: 41) | WTFSGCTGLEIQ (SEQ ID NO: 63) |
| 4E7 | KSVSTSGYSY (SEQ ID NO: 24) | LVS (SEQ ID NO: 202) | CQHIRELTR (SEQ ID NO: 64) |
| 6A9 | ENIYCT (SEQ ID NO: 15) | AAT (SEQ ID NO: 49) | CQHFWDIPYEF (SEQ ID NO: 65) |
| 50B9 | QDISNY (SEQ ID NO: 7) | YTS (SEQ ID NO: 41) | CQQGNMLPWTF (SEQ ID NO: 66) |
| 15C6 | QDIVNY (SEQ ID NO: 13) | YTS (SEQ ID NO: 41) | CQQYSKLPWTF (SEQ ID NO: 67) |
| 17H7 | QDIVKN (SEQ ID NO: 1) | YAT (SEQ ID NO: 35) | CLQFYEFPLTF (SEQ ID NO: 50) |
| 10B10 | QGVDTA (SEQ ID NO: 16) | WAS (SEQ ID NO: 45) | CQQYSSYPLTF (SEQ ID NO: 68) |
| 11A5 | QDIRNY (SEQ ID NO: 18) | YTS (SEQ ID NO: 41) | CQQGNTLPWTF (SEQ ID NO: 69) |
| 4D3 | QGIVNY (SEQ ID NO: 19) | YTS (SEQ ID NO: 41) | CQQYSELPWTF (SEQ ID NO: 70) |
| 5C12 | QDVTNA (SEQ ID NO: 20) | SAS (SEQ ID NO: 39) | CQQHYSFPYTF (SEQ ID NO: 71) |
| 6F1 | QDIVNY (SEQ ID NO: 13) | YTS (SEQ ID NO: 41) | CQQYSKLPWTF (SEQ ID NO: 67) |
| 4A5 | QDVSTA (SEQ ID NO: 21) | WAS (SEQ ID NO: 45) | CQQHYS TPLTF (SEQ ID NO: 72) |
| 5A3 | QVITNY (SEQ ID NO: 22) | YTS (SEQ ID NO: 41) | CQQYGKFPCTF (SEQ ID NO: 73) |
| 51H9 | SSVSY (SEQ ID NO: 23) | LTS (SEQ ID NO: 46) | CQQWSSNPLTF (SEQ ID NO: 74) |
| 12H6 | QDIVNY (SEQ ID NO: 13) | YTS (SEQ ID NO: 41) | CQQYSKLPWTF (SEQ ID NO: 67) |
| 10C5 | KSVSTSGYSY (SEQ ID NO: 24) | LAS (SEQ ID NO: 42) | CQHSRELPYTF (SEQ ID NO: 75) |
| 8G10 | SSVSY (SEQ ID NO: 23) | LTS (SEQ ID NO: 46) | CQQWSSNPLTF (SEQ ID NO: 74) |
| 11B2 | QGISNY (SEQ ID NO: 25) | YTS (SEQ ID NO: 41) | CQQYNTPPWTF (SEQ ID NO: 259) |
| 29G2 | SSVSY (SEQ ID NO: 23) QSLLNSSNQKNY (SEQ | VTS (SEQ ID NO: 47) | CQQWSSNPPTF (SEQ ID NO: 76) |
| 33A12 | ID NO: 26) | FAS (SEQ ID NO: 38) | CQQHYSTPPTF (SEQ ID NO: 130) |
| 15E7 | KSVSTSGYSY (SEQ ID NO: 24) | LAS (SEQ ID NO: 42) | CQHIRELPWTF (SEQ ID NO: 78) |
| 5D6 | QDINSY (SEQ ID NO: 27) | RAN (SEQ ID NO: 48) | CLQYDEFPLTF (SEQ ID NO: 79) |
| 48E1 | ENIYSN (SEQ ID NO: 12) | AAT (SEQ ID NO: 49) | CQHFWGTPPTF (SEQ ID NO: 80) |

TABLE 5-continued

| | | | |
|---|---|---|---|
| 8G8 | QDVGTA (SEQ ID NO: 28) | WAS (SEQ ID NO: 45) | CHQYITYPLTF (SEQ ID NO: 81) |
| 1F6 | QDIVKN (SEQ ID NO: 1) | YAT (SEQ ID NO: 35) | CLQFYEFPLTF (SEQ ID NO: 50) |
| 29H9 | QDIVKN (SEQ ID NO: 1) | YAT (SEQ ID NO: 35) | CLQFYEFPLTF (SEQ ID NO: 50) |
| 5F4 | QDIVKN (SEQ ID NO: 1) | YAT (SEQ ID NO: 35) | CLQFYEFPLTF (SEQ ID NO: 50) |
| 6H12 | QDIVKN (SEQ ID NO: 1) | YAT (SEQ ID NO: 35) | CLQFYEFPLTF (SEQ ID NO: 50) |
| 5H8 | ENIYSN (SEQ ID NO: 12) | AAT (SEQ ID NO: 49) | CQHFWGTPWTF (SEQ ID NO: 82) |
| 6C4 | KSVSTSGFNY (SEQ ID NO: 29) | LAS (SEQ ID NO: 42) | CQHSRELPFTF (SEQ ID NO: 59) |
| 16F12 | QNINVW (SEQ ID NO: 6) | KAS (SEQ ID NO: 40) | CQQGQSYPLTF (SEQ ID NO: 55) |
| 1E6 | QNINVW (SEQ ID NO: 6) | KAS (SEQ ID NO: 40) | CQQGQSYPLTF (SEQ ID NO: 55) |
| 30G7 | QDVTTA (SEQ ID NO: 30) | WAS (SEQ ID NO: 45) | CQQHYNTPLTF (SEQ ID NO: 83) |
| 10D7 | QDVSNA (SEQ ID NO: 31) | SAS (SEQ ID NO: 39) | CQQHYSFPYTF (SEQ ID NO: 71) |
| 12G2 | QSVDYYGDSY (SEQ ID NO: 32) | AAS (SEQ ID NO: 36) | CQQINEDPFTF (SEQ ID NO: 84) |
| 33D10 | QSVDYDGDSY (SEQ ID NO: 3) | AAS (SEQ ID NO: 36) | CQQSNEDPFTF (SEQ ID NO: 52) |
| 3B8 | QSVDYGGDSY (SEQ ID NO: 33) | AAS (SEQ ID NO: 36) | CQQSNEDPFTF (SEQ ID NO: 52) |
| 48G9 | QSIGTS (SEQ ID NO: 4) | FAS (SEQ ID NO: 38) | CQQSNSWPLTF (SEQ ID NO: 57) |
| 7G12 | QSIGTS (SEQ ID NO: 4) | FAS (SEQ ID NO: 38) | CQQSNSWPLTF (SEQ ID NO: 57) |
| 4G3 | QSIGTS (SEQ ID NO: 4) | FAS (SEQ ID NO: 38) | CQQSNSWPLTF (SEQ ID NO: 57) |
| 4B10 | QGISNY (SEQ ID NO: 25) | YTS (SEQ ID NO: 41) | CQQYSEFPWTF (SEQ ID NO: 85) |
| 12E4 | QGISNY (SEQ ID NO: 25) | YTS (SEQ ID NO: 41) | CQQYSEFPWTF (SEQ ID NO: 85) |
| 1F12 | KSVSTSGYSY (SEQ ID NO: 24) | STS (SEQ ID NO: 44) | CQQYSGYPSTF (SEQ ID NO: 86) |
| 3B3 | QDVTKP (SEQ ID NO: 34) | SAS (SEQ ID NO: 39) | CHQHYSFPYTF (SEQ ID NO: 87) |
| 33G2 | SSVSY (SEQ ID NO: 23) | EIS (SEQ ID NO: 260) | CQQWNYPLTF (SEQ ID NO: 88) |
| 15A10 | KSVSTSGYSY (SEQ ID NO: 24) | LAS (SEQ ID NO: 42) | QHIRELPYT (SEQ ID NO: 203) |
| 14E7 | QDIVKN (SEQ ID NO: 1) | YAT (SEQ ID NO: 35) | LQFYEFPLT (SEQ ID NO: 204) |
| 3E5 | QDISNY (SEQ ID NO: 7) | YTS (SEQ ID NO: 41) | QQGNTLPWT (SEQ ID NO: 205) |
| 5A7 | QGISNY (SEQ ID NO: 25) | YTS (SEQ ID NO: 41) | QQYSKLPWT (SEQ ID NO: 206) |

TABLE 5-continued

| | | | |
|---|---|---|---|
| 30A6 | QSVDYDGDSY (SEQ ID NO: 3) | AAS (SEQ ID NO: 36) | QQINEDPFT (SEQ ID NO: 207) |
| 51B8 | QNVGTN (SEQ ID NO: 197) | SAS (SEQ ID NO: 39) | QQYNRYPLT (SEQ ID NO: 208) |
| 15D6 | SSVSSSY (SEQ ID NO: 87) | SIS (SEQ ID NO: 201) | CQQWSSNPILV (SEQ ID NO: 209) |
| 4G8 | QNINVW (SEQ ID NO: 6) | KAS (SEQ ID NO: 40) | QQGQSYPLT (SEQ ID NO: 210) |
| 10D6 | QDVGTA (SEQ ID NO: 28) | WAS (SEQ ID NO: 45) | QQYITYPLT (SEQ ID NO: 211) |
| 6D6 | SSVSSSC (SEQ ID NO: 11) | STS (SEQ ID NO: 44) | QQYSGYPS (SEQ ID NO: 212) |
| 2G11 | QDIVNY (SEQ ID NO: 13) | YTS (SEQ ID NO: 41) | QQYNKLPWT (SEQ ID NO: 213) |
| 50C3_G2A | QDISNY (SEQ ID NO: 7) | YTS (SEQ ID NO: 41) | QQGNMLPWT (SEQ ID NO: 214) |
| 6G8 | QGINNY (SEQ ID NO: 199) | YTS (SEQ ID NO: 41) | QQYSKLPWT |
| 50C3_G1 | QIVDYDGDSY (SEQ ID NO: 200) | AAS (SEQ ID NO: 36) | QQSNEDPFT (SEQ ID NO: 215) |
| 5G5 | KSVSTSGYSY (SEQ ID NO: 24) | LVS (SEQ ID NO: 202) | QHIRELT (SEQ ID NO: 216) |
| 1D6 | QDINSY (SEQ ID NO: 27) | RAN (SEQ ID NO: 48) | CLQYDELLTF (SEQ ID NO: 250) |
| 20D3 | ENIYSN (SEQ ID NO: 12) | GAT (SEQ ID NO: 249) | CQHFWDTPLTF (SEQ ID NO: 251) |
| 4G10 | QDVSIA (SEQ ID NO: 248) | SAS (SEQ ID NO: 39) | CQQHYSFPYTF (SEQ ID NO: 71) |
| 6H2 | QDVSNA (SEQ ID NO: 31) | SAS (SEQ ID NO: 39) | CQQHYSFPYTF (SEQ ID NO: 71) |
| 30F1 | | | |
| 10B4 | QSVDYDGDSY (SEQ ID NO: 3) | AAS (SEQ ID NO: 36) | CQQSNEDPFTF (SEQ ID NO: 52) |
| 4F12 | XSLENSNGNTY, wherein X is any amino acid (SEQ ID NO: 176) | RVS (SEQ ID NO: 253) | CLQVTHVPFTF (SEQ ID NO: 362) |
| 4G7 | | | |
| 7B7 | CSGCTYAWKHL (SEQ ID NO: 374) | RXS, wherein X is any amino acid (SEQ ID NO: 375) | CFQGSHVPWTF (SEQ ID NO: 376) |
| 9B1 | QDISNY (SEQ ID NO: 7) | YTS (SEQ ID NO: 41) | CQQINTLPWTF (SEQ ID NO: 119) |
| 11E5 | QDIRNY (SEQ ID NO: 18) | YTS (SEQ ID NO: 41) | CQQGNTLPWTF (SEQ ID NO: 69) |

| | Heavy chain sequence | | |
|---|---|---|---|
| Clones | CDR1 | CDR2 | CDR3 Junc. |
| 1F1 | GYAFTNFF (SEQ ID NO: 89) | INPGSGGT (SEQ ID NO: 120) | CARNDAMDYW (SEQ ID NO: 158) |
| 10D8 | GYSFTFFW (SEQ ID NO: 90) | IDPSDNYT (SEQ ID NO: 121) | CARRWLLHEMAYW (SEQ ID NO: 159) |
| 10G7 | GYSFTTYW (SEQ ID NO: 91) | IDPSDSYT (SEQ ID NO: 122) | CARRWLLHEMDYW (SEQ ID NO: 160) |

TABLE 5-continued

| | | | |
|---|---|---|---|
| 1H3 | GYTFTDFE (SEQ ID NO: 92) | IDPETGGS (SEQ ID NO: 123) | CTIYFWYFDVW (SEQ ID NO: 161) |
| 6C3 | GYTFTDFE (SEQ ID NO: 92) | IDPTGGS (SEQ ID NO: 124) | CTIYFWYFDVW (SEQ ID NO: 161) |
| 16F4 | GYTFTNYW (SEQ ID NO: 93) | IDPSDTYT (SEQ ID NO: 125) | CGRRWLLLEMDYW (SEQ ID NO: 162) |
| 3G6 | GYTFTNYW (SEQ ID NO: 93) | IDPSDSYT (SEQ ID NO: 122) | CARRWLLHEMDYW (SEQ ID NO: 160) |
| 4E2 | GYTFTSYW (SEQ ID NO: 94) | IHPSDSDT (SEQ ID NO: 126) | CALGSTVPSFVYW (SEQ ID NO: 163) |
| 9H9 | GYIFTSNW (SEQ ID NO: 95) | IYPGSDTT (SEQ ID NO: 127) | CARFFSSPWFAYW (SEQ ID NO: 164) |
| 13H1 | DYTFTGYW (SEQ ID NO: 96) | ILPESGST (SEQ ID NO: 128) | CARRSLGLSFNYW (SEQ ID NO: 165) |
| 6F2 | GYTFTSYW (SEQ ID NO: 94) | IDPSDSYT (SEQ ID NO: 122) | CARRWLLREMDYW (SEQ ID NO: 166) |
| 51A12 | GYTFTDYE (SEQ NO: 97) | IDPETGGS (SEQ ID NO: 123) | CTIYFWYFDVW (SEQ ID NO: 161) |
| 4B6 | GYSFTFFW (SEQ ID NO: 90) | IDPSDNYT (SEQ ID NO: 121) | CARRWLLHKMDYW (SEQ ID NO: 167) |
| 47F11 | GYTFTDYE (SEQ ID NO: 97) | IDPETGGS (SEQ ID NO: 123) | CTIYFWYFDVW (SEQ ID NO: 161) |
| 7H1 | GYSFTNYL (SEQ ID NO: 98) | INPGSGGT (SEQ ID NO: 120) | CARNDAMDYW (SEQ ID NO: 158) |
| 4H5 | GYAFTNYL (SEQ ID NO: 99) | INPGSGGK (SEQ ID NO: 129) | CARNDAMDYW (SEQ ID NO: 158) |
| 29G3 | GYTFTDYN (SEQ ID NO: 100) | INPNNGGT (SEQ ID NO: 258) | CARRPTTVLGGVYFDYW (SEQ ID NO: 168) |
| 51G7 | GYTFTDYE (SEQ ID NO: 97) | IDPETGGS (SEQ ID NO: 123) | CTIYFWYFDVW (SEQ ID NO: 161) |
| 6E7 | GYTFTSYW (SEQ ID NO: 94) | MYPGSGNT (SEQ ID NO: 131) | CARGFLYFDVW (SEQ ID NO: 169) |
| 51D3 | GYTFTDYE (SEQ ID NO: 97) | IDPETGGS (SEQ ID NO: 123) | CTIYFWYFDVW (SEQ ID NO: 161) |
| 6H6 | GYTFTSYW (SEQ ID NO: 94) | INPSNGGT (SEQ ID NO: 77) | CAKEPIYYDYDEAGFDHW (SEQ ID NO: 170) |
| 17A3 | GFTFSNYG (SEQ ID NO: 101) | TSSGGNST (SEQ ID NO: 132) | CARHPYYSYYVEDWFAYW (SEQ ID NO: 171) |
| 8B5 | GYSITSGYY (SEQ ID NO: 102) | ISYEGSN (SEQ ID NO: 133) | CVRYFDFW (SEQ ID NO: 172) |
| 4E7 | GYSITSGYY (SEQ ID NO: 102) | ISYKGSN (SEQ ID NO: 134) | CARYFDVW (SEQ ID NO: 173) |
| 6A9 | GFTFSNYG (SEQ ID NO: 101) | TSSGGNST (SEQ ID NO: 132) | CARHPYYSYYVEDWFAYW (SEQ ID NO: 171) |
| 50B9 | GYTFTGYG (SEQ ID NO: 103) | IYPRSSNT (SEQ ID NO: 135) | CARREGAPYAMDYW (SEQ ID NO: 174) |
| 15C6 | GYSITSGYY (SEQ ID NO: 102) | ISYEGSN (SEQ ID NO: 133) | CVRYFDVW (SEQ ID NO: 175) |
| 17H7 | GYSFTNYF (SEQ ID NO: 104) | INPGSGGI (SEQ ID NO: 136) | CARNDAMDYW (SEQ ID NO: 158) |
| 10B10 | GFTFSNYR (SEQ ID NO: 105) | ITVKSDNYGA (SEQ ID NO: 137) | CSRSYGSSYGFAYW (SEQ ID NO: 177) |
| 11A5 | GYTFTSYG (SEQ ID NO: 107) | IYPRSGNT (SEQ ID NO: 138) | CARREGAPYTMDYW (SEQ ID NO: 178) |

TABLE 5-continued

| | | | |
|---|---|---|---|
| 4D3 | GYSITSGYY (SEQ ID NO: 102) | ISYKGSN (SEQ ID NO: 134) | CARYFDVW (SEQ ID NO: 173) |
| 5C12 | GYTFTSYW (SEQ ID NO: 94) | IYPGSGNT (SEQ ID NO: 139) | CTRGFLYFDVW (SEQ ID NO: 179) |
| 6F1 | GYSITSGYY (SEQ ID NO: 102) | ISYEGSN (SEQ ID NO: 133) | CVRYFDVW (SEQ ID NO: 175) |
| 4A5 | GFTFSDYY (SEQ ID NO: 108) | ISNGGGNT (SEQ ID NO: 140) | CARQGEEWYFDVW (SEQ ID NO: 180) |
| 5A3 | GYSITSGYY (SEQ ID NO: 102) | ISYDGST (SEQ ID NO: 141) | CTRYFDVW (SEQ ID NO: 181) |
| 51H9 | GYTFTSYW (SEQ ID NO: 94) | IHPNSDTT (SEQ ID NO: 142) | CAIRYHYYFDYW (SEQ ID NO: 182) |
| 12H6 | GYSITSGYY (SEQ ID NO: 102) | ISYEGSN (SEQ ID NO: 133) | CVRYFDVW (SEQ ID NO: 175) |
| 10C5 | GYAFSSSW (SEQ ID NO: 109) | IYPGDGDT (SEQ ID NO: 143) | CTPAYYSNYGAWFAYW (SEQ ID NO: 183) |
| 8G10 | GYTFTSYW (SEQ ID NO: 94) | IHPNSDTT (SEQ ID NO: 142) | CAIRYRYYFDYW (SEQ ID NO: 184) |
| 11B2 | GHSITSGYY (SEQ ID NO: 110) | IFYDGSN (SEQ ID NO: 144) | CARYFDVW (SEQ ID NO: 173) |
| 29G2 | GYTFTSYW (SEQ ID NO: 94) | IHPNSGNT (SEQ ID NO: 145) | CARITVVASYYAMDYW (SEQ ID NO: 185) |
| 33A12 | GYTFTTYG (SEQ ID NO: 111) | GYTFTTYG (SEQ ID NO: 111) | CTRMGLRRSLYAMDYW (SEQ ID NO: 186) |
| 15E7 | GYSITSGYY (SEQ ID NO: 102) | ISYEGSN (SEQ ID NO: 133) | CVRYFDVW (SEQ ID NO: 175) |
| 5D6 | GYTFTTYG (SEQ ID NO: 111) | MNTYSGVP (SEQ ID NO: 147) | CARGGLTTVVVDWYFDVW (SEQ ID NO: 187) |
| 48E1 | GYTFTDYY (SEQ ID NO: 112) | INPNNGGT (SEQ ID NO: 258) | CARSYRSSYVDYAMDYW (SEQ ID NO: 188) |
| 8G8 | GYIFTSNW (SEQ ID NO: 95) | IYPGSDTT (SEQ ID NO: 127) | CARFFSSPWFAYW (SEQ ID NO: 164) |
| 1F6 | GYAFTNFF (SEQ ID NO: 89) | INPGSGGT (SEQ ID NO: 120) | CARNDAMDYW (SEQ ID NO: 158) |
| 29H9 | GFPFTNYL (SEQ ID NO: 106) | INPGSGGT (SEQ ID NO: 120) | CARNDAMDYW (SEQ ID NO: 158) |
| 5F4 | GYAFTNYL (SEQ ID NO: 99) | INPGSGGT (SEQ ID NO: 120) | CARNDAMDYW (SEQ ID NO: 158) |
| 6H12 | GYAFTNYL (SEQ ID NO: 99) | INPGSGGT (SEQ ID NO: 120) | CARNDAMDYW (SEQ ID NO: 158) |
| 5H8 | GYTFTTYG (SEQ ID NO: 111) | MNTYSGVP (SEQ ID NO: 147) | CARGGLTTVVVDWYFDVW (SEQ ID NO: 187) |
| 6C4 | GYTFTEYP (SEQ ID NO: 113) | IYTDTGEP (SEQ ID NO: 148) | CVRGVLLS TVFMPEFAYW (SEQ ID NO: 189) |
| 16F12 | GYTFTGYW (SEQ ID NO: 114) | ILSGSDST (SEQ ID NO: 149) | CARRGLGLSFNNW (SEQ ID NO: 190) |
| 1E6 | GNTFTGYW (SEQ ID NO: 115) | ILPGSDST (SEQ ID NO: 150) | CTGRDLGISFNSW (SEQ ID NO: 191) |
| 30G7 | GFTFSDYY (SEQ ID NO: 108) | ISYGGGNT (SEQ ID NO: 151) | CARQGEEWYFDVW (SEQ ID NO: 180) |
| 10D7 | GYAFTSYW (SEQ ID NO: 116) | IYPGTNST (SEQ ID NO: 152) | CARGYLYFDVW (SEQ ID NO: 192) |

TABLE 5-continued

| | | | |
|---|---|---|---|
| 12G2 | GYTFTNYW (SEQ ID NO: 93) | IDPSDTYT (SEQ ID NO: 125) | CARRWLLHEMDYW (SEQ ID NO: 160) |
| 33D10 | GYTFTSYW (SEQ ID NO: 94) | INPSNGGT (SEQ ID NO: 77) | CAKEPIYYDYDEAGFDHW (SEQ ID NO: 170) |
| 3B8 | GYSFTSYW (SEQ ID NO: 117) | IDPYDTYT (SEQ ID NO: 153) | CARRWLLHKMDYW (SEQ ID NO: 167) |
| 48G9 | GYTFTDYE (SEQ ID NO: 97) | IDPETGGS (SEQ ID NO: 123) | CTIYFWYFDVW (SEQ ID NO: 161) |
| 7G12 | GYTFTDFE (SEQ ID NO: 92) | IDPETGGS (SEQ ID NO: 123) | CTIYFWYFDVW (SEQ ID NO: 161) |
| 4G3 | GYTFTDYE (SEQ ID NO: 97) | FDPETGGS (SEQ ID NO: 154) | CTIYFWYFDVW (SEQ ID NO: 161) |
| 4B10 | GYAFTNFF (SEQ ID NO: 89) | INPGSGGT (SEQ ID NO: 120) | CARNDAMDYW (SEQ ID NO: 158) |
| 12E4 | WLPHASGYY (SEQ ID NO: 118) | IIYDGNN (SEQ ID NO: 155) | CGRYFNGW (SEQ ID NO: 193) |
| 1F12 | GYTFTNYW (SEQ ID NO: 93) | INPSNGGT (SEQ ID NO: 77) | CAKEPIYYDYDEAGFDYW (SEQ ID NO: 194) |
| 3B3 | GYTFTSYW (SEQ ID NO: 94) | ILPHIGYP (SEQ ID NO: 156) | CTQPFLYFHVW (SEQ ID NO: 195) |
| 33G2 | GYTFTTYG (SEQ ID NO: 111) | INTYSGVP (SEQ ID NO: 157) | CARRGSYDGFRLDYW (SEQ ID NO: 196) |
| 15A10 | GYAFSSSW (SEQ ID NO: 109) | IYPGDGDT (SEQ ID NO: 143) | TPAYYSNYGAWFAY (SEQ ID NO: 245) |
| 14E7 | GFAFTNYL (SEQ ID NO: 224) | INPGSGGT (SEQ ID NO: 120) | ARNDAMDY (SEQ ID NO: 246) |
| 3E5 | GYTFTSYW (SEQ ID NO: 94) | IYPGSGNT (SEQ ID NO: 139) | TRGFLYFDV (SEQ ID NO: 247) |
| 5A7 | GYTFTAYG (SEQ ID NO: 217) | INTYSGVP (SEQ ID NO: 157) | ARGGLTTVVVDWYFDV (SEQ ID NO: 233) |
| 30A6 | EYTFTDYY (SEQ ID NO: 218) | INPYNGGI (SEQ ID NO: 231) | ARGGRTLT (SEQ ID NO: 234) |
| 51B8 | GYTFTRYW (SEQ ID NO: 219) | IHPNSGST (SEQ ID NO: 232) | GQYGYDVDYFDY (SEQ ID NO: 235) |
| 15D6 | GYIFTSYW (SEQ ID NO: 220) | IDPSDSYT (SEQ ID NO: 122) | ARRWLLREMDY (SEQ ID NO: 236) |
| 4G8 | GYTFTSYW (SEQ ID NO: 94) | FNPNIGNA (SEQ ID NO: 226) | AREGFSAGY (SEQ ID NO: 237) |
| 10D6 | GYTFTSNW (SEQ ID NO: 221) | IYPGGDTT (SEQ ID NO: 227) | ARFFSSPWFAY (SEQ ID NO: 238) |
| 6D6 | GYTFTSYW (SEQ ID NO: 94) | INPSNGGT (SEQ ID NO: 77) | AKEPIYYDYDEAGFDH (SEQ ID NO: 239) |
| 2G11 | GYTFTNYD (SEQ ID NO: 222) | IYPRSGNA (SEQ ID NO: 228) | ASRRRLCYGL (SEQ ID NO: 240) |
| 50C3_G2A | GYTFTGYG (SEQ ID NO: 103) | IYPRSSNT (SEQ ID NO: 135) | ARREGAPYAMDY (SEQ ID NO: 241) |
| 6G8 | GFTFSNYG (SEQ ID NO: 101) | TSSGGNST (SEQ ID NO: 132) | ARHPYYSYYVEDWFAY (SEQ ID NO: 242) |
| 50C3_G1 | GYTFTEYY (SEQ ID NO: 223) | INPYNGGT (SEQ ID NO: 229) | QQPHLSIHWVIXVS (SEQ ID NO: 243) |

TABLE 5-continued

| | | | |
|---|---|---|---|
| 5G5 | GYTFTNHL (SEQ ID NO: 225) | IHPNTTDT (SEQ ID NO: 230) | AREGRGWYFDV (SEQ ID NO: 244) |
| 1D6 | GYTFTGYW (SEQ ID NO: 114) | ILPGSGST (SEQ ID NO: 255) | CARGGIYYGPTGFAYW (SEQ ID NO: 146) |
| 20D3 | GYTFTTYT (SEQ ID NO: 252) | INPNSDYT (SEQ ID NO: 254) | CARGESITTVVADWYFDVW (SEQ ID NO: 257) |
| 4G10 | GYTFTSYW (SEQ ID NO: 94) | INPGSGST (SEQ ID NO: 256) | CARGFLYFDVW (SEQ ID NO: 169) |
| 6H2 | GYTFTTYG (SEQ ID NO: 111) | MYPGSGNT (SEQ ID NO: 131) | CARGFLYFDVW (SEQ ID NO: 169) |
| 30F1 | | | |
| 10B4 | GYSFTNYW (SEQ ID NO: 377) | IDPSDTYT (SEQ ID NO: 125) | CARRWLLXKMDYW, wherein X is any amino acid (SEQ ID NO: 378) |
| 4F12 | GFTFSNYA (SEQ ID NO: 363) | ITDGGTYT (SEQ ID NO: 364) | CARDDYYGSSYLGFAYW (SEQ ID NO: 365) |
| 4G7 | | | |
| 7B7 | GFTFSNYG (SEQ ID NO: 101) | TSSGGNST (SEQ ID NO: 132) | CARHPYYSYYVEDWFAYW (SEQ ID NO: 171) |
| 9B1 | GYTFTNYG (SEQ ID NO: 267) | IYPRSGNT (SEQ ID NO: 138) | CARREGAPYAMDYW (SEQ ID NO: 174) |
| 11E5 | GYTFTSYG (SEQ ID NO: 107) | IYPRSGNT (SEQ ID NO: 138) | CARREGAPYTMDYW (SEQ ID NO: 178) |

TABLE 6

| | Kappa VJ alleles | | heavy chain VJD alleles | | |
|---|---|---|---|---|---|
| ID | V-GENE and allele | J-GENE and allele | V-GENE and allele | J-GENE and allele | D-GENE and allele |
| 1F1 | IGKV14-130*01 F | IGKJ5*01 F | IGHV1-53*01 F | IGHJ2*01 F (a) | IGHD2-4*01 F |
| 10D8 | IGKV3-4*01 F | IGKJ4*01 F | IGHV1-59*01 F | IGHJ4*01 F | IGHD2-3*01 F |
| 10G7 | IGKV3-4*01 F | IGKJ4*01 F | IGHV1-59*01 F | IGHJ4*01 F | IGHD2-3*01 F |
| 1H3 | IGKV5-48*01 F | IGKJ5*01 F | IGHV1-15*01 F | IGHJ1*03 F | IGHD2-1*01 F |
| 6C3 | IGKV5-48*01 F | IGKJ5*01 F | IGHV1-15*01 F | IGHJ1*03 F | IGHD2-1*01 F |
| 16F4 | IGKV3-4*01 F | IGKJ4*01 F | IGHV1-59*01 F | IGHJ4*01 F | IGHD2-3*01 F |
| 3G6 | IGKV3-4*01 F | IGKJ4*01 F | IGHV1-59*01 F | IGHJ4*01 F | IGHD2-3*01 F |
| 4E2 | IGKV6-17*01 F | IGKJ1*01 F | IGHV1-74*01 F | IGHJ3*01 F, IGHJ3*02 P | IGHD2-14*01 F |
| 9H9 | IGKV3-4*01 F | IGKJ4*01 F | IGHV1-59*01 F | IGHJ4*01 F | IGHD2-3*01 F |
| 13H1 | IGKV15-103*01 ORF | IGKJ1*01 F | IGHV1-9*01 F | IGHJ2*01 F (a) | IGHD3-1*01 F |
| 6F2 | IGKV3-4*01 F | IGKJ4*01 F | IGHV1-59*01 F | IGHJ4*01 F | IGHD2-3*01 F |
| 51A12 | IGKV5-48*01 F | IGKJ5*01 F | IGHV1-15*01 F | IGHJ1*03 F | IGHD2-1*01 F |
| 50C3 | IGKV10-96*01 F | IGKJ1*01 F | IGHV1-59*01 F | IGHJ4*01 F | IGHD2-3*01 F |
| 4B6 | IGKV3-4*01 F | IGKJ4*01 F | IGHV1-59*01 F | IGHJ4*01 F | IGHD2-3*01 F |
| 47F11 | IGKV5-48*01 F | IGKJ5*01 F | IGHV1-15*01 F | IGHJ1*03 F | IGHD2-1*01 F |
| 7H1 | IGKV14-130*01 F | IGKJ5*01 F (b) | IGHV1-54*01 F | IGHJ4*01 F | IGHD2-3*01 F |
| 4H5 | IGKV14-130*01 F | IGKJ5*01 F | IGHV1-54*01 F | IGHJ4*01 F | IGHD2-13*01 F |
| 29G3 | IGKV3-12*01 F | IGKJ4*01 F | IGHV1-18*01 F | IGHJ2*01 F | IGHD1-1*01 F |
| 51G7 | IGKV5-48*01 F | IGKJ5*01 F | IGHV1-15*01 F | IGHJ1*03 F | IGHD2-1*01 F |
| 6E7 | IGKV1-88*01 F | IGKJ1*01 F | IGHV1-19*01 F | IGHJ4*01 F | IGHD2-1*01 F |
| 51D3 | IGKV5-48*01 F | IGKJ5*01 F | IGHV1-15*01 F | IGHJ1*03 F | IGHD2-1*01 F |
| 6H6 | IGKV4-78*01 F | IGKJ5*01 F | IGHV1-53*01 F | IGHJ2*01 F (a) | IGHD2-4*01 F |
| 17A3 | IGKV12-46*01 F | IGKJ2*01 F | IGHV5-6*01 F, IGHV5-6-1*01 F | IGHJ3*01 F | IGHD2-5*01 F |
| 8B5 | IGKV10-94*01 F | IGKJ1*01 F | IGHV3-6*01 F | IGHJ1*03 F | IGHD2-1*01 F |
| 4E7 | IGKV10-94*01 F | IGKJ1*01 F | IGHV3-6*01 F | IGHJ1*03 F | IGHD2-1*01 F |
| 6A9 | IGKV12-46*01 F | IGKJ2*01 F | IGHV5-6*01 F, IGHV5-6-1*01 F | IGHJ3*01 F | IGHD2-5*01 F |
| 50B9 | IGKV10-96*01 F | IGKJ1*01 F | IGHV1-81*01 F | IGHJ4*01 F | IGHD6-3*01 F |
| 15C6 | IGKV10-94*01 F | IGKJ1*01 F | IGHV3-6*01 F | IGHJ1*03 F | IGHD2-1*01 F |
| 17H7 | IGKV14-130*01 F | IGKJ5*01 F | IGHV1-54*01 F, IGHV1-54*02 F | IGHJ4*01 F | IGHD2-13*01 F |

TABLE 6-continued

| | Kappa VJ alleles | | heavy chain VJD alleles | | |
|---|---|---|---|---|---|
| ID | V-GENE and allele | J-GENE and allele | V-GENE and allele | J-GENE and allele | D-GENE and allele |
| 10B10 | IGKV6-23*01 F | IGKJ2*01 F | IGHV13-2*01 F | IGHJ3*01 F | IGHD1-1*01 F |
| 11A5 | IGKV10-96*01 F | IGKJ1*01 F | IGHV1-81*01 F | IGHJ4*01 F | IGHD6-3*01 F |
| 4D3 | IGKV10-94*01 F | IGKJ1*01 F | IGHV3-6*01 F, or IGHV3-6*02 F | IGHJ3*01 F | IGHD1-1*01 F |
| 5C12 | IGKV6-17*01 F | IGKJ2*01 F | GHV1-55*01 F | IGHJ1*03 F | IGHD3-1*01 F |
| 6F1 | IGKV10-94*01 F | IGKJ1*01 F | IGHV3-6*01 F | IGHJ1*03 F | IGHD2-1*01 F |
| 4A5 | IGKV6-25*01 F | IGKJ5*01 F | IGHV5-12*01 F | IGHJ1*03 F | IGHD2-14*01 F |
| 5A3 | IGKV10-94*01 F | IGKJ1*01 F | s IGHV3-6*01 F | IGHJ1*03 F | IGHD2-1*01 F |
| 51H9 | IGKV4-68*01 F | IGKJ5*01 F | IGHV1-64*01 F | IGHJ2*01 F | IGHD1-1*01 F |
| 12H6 | IGKV10-94*01 F | IGKJ1*01 F | IGHV3-6*01 F | IGHJ1*03 F | IGHD2-1*01 F |
| 10C5 | IGKV3-12*01 F | IGKJ2*01 F | IGHV1-82*01 F | IGHJ3*01 F | IGHD2-5*01 F |
| 8G10 | IGKV4-68*01 F | IGKJ5*01 F | IGHV1-64*01 F | IGHJ2*01 F | IGHD1-1*01 F |
| 11B2 | IGKV10-94*01 F | IGKJ1*01 F | IGHV3-6*01 F | IGHJ1*03 F | IGHD2-1*01 F |
| 29G2 | IGKV4-72*01 F | IGKJ2*01 F | IGHV1-64*01 F | IGHJ4*01 F | IGHD1-1*01 F |
| 33A12 | IGKV8-24*01 F | IGKJ5*01 F | IGHV9-3*01 F | IGHJ4*01 F | IGHD2-4*01 F |
| 15E7 | IGKV3-12*01 F | IGKJ1*01 F | IGHV1-26*01 F | IGHJ3*01 F | IGHD1-1*01 F |
| 5D6 | IGKV14-111*01 F | IGKJ5*01 F | IGHV9-3*01 F | IGHJ1*03 F | IGHD1-1*01 F |
| 48E1 | IGKV12-46*01 F | IGKJ1*01 F | IGHV1-26*01 F | IGHJ4*01 F | IGHD1-1*01 F |
| 8G8 | IGKV6-23*01 F | IGKJ5*01 F | IGHV1-55*01 F | IGHJ3*01 F | IGHD1-2*01 F |
| 1F6 | IGKV14-130*01 F | IGKJ5*01 F | IGHV1-54*01 F | IGHJ4*01 F | IGHD2-13*01 F |
| 29H9 | IGKV14-130*01 F | IGKJ5*01 F | IGHV1-54*01 F | IGHJ4*01 F | IGHD2-13*01 F |
| 5F4 | IGKV14-130*01 F | IGKJ5*01 F | IGHV1-54*01 F | IGHJ4*01 F | IGHD2-13*01 F |
| 6H12 | IGKV14-130*01 F | IGKJ5*01 F | IGHV1-54*01 F | IGHJ4*01 F | IGHD2-13*01 F |
| 5H8 | IGKV12-46*01 F | IGKJ1*01 F | IGHV9-3*01 F | IGHJ1*03 F | IGHD1-1*01 F |
| 6C4 | IGKV3-12*01 F | IGKJ4*01 F | IGHV9-1*01 F | IGHJ3*01 F | IGHD2-2*01 F |
| 16F12 | IGKV15-103*01 ORF | IGKJ1*01 F | IGHV1-9*01 F | IGHJ2*01 F (a) | IGHD3-1*01 F |
| 1E6 | IGKV15-103*01 ORF | IGKJ1*01 F | IGHV1-9*01 F | IGHJ2*01 F (a) | IGHD1-1*02 F |
| 30G7 | IGKV6-25*01 F | IGKJ5*01 F | IGHV5-12*01 F | IGHJ1*03 F | IGHD2-14*01 F |
| 10D7 | IGKV6-17*01 F | IGKJ2*01 F | IGHV1-55*01 F | IGHJ1*03 F | IGHD3-3*01 F |
| 12G2 | IGKV3-4*01 F | IGKJ4*01 F | IGHV1-59*01 F | IGHJ4*01 F | IGHD2-3*01 F |
| 33D10 | IGKV3-4*01 F | IGKJ4*01 F | IGHV1-53*01 F | IGHJ2*01 F (a) | IGHD2-4*01 F |
| 3B8 | IGKV3-4*01 F | IGKJ4*01 F | IGHV1-59*01 F | IGHJ4*01 F | IGHD2-3*01 F |
| 48G9 | IGKV5-48*01 F | IGKJ5*01 F | IGHV1-15*01 F | IGHJ1*03 F | IGHD2-1*01 F |
| 7G12 | IGKV5-48*01 F | IGKJ5*01 F | IGHV1-15*01 F | IGHJ1*03 F | IGHD2-1*01 F |
| 4G3 | IGKV5-48*01 F | IGKJ5*01 F | IGHV1-15*01 F | IGHJ1*03 F | IGHD2-1*01 F |
| 4B10 | IGKV10-94*01 F | IGKJ1*01 F | IGHV1-54*01 F | IGHJ4*01 F | IGHD2-13*01 F |
| 12E4 | IGKV10-94*01 F | IGKJ1*01 F | IGHV3-6*01 F | IGHJ1*03 F | IGHD2-1*01 F |
| 1F12 | IGKV4-78*01 F | IGKJ5*01 F | IGHV1-53*01 F | IGHJ2*01 F (a) | IGHD2-4*01 F |
| 3B3 | IGKV6-17*01 F | IGKJ2*01 F | IGHV1S20*02 F | IGHJ1*03 F | IGHD6-2*02 F |
| 33G2 | IGKV4-86*01 F | IGKJ5*01 F | IGHV9-3*01 F | IGHJ2*01 F (a) | IGHD1-1*01 F |
| 5G5 | IGKV4-59*01 F | IGKJ2*01 F | IGHV1-64*01 F | IGHJ1*03 F | IGHD2-14*01 F |
| 15A10 | IGKV3-12*01 F | IGKJ2*01 F | IGHV1-82*01 F | IGHJ3*01 F | IGHD2-5*01 F |
| 14E7 | IGKV14-130*01 F | IGKJ5*01 F | IGHV4-1*01 F | IGHJ3*01 F | IGHD2-5*01 F |
| 3E5 | IGKV10-96*01 F | IGKJ1*01 F | IGHV1-55*01 F | IGHJ1*03 F | IGHD3-1*01 F |
| 5A7 | IGKV10-94*01 F | IGKJ1*01 F | IGHV9-3*01 F | IGHJ1*03 F | IGHD1-1*01 F |
| 30A6 | IGKV3-4*01 F | IGKJ4*01 F | IGHV1-59*01 F | IGHJ4*01 F | IGHD2-3*01 F |
| 51B8 | IGKV3-4*01 F | IGKJ4*01 F | IGHV1-64*01 F | IGHJ2*01 F | IGHD2-2*01 F |
| 15D6 | IGKV3-4*01 F | IGKJ4*01 F | IGHV1-59*01 F | IGHJ4*01 F | IGHD2-3*01 F |
| 4G8 | IGKV6-23*01 F | IGKJ2*01 F | IGHV1-53*01 F | IGHJ2*01 F (a) | IGHD1-2*01 F |
| 10D6 | IGKV6-23*01 F | IGKJ5*01 F | IGHV1-55*01 F | IGHJ3*01 F | IGHD1-2*01 F |
| 6D6 | IGKV3-4*01 F | IGKJ4*01 F | IGHV1-53*01 F | IGHJ2*01 F (a) | IGHD2-4*01 F |
| 2G11 | IGKV10-94*01 F | IGKJ1*01 F | IGHV1-81*01 F | IGHJ4*01 F | IGHD2-4*01 F |
| 50C3_G2A | IGKV10-96*01 F | IGKJ1*01 F | IGHV1-81*01 F | IGHJ4*01 F | IGHD6-3*01 F |
| 6G8 | IGKV10-94*01 F | IGKJ1*01 F | IGHV5-6*01 F or IGHV5-6-1*01 F | IGHJ3*01 F | IGHD2-5*01 F |
| 50C3_G1 | IGKV3-4*01 F | IGKJ4*01 F | IGHV1-19*01 F | IGHJ3*01 F (b) | IGHD1-2*01 F |
| 1D6 | IGKV14-111*01 F | IGKJ5*01 F | IGHV1-9*01 F | IGHJ3*01 F | IGHD2-1*01 F |
| 20D3 | IGKV12-46*01 F | IGKJ5*01 F | IGHV1-4*01 F | IGHJ1*03 F | IGHD1-1*01 F |
| 4G10 | IGKV6-17*01 F | IGKJ2*01 F | IGHV1-55*01 F | IGHJ1*03 F | IGHD3-1*01 F |
| 6H2 | IGKV6-17*01 F | IGKJ2*01 F | IGHV1-55*01 F | IGHJ1*03 F | IGHD3-1*01 F |
| 30F1 | | | | | |
| 10B4 | | | | | |
| 4F12 | | | | | |
| 4G7 | | | | | |
| 7B7 | | | | | |
| 11E5 | | | | | |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to leukocyte immunoglobulin-like receptor B2 (LILRB2), comprising (a) a heavy chain variable region (VH) comprising a heavy chain complementarity determining region 1 (HCDR1) comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and a light chain variable region (VL) comprising: a light chain CDR 1 (LCDR1) comprising the amino acid sequence set forth in SEQ ID NO:1, a LCDR2 comprising the amino acid sequence set forth in SEQ ID NO:35, and a LCDR3 comprising SEQ ID NO:50;

(b) a VH comprising: a HCDR1 comprising the amino acid sequence set forth in SEQ ID NO:92, a HCDR2 comprising the amino acid sequence set forth in SEQ ID NO:124, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:53;

(c) a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:159; and a VL comprising: a LCDR1 comprising the amino acid sequence set forth in SEQ ID NO:2, a LCDR2 comprising the amino acid sequence set forth in SEQ ID NO:36, and a LCDR3 comprising the amino acid sequence set forth in SEQ ID NO:51;

(d) a VH comprising: a HCDR1 comprising the amino acid sequence set forth in SEQ ID NO:91, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52;

(e) a VH comprising: a HCDR1 comprising the amino acid sequence set forth in SEQ ID NO:92, a HCDR2 comprising the amino acid sequence set forth in SEQ ID NO:123, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:37, and a LCDR3 comprising the amino acid sequence set forth in SEQ ID NO:53;

(f) a VH comprising: a HCDR1 comprising the amino acid sequence set forth in SEQ ID NO:225, a HCDR2 comprising the amino acid sequence set forth in SEQ ID NO:230, and a HCDR3 comprising the amino acid sequence set forth in SEQ ID NO:244; and a VL comprising: a light chain CDR 1 (LCDR1) comprising the amino acid sequence set forth in SEQ ID NO:24, a LCDR2 comprising the amino acid sequence set forth in SEQ ID NO:202, and a LCDR3 comprising the amino acid sequence set forth in SEQ ID NO:216;

(g) a VH comprising: a HCDR1 comprising the amino acid sequence set forth in SEQ ID NO:93, a HCDR2 comprising the amino acid sequence set forth in SEQ ID NO:125, and a HCDR3 comprising the amino acid sequence set forth in SEQ ID NO:162; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52;

(h) a VH comprising: a HCDR1 comprising the amino acid sequence set forth in SEQ ID NO:93, a HCDR2 comprising the amino acid sequence set forth in SEQ ID NO:122, and a HCDR3 comprising the amino acid sequence set forth in SEQ ID NO:160; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52;

(i) a VH comprising: a HCDR1 comprising the amino acid sequence set forth in SEQ ID NO:95, a HCDR2 comprising the amino acid sequence set forth in SEQ ID NO:127, and a HCDR3 comprising the amino acid sequence set forth in SEQ ID NO:164; and a VL comprising: a LCDR1 comprising the amino acid sequence set forth in SEQ ID NO:3, a LCDR2 comprising the amino acid sequence set forth in SEQ ID NO:36, and a LCDR3 comprising the amino acid sequence set forth in SEQ ID NO:52; or (j) a VH comprising: a HCDR1 comprising the amino acid sequence set forth in SEQ ID NO:96, a HCDR2 comprising the amino acid sequence set forth in SEQ ID NO:128, and a HCDR3 comprising the amino acid sequence set forth in SEQ ID NO:165; and a VL comprising: a LCDR1 comprising the amino acid sequence set forth in SEQ ID NO:6, a LCDR2 comprising the amino acid sequence set forth in SEQ ID NO:40, and a LCDR3 comprising the amino acid sequence set forth in SEQ ID NO:55.

2. The antibody or antigen-binding fragment thereof of claim 1, comprising:

(a) a VH comprising: a HCDR1 comprising the amino acid sequence set forth in SEQ ID NO:89, a HCDR2 comprising the amino acid sequence set forth in SEQ ID NO:120, and a HCDR3 comprising the amino acid sequence set forth in SEQ ID NO:158; and VL comprising: a LCDR1 comprising the amino acid sequence set forth in SEQ ID NO:1, a LCDR2 comprising the amino acid sequence set forth in SEQ ID NO:35, and a LCDR3 comprising SEQ ID NO:50;

(b) a VH comprising: a HCDR1 comprising the amino acid sequence set forth in SEQ ID NO:92, a HCDR2 comprising the amino acid sequence set forth in SEQ ID NO:124, and a HCDR3 comprising the amino acid sequence set forth in SEQ ID NO:161; and a VL comprising: a LCDR1 comprising the amino acid sequence set forth in SEQ ID NO:4, a LCDR2 comprising the amino acid sequence set forth in SEQ ID NO:38, and a LCDR3 comprising the amino acid sequence set forth in SEQ ID NO:53; or (c) a VH comprising: a HCDR1 comprising the amino acid sequence set forth in SEQ ID NO:90, a HCDR2 comprising the amino acid sequence set forth in SEQ ID NO:121, and a HCDR3 comprising the amino acid sequence set forth in SEQ ID NO:159; and a VL comprising: a LCDR1 comprising the amino acid sequence set forth in SEQ ID NO:2, a LCDR2 comprising the amino acid sequence set forth in SEQ ID NO:36, and a LCDR3 comprising the amino acid sequence set forth in SEQ ID NO:51.

3. The antibody or antigen-binding fragment thereof of claim 1, wherein the antibody or antigen-binding fragment thereof of comprises an IgG1 or an IgG2 heavy chain constant region.

4. The antibody or antigen-binding fragment thereof of claim 1, wherein the antibody or antigen-binding fragment thereof comprises a kappa light chain constant region.

5. An isolated nucleic acid molecule encoding the antibody or antigen-binding fragment thereof of claim 1.

6. A vector comprising the nucleic acid molecule of claim 5.

7. A host cell comprising the vector of claim 6.

8. A method for producing the antibody or antigen-binding fragment thereof of claim 1, comprising:

(a) culturing a host cell under conditions suitable for expression of the antibody or antigen-binding fragment thereof by the host cell, wherein the host cell comprises a vector comprising a nucleic acid encoding the antibody or antigen-binding fragment thereof; and (b) recovering the antibody or antigen-binding fragment thereof.

9. A pharmaceutical composition comprising the antibody or antigen-binding fragment thereof of claim 1 and a suitable pharmaceutical carrier.

10. The pharmaceutical composition of claim 9, further comprising a chemotherapeutic agent or an analgesic.

11. The pharmaceutical composition of claim 9, further comprising one or more additional agents selected from the group consisting of: a myeloid-derived suppressor cell, a mobilizing agent, a c-jun N-terminal kinase inhibitor, an anti-inflammatory agent, and an immunosuppressive agent.

12. The pharmaceutical composition of claim 9, wherein the composition is formulated for intravenous, intramuscular, oral, subcutaneous, intraperitoneal, intrathecal, intratumoral or intramuscular administration to a subject.

13. A method of treating cancer in a mammal in need thereof, the method comprising administering to the mammal a therapeutically effective amount of the antibody or antigen-binding fragment thereof of claim 1.

14. The method of claim 13, further comprising administering to the mammal a chemotherapeutic agent or an analgesic.

15. The method of claim 13, further comprising administering to the mammal an immune checkpoint inhibitor.

16. The method of claim 15, wherein the immune checkpoint inhibitor is a PD-1 or PD-L1 inhibitor.

17. The method of claim 13, wherein the cancer is a lymphoma, a leukemia, a colon cancer, or a breast cancer.

18. A method of treating an infection in a mammal in need thereof, comprising administering to the mammal the antibody or antigen-binding fragment thereof of claim 1.

19. The method of claim 18, wherein the infection is a bacterial infection.

* * * * *

UNITED STATES PATENT AND TRADEMARK OFFICE

CERTIFICATE OF CORRECTION

PATENT NO. : 12,157,768 B2
APPLICATION NO. : 17/276324
DATED : December 3, 2024
INVENTOR(S) : Shu-Hsia Chen et al.

It is certified that error appears in the above-identified patent and that said Letters Patent is hereby corrected as shown below:

On the Title Page

At (71), please correct the Applicant name to read “ICAHN SCHOOL OF MEDICINE AT MOUNT SINAI.”

Signed and Sealed this
Eleventh Day of February, 2025

Coke Morgan Stewart
*Acting Director of the United States Patent and Trademark Office*